US012631624B2

(12) United States Patent
Routenberg et al.

(10) Patent No.: US 12,631,624 B2
(45) Date of Patent: May 19, 2026

(54) METHODS FOR ISOLATING SURFACE MARKER DISPLAYING AGENTS

(71) Applicant: Meso Scale Technologies, LLC., Rockville, MD (US)

(72) Inventors: David Routenberg, Gaithersburg, MD (US); Alexander K. Tucker-Schwartz, Bethesda, MD (US); Sigal Shachar, North Bethesda, MD (US)

(73) Assignee: MESO SCALE TECHNOLOGIES, LLC., Rockville, MD (US)

( * ) Notice: Subject to any disclaimer, the term of this patent is extended or adjusted under 35 U.S.C. 154(b) by 1230 days.

(21) Appl. No.: 17/287,341

(22) PCT Filed: Oct. 23, 2019

(86) PCT No.: PCT/US2019/057713
§ 371 (c)(1),
(2) Date: Apr. 21, 2021

(87) PCT Pub. No.: WO2020/086751
PCT Pub. Date: Apr. 30, 2020

(65) Prior Publication Data
US 2021/0382043 A1      Dec. 9, 2021

Related U.S. Application Data

(60) Provisional application No. 62/749,640, filed on Oct. 23, 2018.

(30) Foreign Application Priority Data

May 17, 2019    (WO) ............... PCT/US2019/032995

(51) Int. Cl.
*G01N 33/543*        (2006.01)
*C12N 15/10*        (2006.01)
*C12Q 1/6834*        (2018.01)

(52) U.S. Cl.
CPC ...  *G01N 33/54306* (2013.01); *C12N 15/1065* (2013.01); *C12Q 1/6834* (2013.01)

(58) Field of Classification Search
None
See application file for complete search history.

(56) References Cited

U.S. PATENT DOCUMENTS

| | | |
|---|---|---|
| 5,238,808 A | 8/1993 | Bard |
| 5,240,863 A | 8/1993 | Shibue et al. |
| 5,641,623 A | 6/1997 | Martin |
| 5,846,485 A | 12/1998 | Leland et al. |
| 6,054,274 A | 4/2000 | Sampson et al. |
| 6,291,187 B1 | 9/2001 | Kingsmore et al. |
| 6,323,009 B1 | 11/2001 | Lasken et al. |
| 6,344,329 B1 | 2/2002 | Lizardi |
| 6,368,801 B1 | 4/2002 | Faruqi |
| 6,939,720 B2 | 9/2005 | Chandler et al. |
| 6,977,722 B2 | 12/2005 | Wohlstadter et al. |
| 7,842,246 B2 | 11/2010 | Wohlstadter et al. |
| 10,201,812 B2 | 2/2019 | Glezer et al. |
| 10,655,162 B1 | 5/2020 | Alon et al. |
| 12,480,940 B2 | 11/2025 | Routenberg |
| 2010/0261292 A1 | 10/2010 | Glezer et al. |
| 2015/0119278 A1 | 4/2015 | Goetzl |
| 2015/0125477 A1 | 5/2015 | Kuttruff-Coqui et al. |
| 2016/0003835 A1 | 1/2016 | Halbert et al. |
| 2017/0211133 A1* | 7/2017 | Landegren ........... C12Q 1/6876 |
| 2019/0203275 A1* | 7/2019 | Frisén .................. C12Q 1/6834 |
| 2021/0389304 A1 | 12/2021 | Routenberg |
| 2023/0349920 A1 | 11/2023 | Routenberg et al. |
| 2025/0035615 A1 | 1/2025 | Routenberg |
| 2025/0354198 A1 | 11/2025 | Gizzie et al. |

FOREIGN PATENT DOCUMENTS

| | | | |
|---|---|---|---|
| EP | 3246703 A1 | 11/2017 | |
| WO | 2015/175856 A1 | 10/2010 | |
| WO | 2011/062933 A2 | 5/2011 | |
| WO | 2015/130956 A2 | 9/2015 | |
| WO | WO-2016193695 A1 * | 12/2016 | ........... C12Q 1/6806 |
| WO | 2017/053516 A1 | 3/2017 | |
| WO | 2017/124000 A1 | 7/2017 | |
| WO | 2018/213847 A1 | 11/2018 | |
| WO | 2019/014486 A1 | 1/2019 | |
| WO | 2019/113499 A1 | 6/2019 | |
| WO | 2019/222708 A2 | 11/2019 | |
| WO | 2020/086751 A1 | 4/2020 | |
| WO | 2020/142313 A1 | 7/2020 | |
| WO | 2022/011197 A1 | 1/2022 | |
| WO | 2022/051481 A2 | 3/2022 | |
| WO | 2023/212315 A2 | 11/2023 | |

OTHER PUBLICATIONS

Jwa-Min Nam et al "Nanoparticle-Based Bio-Bar Codes for the Ultrasensitive Detection of Proteins" Science, vol. 301, 1884-1886. (Year: 2003).*
Hammond et al, Profiling Cellular Protein Complexes by Proximity Ligation with Dual Tag Microarray Readout, PlosONE, 7(7): e40405 (Year: 2012).*
ProteinSeq: High-Performance Proteomic Analyses by Proximity Ligation and Next Generation Sequencing, PLoS ONE 6(9): e25583 (Year: 2011).*

(Continued)

*Primary Examiner* — Juliet C Switzer
*Assistant Examiner* — Brian Ellis Young
(74) *Attorney, Agent, or Firm* — MEDLER FERRO WOODHOUSE & MILLS PLLC

(57)            ABSTRACT

The invention relates to method and kits for highly specific isolation of surface marker displaying agents by targeting at least two surface markers. The invention further relates to methods and kits for analyzing surface marker displaying agents and their contents.

11 Claims, 72 Drawing Sheets

(56)            References Cited

OTHER PUBLICATIONS

Tavoosidana et al, Multiple recognition assay reveals prostasomes as promising plasma biomarkers for prostate cancer, 108(21) 8809-8814 (Year: 2011).*

Lof et al, Detection of Extracellular Vesicles Using Proximity Ligation Assay with Flow Cytometry Readout-ExoPLA, Current Protocols in Cytometry 4.8.1-4.8.10 (Year: 2017).*

Edith et al, Sensitive protein detection via triple-binder proximity ligation assays, Nature Methods, 4(2), 135-137. (Year: 2007).*

Darmanis et al, ProteinSeq: High-Performance Proteomic Analyses by Proximity Ligation and Next Generation Sequencing, PLoS ONE 6(9): e25583 (Year: 2011).*

Aureli, M. et al., "GM Ganglioside: Past Studies and Future Potential", Mol. Neurobiol. 53:1824-1842 (2016).

Lauc, G. et al., "Shedding and Uptake of Gangliosides and Glycosylphosphatidylinositol-Anchored Proteins", Biochimica et Biophysica Acta 1760(4):584-602 (2006).

Final Office Action in U.S. Appl. No. 17/055,829, dated Aug. 26, 2024.

Bombera et al., "DNA-directed capture of primary cells from a complex mixture and controlled orthogonal release monitored by SPR imaging." Biosensors and Bioelectronics 15:33(1):10-16 (2012).

Zhang et al., "A membrane form of TNF-alpha presented by exosome delays T cell activation-induced cell death," The Journal of Immunology 176(12):7385-93 (2006).

Armstrong et al., "Extracellular Vesicles and the Promise of Continuous Liquid Biopsies," Journal of Pathology and Translational Medicine 52:1-8 (2018).

Baner et al., "Signal amplification of padlock probes by rolling circle replication," Nucleic Acids Res. 26:5073-5078 (1998).

Bugeon et al., "Costimulation of Cells," Am. J. Respir. Crit. Care Med. 162:S164-S168 (2000).

Dean et al., "Rapid Amplification of Plasmid and Phage DNA Using Phi29 DNA Polymerase and Multiply-Primed Rolling Circle Amplification," Genome Res. 11:1095-1099 (2001).

Eason et al., "Characterization of synthetic DNA bar codes in *Saccharomyces cerevisiae* gene-deletion strains," Proc Natl Acad Sci USA 101(30):11046-11051 (2004).

Faruqi et al., "High-throughput genotyping of single nucleotide polymorphisms with rolling circle amplification," BMC Genomics 2:4 (2000).

Fredriksson et al., "Multiplexed protein detection by proximity ligation for cancer biomarker validation," Nature Methods 4(4):327-329 (2007).

Gardiner et al., "Techniques used for the isolation and characterization of extracellular vesicles: Results of a worldwide survey," Journal of Extracellular Vesicles 5(1):32945 (2016).

Hein et al., "Click Chemistry, a Powerful Tool for Pharmaceutical Sciences," Pharm. Res. 25(10):2216-2230 (2008).

Hill et al., "The bio-barcode assay for the detection of protein and nucleic acid targets using DTT-induced ligand exchange," Nature Protocols 1(1):324-336 (2006).

Hodge et al., "Costimulatory Molecules as Adjuvants for Immunotherapy," Frontiers in Bioscience 11:788-803 (2006).

Kalra et al., "Vesiclepedia: a compendium for extracellular vesicles with continuous community annotation," PLoS Biol 10(12):e1001450 (2012).

Kim et al., "EVpedia: an integrated database of high-throughput data for systemic analyses of extracellular vesicles," Journal of Extracellular Vesicles 2:20384 (2013).

Koliha et al., "A novel multiplex bead-based platform highlights the diversity of extracellular vesicles," Journal of Extracellular Vesicles, 5:29975 (2016).

Lizardi et al., "Mutation detection and single-molecule counting using isothermal rolling-circle amplification," Nature Genetics 19:225-232 (1998).

Mathivanan et al., "ExoCarta: a compendium of exosomal proteins and RNA," Proteomics 9:4997-5000 (2009).

Mathivanan et al., "ExoCarta 2012: database of exosomal proteins RNA and lipids," Nucleic Acids Res. 40(D1): D1241-D1244 (2012).

Nallur et al., "Signal amplification by rolling circle amplification on DNA microarrays," Nucleic Acids Res. 29:e118 (2001).

Nam et al., "Nanoparticle-Based Bio-Bar Codes for the Ultrasensitive Detection of Proteins," Science 301(5641):1884-1886 (2003).

Schweitzer et al., "Immunoassays with rolling circle DNA amplification: a versatile platform for ultrasensitive antigen detection," Proc Natl Acad Sci USA 97:10113-10119 (2000).

Schweitzer et al., "Multiplexed protein profiling on microarrays by rolling-circle amplification," Nature Biotechnol. 20:359-365 (2002).

Simpson et al., "ExoCarta as a resource for exosomal research," Journal of Extracellular Vesicles 1:18374 (2012).

Thermofisher, "Crosslinking Technical Handbook," Oct. 2012 printed in the U.S.

Winzeler et al., "Functional characterization of the *S. cerevisiae* genome by gene deletion and parallel analysis," Science 285:901-906 (1999).

International Search Report in PCT/US19/57713, dated Dec. 20, 2019.

International Search Report in PCT/US19/32995, dated Nov. 20, 2019.

International Search Report in PCT/US2023/020399 dated Oct. 23, 2023.

Non-Final Office Action in U.S. Appl. No. 17/055,829, United States Patent and Trademark Office, dated Apr. 5, 2024.

International Search Report in PCT/US2021/048849, dated Feb. 25, 2022.

Non-Final Office Action issued in U.S. Appl. No. 17/055,829, filed Feb. 12, 2025.

Notice of Allowance in U.S. Appl. No. 17/055,829, dated Jul. 31, 2025.

Corrected Notice of Allowability in U.S. Appl. No. 17/055,829, dated Oct. 7, 2025.

\* cited by examiner

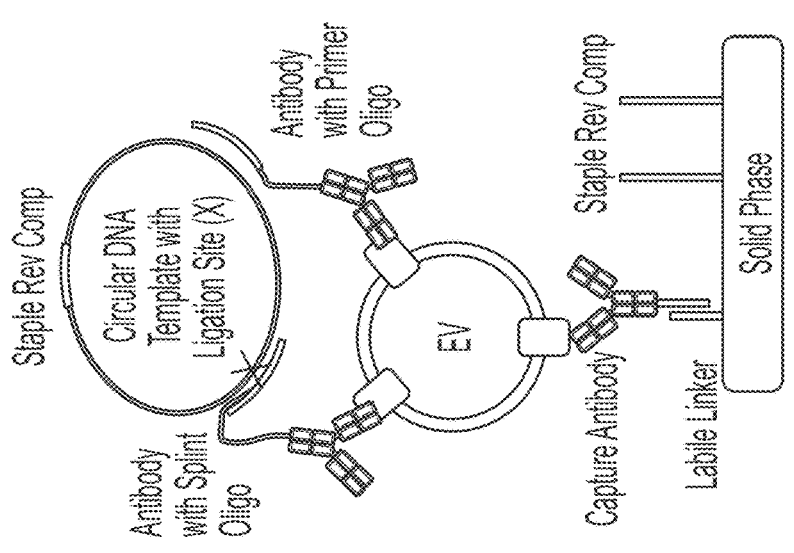
FIG. 1E
| Staple Antibody Specificity | EV Fraction Remaining after Elution |
|---|---|
| CD81 (High Expression) | 101.2% ±13.9% |
| CD63 (Low Expression) | 70.7% ±10.9% |
| Irrelevant Control | 39.3% ±5.3% |
| No Stapling | 19.9% ±1.2% |
FIG. 1D
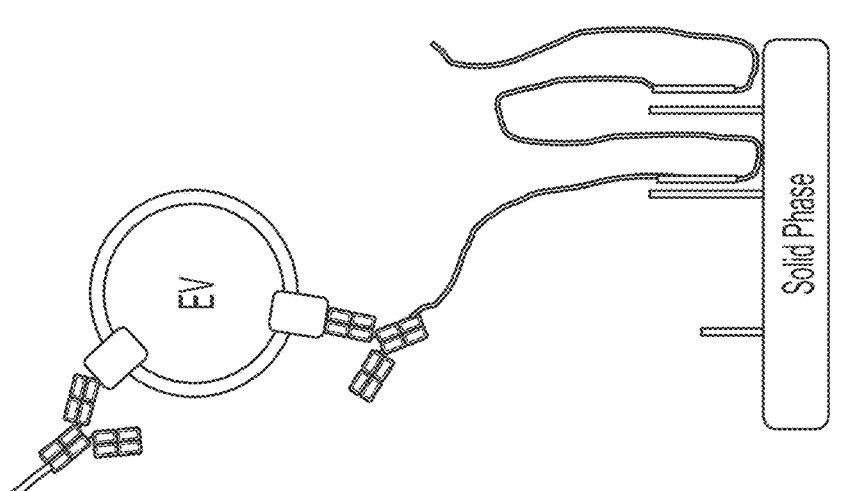
FIG. 1C

| Position of Irrelevant Control Ab | Relative Signal |
|---|---|
| None | 100% |
| Negative Control Capture Antibody | 0.9% |
| Negative Control Splint Antibody | 1.8% |
| Negative Control Primer Antibody | 1.6% |

1. Selective capture of EVs and wash     2. Lyse EVs and transfer to ultrasensitive assay

| EV Capture Antibody | Relative EDFR cytoplasmic domain assay signal |
|---|---|
| No EV capture w/lysis | 100% |
| No EV capture w/o lysis | 34% ± 0.2% |
| CD63 | 31% ± 4.6% |
| CD81 | 37% ± 3.2% |
| CD9 | 64% ± 11.4% |
| Irrelevant Control | 3.5% ± 0.8% |

| EV Capture Antibody | Protease treatment | Relative HSP70 assay signal |
|---|---|---|
| No Capture | None | 100% |
| CD81 | None | 0.45% ± 0.01% |
| CD81 | Before Lysis | 0.16% ± 0.03% |
| CD81 | After Lysis | 0.001% ± 0.01% |
| Irrelevant Control | None | 0.21% ± 0.03% |
| Irrelevant Control | Before Lysis | 0.000% ± 0.003% |
| Irrelevant Control | After Lysis | 0.000% ± 0.003% |

1. Selective capture of EVs and wash

2. Protease digestion, then add inhibitor

3. Lyse EVs and transfer to ultrasensitive assay

| | CD63 Cap | CD81 Cap | CD9 Cap | EpCAM Cap |
|---|---|---|---|---|
| MC01 - PANC1-1 Exosomes 1/100 | | | | |
| CD63 Detection | 16894.5 | 27497 | 9980 | 1855 |
| CD81 Detection | 25106.5 | 31456 | 17407 | 3153 |
| CD9 Detection | 24438.5 | 47679 | 12087 | 4042.5 |
| EpCAM detection | 1450.5 | 2938.5 | 1167.5 | |
| MC02 - PANC-1 CCM, neat | | | | |
| CD63 Detection | 28849 | 39941 | 8290 | 4068.5 |
| CD81 Detection | 41466 | 38604.5 | 13566 | 6299 |
| CD9 Detection | 27489.5 | 40460.5 | 8165.5 | 7999.5 |
| EpCAM detection | 3236 | 5838 | 1923 | |
| MC03 - HUVEC Exosomes 1/100 | | | | |
| CD63 Detection | 16713 | 13316 | 13340 | 63.5 |
| CD81 Detection | 10928.5 | 9578.5 | 17309.5 | 47 |
| CD9 Detection | 27374 | 46228 | 39523.5 | 63 |
| EpCAM detection | 163 | 137 | 139.5 | |
| MC04 - HUVEC CCM, neat | | | | |
| CD63 Detection | 15143.5 | 12564 | 15325 | 49.5 |
| CD81 Detection | 9920 | 6187 | 16376 | 39 |
| CD9 Detection | 32941.5 | 54121 | 50560.5 | 52.5 |
| EpCAM detection | 143 | 133.5 | 123.5 | |
| MC05 - HPDEC Exosomes, 1/100 | | | | |
| CD63 Detection | 3338 | 2314 | 3904 | 1648 |
| CD81 Detection | 1699.5 | 1056 | 6493 | 2505 |
| CD9 Detection | 8394 | 25679 | 25273.5 | 16320.5 |
| EpCAM detection | 1577 | 3675 | 6879 | |
| MC07 - Pancreatic Tumor Exosomes, 1/100 | | | | |
| CD63 Detection | 719.5 | 53.5 | 1762.5 | 3080.5 |
| CD81 Detection | 211 | 48 | 48 | 43 |
| CD9 Detection | 4154 | 74.5 | 17599 | 56415.5 |
| EpCAM detection | 2322.5 | 148.5 | 20643 | |
| MC08 - Pancreatic Tumor CCM, neat | | | | |
| CD63 Detection | 22513 | 3738.5 | 2270.5 | 207 |
| CD81 Detection | 3920 | 4196 | 3470 | 57.5 |
| CD9 Detection | 3983 | 6670.5 | 3233 | 7104.5 |
| EpCAM Detection | 278.5 | 143.5 | 2762 | |
| Expi293 CCM, neat | | | | |
| CD63 Detection | 5359 | 38393.5 | 20234 | 564.5 |
| CD81 Detection | 65068 | 161165 | 119507.5 | 3770.5 |
| CD9 Detection | 41604 | 141440.5 | 18436 | 3031.5 |
| EpCAM detection | 974.5 | 4382 | 2420 | |

FIG. 12

IgG1 control detection
antibody
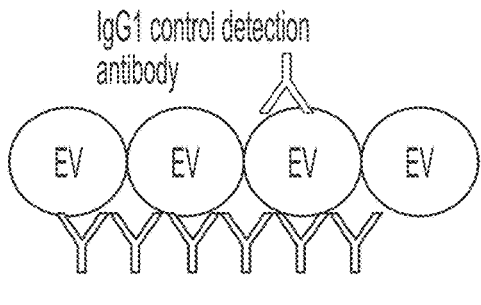
CD81 Capture
FIG. 13A
CD81 Detector antibody
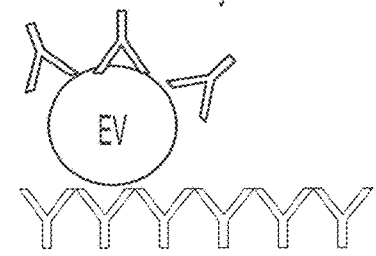
IgG1 control capture antibody
FIG. 13B
| | | CD63 cap | CD81 cap | CD9 cap | IbgG1-KLH cap |
|---|---|---|---|---|---|
| 1X Expi 293 CCM | CD63 det | 5196 | 25718 | 20622 | 47 |
| | CD81 det | 92180 | 295759 | 191870 | 39 |
| | CD9 det | 50739 | 139502 | 29587 | 41 |
| | IgG1-KLH det | 164 | 139 | 42 | 40 |
| Blank | CD63 det | 43 | 39 | 37 | 41 |
| | CD81 det | 56 | 52 | 40 | 52 |
| | CD9 det | 271 | 41 | 42 | 44 |
| | IgG1-KLH det | 208 | 158 | 36 | 40 |
FIG. 13C

| Ratio multiplex signal to singleplex | | | | |
|---|---|---|---|---|
| Cature Ab | CCM dilution | CD63 Detection | CD81 Detection | CD9 Detection |
| CD63 capture | 1 | 102% | 94% | 93% |
| | 4 | 104% | 91% | 93% |
| | 16 | 107% | 93% | 91% |
| | 64 | 108% | 95% | 93% |
| | 256 | BLD | 98% | 91% |
| | 1024 | BLD | 100% | 105% |
| | 4096 | BLD | 127% | 97% |
| | NSB | BLD | BLD | BLD |
| Cature Ab | CCM dilution | CD63 Detection | CD81 Detection | CD9 Detection |
| CD81 capture | 1 | 90% | 93% | 92% |
| | 4 | 90% | 94% | 95% |
| | 16 | 91% | 91% | 93% |
| | 64 | 91% | 97% | 93% |
| | 256 | BLD | 97% | 87% |
| | 1024 | BLD | 105% | 96% |
| | 4096 | BLD | BLD | 99% |
| | NSB | BLD | BLD | BLD |
| Cature Ab | CCM dilution | CD63 Detection | CD81 Detection | CD9 Detection |
| CD9 capture | 1 | 101% | 98% | 95% |
| | 4 | 89% | 93% | 90% |
| | 16 | 90% | 88% | 83% |
| | 64 | 97% | 92% | 89% |
| | 256 | 126% | 95% | 95% |
| | 1024 | 106% | 98% | 109% |
| | 4096 | BLD | 121% | 113% |
| | NSB | BLD | BLD | BLD |

FIG. 14

| Column1 | CA125-RSET | CA15.3-Hytest | CA19.9-Hytest | CA50-Fujirebio | CEA-RSET | E-Cadherin-RSET | EGFR-Labvision | EpCAM-R&D | EphA2-R&D | NCAM1-Ansell 7C7 | P-Cadherin-RSET | Avg Blank Spot |
|---|---|---|---|---|---|---|---|---|---|---|---|---|
| BeWo, Serum Free | | | | | | | | | | | | |
| 3 - CD63 | 30 | 2 | 53 | 21 | 56 | 961 | 647 | 7913 | 17 | 117 | 39 | 81 |
| 8 - CD81 | 20 | 20 | 51 | 14 | 156 | 1770 | 998 | 22870 | 81 | 128 | 39 | 97 |
| 14 - CD9 | 35 | 78 | 52 | 37 | 812 | 9061 | 4657 | 75958 | 98 | 232 | 107 | 162 |
| Caco-2, Basal | | | | | | | | | | | | |
| 3 - CD63 | 16 | 29 | 62 | 16 | 76 | 1142 | 236 | 59582 | 58 | 172 | 61 | 70 |
| 8 - CD81 | 30 | 23 | 21 | 29 | 62 | 1436 | 304 | 73571 | 76 | 174 | 92 | 67 |
| 14 - CD9 | 38 | 49 | 43 | 32 | 215 | 2685 | 631 | 134675 | 105 | 278 | 141 | 131 |
| Caco-2, Apical | | | | | | | | | | | | |
| 3 - CD63 | 22 | 31 | 62 | 60 | 3420 | 202 | 81 | 6556 | 84 | 96 | 37 | 70 |
| 8 - CD81 | 34 | 22 | 22 | 33 | 782 | 175 | 63 | 4525 | 97 | 83 | 46 | 65 |
| 14 - CD9 | 42 | 8 | 52 | 59 | 4760 | 528 | 158 | 16581 | 223 | 132 | 79 | 105 |
| Caco-2, Undifferentiated | | | | | | | | | | | | |
| 3 - CD63 | 73 | 60 | 75 | 69 | 730 | 197 | 128 | 3648 | 290 | 117 | 74 | 74 |
| 8 - CD81 | 80 | 65 | 80 | 60 | 333 | 138 | 100 | 2077 | 208 | 155 | 75 | 80 |
| 14 - CD9 | 75 | 75 | 71 | 68 | 1798 | 384 | 210 | 8782 | 649 | 146 | 133 | 101 |
| Calu-3, Untreated | | | | | | | | | | | | |
| 3 - CD63 | 58 | 81 | 1568 | 3325 | 475 | 114 | 135 | 2544 | 116 | 144 | 77 | 90 |
| 8 - CD81 | 61 | 63 | 956 | 2118 | 416 | 118 | 117 | 2527 | 130 | 140 | 90 | 77 |
| 14 - CD9 | 71 | 130 | 6792 | 15650 | 3108 | 614 | 579 | 15675 | 401 | 150 | 276 | 223 |
| HT-1376 | | | | | | | | | | | | |
| 3 - CD63 | 326 | 1072 | 135 | 103 | 113 | 182 | 637 | 848 | 693 | 150 | 204 | 208 |
| 8 - CD81 | 668 | 1531 | 164 | 180 | 128 | 494 | 1704 | 2462 | 1746 | 192 | 382 | 419 |
| 14 - CD9 | 1430 | 4144 | 357 | 399 | 255 | 1331 | 4176 | 5177 | 4111 | 231 | 1016 | 723 |
| TT, Untreated | | | | | | | | | | | | |
| 3 - CD63 | 76 | 3897 | 238 | 440 | 20695 | 165 | 304 | 21747 | 157 | 297 | 122 | 72 |
| 8 - CD81 | 63 | 89 | 63 | 78 | 192 | 68 | 58 | 436 | 80 | 128 | 54 | 32 |
| 14 - CD9 | 116 | 14518 | 945 | 1834 | 97024 | 850 | 1705 | 185673 | 508 | 1338 | 566 | 608 |

FROM FIG. 15A

| | | | | | | | | | | | |
|---|---|---|---|---|---|---|---|---|---|---|---|
| HaCat, Differentiated | | | | | | | | | | | |
| 3 - CD63 | 142 | 133 | 117 | 87 | 4105 | 415 | 2551 | 2927 | 155 | 146 | 473 | 101 |
| 8 - CD81 | 110 | 81 | 42 | 72 | 2539 | 391 | 1685 | 2723 | 125 | 147 | 441 | 107 |
| 14 - CD9 | 1203 | 246 | 172 | 133 | 66109 | 6610 | 21513 | 49425 | 909 | 297 | 6014 | 690 |
| HaCat, Untreated | | | | | | | | | | | |
| 3 - CD63 | 92 | 72 | 101 | 72 | 369 | 241 | 838 | 3731 | 101 | 117 | 284 | 67 |
| 8 - CD81 | 85 | 48 | 76 | 70 | 291 | 418 | 875 | 6490 | 126 | 159 | 490 | 89 |
| 14 - CD9 | 744 | 84 | 149 | 117 | 7509 | 7237 | 11802 | 108124 | 645 | 370 | 7937 | 413 |
| U2-OS, Untreated | | | | | | | | | | | |
| 3 - CD63 | 99 | 127 | 100 | 104 | 84 | 45 | 93 | 92 | 1284 | 139 | 45 | 221 |
| 8 - CD81 | 96 | 127 | 81 | 106 | 103 | 89 | 96 | 168 | 1646 | 148 | 75 | 225 |
| 14 - CD9 | 93 | 142 | 129 | 125 | 104 | 139 | 157 | 350 | 4006 | 261 | 88 | 454 |
| HCT-15, Untreated | | | | | | | | | | | |
| 3 - CD63 | 117 | 189 | 164 | 137 | 137 | 2403 | 1312 | 154668 | 2940 | 344 | 440 | 250 |
| 8 - CD81 | 185 | 279 | 285 | 261 | 309 | 9059 | 4425 | 483341 | 8303 | 806 | 1304 | 661 |
| 14 - CD9 | 411 | 659 | 666 | 616 | 791 | 36278 | 15343 | 1535689 | 25811 | 2397 | 4378 | 1941 |
| Expi293, March 10 | | | | | | | | | | | |
| 3 - CD63 | 96 | 112 | 134 | 109 | 92 | 86 | 238 | 490 | 358 | 153 | 82 | 126 |
| 8 - CD81 | 209 | 276 | 216 | 230 | 247 | 311 | 1866 | 3908 | 3405 | 433 | 294 | 526 |
| 14 - CD9 | 147 | 190 | 180 | 177 | 155 | 213 | 1147 | 2967 | 2136 | 378 | 207 | 320 |
| 10% FBS | | | | | | | | | | | |
| 3 - CD63 | 71 | 61 | 124 | 90 | 103 | 64 | 74 | 82 | 79 | 138 | 53 | 62 |
| 8 - CD81 | 102 | 70 | 85 | 95 | 122 | 74 | 92 | 123 | 85 | 125 | 56 | 58 |
| 14 - CD9 | 84 | 81 | 115 | 112 | 106 | 116 | 99 | 213 | 79 | 106 | 42 | 143 |

FIG. 15B

| Sample | EphA2 | CA50 | CEA | P-Cadherin | EpCAM | EGFR | CA15.3 | E-Cadherin | CA19-9 | CA125 | CD63-Biolegend | CD81-Biolegend | CD9-Biolegend | Avg Blank |
|---|---|---|---|---|---|---|---|---|---|---|---|---|---|---|
| MC01 | 49082 | 377 | 389 | 5532 | 24802 | 33181 | 1294 | 3139 | 700 | 1387 | 44000 | 70611 | 13399 | 4657 |
| MC03 | 5213 | 101 | 102 | 83 | 825 | 267 | 86 | 98 | 150 | 124 | 27102 | 40207 | 37473 | 244 |
| MC05 | 5559 | 22122 | 4046 | 2019 | 179415 | 17082 | 631 | 2253 | 5992 | 701 | 4846 | 80 | 13373 | 187 |
| MC07 | 780 | 11622 | 3825 | 291 | 54274 | 3943 | 155 | 751 | 3863 | 356 | 11507 | 16265 | 10344 | 85 |
| 7/16/11 Exo | 8646 | 34298 | 7614 | 1979 | 333076 | 27531 | 1176 | 3880 | 8088 | 1267 | 9646 | 125 | 23727 | 242 |
| 7/30/10 Exo | 182 | 337 | 186 | 12 | 1554 | 148 | 41 | 64 | 106 | 104 | 340 | 21 | 569 | 44 |
| 4041 Sup | 13787 | 35092 | 21866 | 439 | 70358 | 2364 | 3080 | 1971 | 14752 | 163 | 18557 | 144 | 16177 | 80 |
| 4636 Sup | 15613 | 11393 | 22700 | 298 | 127414 | 9292 | 2175 | 1867 | 6754 | 763 | 19112 | 164 | 17632 | 88 |
| 5289 Sup | 3517 | 35670 | 23686 | 159 | 40691 | 1205 | 2076 | 1252 | 12725 | 28 | 7016 | 2882 | 6275 | 88 |
| 5548 Sup | 7037 | 20778 | 18944 | 926 | 87782 | 4850 | 1674 | 2570 | 10401 | 472 | 13798 | 11313 | 14414 | 67 |
| 6413 Sup | 10850 | 145468 | 90124 | 2858 | 253285 | 13940 | 1087 | 6865 | 55839 | 437 | 111617 | 69914 | 50531 | 199 |
| Blank | 57 | 91 | 45 | 98 | 176 | 70 | 87 | 62 | 105 | 43 | 108 | 68 | 16 | 71 |

Cell Culture Control Samples

FIG. 16A

| Condition | Sample | EphA2 | CA50 | CEA | P-Cadherin | EpCAM | EGFR | CA15.3 | E-Cadherin | CA19-9 | CA125 | CD63 | CD81 | CD9 |
|---|---|---|---|---|---|---|---|---|---|---|---|---|---|---|
| Normal | DMEX1 | 80 | 90 | 506 | 196 | 118 | 125 | 277 | 120 | 105 | 232 | 23148 | 6338 | 49764 |
| Normal | DMEX2 | 112 | 86 | 349 | 140 | 116 | 101 | 130 | 212 | 132 | 185 | 18298 | 6829 | 37513 |
| Normal | DMEX4 | 91 | 72 | 865 | 228 | 104 | 91 | 223 | 146 | 107 | 206 | 15460 | 5261 | 34118 |
| Normal | DMEX8 | 124 | 127 | 501 | 145 | 135 | 99 | 238 | 183 | 125 | 227 | 93522 | 8822 | 168841 |
| Normal | DMEX11 | 94 | 141 | 496 | 107 | 186 | 126 | 80 | 110 | 141 | 79 | 42107 | 5188 | 73606 |
| Normal | DMEX25 | 40 | 79 | 383 | 94 | 100 | 105 | 56 | 361 | 156 | 55 | 27305 | 13341 | 42032 |
| Normal | DMEX26 | 75 | 77 | 365 | 110 | 130 | 83 | 123 | 87 | 129 | 125 | 20233 | 4477 | 36807 |
| Normal | DMEX27 | 62 | 66 | 512 | 176 | 113 | 79 | 243 | 96 | 137 | 197 | 43734 | 6874 | 82173 |
| Normal | DMEX28 | 57 | 85 | 414 | 82 | 99 | 84 | 131 | 147 | 149 | 146 | 8138 | 7245 | 24874 |
| Normal | DMEX29 | 131 | 96 | 506 | 870 | 154 | 98 | 303 | 206 | 133 | 311 | 41757 | 8209 | 79118 |
| IIA Adenocarcinoma | DMEX12 | 89 | 82 | 1202 | 89 | 124 | 64 | 114 | 194 | 76 | 78 | 5237 | 5736 | 13662 |
| IIA Adenocarcinoma | DMEX14 | 111 | 137 | 6062 | 106 | 110 | 87 | 136 | 639 | 108 | 121 | 24873 | 7715 | 51383 |
| IIB Adenocarcinoma | DMEX15 | 115 | 205 | 1226 | 103 | 155 | 131 | 82 | 374 | 233 | 138 | 205516 | 15796 | 282328 |
| IIB Adenocarcinoma | DMEX13 | 75 | 102 | 212 | 90 | 221 | 115 | 74 | 138 | 131 | 117 | 7151 | 4214 | 18249 |
| III Adenocarcinoma | DMEX5 | 156 | 82 | 5677 | 5037 | 283 | 327 | 3603 | 274 | 106 | 3612 | 11172 | 4181 | 21359 |
| III Adenocarcinoma | DMEX6 | 110 | 163 | 1505 | 78 | 82 | 93 | 62 | 114 | 175 | 77 | 13698 | 5251 | 22416 |
| III Adenocarcinoma | DMEX7 | 165 | 132 | 7641 | 55 | 222 | 165 | 86 | 1267 | 159 | 53 | 23531 | 4904 | 48957 |
| IV Adenocarcinoma | DMEX3 | 102 | 127 | 327 | 47 | 148 | 114 | 87 | 125 | 166 | 58 | 49646 | 5206 | 98035 |
| IV Adenocarcinoma | DMEX10 | 96 | 110 | 1746 | 218 | 259 | 113 | 213 | 265 | 132 | 194 | 47743 | 6174 | 81212 |
| IV Adenocarcinoma | DMEX33 | 55 | 119 | 3761 | 89 | 163 | 92 | 140 | 363 | 88 | 137 | 14113 | 4171 | 23237 |

1:10 Diluted Patient Plasma

FIG. 16B

| Mixed Tetraspanins | BSA | cMET | EGFR | Flt-3L | Mesothelin | S100A6 | TNFR-2 |
|---|---|---|---|---|---|---|---|
| Sample Set A: MC02 - CCM, Neat | 47 | 86 | 1192 | 29 | 117 | 55 | 146 |
| Sample Set A: MC01 - Exosomes, 1/100X | 15 | 28 | 807 | 22 | 38 | 59 | 15 |
| Sample Set B: MC04 - CCM, Neat | 18 | 41 | 24 | 17 | 17 | 26 | 20 |
| Sample Set B: MC03 - Exosomes, 1/100X | 36 | 28 | 30 | 30 | 33 | 84 | 23 |
| Sample Set C: MC05 - Exosomes, 1/100X | 26 | 36 | 100 | 18 | 60 | 219 | 20 |
| Sample Set D: MC08 - CCM, Neat | 21 | 12 | 140 | 34 | 30 | 27 | 40 |
| Sample Set D: MC07 - Exosomes, 1/100X | 16 | 37 | 911 | 28 | 27 | 45 | 13 |
| Reference Sample: Expi293 - CCM, Neat | 40 | 63 | 236 | 41 | 24 | 35 | 22 |
| Normal Pool, 12 donor sera | 33 | 69 | 94 | 173 | 55 | 31 | 250 |
| OvC Benign Pool, 12 donor sera | 38 | 474 | 97 | 1121 | 198 | 40 | 2068 |
| OvC Early Pool, 12 donor sera | 26 | 55 | 77 | 101 | 52 | 41 | 482 |
| OvC Late Pool, 12 donor sera | 23 | 56 | 52 | 306 | 49 | 29 | 813 |
| A: H-1650 Untreated CCM, Neat | 26 | 24 | 115 | 19 | 28 | 21 | 13 |
| B: HCC827 Untreated CCM, Neat | 17 | 30 | 835 | 13 | 21 | 20 | 46 |
| C: Caco-2 Untreated Apical CCM, Neat | 23 | 41 | 40 | 32 | 34 | 36 | 43 |
| D: Caco-2 Untreated Basal CCM, Neat | 47 | 27 | 66 | 42 | 43 | 34 | 26 |
| E: Caco-2 Undifferentiated Untreated CCM, Neat | 29 | 42 | 44 | 20 | 29 | 30 | 22 |
| F: HaCat, Undifferentiated Untreated CCM, Neat | 54 | 63 | 904 | 35 | 51 | 45 | 57 |
| G: HaCat, Partially Diff, CCM, Neat | 32 | 33 | 390 | 48 | 43 | 39 | 25 |
| H: HaCat, Diff, CCM, Neat | 30 | 13 | 970 | 42 | 25 | 41 | 25 |
| I: HCT-15 Untreated CCM, 1/4X | 25 | 55 | 166 | 36 | 43 | 29 | 25 |
| J: HepG2 Untreated CCM, Neat | 40 | 43 | 44 | 41 | 37 | 37 | 36 |
| K: HT-1376 Untreated CCM, Neat | 31 | 62 | 271 | 39 | 31 | 40 | 30 |
| L: Blank Media, 10% FBS in RPMI | 47 | 110 | 424 | 51 | 72 | 66 | 45 |
| Expi293 CCM 6X concentrate | 30 | 81 | 1122 | 83 | 69 | 24 | 33 |
| Normal Serum Pool P6P6 precipitate 10X | 53 | 194 | 143 | 1886 | 121 | 67 | 2239 |
| Blank, 2% BSA in DPBS | 13 | 31 | 35 | 28 | 30 | 36 | 33 |
| Normal Serum Pool, Neat | 25 | 109 | 102 | 233 | 94 | 37 | 333 |

| BSA | CA15-3 | CA50 | cKit | E-Cadherin | MMP-3 | OPN | BSA | CA19-9 | ErbB2 | HGF | M-CSF | MMP-2 | MMP-9 |
|---|---|---|---|---|---|---|---|---|---|---|---|---|---|
| 35 | 2904 | 605 | 47 | 390 | 4994 | 100 | 34 | 34 | 423 | 105 | 154 | 75 | 69 |
| 43 | 358 | 48 | 51 | 340 | 4992 | 98 | 23 | 30 | 427 | 76 | 288 | 71 | 30 |
| 47 | 44 | 45 | 50 | 68 | 4907 | 109 | 14 | 23 | 148 | 89 | 52 | 73 | 16 |
| 28 | 52 | 40 | 40 | 66 | 4791 | 119 | 21 | 28 | 118 | 96 | 49 | 76 | 37 |
| 27 | 37 | 64 | 33 | 679 | 4249 | 112 | 29 | 19 | 111 | 88 | 33 | 63 | 37 |
| 40 | 60 | 2263 | 44 | 237 | 4752 | 104 | 20 | 169 | 175 | 67 | 46 | 61 | 35 |
| 41 | 131 | 10905 | 47 | 1847 | 4690 | 111 | 30 | 1028 | 615 | 82 | 66 | 77 | 40 |
| 42 | 97 | 134 | 42 | 167 | 4097 | 107 | 35 | 42 | 744 | 256 | 118 | 89 | 42 |
| 63 | 626 | 108 | 525 | 544 | 3971 | 136 | 46 | 489 | 419 | 358 | 305 | 102 | 278 |
| 48 | 4014 | 130 | 5779 | 673 | 3935 | 201 | 45 | 2432 | 832 | 3284 | 444 | 129 | 3031 |
| 45 | 1418 | 98 | 712 | 350 | 3824 | 120 | 51 | 689 | 241 | 906 | 155 | 84 | 330 |
| 44 | 1986 | 57 | 2008 | 314 | 3049 | 113 | 32 | 1060 | 218 | 2016 | 80 | 67 | 292 |
| 37 | 185 | 46 | 30 | 1074 | 4342 | 99 | 24 | 19 | 259 | 75 | 33 | 67 | 38 |
| 41 | 134 | 42 | 37 | 397 | 4302 | 103 | 30 | 72 | 137 | 89 | 55 | 57 | 34 |
| 59 | 62 | 60 | 67 | 448 | 3437 | 132 | 32 | 38 | 167 | 88 | 38 | 66 | 37 |
| 51 | 53 | 55 | 62 | 1694 | 3366 | 145 | 40 | 65 | 1381 | 73 | 52 | 78 | 42 |
| 38 | 60 | 42 | 47 | 268 | 3899 | 106 | 24 | 10 | 110 | 59 | 47 | 66 | 41 |
| 84 | 83 | 82 | 118 | 627 | 3395 | 146 | 101 | 86 | 203 | 95 | 86 | 115 | 83 |
| 63 | 69 | 40 | 62 | 680 | 3433 | 115 | 41 | 40 | 251 | 73 | 53 | 78 | 52 |
| 45 | 51 | 36 | 53 | 1874 | 3980 | 103 | 39 | 34 | 384 | 67 | 43 | 34 | 34 |
| 50 | 78 | 54 | 47 | 3770 | 4622 | 130 | 36 | 53 | 540 | 82 | 167 | 81 | 24 |
| 64 | 65 | 77 | 97 | 91 | 3695 | 133 | 44 | 42 | 160 | 89 | 64 | 85 | 86 |
| 71 | 1553 | 136 | 74 | 537 | 3601 | 131 | 58 | 50 | 129 | 73 | 58 | 110 | 60 |
| 96 | 148 | 99 | 67 | 10770 | 4109 | 176 | 73 | 94 | 1599 | 111 | 329 | 96 | 72 |
| 63 | 370 | 1215 | 62 | 661 | 4196 | 155 | 50 | 51 | 3589 | 2144 | 272 | 101 | 57 |
| 87 | 7877 | 170 | 2925 | 574 | 4105 | 219 | 70 | 4045 | 2498 | 4762 | 282 | 75 | 1378 |
| 33 | 19 | 46 | 41 | 66 | 4522 | 112 | 37 | 26 | 73 | 86 | 36 | 202 | 27 |
| 38 | 1205 | 116 | 606 | 396 | 3938 | 158 | 28 | 774 | 491 | 677 | 215 | 72 | 501 |

FROM FIG. 17A

Homo-pair of PPs (CD9/CD9)          Hetero-pair of PPs (CD9/CD9)
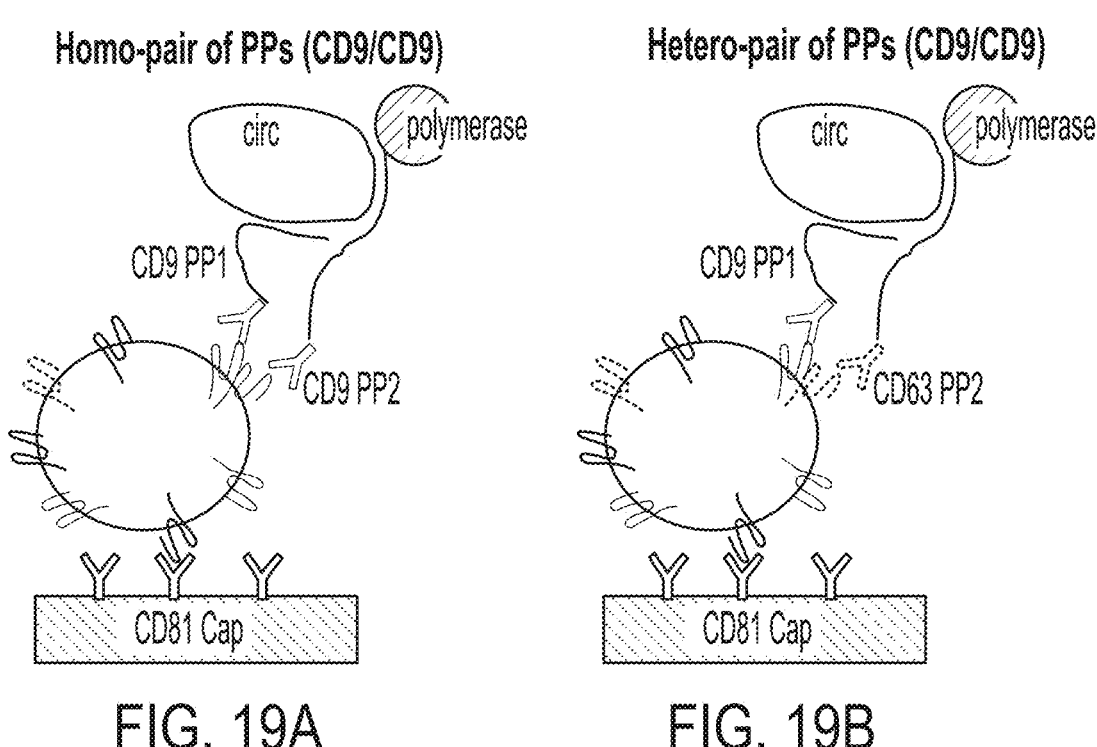
FIG. 19A                    FIG. 19B
Homo- and Hetero-pair Proximity Ligation Detection
of Evs captured on CD81
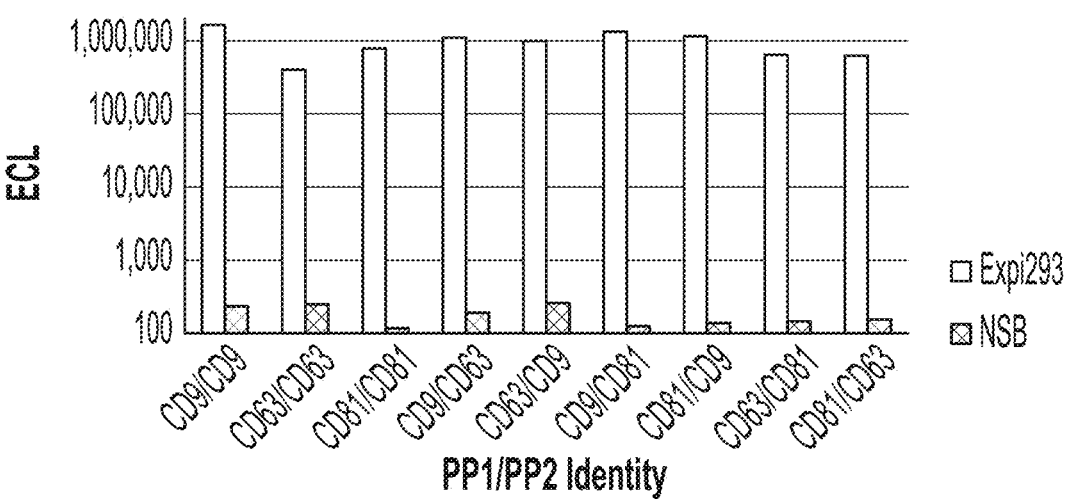
FIG. 19C

| Panel 2 | | CA125-MSD R-SET | CA15.3-Hytest | CA19.9-Hytest | CA50-Fujirebio | CEA-MSD R-SET | GPC1-Sigma | IgG1-R&D |
|---|---|---|---|---|---|---|---|---|
| HaCat Diff | CD63/CD63 | 1275 | 264 | 154 | 178 | 79856 | 5377 | 213 |
| | CD81/CD81 | 687 | 156 | 112 | 149 | 47837 | 5252 | 125 |
| | CD9/CD9 | 19891 | 1846 | 577 | 813 | 1390020 | 9455 | 1005 |
| MST76 | CD63/CD63 | 3888 | 12492 | 459 | 480 | 414 | 6793 | 507 |
| | CD81/CD81 | 9080 | 20092 | 973 | 1081 | 786 | 9207 | 1183 |
| | CD9/CD9 | 22254 | 58594 | 2831 | 3735 | 2115 | 13909 | 2196 |
| MC02 | CD63/CD63 | 14105 | 36325 | 354 | 7837 | 1296 | 6101 | 667 |
| | CD81/CD81 | 47282 | 67024 | 555 | 6862 | 1969 | 7588 | 868 |
| | CD9/CD9 | 36490 | 63051 | 477 | 3267 | 1948 | 6896 | 540 |
| MC08 | CD63/CD63 | 313 | 126 | 564 | 652 | 630 | 3938 | 91 |
| | CD81/CD81 | 98 | 119 | 72 | 95 | 123 | 3993 | 74 |
| | CD9/CD9 | 2749 | 464 | 21655 | 32560 | 37338 | 4300 | 106 |
| TT | CD63/CD63 | 224 | 51186 | 1689 | 1880 | 560149 | 6914 | 301 |
| | CD81/CD81 | 87 | 191 | 65 | 88 | 1920 | 5255 | 65 |
| | CD9/CD9 | 688 | 171546 | 6659 | 7537 | 1736015 | 12687 | 1035 |
| RPMI + 10%FBS | CD63/CD63 | 73 | 43 | 75 | 84 | 101 | 4358 | 61 |
| | CD81/CD81 | 23 | 56 | 28 | 2 | 49 | 4510 | 18 |
| | CD9/CD9 | 80 | 26 | 60 | 78 | 51 | 4798 | 118 |

FIG. 22A

| Panel 3 | | E-Cadherin - MSD R-set | EGFR - Labvision | EpCAM - R&D | EphA2 - R&D | L1CAM - Biolegend | NCAM1 - Biolegend | P-Cadherin - MSD R-Set | IgG1 - R&D |
|---|---|---|---|---|---|---|---|---|---|
| HaCat Diff | CD63/CD63 | 8731 | 58455 | 62202 | 3504 | 412 | 1288 | 10866 | 791 |
| | CD81/CD81 | 8995 | 34881 | 56179 | 2362 | 274 | 830 | 10395 | 609 |
| | CD9/CD9 | 121593 | 465080 | 816961 | 25814 | 1651 | 9207 | 136165 | 5506 |
| HCT-15 | CD63/CD63 | 49974 | 28531 | 2736172 | 106984 | 4099 | 5582 | 8982 | 4118 |
| | CD81/CD81 | 145312 | 84338 | 3932881 | 260481 | 17110 | 14279 | 23646 | 10709 |
| | CD9/CD9 | 340676 | 186152 | 4741533 | 575859 | 45372 | 31202 | 54935 | 20236 |
| MC02 | CD63/CD63 | 4793 | 135508 | 99089 | 912412 | 31933 | 4022 | 4395 | 4076 |
| | CD81/CD81 | 10599 | 314822 | 266724 | 1773055 | 98772 | 7337 | 10932 | 5903 |
| | CD9/CD9 | 11895 | 387017 | 320998 | 1765080 | 113264 | 8447 | 11099 | 5120 |
| PANC-1 | CD63/CD63 | 785 | 11607 | 3863 | 119527 | 6573 | 464 | 425 | 289 |
| | CD81/CD81 | 1011 | 20468 | 7842 | 165874 | 9223 | 635 | 627 | 372 |
| | CD9/CD9 | 1833 | 61155 | 21053 | 351655 | 26403 | 1910 | 1188 | 1218 |
| U-87-MG | CD63/CD63 | 462 | 14155 | 507 | 19373 | 254 | 10898 | 201 | 420 |
| | CD81/CD81 | 377 | 9232 | 393 | 13040 | 185 | 10443 | 140 | 321 |
| | CD9/CD9 | 482 | 9802 | 369 | 13616 | 223 | 12500 | 169 | 566 |
| RPMI + 10%FBS | CD63/CD63 | 294 | 103 | 156 | 94 | 49 | 130 | 75 | 58 |
| | CD81/CD81 | 269 | 66 | 113 | 91 | 88 | 99 | 78 | 53 |
| | CD9/CD9 | 279 | 135 | 187 | 158 | 89 | 161 | 82 | 150 |

FIG. 22B

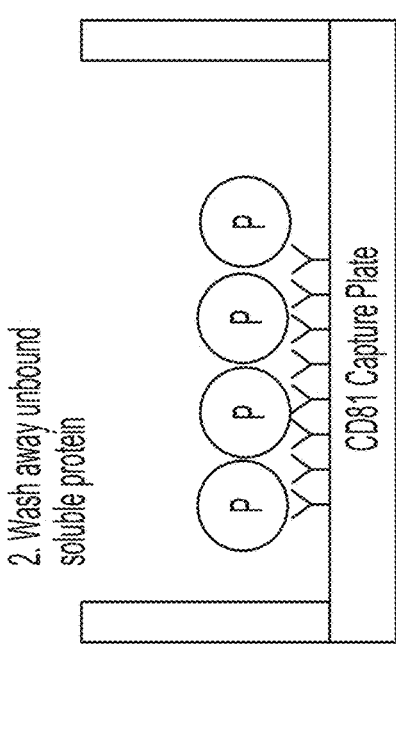
2. Wash away unbound soluble protein
CD81 Capture Plate
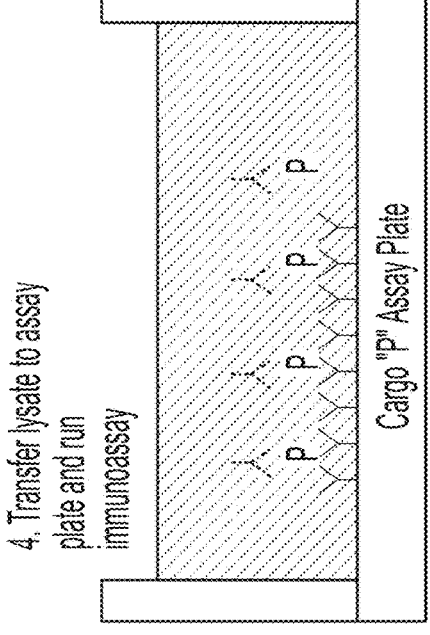
4. Transfer lysate to assay plate and run immunoassay
Cargo "P" Assay Plate
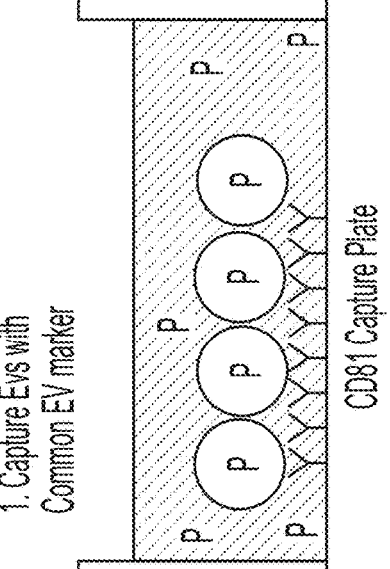
1. Capture Evs with Common EV marker
CD81 Capture Plate
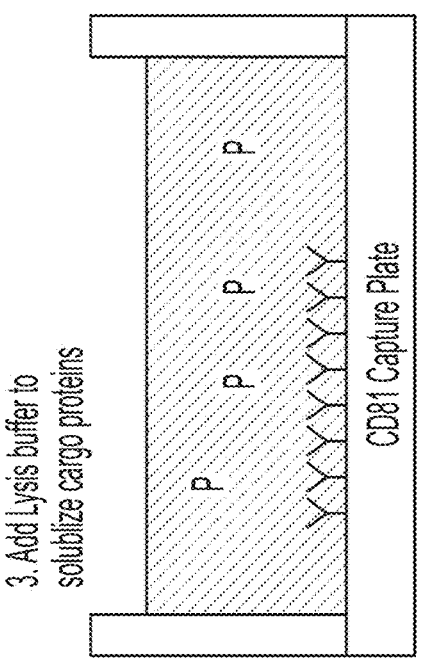
3. Add Lysis buffer to solublize cargo proteins
CD81 Capture Plate
FIG. 23

1. Transfected cells overexpress IL-6

| | Wild Type Expi293 CCM 1/10 dilution | | Transfected Expi293 CCM 1/10 dilution | |
|---|---|---|---|---|
| | No Triton | 1%Triton | No Triton | 1%Triton |
| Day 1 | 93 | 41 | 3897 | 5636 |
| Day 2 | 85 | 49 | 25378 | 39333 |
| Day 3 | 128 | 102 | 104360 | 170862 |
| Day 4 | 107 | 94 | 201140 | 302404 |
| Day 5 | 110 | 110 | 264572 | 375864 |

FIG. 24A

2. Recombinant IL-6 appears to be present within EVs

| | Day 1 CCM | Day 2 CCM | Day 2 CCM | Day 2 CCM | Day 2 CCM |
|---|---|---|---|---|---|
| CD63 Capture | 468 | 1516 | 3831 | 5520 | 5382 |
| CD81 Capture | 7203 | 26660 | 50607 | 53562 | 51865 |
| CD9 Capture | 3779 | 22732 | 56943 | 62227 | 55676 |
| Isotype Control Capture | 247 | 888 | 2109 | 2960 | 4464 |

FIG. 24B

3. Non-Specific binding of soluble IL-6 cannot account for CD81 and CD9 associated IL-6 in step 2

| Sample Treatment | 4ng/mL IL-6 |
|---|---|
| CD63 cap/lys | 502 |
| CD81 cap/lys | 499 |
| CD9 cap/lys | 354 |
| Iso Control Cap/Lys | 457 |
| Direct Assay (No IP) | 1004508 |
| Carryover Ratio | 0.05% |

FIG. 24C

EGFR Cytoplasmic Domain in HaCaT CCM
with and without EV Lysis

Calibration curve for EGFR Cytoplasmic
Domain

EGFR Cytoplasmic domain within Evs
captured from HaCaT CCM

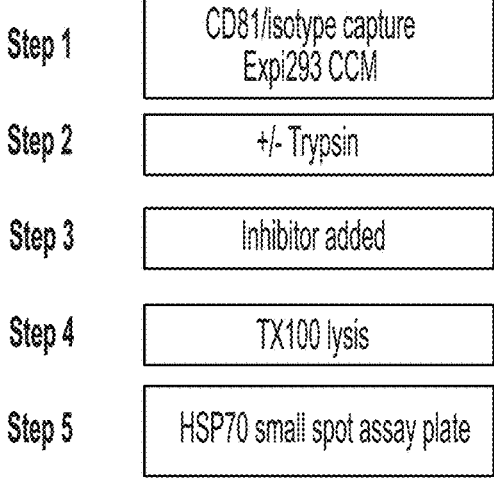

Step 1 — CD81/isotype capture Expi293 CCM

Step 2 — +/- Trypsin

Step 3 — Inhibitor added

Step 4 — TX100 lysis

Step 5 — HSP70 small spot assay plate

FIG. 26A

| HSP70 in 1xExpi293 CCM sample (March 10) | | | | |
|---|---|---|---|---|
| Enzyme +/- | Lysis type | Capture CD81 | Capture Isotype | HSP70 Cargo ECL |
| NONE | No pre-lyse | 7204 | 3617 | 3587 |
| | Pre-Lyse | 2281 | 1971 | 310 |
| 5 mg/ml | No pre-lyse | 2834 | 501 | 2332 |
| | Pre-Lyse | 519 | 455 | 64 |
| 1 mg/ml | No pre-lyse | 3788 | 790 | 2998 |
| | Pre-Lyse | 746 | 737 | 9 |

FIG. 26B

| IL-6 in 200 mL, X-Pack CCM 2nd round, Day 3 | | | | |
|---|---|---|---|---|
| Enzyme +/- | Lysis type | Capture CD81 | Capture Isotype | IL-6 Cargo ECL |
| NONE | No pre-lyse | 16515 | 3435 | 13079 |
| | Pre-Lyse | 3245 | 1865 | 1380 |
| 5 mg/ml | No pre-lyse | 13103 | 661 | 12442 |
| | Pre-Lyse | 427 | 393 | 33 |
| 1 mg/ml | No pre-lyse | 12444 | 670 | 11774 |
| | Pre-Lyse | 588 | 476 | 111 |

FIG. 26C

Formalin Fix: Proteins and Nucleic acids are crosslinked

Detergent Perm: Exosomal membrane is partially or fully dissolved

HSP70 in EVs captured by CD81 from Expi293 CCM with and without fixation and permeablization

| Capture Ab | Time (min) | CD81 | | | | | | |
|---|---|---|---|---|---|---|---|---|
| | | RBB-0.02% | RBB-0.015% | RBB-0.01% | RBB-0.005% | SurfFree RBB | 2mM Tween RBB | 0.5mM Tween RBB |
| CD63 | 0 min | 12,667 | 58,067 | 172,959 | 182,017 | 178,251 | 213,005 | 210,575 |
| | 15 min | 3,050 | 9,868 | 130,332 | 141,703 | 133,004 | 162,868 | 161,807 |
| CD81 | 0 min | 134,143 | 355,827 | 660,121 | 564,044 | 587,361 | 711,847 | 685,249 |
| | 15 min | 51,729 | 113,546 | 469,218 | 431,632 | 434,418 | 506,233 | 500,672 |
| CD9 | 0 min | 52,712 | 140,657 | 239,393 | 214,443 | 214,641 | 230,564 | 251,954 |
| | 15 min | 7,387 | 18,587 | 181,683 | 173,502 | 166,088 | 208,780 | 205,780 |
| IgG1 Isotype | 0 min | 131 | 239 | 875 | 897 | 1,011 | 1,088 | 1,088 |
| | 15 min | 68 | 117 | 514 | 646 | 729 | 693 | 661 |

FIG. 28

| | CD63 Capture | CD81 Capture | CD9 Capture | EpCAM Capture |
|---|---|---|---|---|
| Sample Set A: MC01 - Exosomes, 1/100X | | | | |
| CD63 Det | 16895 | 27497 | 9980 | 1856 |
| CD81 Det | 25107 | 31456 | 17407 | 3153 |
| CD9 Det | 24439 | 47679 | 12087 | 4042 |
| EpCAM Det | 1451 | 2939 | 1168 | |
| Tetraspanin Det Mix | | | | 7365 |
| Sample Set B: MC03 - Exosomes, 1/100 | | | | |
| CD63 Det | 16713 | 13316 | 13340 | 64 |
| CD81 Det | 10929 | 9579 | 17310 | 47 |
| CD9 Det | 27374 | 46228 | 39524 | 63 |
| EpCAM Det | 163 | 137 | 140 | |
| Tetraspanin Det Mix | | | | 94 |
| Sample Set C: MC05 - Exosomes, 1/100 | | | | |
| CD63 Det | 3338 | 2314 | 3904 | 1648 |
| CD81 Det | 1700 | 1056 | 6493 | 2505 |
| CD9 Det | 8394 | 25679 | 25274 | 16321 |
| EpCAM Det | 1577 | 3675 | 6879 | |
| Tetraspanin Det Mix | | | | 19349 |
| Sample Set D: MC07 - Exosomes, 1/100 | | | | |
| CD63 Det | 720 | 54 | 1763 | 3081 |
| CD81 Det | 211 | 48 | 48 | 43 |
| CD9 Det | 4154 | 75 | 17599 | 56416 |
| EpCAM Det | 2323 | 149 | 20643 | |
| Tetraspanin Det Mix | | | | 57387 |

FIG. 29

| Cell Line | CD63 | CD81 | CD9 |
|---|---|---|---|
| MOLT-4 | 3977 | 46869 | 29159 |
| MOLT-4, Stimulated | 4130 | 49491 | 15048 |
| Jurkat E6.1 | 20988 | 139169 | 22281 |
| HL60 | 18380 | 26479 | BLD |
| HL60, Differentiated | 26953 | 36273 | 6398 |
| HL60, Differentiated, Stimulated | 67296 | 57899 | 504 |
| U-937 | 8518 | BLD | 7284 |
| U-937, Differentiated | 10627 | BLD | BLD |
| U-937, Differentiated, Stimulated | 29581 | BLD | BLD |
| HDLM-2 | 13877 | 7958 | BLD |
| THP-1 | 38964 | 16083 | BLD |
| THP-1, Differentiated | 22957 | 53908 | 20522 |
| THP-1, Differentiated, Stimulated | 38968 | 63691 | 29563 |
| GA10 clone 20 | 9570 | 10196 | BLD |
| Ramos | 17036 | 22192 | BLD |
| HUVEC | 46034 | 64863 | 98650 |
| PANC-1 | 118161 | 139154 | 90892 |
| Expi293 | 320545 | 791724 | 428926 |
| HaCat | 95844 | 53971 | 384067 |
| HCT-15 | 740486 | 1569461 | 1457143 |
| H-2228 | 191899 | 49419 | 43604 |

FIG. 37A

| Seeding Density | Time in Culture (h) | CD63/CD63 | | CD81/CD81 | | CD9/CD9 | |
|---|---|---|---|---|---|---|---|
| | | Unstim. | PMA stim. | Unstim. | PMA stim. | Unstim. | PMA stim. |
| 10M cells/ flask | 24 | 3959 | 8892 | 1353 | 1747 | 204 | 944 |
| | 48 | 6570 | 15522 | 2796 | 4402 | 641 | 4751 |
| | 72 | 9027 | 28937 | 4985 | 14862 | 1378 | 18080 |
| | 96 | 10948 | 24890 | 7009 | 13394 | 1947 | 19833 |
| 30M cells/ flask | 24 | 8133 | 20119 | 5279 | 7651 | 382 | 3072 |
| | 48 | 13209 | 28813 | 9241 | 15031 | 858 | 11545 |
| | 72 | 19138 | 29549 | 13581 | 14831 | 1595 | 18676 |
| | 96 | 26967 | 44185 | 20112 | 30121 | 2743 | 30322 |
| 50M cells/ flask | 24 | 10515 | 22911 | 8575 | 14476 | 448 | 6626 |
| | 48 | 18841 | 34261 | 13545 | 26718 | 1015 | 22026 |
| | 72 | 28316 | 48156 | 19744 | 35257 | 2168 | 37537 |
| | 96 | 37693 | 52750 | 28102 | 41260 | 3500 | 43490 |

FIG. 37B

| Sample Type | Assay | Recommended Dilution | Spike Recovery at Recommended dilution | Linear Range of Assay (80%-120% dilution linearity) |
|---|---|---|---|---|
| Human Serum | CD9/CD9 | 10-fold | 96% | Neat to 1024-fold |
| | CD63/CD63 | 10-fold | 77% | Neat to 256-fold |
| | CD81/CD81 | 4-fold | 90% | Neat to 256-fold |
| Human Plasma | CD9/CD9 | 50-fold | 118% | 16 to 1024-fold |
| | CD63/CD63 | 20-fold | 82% | 8 to 32 fold |
| | CD81/CD81 | 10-fold | 104% | Neat to 256-fold |
| Human CSF | CD9/CD9 | 10-fold | 96% | 4 to 256-fold |
| | CD63/CD63 | 10-fold | 104% | 4 to 256-fold |
| | CD81/CD81 | 10-fold | 102% | Neat to 256-fold |
| Human Urine | CD9/CD9 | 4-fold | 94% | Neat to 256-fold |
| | CD63/CD63 | 4-fold | 94% | Neat to 8-fold |
| | CD81/CD81 | 4-fold | 87% | Neat to 4 fold |

FIG. 38

Dilution Curves for Two-Marker EV-associated
Tetraspanins in THP-1 Culture
Medium (Capture/Detector)

Capture Antibody

| | | CD63 | CD81 | CD9 | |
|---|---|---|---|---|---|
| Cell line | BeWo | 7,039 | 14,319 | 12,731 | CD63 |
| | | 29,709 | 10,374 | 29,668 | CD81 |
| | | 78,407 | 85,704 | 66,220 | CD9 |
| | TT | 5,704 | 189 | 21,435 | CD63 |
| | | 293 | 56 | 280 | CD81 |
| | | 127,258 | 2,109 | 124,446 | CD9 |
| | HCT-15 | 12,248 | 62,593 | 83,384 | CD63 |
| | | 119,232 | 55,215 | 256,598 | CD81 |
| | | 317,828 | 556,064 | 652,899 | CD9 |
| | Expi293 | 2,679 | 31,688 | 12,161 | CD63 |
| | | 104,814 | 190,996 | 122,606 | CD81 |
| | | 57,770 | 171,455 | 26,891 | CD9 |

Detection Antibody

Single Marker and Two-Marker EV-Associate Tetraspanin Assays in SEC-purified EVs from Matched Serum and Plasma Samples from Healthy Donors

TO

| Sample | Sample Type | Negative Control IgG1 | CD4 Clone A | CD4 Clone B | CD4 Clone C | CD4 Clone D |
|---|---|---|---|---|---|---|
| DPBS | Negative Control | 175 | 89 | 193 | 126 | 172 |
| Media (RPMI+10% FBS) | Negative Control | 162 | 68 | 184 | 115 | 129 |
| Jurkat E6.1 | Positive Cell Line | 195 | 1575 | 888 | 1514 | 9675 |
| HL60 | Positive Cell Line | 191 | 1444 | 738 | 1252 | 10914 |
| THP-1 | Positive Cell Line | 353 | 2201 | 1452 | 3611 | 25537 |
| U-937 | Positive Cell Line | 178 | 167 | 223 | 216 | 934 |
| MOLT-4 | Positive Cell Line | 198 | 209 | 192 | 199 | 770 |
| HDLM-2 | Positive Cell Line | 217 | 131 | 220 | 175 | 460 |
| Primary PBMCs | Positive Primary | 237 | 538 | 489 | 785 | 4784 |
| GA10 clone 20 | Negative Cell Line | 204 | 83 | 161 | 114 | 160 |
| Ramos | Negative Cell Line | 173 | 64 | 172 | 102 | 90 |
| HUVEC | Negative Cell Line | 179 | 53 | 185 | 115 | 161 |
| PANC-1 | Negative Cell Line | 178 | 108 | 208 | 135 | 180 |
| HaCat | Negative Cell Line | 186 | 582 | 182 | 117 | 160 |
| HCT-15 | Negative Cell Line | 204 | 366 | 778 | 206 | 227 |
| H-2228 | Negative Cell Line | 195 | 87 | 162 | 136 | 148 |

FIG. 42A

| Panel 1 | Panel 2 | Panel 3 | Panel 4 | Panel 5 |
|---|---|---|---|---|
| CD81 | E-Cadherin | Endoglin | CD3 | Nectin-4 |
| CD15 | EGFR | PSGL-1 | MET | FasL |
| IgG1 | IgG1 | IgG1 | IgG1 | IgG1 |
| CD9 | EphA2 | SCFR/Kit | CD5 | TNF-RII |
| EpCAM | CA-50 | sFAS (FASR) | CD8 | CD27 |
| CD54 (ICAM-1) | CA-125 | FAP-a | CD19 | IL-6R |
| CD31 (PECAM) | CEA | CD4 | CD56 (NCAM) | Flt-1/VEGRF1 |
| CD276 (B7-H3 | CD50 (ICAM-3) | CA-19.9 | CD171 (L1CAM) | Osteoactivin |
| P-Selectin | Mesothelin | Thrombomodulin | DPPIV | TNF-RI |
| CD63 | E-Selectin | sTfR-1 (TFRC) | CA-15.3 | CD144 (VE-Cadherin) |

FIG. 42B

Source of EVs (Cell Line)

| Surface Marker | MCF-7 | HCT116 | HCT-15 | Expi293 | Calu-3 | H2228 | PANC-1 | GA-10 | Ramos | KU-812 | THP-1 | HL60 | Jurkat E 6.1 | MOLT-4 | Hacat | TT | HUVEC | MC-04 | HT-1376 |
|---|---|---|---|---|---|---|---|---|---|---|---|---|---|---|---|---|---|---|---|
| CD81 | 703.8 | 871.1 | 728.7 | 1332.1 | 207.9 | 186.9 | 389.4 | 67.2 | 173.7 | 256.8 | 752.0 | 335.6 | 845.9 | 258.6 | 104.9 | 11.9 | 266.1 | 500.4 | 613.9 |
| CD15 | 791.9 | 1.4 | 246.1 | 170.3 | 15.9 | 1.4 | 120.8 | 0.1 | 0.2 | 0.4 | 323.9 | 1603.8 | 3.7 | 0.9 | 2.0 | 350.1 | 0.3 | 1.1 | 32.4 |
| CD9 | 599.8 | 830.2 | 815.2 | 813.5 | 333.6 | 305.9 | 377.6 | 236.8 | 275.7 | 268.3 | 513.4 | 255.8 | 355.0 | 429.3 | 922.2 | 870.8 | 539.2 | 609.7 | 613.2 |
| EpCAM | 214.7 | 245.0 | 504.0 | 8.9 | 74.2 | 7.9 | 5.4 | 0.1 | 0.0 | 0.8 | 1.8 | 0.0 | 0.0 | 0.4 | 24.5 | 127.9 | 0.5 | 3.2 | 13.0 |
| CD54 | 2.9 | 3.3 | 89.8 | 2.0 | 23.6 | 23.9 | 101.3 | 0.3 | 26.2 | 15.8 | 187.1 | 5.2 | 1.2 | 0.7 | 1.6 | 7.0 | 1.8 | 112.2 | 1.8 |
| CD31 | 1.6 | 1.6 | 2.0 | 1.8 | 0.6 | 0.6 | 0.9 | 0.4 | 0.1 | 2.1 | 312.0 | 9.9 | 164.5 | 8.3 | 1.3 | 1.8 | 201.8 | 124.4 | 1.3 |
| CD276 | 199.7 | 36.3 | 41.4 | 160.5 | 33.5 | 19.3 | 50.7 | 0.0 | 0.0 | 0.0 | 65.9 | 0.0 | 0.0 | 0.0 | 67.4 | 28.4 | 29.5 | 36.6 | 23.7 |
| CD63 | 215.1 | 331.7 | 275.6 | 615.1 | 153.5 | 472.3 | 286.8 | 33.3 | 101.3 | 180.5 | 541.9 | 292.3 | 89.4 | 18.6 | 139.0 | 379.7 | 137.9 | 271.3 | 342.6 |
| E-Cadherin | 23.3 | 6.3 | 191.8 | 1.9 | 6.4 | 0.3 | 0.2 | 0.0 | 0.0 | 2.4 | 2.0 | 0.0 | 0.0 |  | 17.8 | 3.8 | 0.0 | 0.0 | 11.9 |
| EGFR | 2.5 | 40.1 | 141.8 | 65.6 | 18.0 | 21.8 | 52.6 | 0.0 | 0.2 | 0.0 | 1.9 | 0.2 | 0.9 |  | 103.3 | 27.6 | 1.3 | 3.0 | 70.0 |
| EphA2 | 17.1 | 291.3 | 174.8 | 81.9 | 7.7 | 6.0 | 143.2 | 0.1 | 0.0 | 0.1 | 3.5 | 0.3 | 1.0 |  | 1.5 | 4.6 | 37.0 | 142.2 | 38.3 |
| CA50 | 0.7 | 0.5 | 1.5 | 0.8 | 312.6 | 11.3 | 0.4 | 0.0 | 0.0 | 0.0 | 0.7 | 0.1 | 0.5 |  | 0.4 | 10.5 | 0.0 | 0.3 | 3.0 |
| CA125 | 1.0 | 2.0 | 2.5 | 1.5 | 0.8 | 3.5 | 1.2 | 0.0 | 0.0 | 0.1 | 6.8 | 0.0 | 0.1 |  | 26.2 | 1.6 | 0.2 | 0.7 | 16.7 |
| CEA | 8.8 | 1.7 | 2.6 | 0.7 | 17.5 | 7.3 | 0.6 | 0.4 | 0.4 | 0.5 | 1.0 | 0.8 | 0.4 |  | 193.3 | 364.0 | 0.4 | 0.7 | 0.8 |
| CD50 | 0.5 | 0.1 | 0.7 | 0.4 | 1.1 | 0.3 | 0.3 | 2.9 | 34.4 | 111.4 | 301.1 | 52.4 | 211.6 |  | 0.4 | 8.2 | 0.2 | 0.5 | 0.2 |
| E-Selectin | 2.9 | 8.1 | 15.6 | 5.5 | 0.9 | 0.1 | 0.5 | 0.0 | 0.0 | 0.0 | 4.2 | 0.1 | 0.0 |  | 2.7 | 5.3 | 1.4 | 6.2 | 1.6 |

FIG. 43A

Source of EVs (Cell Line)

| Surface Marker | MCF-7 | HCT116 | HCT-15 | Expi293 | Calu-3 | H2228 | PANC-1 | GA-10 | Ramos | KU-812 | THP-1 | HL60 | Jurkat E 6.1 | MOLT-4 | Hacat | TT | HUVEC | MC-04 | HT-1376 |
|---|---|---|---|---|---|---|---|---|---|---|---|---|---|---|---|---|---|---|---|
| Endoglin | 0.6 | 0.6 | 0.8 | 0.7 | 0.9 | 5.4 | 7.0 | 0.3 | 0.3 | 4.9 | 181.0 | 1.9 | 0.5 | | 0.1 | 1.4 | 443.0 | 1019.2 | 4.4 |
| PSGL-1 | 0.3 | 0.3 | 0.8 | 0.6 | 0.9 | 0.2 | 0.1 | 0.5 | 11.1 | 39.1 | 289.1 | 19.4 | 28.9 | | 0.1 | 1.1 | 0.1 | 0.0 | 0.3 |
| SCFR/Kit | 0.4 | 0.2 | 4.3 | 44.7 | 0.5 | 0.0 | 1.3 | 0.0 | -0.5 | 85.6 | 3.2 | 0.7 | 0.2 | | 0.0 | 116.7 | 0.2 | 4.0 | 0.0 |
| sFAS | 3.4 | 34.2 | 128.7 | 154.1 | 2.4 | 9.1 | 3.1 | 0.3 | 1.9 | 0.0 | 3.2 | 4.9 | 31.4 | | 3.7 | 9.6 | 2.3 | 4.7 | 5.3 |
| FAP-a | 0.4 | 0.3 | 0.7 | 0.8 | 0.5 | 85.2 | 0.2 | 0.0 | 0.0 | 0.2 | 4.0 | 0.3 | 0.3 | | 0.3 | 1.4 | 145.5 | 0.4 | 0.4 |
| CD4 | 0.6 | 0.3 | 1.1 | 1.5 | 0.9 | 0.2 | 0.3 | 0.0 | 0.0 | 26.5 | 362.5 | 109.5 | 92.0 | | 0.0 | 2.4 | 0.2 | 0.0 | 0.4 |
| CA19.9 | 0.3 | 0.1 | 0.4 | 0.5 | 0.9 | 3.5 | 0.1 | 0.1 | 0.1 | 0.3 | 1.1 | 0.2 | 0.0 | | 0.3 | 4.5 | 0.4 | 0.1 | 0.9 |
| Thrombo-modulin | 7.5 | 0.4 | 0.6 | 12.7 | 87.5 | 27.1 | 0.2 | 0.0 | 0.0 | 0.8 | 107.0 | 0.1 | 0.0 | | 42.7 | 16.7 | 11.5 | 7.6 | 36.2 |
| sTfR-1 | 61.1 | 13.6 | 117.5 | 148.7 | 8.8 | 45.0 | 82.1 | 12.3 | 53.4 | 286.0 | 35.5 | 83.4 | 32.3 | | 49.1 | 64.8 | 6.5 | 41.8 | 95.1 |
| CD3 | 0.4 | 0.0 | 3.6 | 0.8 | 0.4 | 0.0 | 0.0 | 0.0 | 0.0 | 0.0 | 0.8 | 0.0 | 364.5 | 0.7 | 0.0 | 1.0 | 0.0 | 0.2 | 0.0 |
| MET | 0.1 | 2.7 | 6.8 | 18.4 | 0.3 | 0.0 | 0.0 | 0.0 | 0.0 | 0.0 | 0.5 | 0.0 | 0.0 | 0.0 | 0.3 | 0.0 | 0.0 | 0.0 | 0.7 |
| CD5 | 1.0 | 0.3 | 1.3 | 0.3 | 0.9 | 0.1 | 1.3 | 0.1 | 0.7 | 0.3 | 0.7 | 0.5 | 196.1 | 23.4 | 0.4 | 1.4 | 0.7 | 0.6 | 0.4 |
| CD8 | 1.2 | 1.9 | 5.1 | 1.7 | 0.7 | 0.3 | 0.6 | 0.0 | 0.3 | 0.0 | 2.9 | 0.2 | 0.2 | 16.8 | 1.8 | 2.4 | 0.5 | 1.0 | 0.7 |
| CD19 | 0.5 | 0.2 | 0.7 | 0.6 | 0.2 | 0.1 | 0.2 | 0.0 | 120.7 | 0.2 | 3.8 | 0.1 | 0.3 | 0.2 | 0.1 | 0.3 | 0.0 | 0.2 | 0.1 |
| CD56/ NCAM | 0.8 | 0.1 | 0.8 | 33.1 | 0.5 | 0.0 | 0.4 | 32.3 | 0.5 | 0.0 | 1.8 | 0.3 | 0.2 | 0.9 | 0.3 | 25.9 | 0.5 | 0.8 | 0.1 |
| CD171/ L1CAM | 24.5 | 2.1 | 28.6 | 1.9 | 1.3 | 0.5 | 15.3 | 0.0 | 0.5 | 0.1 | 35.4 | 0.2 | 0.3 | 1.3 | 1.7 | 3.3 | 1.0 | 1.4 | 1.7 |
| DPPIV | 1.6 | 4.6 | 5.4 | 8.5 | 1.4 | 74.1 | 0.7 | 0.1 | 0.3 | 0.1 | 2.4 | 0.3 | 0.3 | 1.2 | 2.6 | 1.5 | 0.9 | 10.2 | 1.1 |
| CA15.3 | 1.2 | 0.1 | 1.3 | 0.6 | 0.4 | 2.4 | 2.9 | 0.0 | 0.0 | 0.5 | 0.7 | 0.0 | 0.1 | 0.7 | 0.0 | 23.6 | 0.0 | 0.0 | 16.4 |
| TNF-RII | 0.4 | 0.1 | 1.1 | 0.4 | 0.4 | 0.0 | 1.0 | 0.0 | 0.0 | 0.0 | 16.9 | 1.2 | 0.0 | | 0.0 | 3.1 | 0.0 | 0.4 | 0.2 |
| IL-6R | 1.1 | 1.1 | 2.8 | 5.8 | 0.7 | 0.4 | 1.2 | 0.4 | 0.0 | 0.6 | 9.1 | 2.2 | 0.4 | | 0.6 | 2.6 | 0.2 | 1.0 | 0.7 |
| TNF-RI | 1.6 | 1.4 | 5.0 | 17.7 | 0.7 | 0.4 | 0.9 | 0.0 | 0.0 | 1.0 | 98.3 | 3.2 | 4.3 | | 1.2 | 1.4 | 0.5 | 0.9 | 4.0 |
| Flt-1/VEGRF1 | 0.6 | 0.2 | 5.8 | 7.5 | 0.4 | 0.0 | 0.2 | 0.2 | 0.1 | 0.1 | 2.8 | 0.4 | 6.1 | | 0.1 | 2.5 | 1.2 | 4.4 | 0.0 |
| CD144/VE-Cadherin | 0.7 | 0.2 | 1.0 | 0.4 | 0.8 | 0.0 | 0.0 | 0.0 | 0.0 | 0.0 | 1.3 | 0.0 | 0.0 | | 0.1 | 0.6 | 4.1 | 10.1 | 0.2 |

Human Sample Type

| Surface Marker | Urine | CSF | PBMC CCM 1 | PBMC CCM 2 | Raw Plasma Pool | Precipitated Plasma EVs | Raw Serum Pool | Precipitated Serum EVs |
|---|---|---|---|---|---|---|---|---|
| CD81 | 41.8 | 799.1 | 46.3 | 112.8 | 41.2 | 32.2 | 276.1 | 152.6 |
| CD15 | 22.8 | 3.3 | 112.5 | 3.6 | 3.8 | 4.7 | 6.3 | 6.3 |
| CD9 | 295.6 | 448.4 | 211.2 | 377.9 | 243.4 | 230.4 | 342.5 | 115.5 |
| CD54/ICAM-1 | 0.5 | 3.1 | 5.7 | 4.2 | 1.6 | 2.8 | 1.9 | 3.8 |
| CD31/PECAM | 0.4 | 3.0 | 42.8 | 140.6 | 226.1 | 276.6 | 181.4 | 47.5 |
| CD276/B7-H3 | 0.0 | 13.6 | 1.1 | 0.2 | 1.7 | 1.4 | 0.3 | 1.2 |
| P-Selectin | 0.0 | 0.7 | 14.4 | 14.6 | 205.6 | 502.9 | 49.0 | 277 |
| CD63 | 261.5 | 214.2 | 331.9 | 83.2 | 115.9 | 110.0 | 249.3 | 60.3 |
| CEA | 10.0 | 1.0 | 0.9 | 0.6 | 1.8 | 1.9 | 4.2 | 0.8 |
| CD50 (ICAM-3) | 0.1 | 12.1 | 9.6 | 25.5 | 2.9 | 9.8 | 7.9 | 2.9 |
| Endogin | 0.3 | 2.3 | 0.5 | 3.5 | 7.1 | 20.8 | 9.1 | 1.5 |
| PSGL-1 | 0.2 | 1.5 | 22.1 | 15.5 | 3.6 | 16.9 | 12.4 | 2.9 |
| sFAS (FASR) | 0.4 | 224.4 | 2.3 | 2.8 | 1.5 | 2.8 | 0.9 | 0.7 |
| CD4 | 0.1 | 2.3 | 27.4 | 20.3 | 3.6 | 7.0 | 11.8 | 1.3 |
| Thrombo-modulin | 0.0 | 0.4 | 0.8 | 0.6 | 6.2 | 9.6 | 3.5 | 1.0 |
| sTfR-1 (TFRC) | 0.1 | 1.4 | 2.6 | 0.3 | 1.5 | 15.1 | 0.6 | 0.5 |
| CD3 | 0.6 | 0.2 | 10.9 | 8.0 | 18.9 | 6.1 | 2.0 | 1.0 |
| CD5 | 0.5 | 0.1 | 7.3 | 6.6 | 14.4 | 2.9 | 1.8 | 3.8 |
| CD8 | 0.3 | 0.3 | 87.3 | 24.4 | 27.6 | 6.6 | 14.1 | 11.0 |
| CD19 | 0.2 | 0.1 | 1.1 | 8.0 | 57.6 | 3.5 | 3.6 | 5.2 |
| DPPIV | 10.5 | 0.1 | 0.9 | 1.0 | 22.2 | 1.4 | 0.4 | 2.2 |
| CA15.3 | 56.7 | 0.1 | 0.3 | 0.4 | 5.6 | 0.6 | 0.2 | 1.5 |
| TNF-RI | 0.2 | 5.2 | 0.9 | 2.3 | 3.2 | 1.4 | 0.8 | 0.7 |

C.

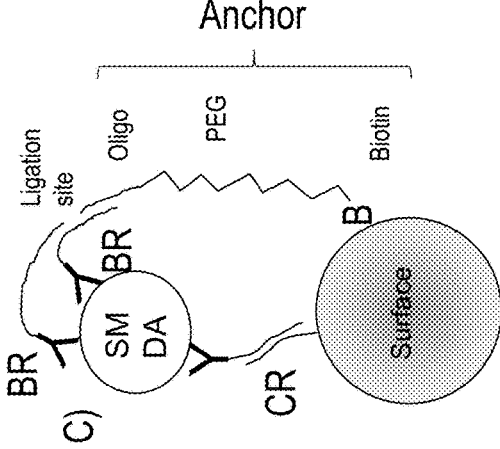
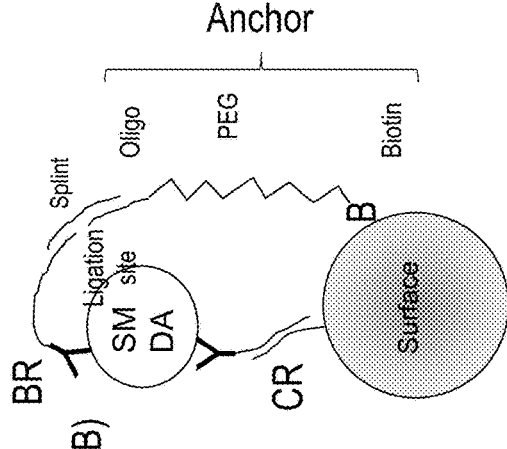
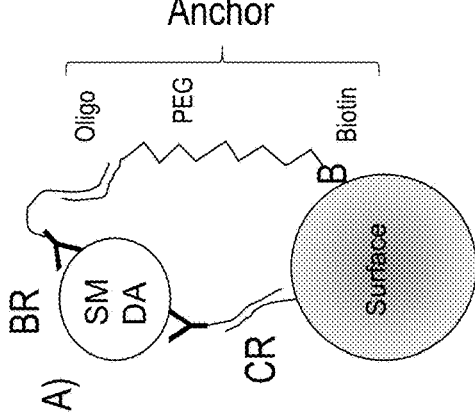
FIG. 49

IL-8 is Associated with HL-60 EVs

Legend:
- CD9 Capture/Membrane Detector
- CD81 Capture/Tetraspanin Cocktail
- IL-8 Assay x-axis: SEC Fraction
left y-axis: ECL (Counts)
right y-axis: [IL-8 (pg/mL)]

B.

| Cytokine | Concentration(pg/mL) | % Digested |
|----------|----------------------|------------|
| IL8 | 480 | 99% |
| IL-1B | 1.3 | 77% |
| TNF-a | 14 | 54% |
| IL-13 | 3.0 | >90% |

1, 2, 3, ... = library pool
A, B, C, ... = unique binding reagents

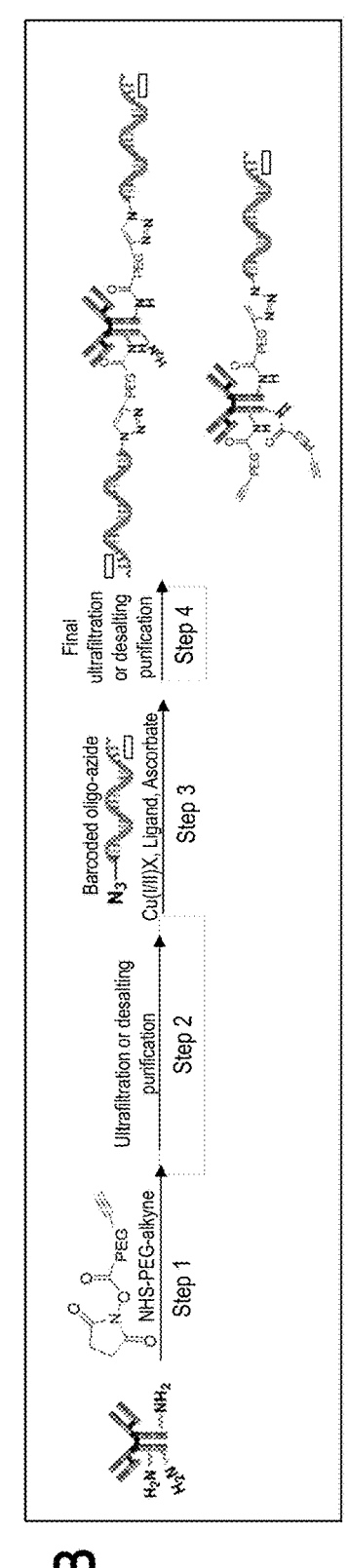
FIG. 58A
FIG. 58B
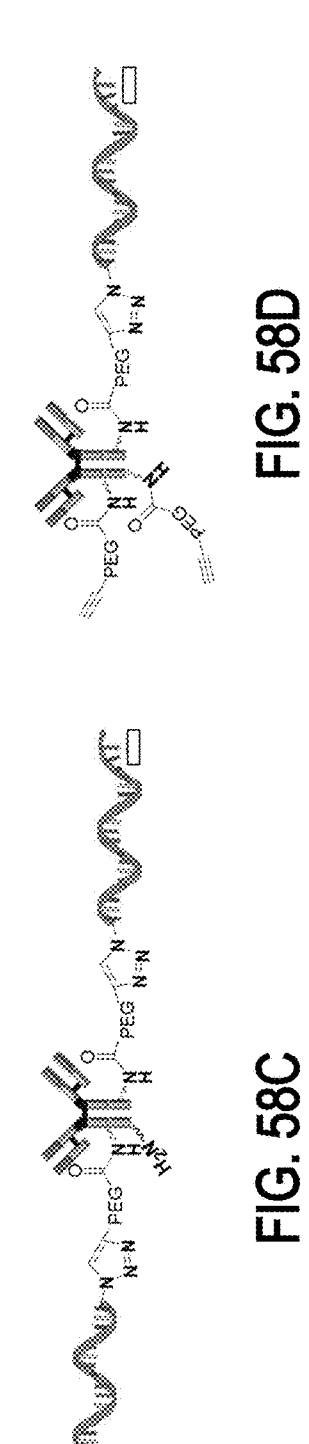
FIG. 58C
FIG. 58D

METHODS FOR ISOLATING SURFACE MARKER DISPLAYING AGENTS

GOVERNMENT LICENSE RIGHTS

This invention was made with government support under grant number UG3TR002886 awarded by the National Institutes of Health and National Center for Advancing Translational Sciences. The government has certain rights in the invention.

FIELD OF THE INVENTION

The invention relates to methods and kits for highly specific isolation and analysis of surface marker displaying agents such as extracellular vesicles (EVs) and/or their cargo by targeting at least two surface markers.

BACKGROUND

Surface marker displaying agents include cells, viruses and viral particles, cellular organelles, and vesicles, including extracellular vesicles (EVs) and exosomes. Surface marker displaying agents may include biologically relevant materials or components; therefore, methods of isolating and/or characterizing various types of surface marker displaying agents are actively being developed and improved.

Extracellular vesicles (EVs) are a diverse group of cell-secreted membrane vesicles implicated in a wide variety of physiological and pathological processes, many of which are only beginning to be understood. These include immune regulation, antigen presentation, tumor progression and metastasis, modulation of inflammation, stem cell regulation, neuronal development and regeneration, and cell-to-cell transfer of pathogenic proteins and nucleic acids. EVs are secreted from nearly all cell types through multiple mechanisms including the fusion of specific endosomal compartments called multivesicular bodies (MVB) with the plasma membrane and by budding/shedding directly from the plasma membrane. EVs are present in nearly all body fluids including blood, urine, cerebral spinal fluid, and saliva, and are secreted by most in vitro cultured cells as well. Because of the EV formation mechanisms, EVs contain specific lipids, membrane proteins, and internalized proteins, nucleic acids and metabolites derived from their cells of origin and are thus a rich source of potential biomarkers.

Recent research suggests a role for EVs in the function of the healthy central nervous system (CNS) as well as a role in numerous diseases of the CNS. Many cells of the CNS including neurons, astrocytes, oligodendroglia and microglia have been shown to secrete EVs in vitro. In neurons, synaptic activity-dependent EV release and reuptake has been observed and has been proposed as a possible mechanism of synaptic plasticity and inter-neuronal transfer of complex information. Neurons have also been shown to transfer miRNA via EVs to astrocytes, modulating the level of an important functional synaptic protein, EAAT2/GLT1. EV secretion by oligodendrocytes has been found to modulate myelin biogenesis, promote neuronal viability under stress and enable degradation of oligodendroglial membrane proteins by a subset of microglia through an "immunologically silent" macropinocytotic mechanism. Astrocyte-derived EVs have been shown to promote neuronal survival under stress by transferring heat-shock proteins and synapsin I. EV secretion by microglia has been shown to be inducible by Wnt-signaling and to stimulate synaptic activity by enhancing sphingosine metabolism in neurons and to represent a unique secretion mechanism for IL-1beta, an important neuroinflammatory cytokine.

In addition to promoting healthy CNS function, EVs appear to play several roles in various CNS diseases and disorders. Broadly these include the export of toxic proteins and possibly promotion of toxic isoform formation, mediation of neuroinflammation, and the transfer of disease associated miRNAs. Numerous studies have demonstrated that EVs can mediate the transfer of toxic proteins between cells both in-vitro and in animal studies. This includes the misfolded prion protein PrPSc, the infectious agent in human diseases Creutzfeldt-Jakob disease (CJD) and Gerstmann-Straussler-Scheinker syndrome (GSS), aggregated alpha-synuclein, the pathogenic species associated with Parkinson's disease and Lewy body dementia, aggregated Tau and beta-amyloid peptides hallmarks of Alzheimer's disease (AD), frontotemporal lobar degeneration (FTD) and progressive supranuclear palsy (PSP), and mutated SOD1, linked to the development of amyotrophic lateral sclerosis (ALS). There is also some evidence that the secretion of toxic proteins in EVs may actually have a protective role, facilitating clearing of these pathogenic species by microglia.

Assessing the composition of EVs and their cargo generally requires isolating a pure population of EVs and separating it from non-EV associated factors. Some demonstrations of this idea have focused on enriching CNS-derived extracellular vesicles (CNS-EVs) from plasma or serum based on immunoaffinity capture of specific EV surface proteins and measuring disease-associated proteins within the enriched EV population.

EVs are also emerging as useful indicators of disease. For example, cellular stresses including ischemia and glucose starvation have been shown to enhance the secretion of EVs by cardiomyocytes. EVs from serum or plasma have also recently become useful biomarkers for numerous cardiac-related conditions, including acute coronary syndrome, chronic ischemic heart disease, myocardial infarction, and atrial fibrillation. Certain EVs may also be associated with aging and health span.

Despite its utility, this method has significant fundamental and technical drawbacks. Fundamentally, the use of a single marker for EV isolation presents a great challenge. Most surface proteins are expressed on a variety of cell types; thus, multiple markers are usually needed to define a specific cell population. This is often apparent in flow cytometry, wherein multiple markers are usually employed despite the benefit of a predefined input cell population (e.g. PBMCs, or cultured cells). When isolating EVs from blood, nearly all cell types of the organism may be represented within the EV population, increasing the challenge of identifying a single marker specific for EVs from one cell type. Technical challenges of the existing approach are illustrated by the dramatic differences in levels of circulating L1CAM+ EVs and associated cargo molecules (e.g. Tau) reported by multiple groups using nearly identical protocols. This variability, which likely stems from minor variations in protocols from lab to lab (e.g. wash or mixing steps) speaks to the need for protocol standardization and simplification.

SUMMARY OF THE INVENTION

In embodiments, the disclosure provides methods and kits for determining surface markers of a surface marker displaying agent. In embodiments, the disclosure provides methods and kits for identifying a surface marker displaying agent in a sample. In embodiments, the disclosure provides methods and kits for isolating, detecting, or both, a surface marker displaying agent in a sample.

In embodiments, the disclosure provides a library comprising multiple pools of oligonucleotides. In embodiments, the disclosure provides a library comprising multiple pools of binding reagents conjugated to oligonucleotides.

In embodiments, the disclosure provides methods and kits for generating an oligonucleotide library. In embodiments, the disclosure provides methods and kits for generating a binding reagent library.

BRIEF DESCRIPTION OF THE DRAWINGS

The following drawings form part of the present specification and are included to further demonstrate exemplary embodiments of certain aspects of the present invention.

FIGS. 1A-1E—example of the "EV Stapling" method for multi-marker EV isolation. FIG. 1A: Capture antibodies are displayed on the plate surface using labile linker. EVs are captured via the first surface marker. The second surface marker is then decorated by an oligonucleotide-labeled antibody that serves as amplification primer. FIG. 1B: When this primer is present on captured EVs, rolling circle amplification can occur. An additional sequence in the circular template produces a "staple sequence" which hybridizes to complementary oligonucleotides on the surface, "stapling" the EV down to the surface. A typical amplification reaction may produce many copies of the staple sequence yielding a highly stable complex. FIG. 1C: The labile linker is denatured, releasing capture antibodies from the surface. EVs that are stapled remain surface-bound, while those that lacked the second surface marker and thus were not stapled are eluted from the surface and washed away. FIG. 1D: The stapling technique was demonstrated on cell culture derived EVs known to express high levels of CD9 and CD81 and low levels of CD63. EVs were captured with a CD9 antibody followed by stapling with CD81, CD63 or irrelevant antibody or no stapling at all. Captured EVs were detected with CD9 antibodies before and after elution. CD81 stapling resulted in complete retention of EVs, while CD63 resulted in retention of a fraction of the EVs. Irrelevant control and no stapling allowed elution of most of the captured EVs. Optimization will be needed to achieve close to 100% elution for these control conditions. FIG. 1E: Schematic of example of three marker isolation.

FIG. 4 is a schematic of an example of Assaying EV Cargo.

FIGS. 5A and 5B show ECL signal from tetraspanin (CD63, CD81, and CD9) sandwich assays performed on cell culture media depleted in 2 hours and 4 hours, respectively. Bar graphs represent the depleted fraction, calculated as the difference in signal between fresh media and depleted media as a fraction of the signal from fresh media.

FIG. 6A shows ECL signal from tetraspanin (CD63, CD81, and CD9) sandwich assays performed on non-eluted wells using various dilutions of capture antibodies. FIG. 6B shows the correlation between the elution efficiency (percent eluted) and capture antibody dilution.

FIG. 12 shows the results of the experiments described in Example 2.2.1. Cell conditioned medium from different biological samples and purified EVs ($1^{st}$ column) were evaluated by intact EV assays using all pairwise combinations of CD63, CD81, CD9, and EpCAM as capture and detection antibodies.

FIGS. 13A-13C relate to the experiments described in Example 2.2.2. FIG. 13A illustrates using a tetraspanin capture antibody with an isotype-matched non-specific control antibody as the detection antibody to assess non-specific binding of detection antibodies to specifically captured EVs. FIG. 13B illustrates using isotype-matched non-specific control antibody as the capture antibody with a tetraspanin detection antibody to assess non-specific binding of exosomes to the surface. The results of the intact EV assays in FIG. 13C show low non-specific binding of EVs to IgG1 control capture antibody (last column) and low binding of IgG1 control antibody to captured EVs (4$^{th}$ row).

FIG. 14 relates to the experiments described in Example 2.3.1. Capture antibodies targeting CD63, CD81, and CD9 were displayed within the same well for multiplex assays. Singleplex and multiplex intact EV assays were performed on Expi293 cell conditioned medium, using all pairwise combinations of tetraspanin (CD63, CD81, and CD9) capture and detection antibodies. FIG. 14 shows the ratios of the multiplex signal to the singleplex signal. In most cases, the multiplex assay signal is within 10% of the singleplex assay signal.

FIG. 15 shows the results of the experiments described in Example 2.3.2 (A). Two 8-plex capture multiplexes were used to screen 15 different culture conditions representing 10 different cell lines. Each sample and capture multiplex were used in combination with each of the tetraspanin detectors. Cell lines that produced EVs with 11 of the 13 tumor markers were identified.

FIGS. 16A-16B relate to the experiments described in Example 2.3.2 (B). FIG. 16A shows the results of a 10-plex assay of cell culture control samples with cancer antigen capture antibodies and a triplex of tetraspanin (CD63, CD81, and CD9) capture antibodies. Each sample and capture multiplex was combined with a cocktail of all three tetraspanin detectors to maximize signal. FIG. 16B shows the results of the same 10-plex assay on plasma samples from 10 pancreatic ductal adenocarcinoma patents and 10 healthy subjects.

FIG. 17 shows the results of the experiments described in Example 2.3.2 (C). Samples of cell conditioned media and exosomes from various cell lines and serum pools (1st column) were captured using three 6-plex panels of cancer antigens and detected using a cocktail of tetraspanin (CD63, CD81, and CD9) detection antibodies. Several expected surface markers were detected in pancreatic cancer cell lines.

FIG. 18A illustrates a single antibody RCA detection assay of EV-associated antigen. The results of the assay in FIG. 18B show linear amplification across a wide range of dilutions with no observable elevation in background signal.

FIGS. 19A-19C relate to the experiments described in Example 2.4.1 (B). FIG. 19A illustrates a homo-pair proximity ligation/RCA. FIG. 19B illustrates a hetero-pair proximity ligation/RCA. The results of the assays in FIG. 19C demonstrate low non-specific binding and high specific signal for all combinations of proximity probes.

CD9), hetero-pairs (e.g., CD9/CD81), or cocktails comprising CD63, CD81, and CD9 PP1s and CD63, CD81, and CD9 PP2s at two different concentrations.

Figure 21A:
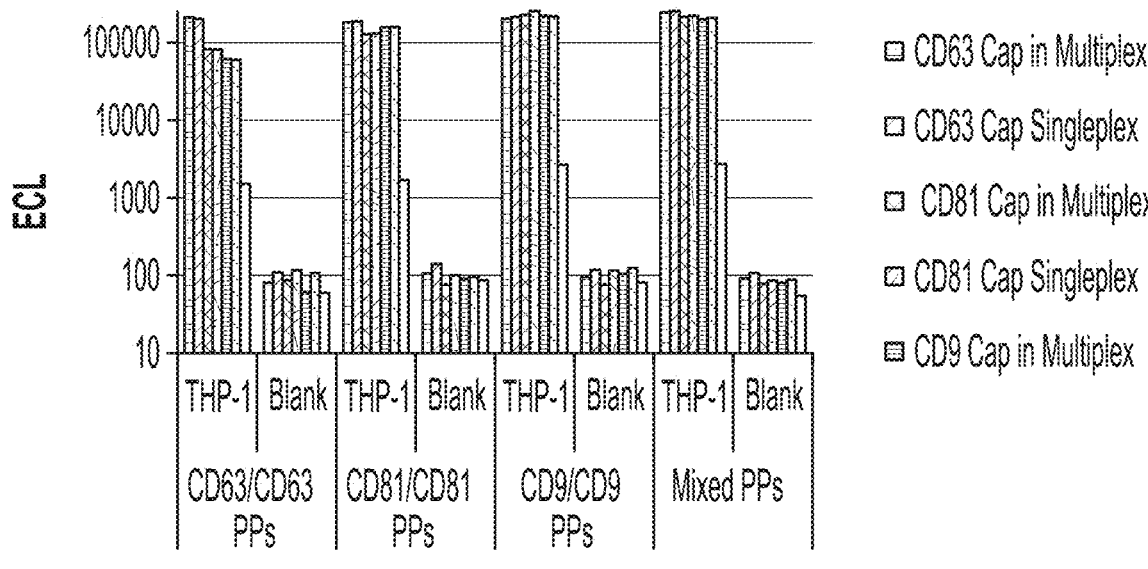
Figure 21B:
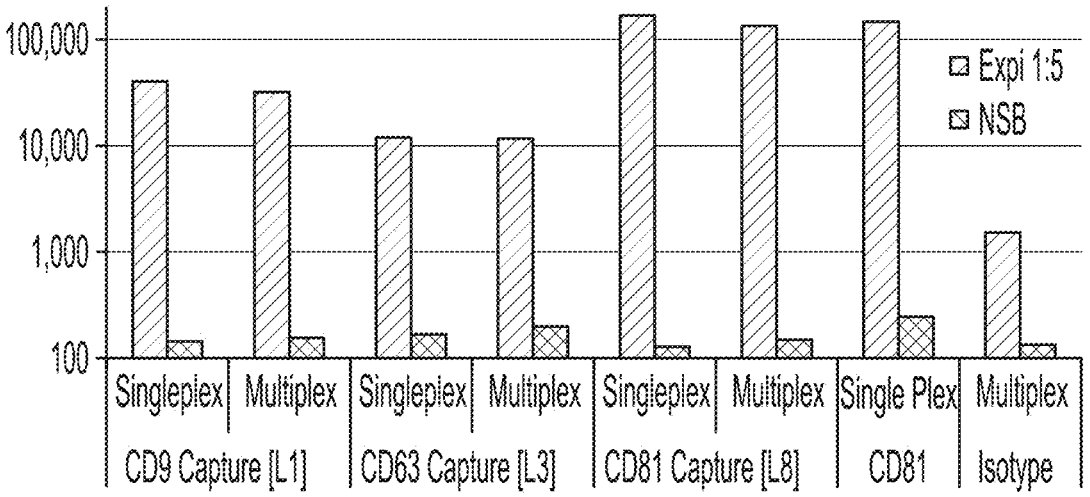

FIGS. 21A-21B show the results of the experiments described in Example 2.4.2 (A). FIG. 21A is a comparison of singleplex and multiplex PLA/RCA tetraspanin (CD63, CD81, and CD9) assays performed with a blocking step. FIG. 21B is a comparison of singleplex and multiplex PLA/RCA assays performed without the blocking step.

FIGS. 22A-22B show the results of the experiments described in Example 2.4.2 (B). Multiplex assays were performed using cell conditioned medium from 12 different cell lines. FIG. 22A shows the assay results using a multiplex capture panel containing 6 proteoglycan surface markers and the isotype control. FIG. 22B shows the assay results using a multiplex capture panel containing 5 cell adhesion proteins and 2 surface receptors and the isotype control.

FIG. 23 illustrates a method for assaying EV cargo proteins as described in Example 3.

FIGS. 24A-24C show the results of the experiments described in Example 3.1.1. FIG. 24A compares IL-6 levels in cell conditioned medium from wild-type and transfected Expi293 cells. FIG. 24B shows the results of IL-6 assays on captured EVs to determine whether the IL-6 was present in the exosome. FIG. 24C shows the levels of non-specific binding of soluble IL-6 in the assays of captured EVs.

Figure 25A:
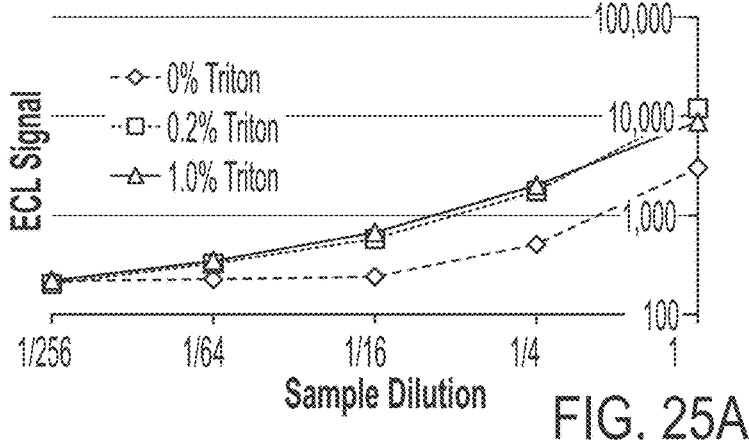
Figure 25B:
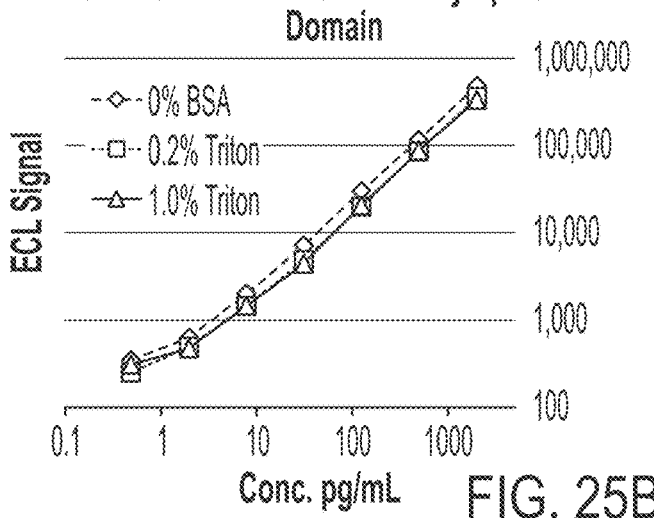
Figure 25C:
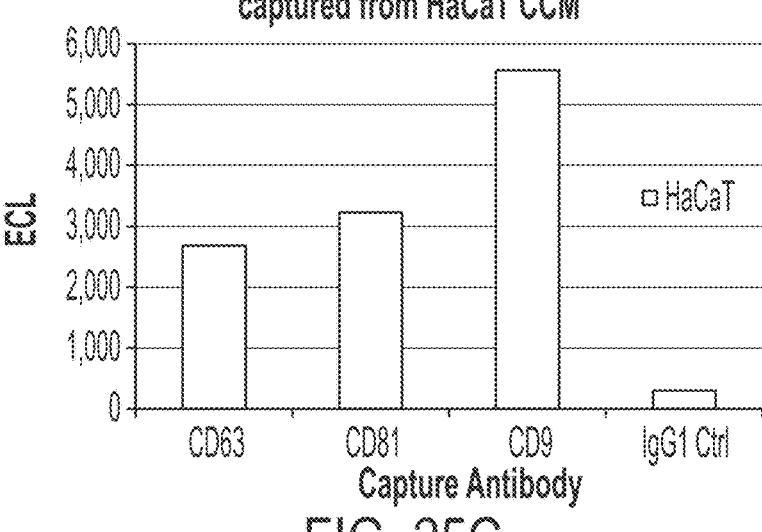

FIGS. 25A-25C show the results of the experiments described in Example 3.1.2. FIG. 25A shows the results of an ultrasensitive assay for EGFR (cytoplasmic domain) with and without lysis. FIG. 25B shows a calibration curve for the EGFR cytoplasmic domain assay. FIG. 25C shows the results of an ultrasensitive assay for EGFR cytoplasmic domain from captured and lysed EVs.

FIGS. 26A-26C relate to the experiments described in Example 3.2. FIG. 26A illustrates the procedure of an enzymatic digestion of non-cargo proteins in an EV-containing sample. FIG. 26B shows the results of an immunoassay of captured EVs detecting for EV-cargo HSP70. FIG. 26C shows the results of an immunoassay of captured EVs detecting for EV-cargo IL-6.

Figure 27A:
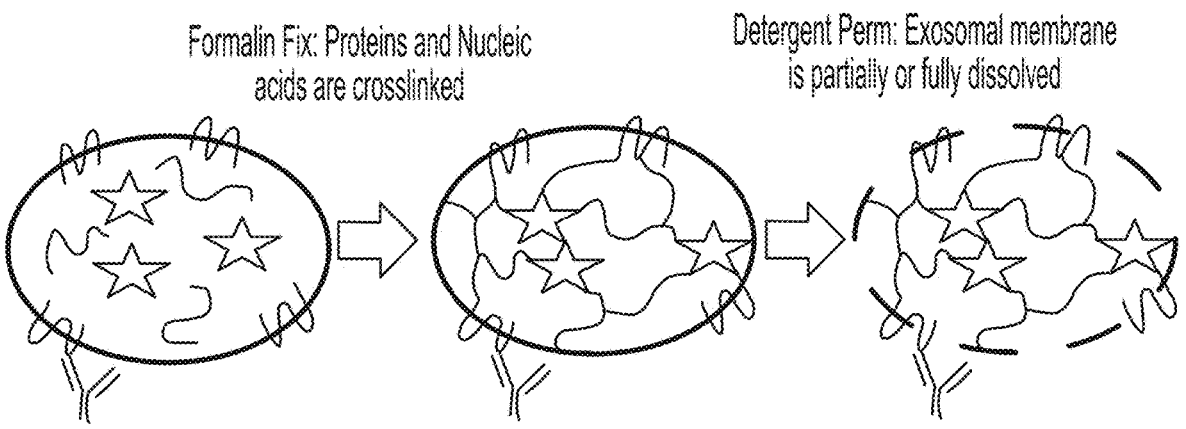
Figure 27B:
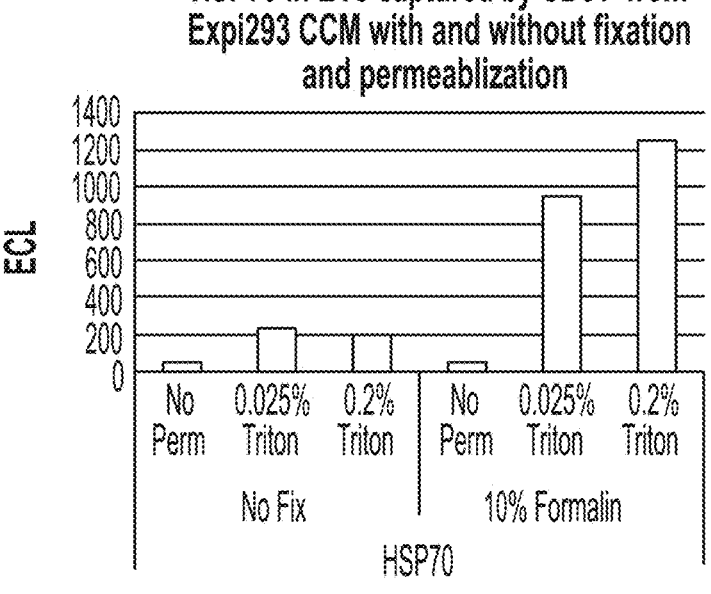

FIGS. 27A-27B relate to the experiments described in Example 3.3. FIG. 27A illustrates the procedure of fixing and permeabilizing captured EVs. Results in FIG. 27B show the effect of fixation and permeabilization on the detection of HSP70 in captured EVs.

FIG. 28 shows the results of the experiments described in Example 4. MSD Read Buffer B with varying concentrations of TRITON X-100 and Tween-20 were tested in EV assays using tetraspanin (CD63, CD81, and CD9) and isotype control capture antibodies and CD81 detection antibody.

FIG. 29 shows the results of the experiments described in Example 5.1. EV assays were performed on four different samples sets using all combinations of tetraspanin (CD63, CD81, and CD9) and EpCAM capture and detection antibodies.

Figure 30A:
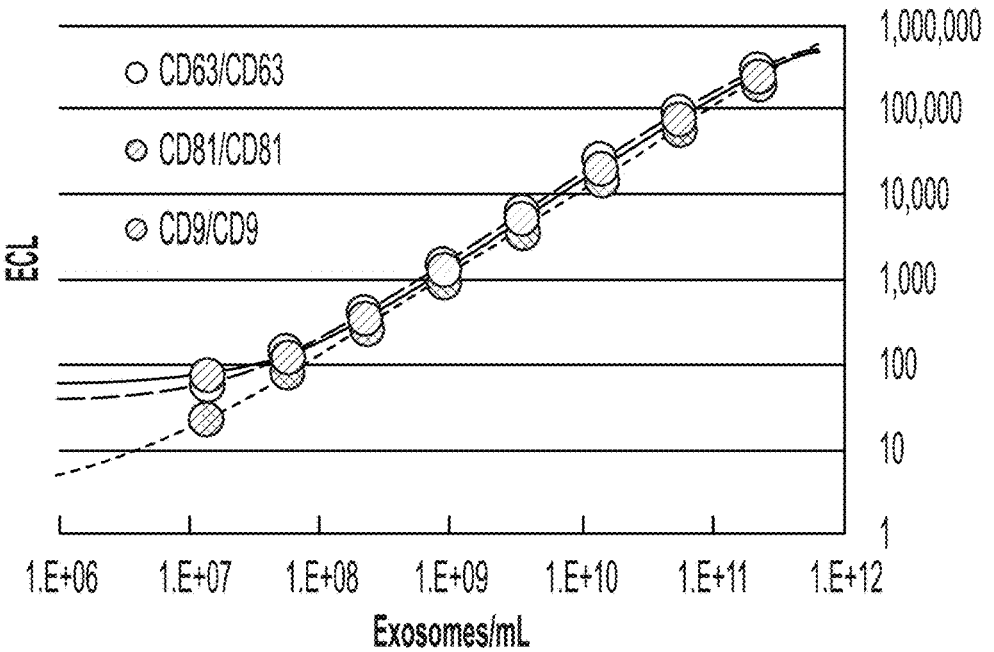
Figure 30B:
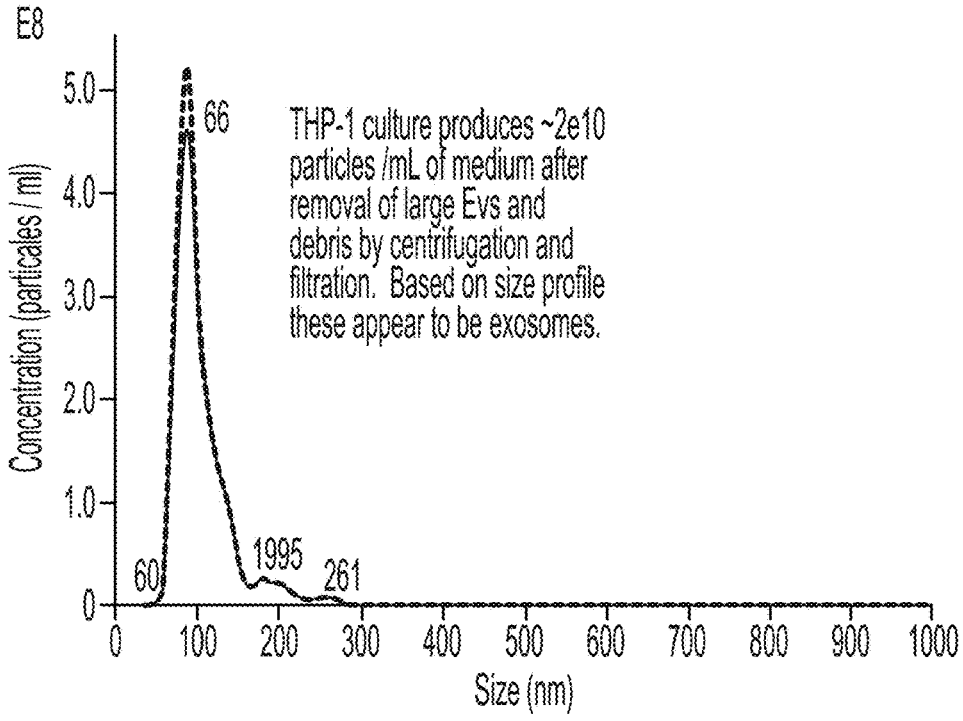

FIGS. 30A-30B show the results of the experiments described in Example 5.2. FIG. 30A shows the ECL signal from EV-associated tetraspanins (CD63, CD81, and CD9) in cell conditioned medium from THP-1 cells. FIG. 30B shows nanoparticle tracking analysis results of EVs in THP-1 cell culture.

Figure 31:
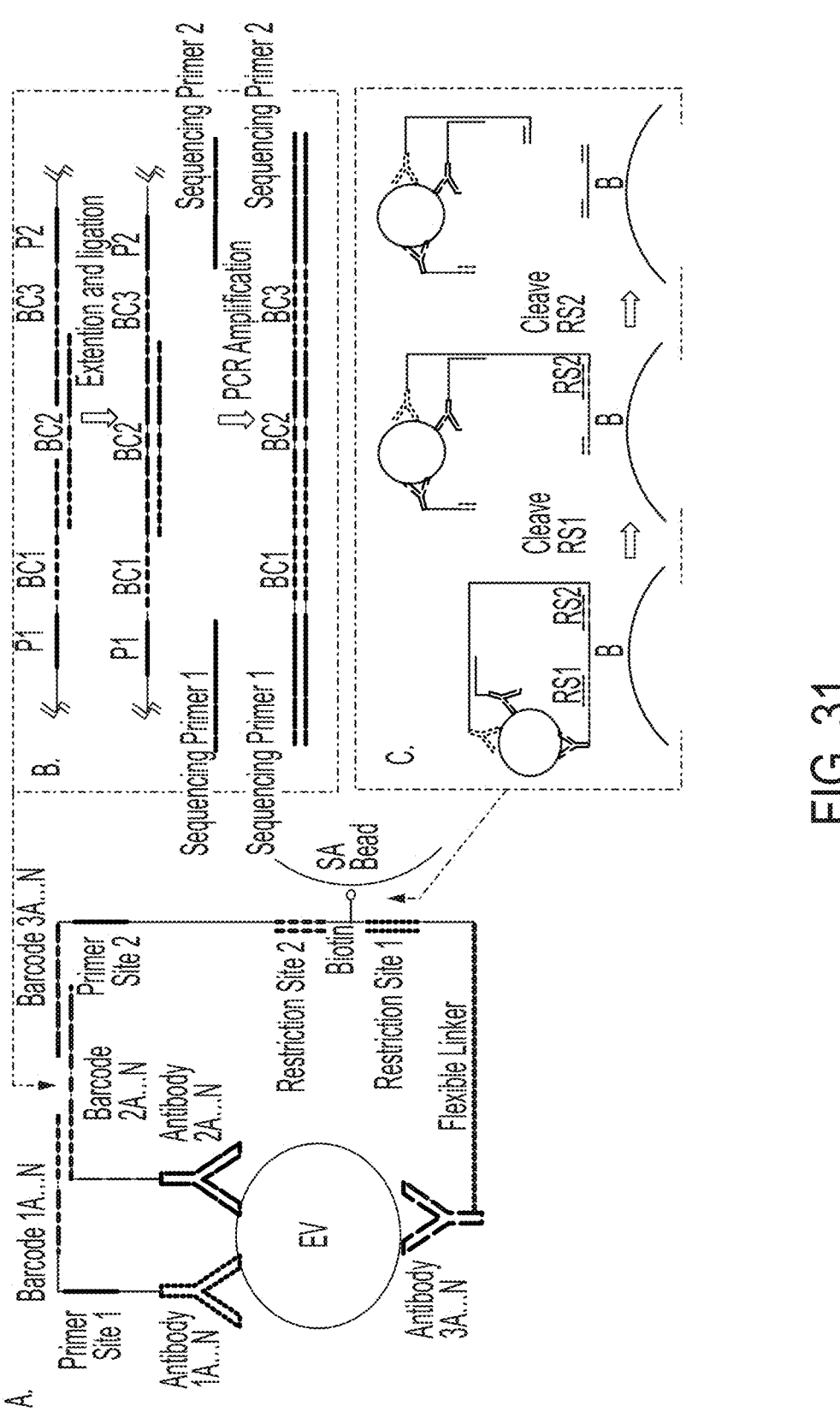

FIGS. 31A-31C illustrate a method for determining EV surface markers as described herein. FIG. 31A shows an EV bound to three antibodies from a pool of antibodies (not shown). At least one antibody is biotinylated, allowing the EV to be captured on a streptavidin bead, and washed to remove unbound EVs and antibodies. Extension and ligation reagents are added to ligate and join the barcodes into a single oligonucleotide. FIG. 31B shows the barcode screening process for EV surface markers. For screening, sequencing adapters are added by PCR, and each 3-barcode combination is read by next-generation sequencing. FIG. 31C shows the isolation process, which includes cleaving the first restriction endonuclease site ("RS1"). After cleavage at RS1, only the EVs tethered by the extension/ligation process are retained on the streptavidin bead, and non-specifically-bound EVs or other undesired components are removed by washing. Finally, retained EVs are eluted by cleaving at the second restriction endonuclease site ("RS2"), or by eluting from the antibodies at low pH.

Figure 32:
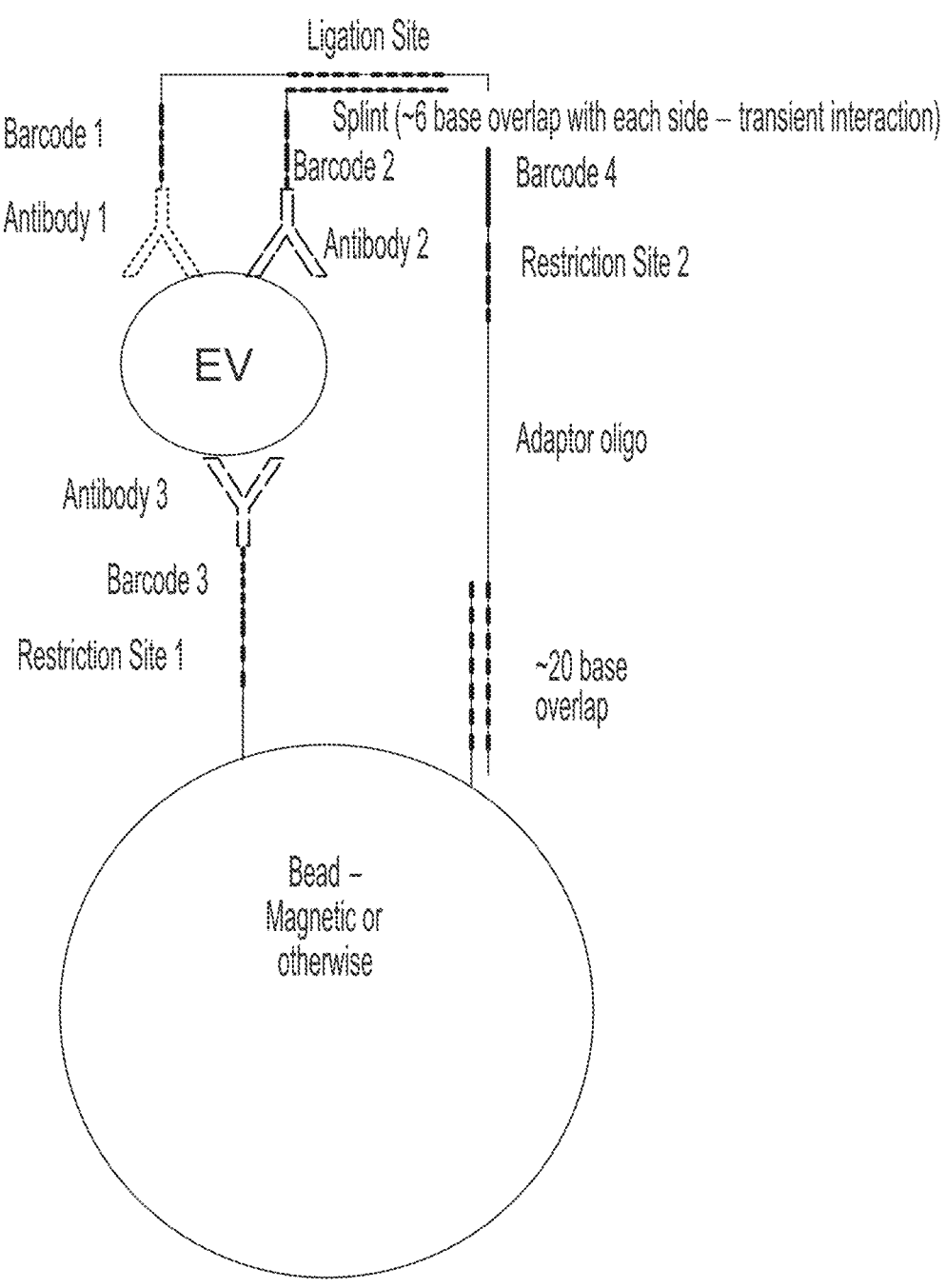

FIG. 32 illustrates an exemplary method of isolating an EV of interest from a sample using multiple (e.g., three) markers and a single solid phase, as described herein.

Figure 33:
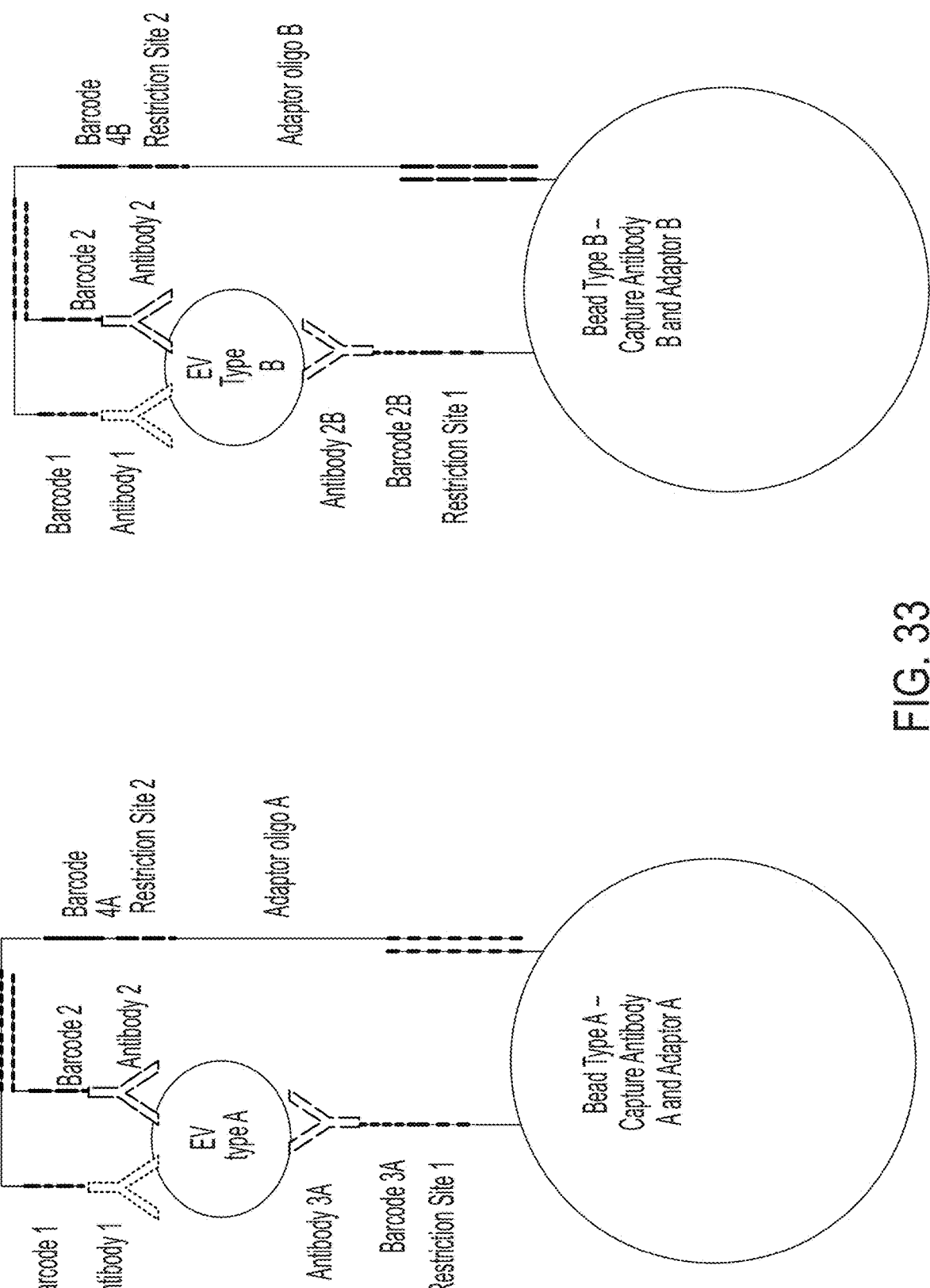

FIG. 33 illustrates an exemplary method of isolating two different EV populations of interest from a sample using multiple markers and a single solid phase, wherein the two different EV populations bind to two of the same binding reagents and one different binding reagent, as described herein.

Figure 34:
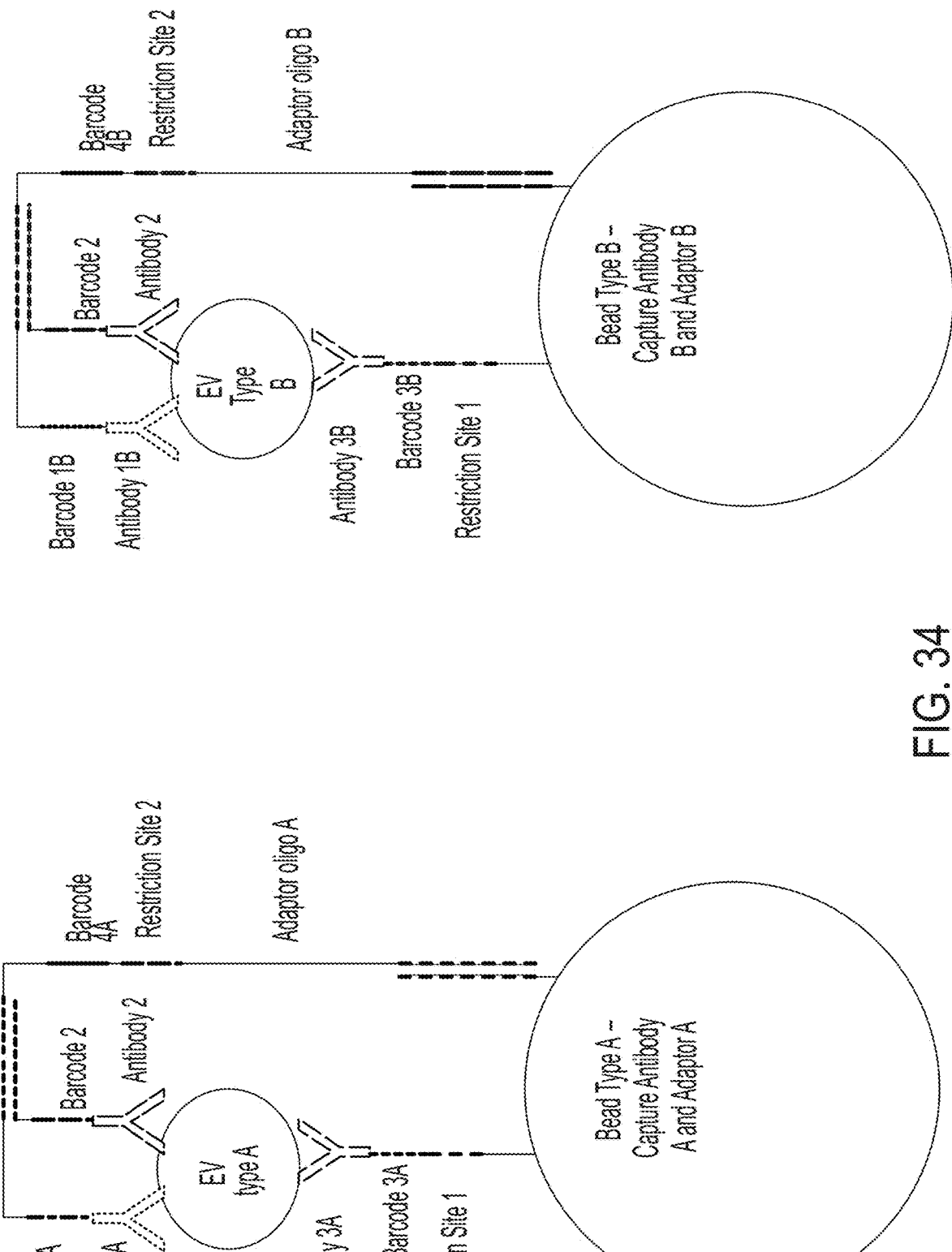

FIG. 34 illustrates an exemplary method of isolating two different EV populations of interest from a sample using multiple markers and a single solid phase, wherein the two different EV populations bind to one of the same binding reagents and two different binding reagents, as described herein.

Figure 35:
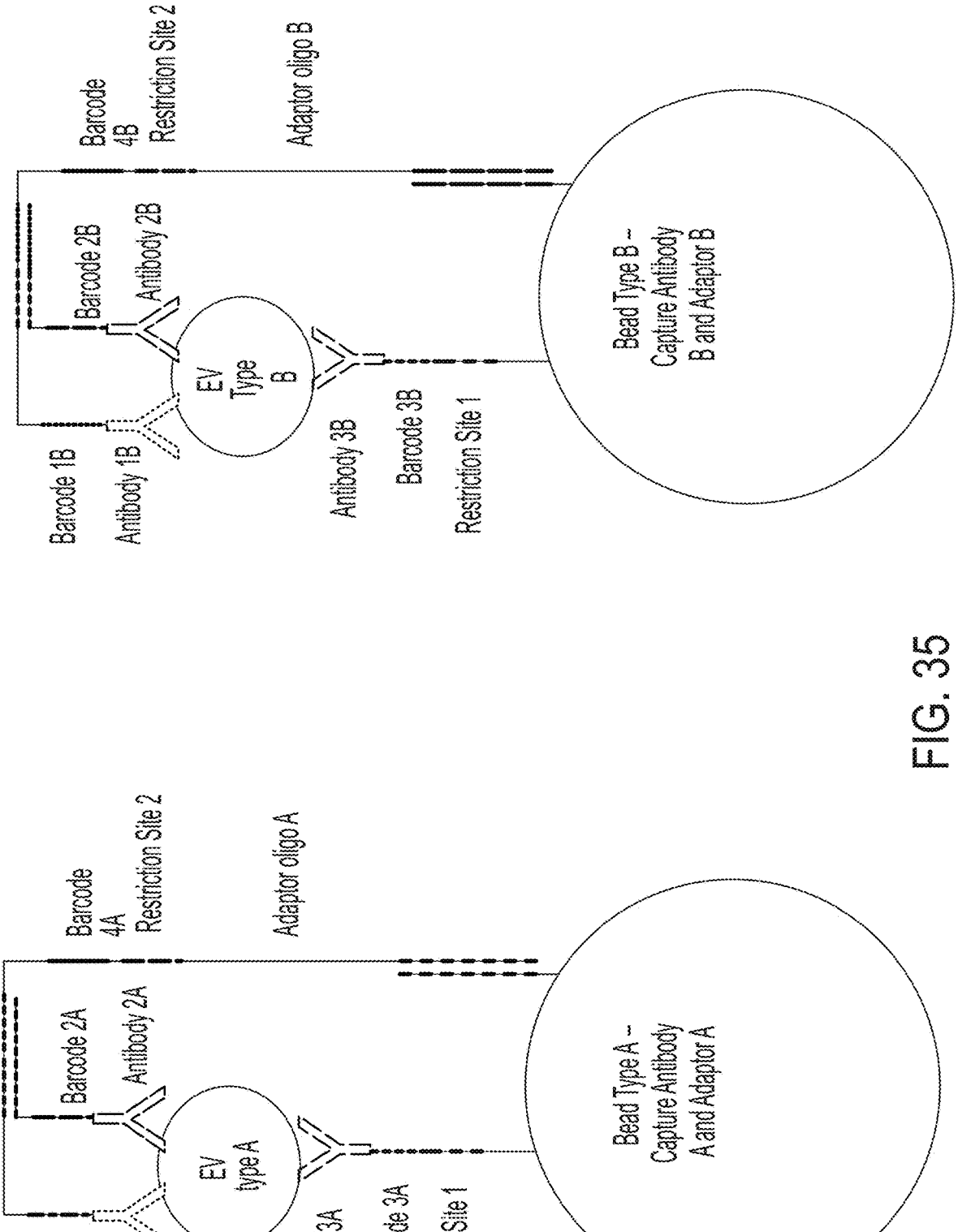

FIG. 35 illustrates an exemplary method of isolating two different EV populations of interest from a sample using multiple markers and a single solid phase, wherein the two different EV populations bind to three different binding reagents, as described herein.

Figure 36:
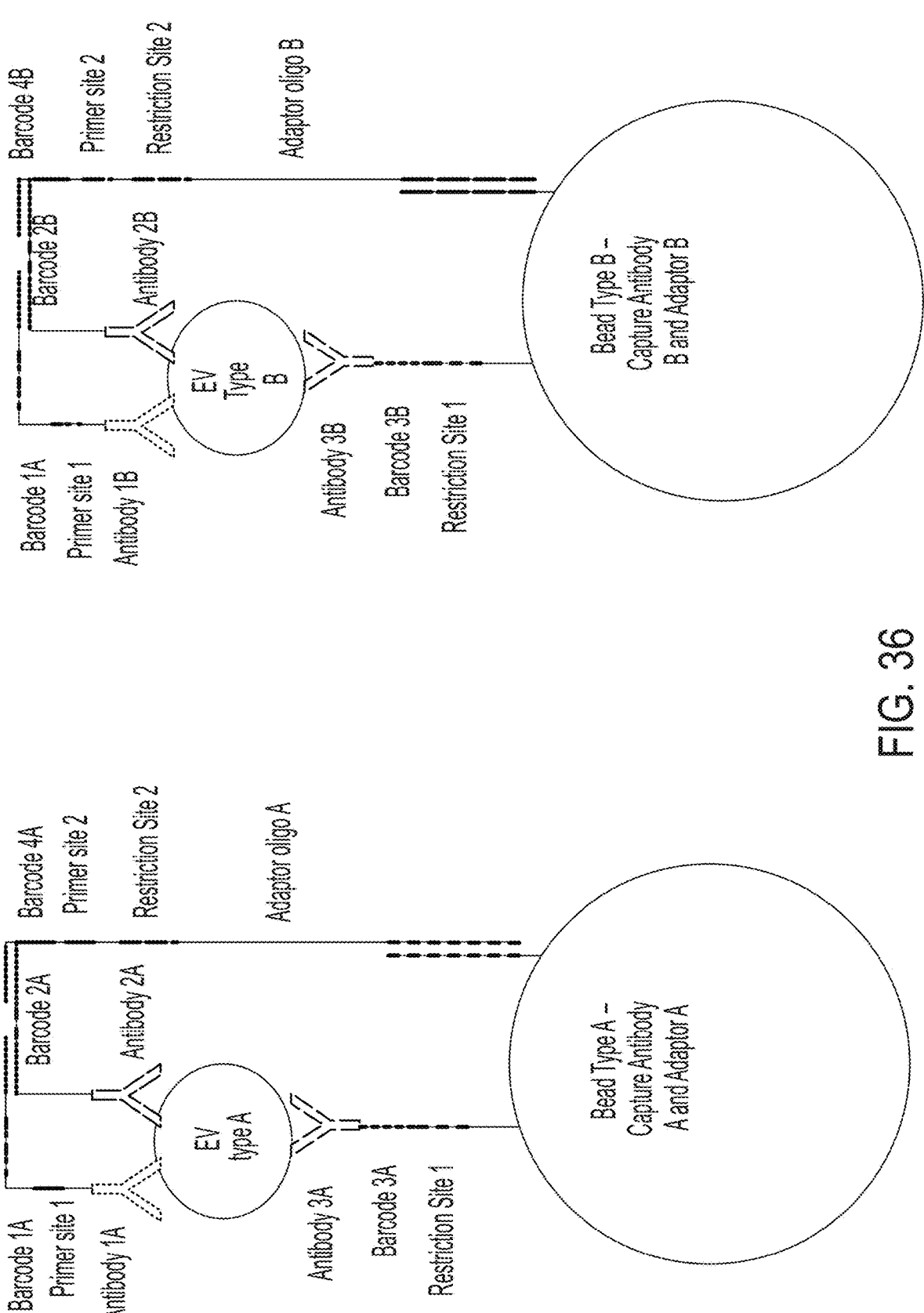

FIG. 36 illustrates another exemplary method of isolating two different EV populations of interest from a sample using multiple markers and a single solid phase, wherein the two different EV populations bind to three different binding reagents, as described herein.

FIGS. 37A and 37B relate to Example 12. FIG. 37A shows the results of an EV assay used to compared EV secretion from various cell lines in different cellular states. FIG. 37B shows the results of an EV assay used to compare multiple growth or stimulation conditions on a single cell line, THP-1.

FIG. 38 relates to Example 13. FIG. 38 shows results of an EV assay with different biofluid samples spiked with EV: human serum, plasma, CSF, and urine.

Figures 39A, 39B:
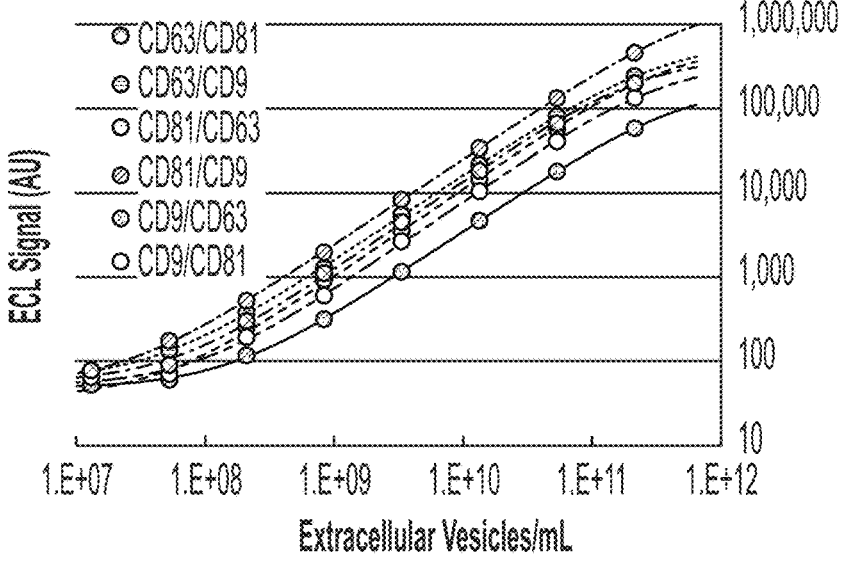

FIGS. 39A and 39B relate to Example 14. FIG. 39A shows a dilution curve for a two-marker EV assay for all combinations of CD63, CD81, and CD9 capture and detection antibodies. FIG. 39B shows the results of a single-marker and two-marker EV assays to compare EV subpopulation abundance and relative levels of each EV-associated marker.

Figure 40:
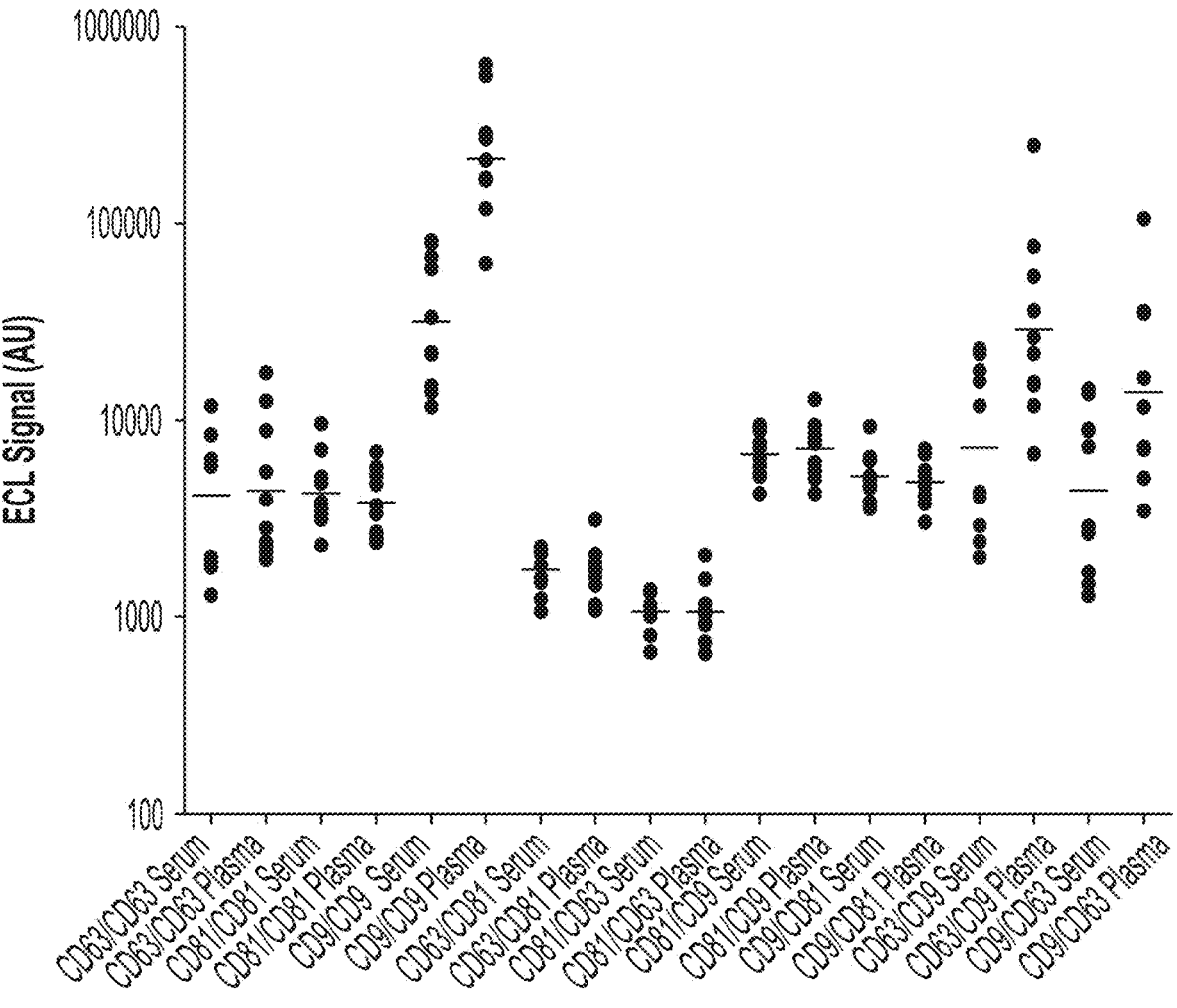

FIG. 40 relates to Example 15. FIG. 40 shows the results of single-marker and two-marker EV assays to determine assay performance with matched serum and plasma samples.

Figures 41A, 41B:
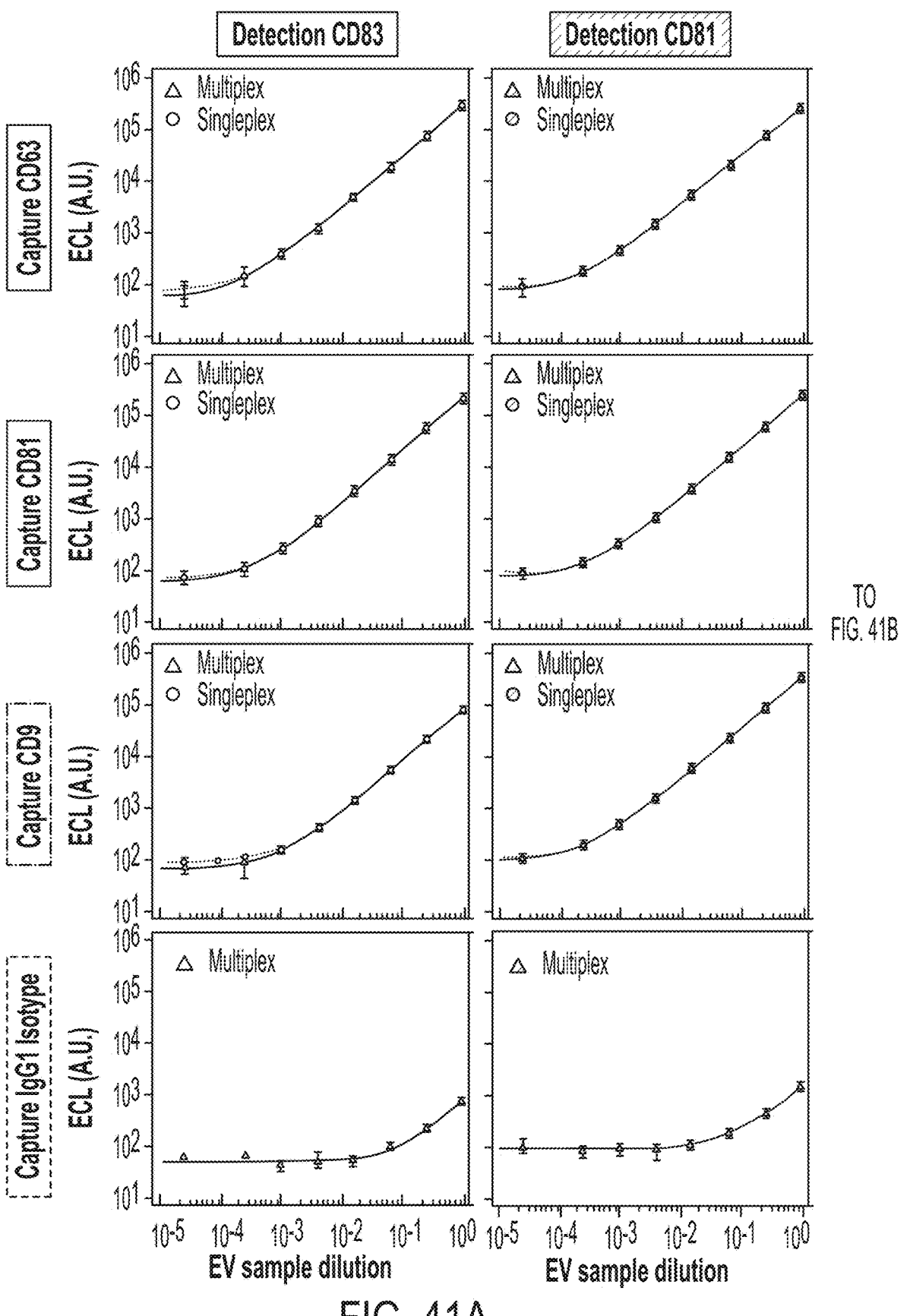
Figure 41B:
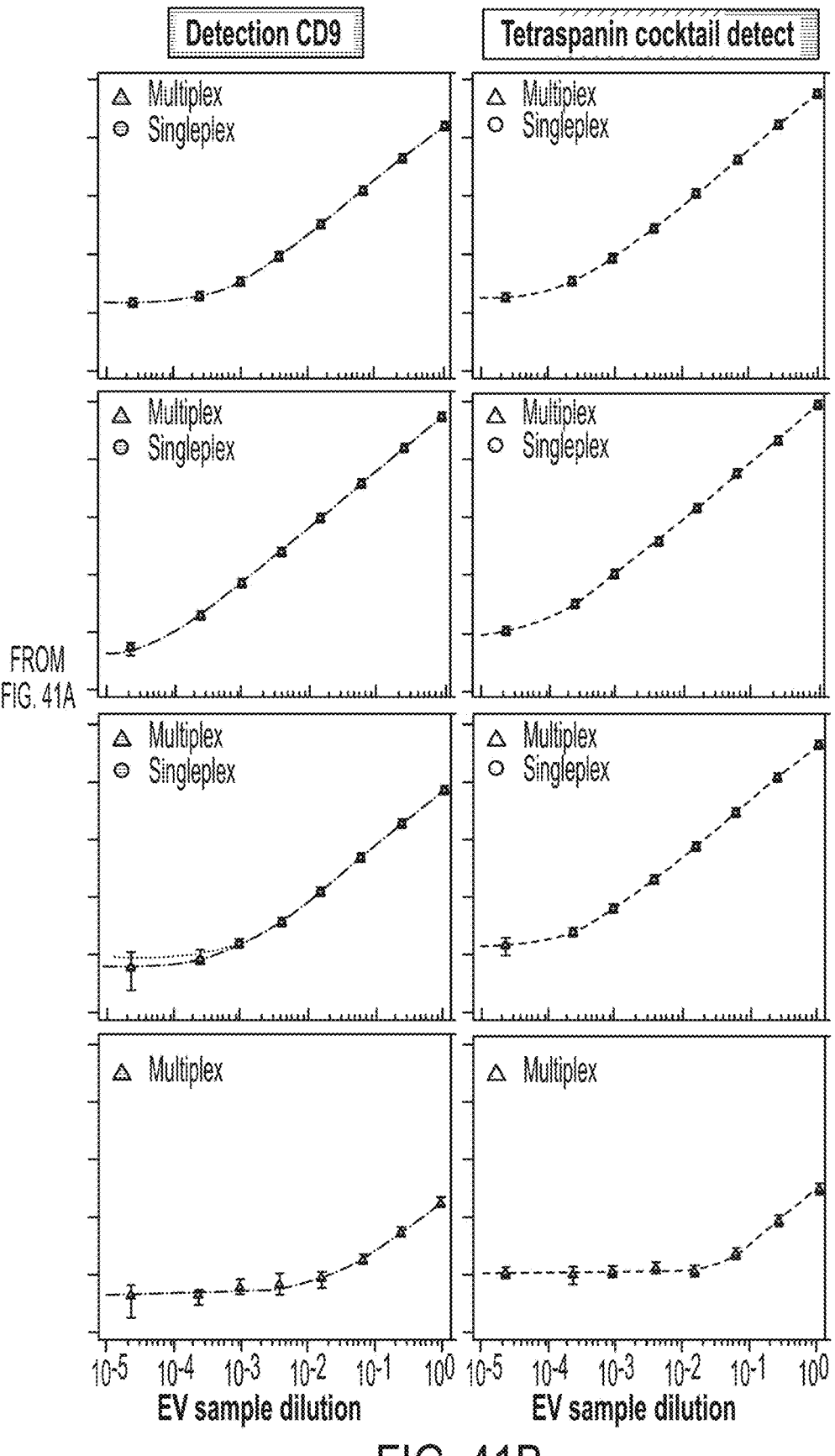

FIG. 41 relates to Example 16. FIG. 41 shows the results of a comparison of singleplex and multiplex EV assays.

FIGS. 42A and 42B relate to Example 17. FIG. 42A shows the results from the development of an EV-marker screening panel in a multiplex format. FIG. 42B shows panels of markers that were screened.

FIGS. 43A and 43B relate to Example 18. FIGS. 43A and 43B show the results of an EV assay for EVs captured from cell conditioned medium using the antibody panels from FIG. 42B.

FIG. 44 relates to Example 19. FIG. 44 shows the results of an EV assay for EVs captured from human biofluids using the antibody panels from FIG. 42B.

Figure 45:
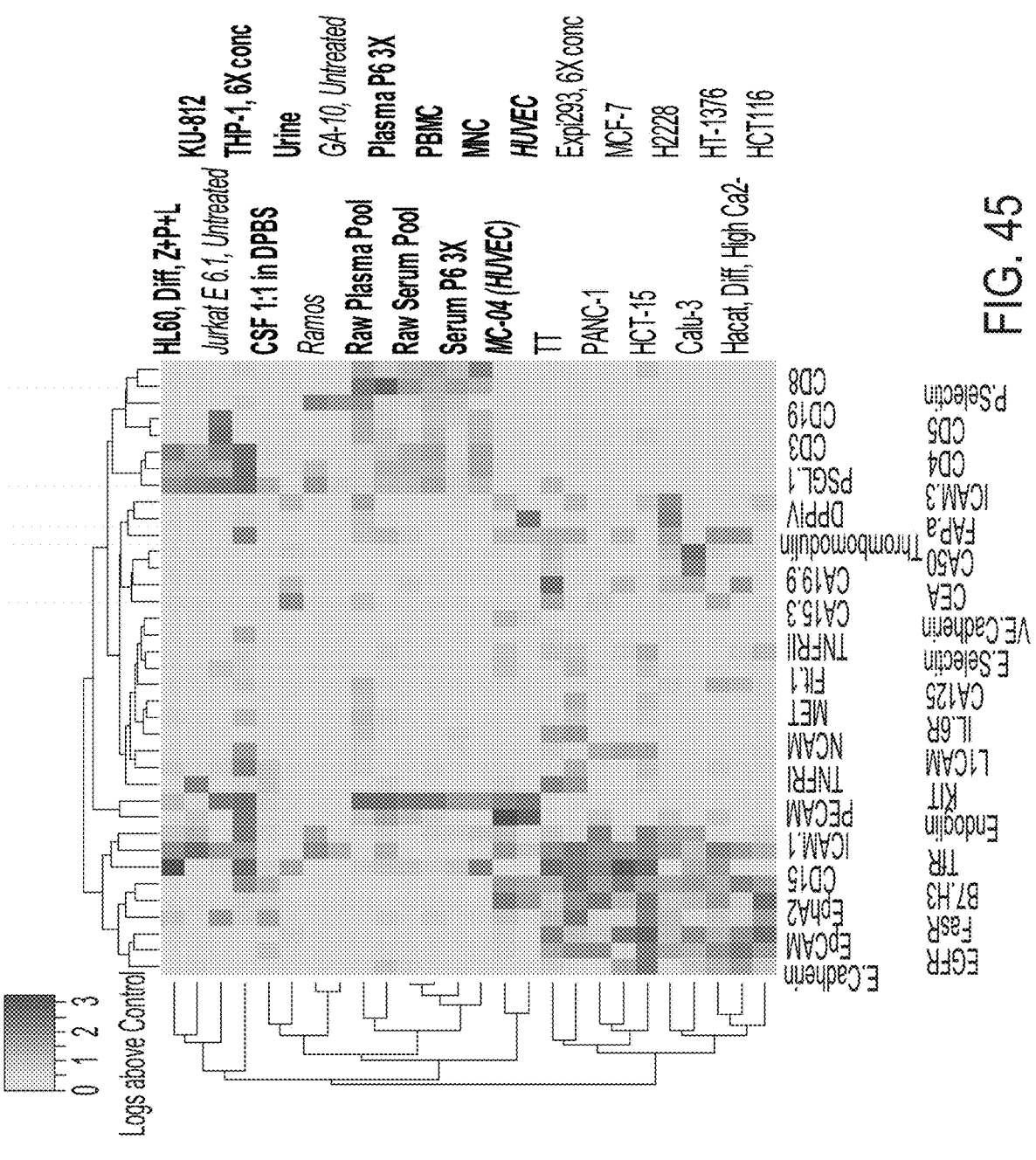

FIG. 45 relates to Example 20. FIG. 45 shows the results of the cluster analysis of the EV screening data from Examples 18 and 19.

Figure 46:
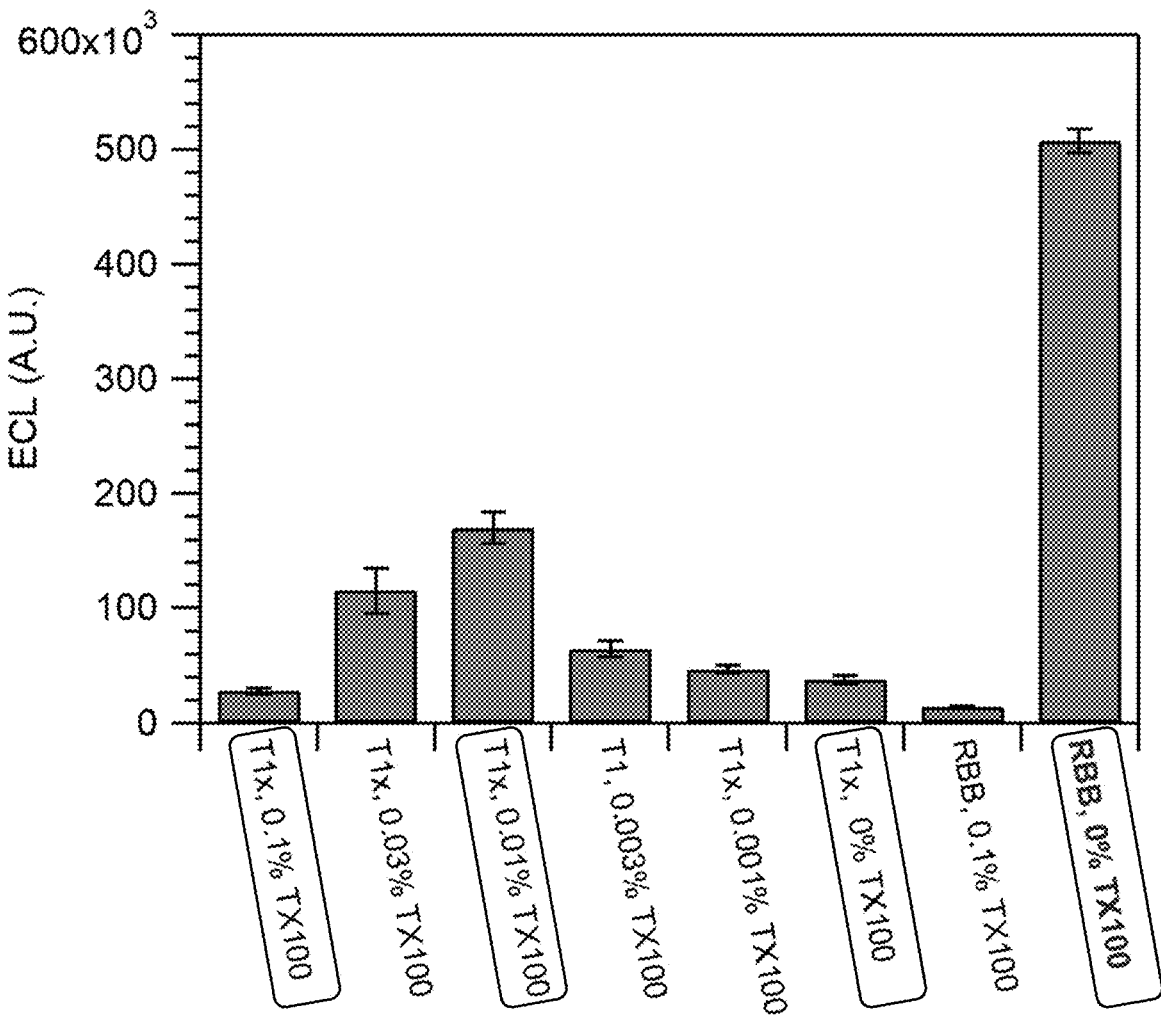
Figure 47:
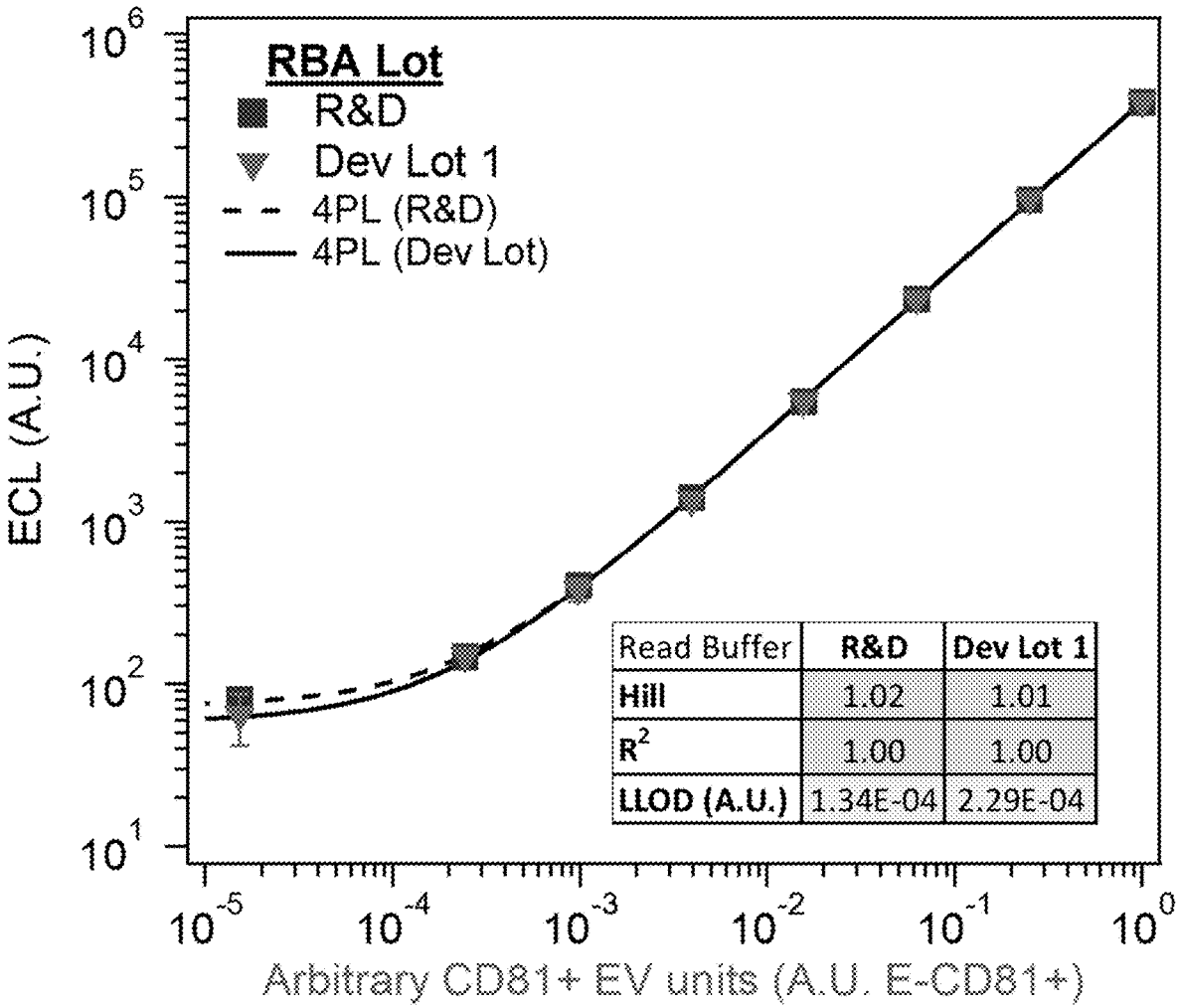

FIGS. 46 and 47 relate to Example 4.1. FIG. 46 shows the signal change in an EV assay based on the read buffer type and concentration of TRITON X-100. FIG. 47 shows a titration curve for known concentrations of EV tested with two different lots of MSD read buffer A.

FIGS. 48A-48C illustrate a method for determining EV surface markers as described in embodiments herein. FIG. 48A shows an EV bound to four antibodies from a pool of antibodies, each of which comprises a detection sequence that includes a unique barcode sequence. At least one antibody comprises a biotin, allowing the EV be captured on a streptavidin bead. Extension and ligation reagents are added to ligate and join the four barcodes into a single oligonucleotide. Adaptor sequences are added for PCR amplification and sequencing. FIG. 48B shows an EV bound to four antibodies from a pool of antibodies. Three of the antibodies have a detection sequence that includes a unique barcode sequence, and the fourth antibody comprises a biotin, allowing the EV to be captured on a streptavidin bead. Extension and ligation reagents are added to ligate and join the three barcodes into a single oligonucleotide. Adaptor sequences are added for PCR amplification and sequencing. FIG. 48C shows an EV bound to four antibodies as in FIG. 48B, and with a circular DNA template that has two ligation sites. The detection sequences from two of the antibodies bound to the EV serve as the splint oligonucleotides for the DNA template. The circular DNA template includes a detectable region that can be used in an ECL assay described herein.

FIGS. 49A-49C illustrate a method for isolating a surface marker displaying agent of interest from a sample as described in embodiments herein. In FIGS. 49A-49C, an anchoring reagent comprises an oligonucleotide moiety, a hydrophilic polymer moiety, and a biotin. The oligonucleotide moiety can have a complementary sequence to an oligonucleotide of the binding reagent (FIG. 49A). The oligonucleotide moiety of the anchoring reagent and an oligonucleotide of the binding reagent can also be complementary to portions of a splint oligonucleotide (FIG. 49B). The method can further use two binding reagents, each comprising an oligonucleotide, and the oligonucleotide moiety of the anchoring reagent and the oligonucleotide of the first binding reagent can be complementary to portions of an oligonucleotide of the second binding reagent (FIG. 49C).

Figure 50A:
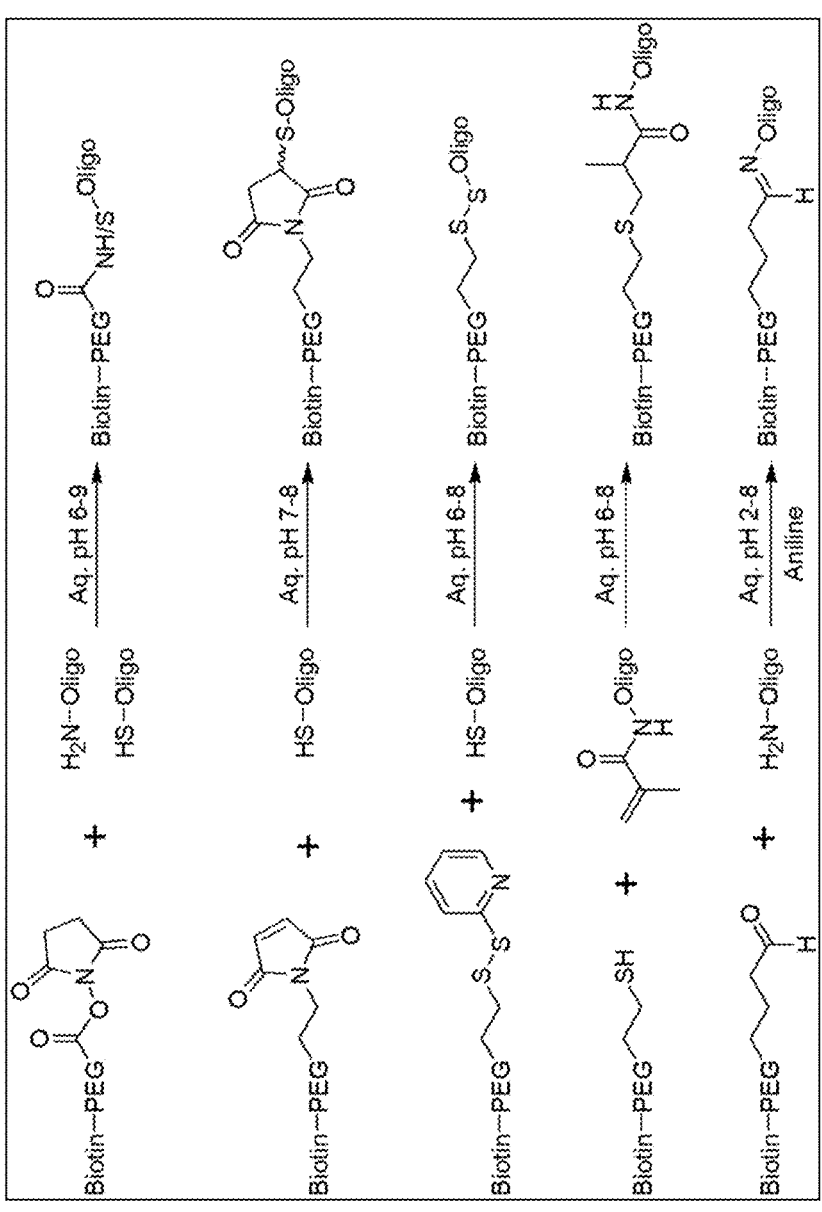
Figure 50B:
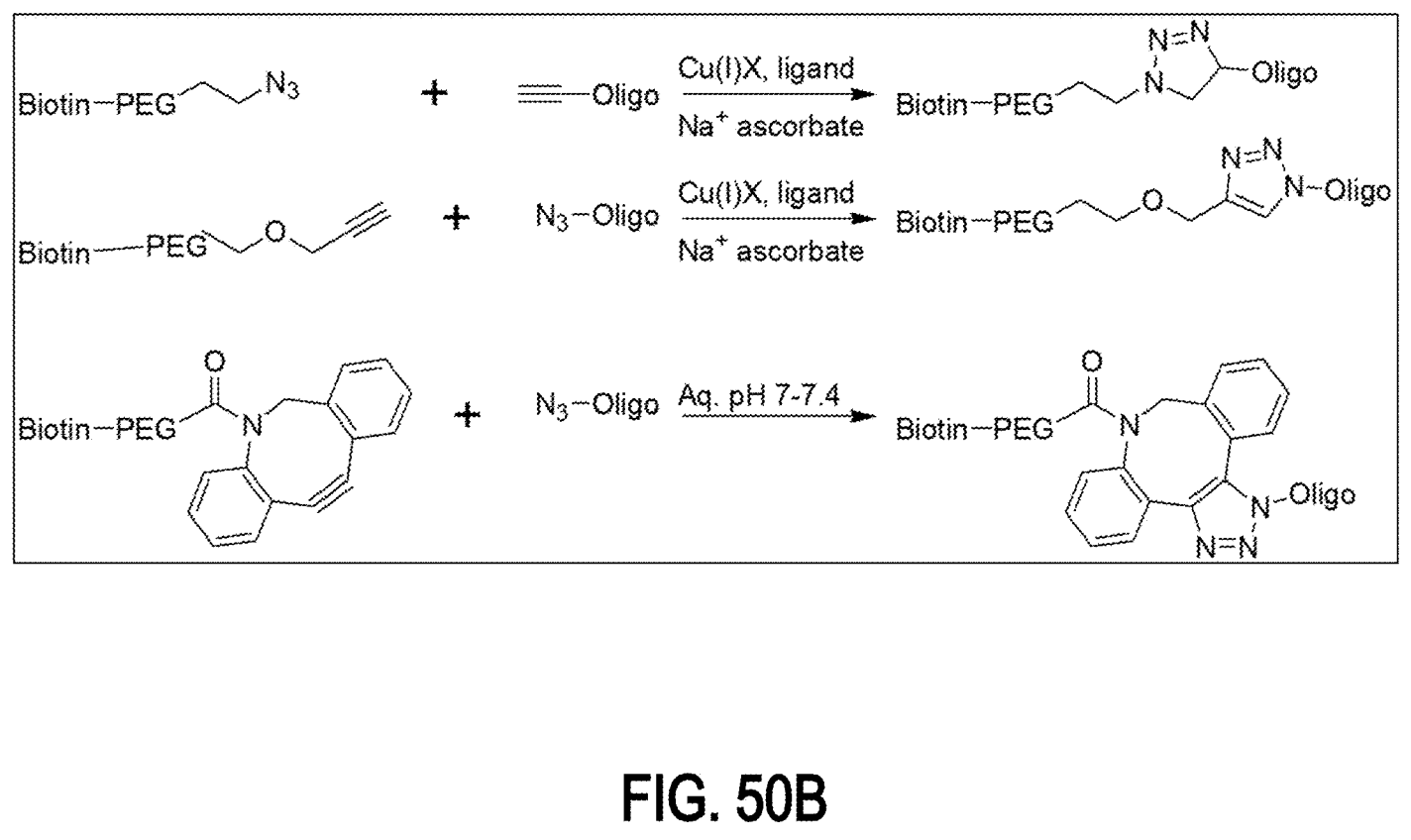

FIGS. 50A and 50B illustrate exemplary conjugation reactions for the anchoring reagents comprising an oligonucleotide moiety and a hydrophilic polymer moiety, as described in embodiments herein. FIG. 50A shows exemplary polar conjugation reactions. FIG. 50B shows exemplary cycloaddition conjugation reactions.

Figure 51A:
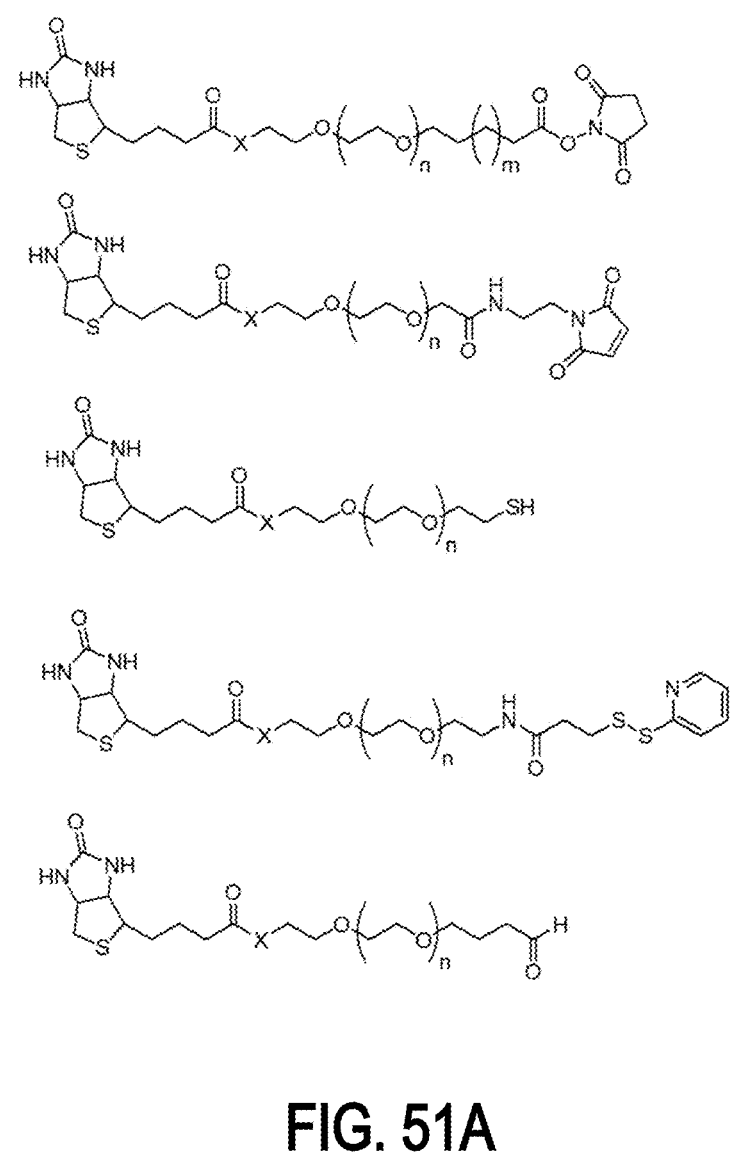
Figure 51B:
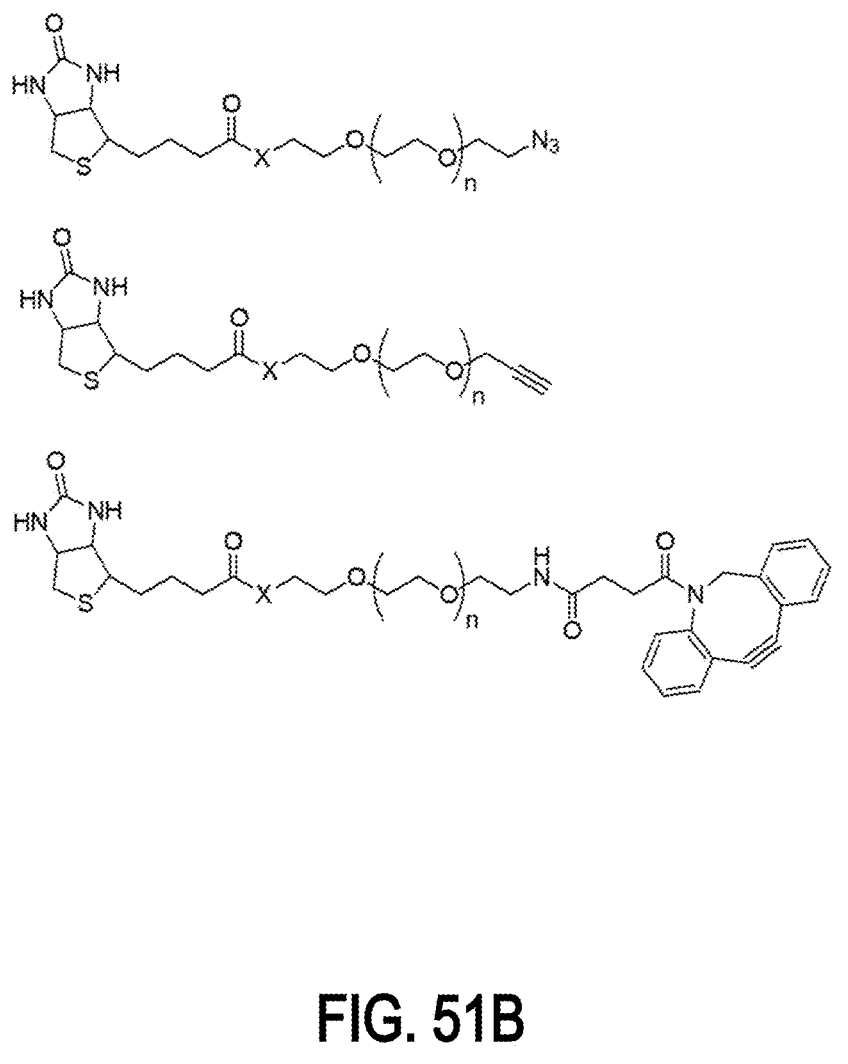

FIGS. 51A and 51B illustrate exemplary hydrophilic polymer moieties described in embodiments herein for use in polar conjugation reactions (FIG. 51A) or cycloaddition conjugation reactions (FIG. 51B).

Figure 52:
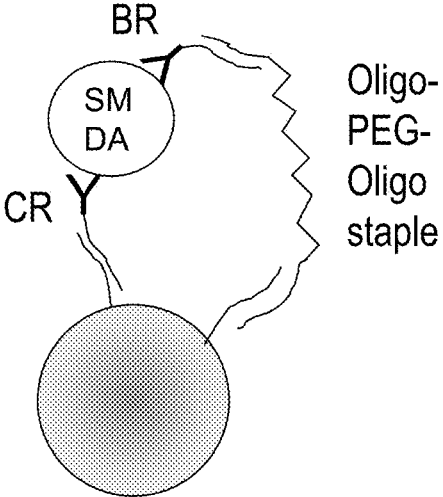

FIG. 52 illustrates a further method for isolating a surface marker displaying agent of interest from a sample as described in embodiments herein. In FIG. 52, a anchor linking reagent comprises a first oligonucleotide moiety, a hydrophilic polymer moiety, and a second oligonucleotide moiety. The first oligonucleotide moiety comprises a sequence complementary to an oligonucleotide of the binding reagent. The second oligonucleotide moiety comprises a sequence complementary to an oligonucleotide of the anchoring reagent.

Figure 53A:
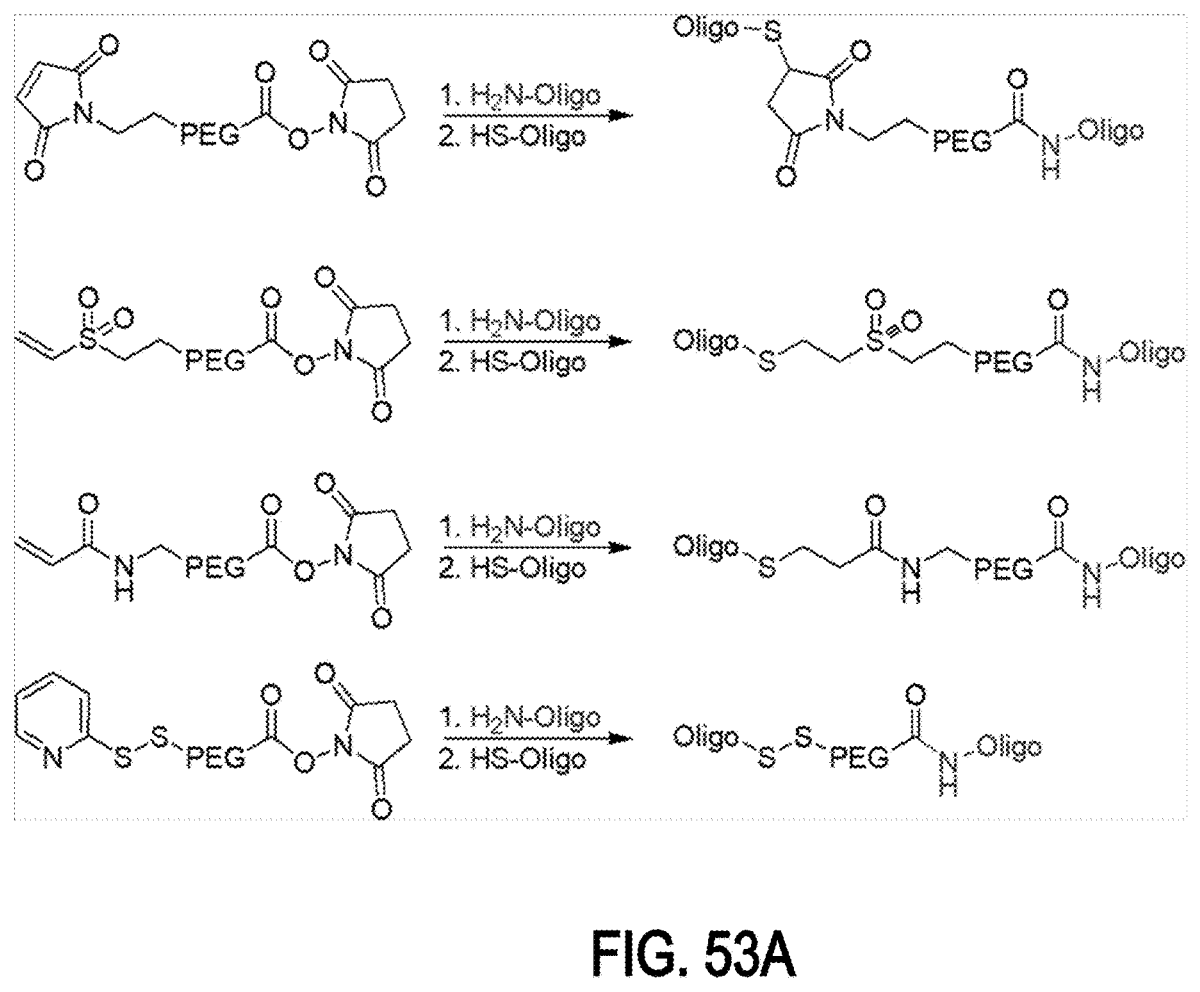
Figure 53B:
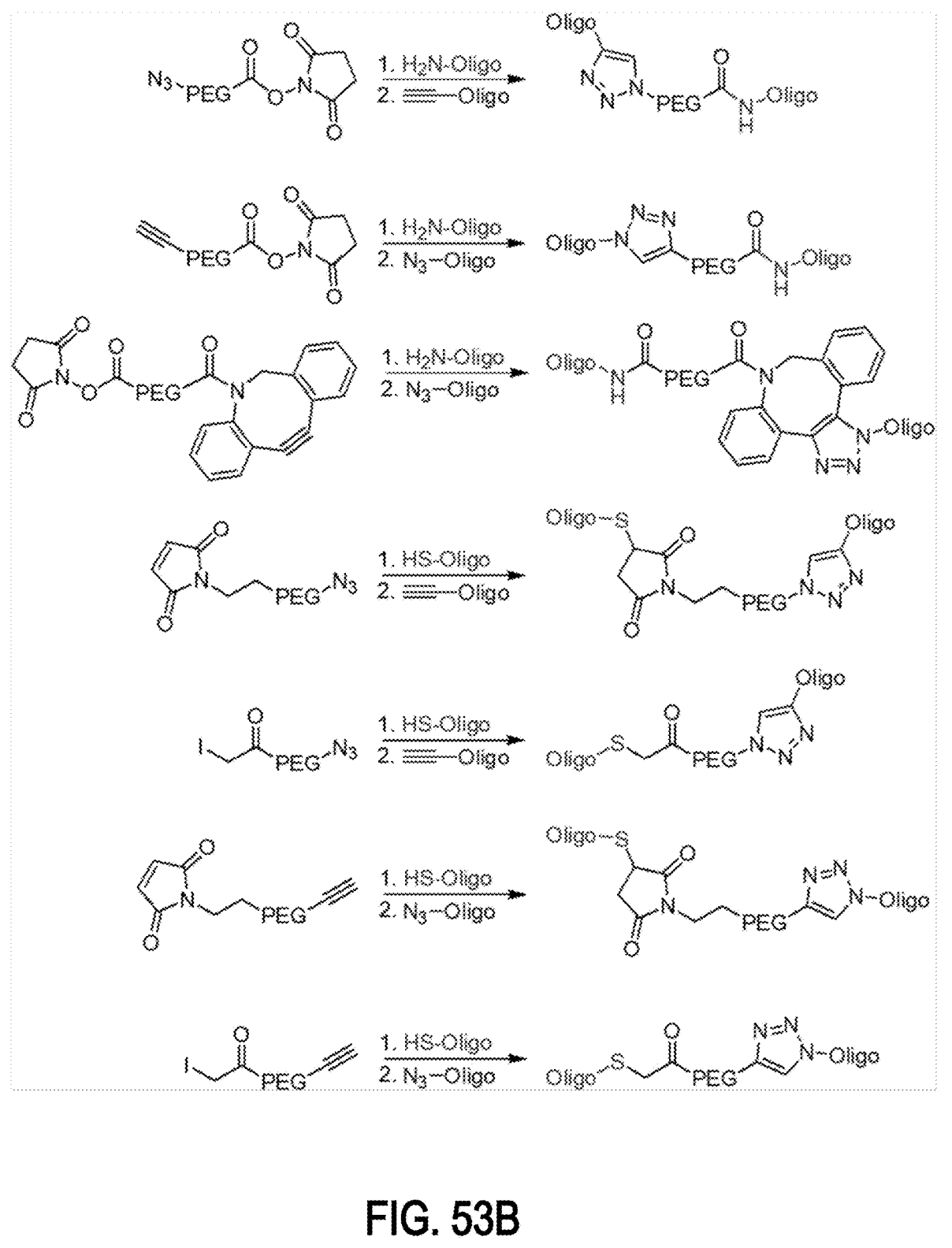

FIGS. 53A and 53B illustrate exemplary conjugation reactions for the anchor linking reagents comprising a first oligonucleotide moiety, a hydrophilic polymer moiety, and a second oligonucleotide moiety, as described in embodiments herein. FIG. 53A shows exemplary polar conjugation reactions. FIG. 53B shows exemplary polar, followed by cycloaddition conjugation reactions.

Figure 54A:
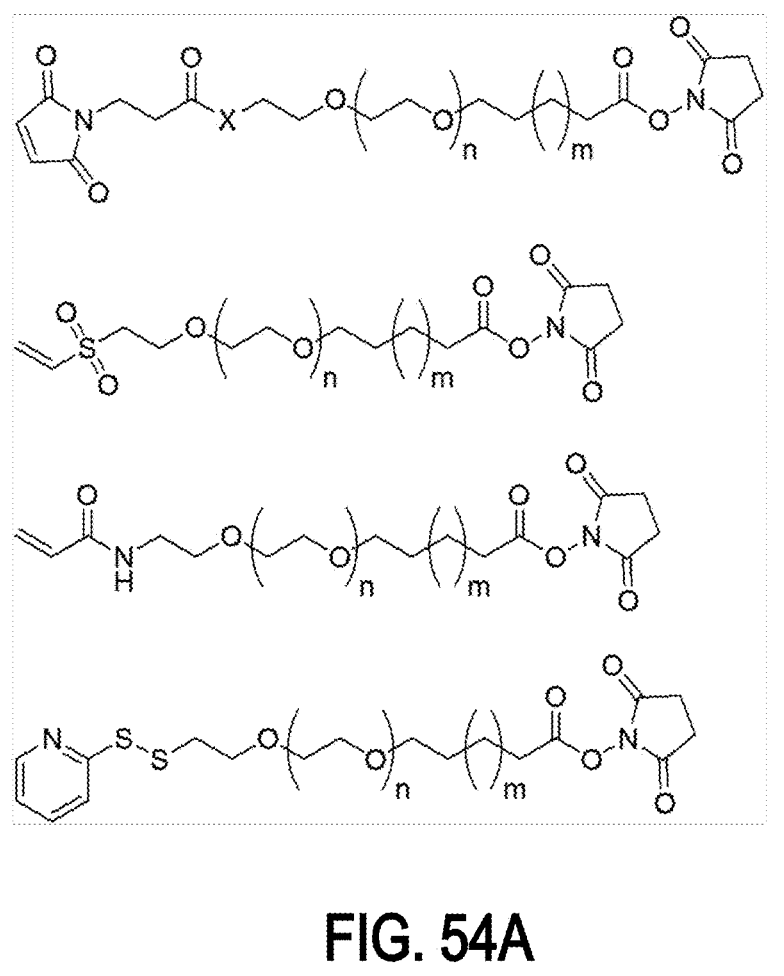
Figure 54B:
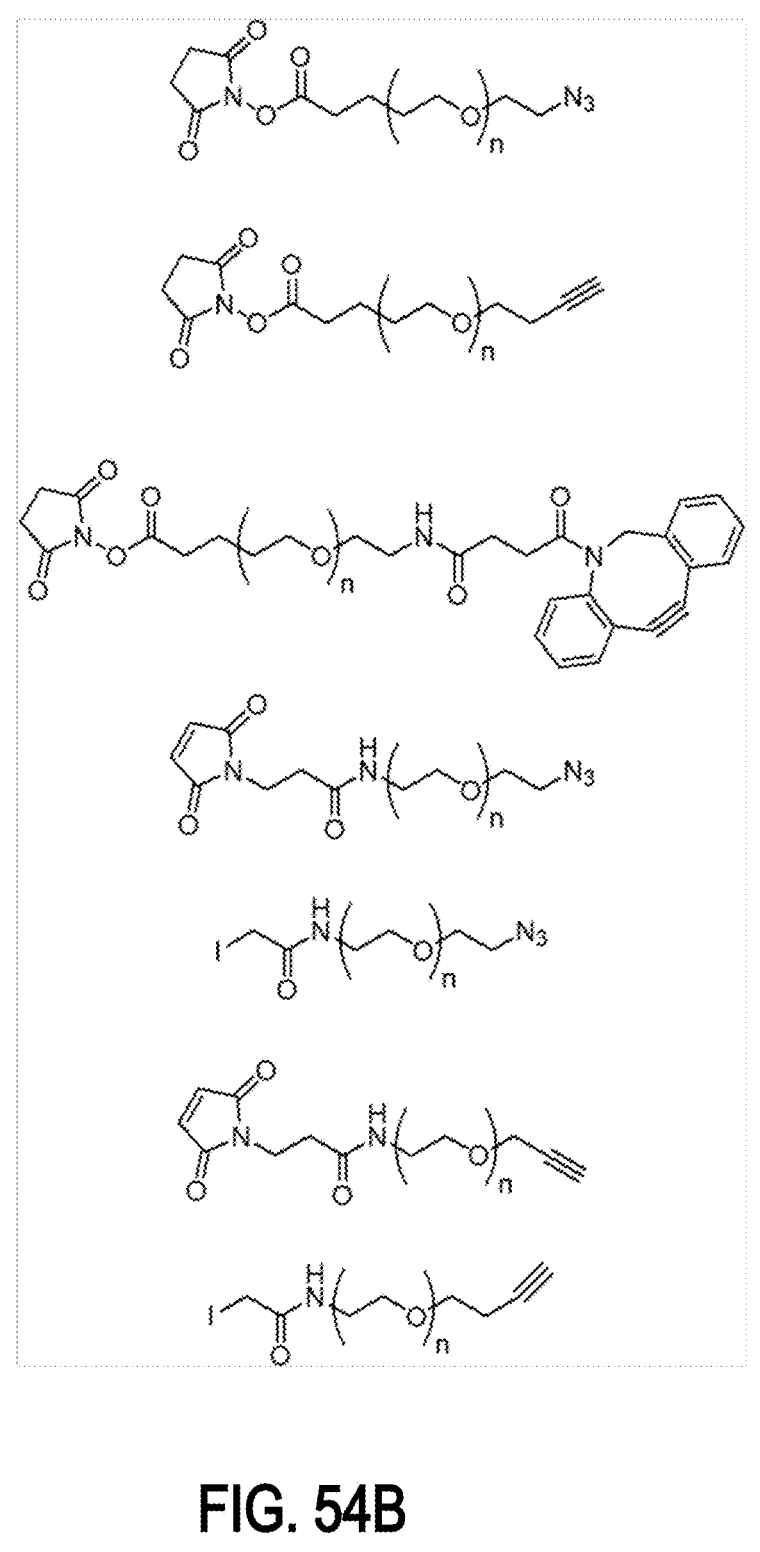

FIGS. 54A and 54B illustrate exemplary hydrophilic polymer moieties described in embodiments herein for use in polar conjugation reactions (FIG. 54A) and polar and cycloaddition conjugation reactions (FIG. 54B).

Figure 55:
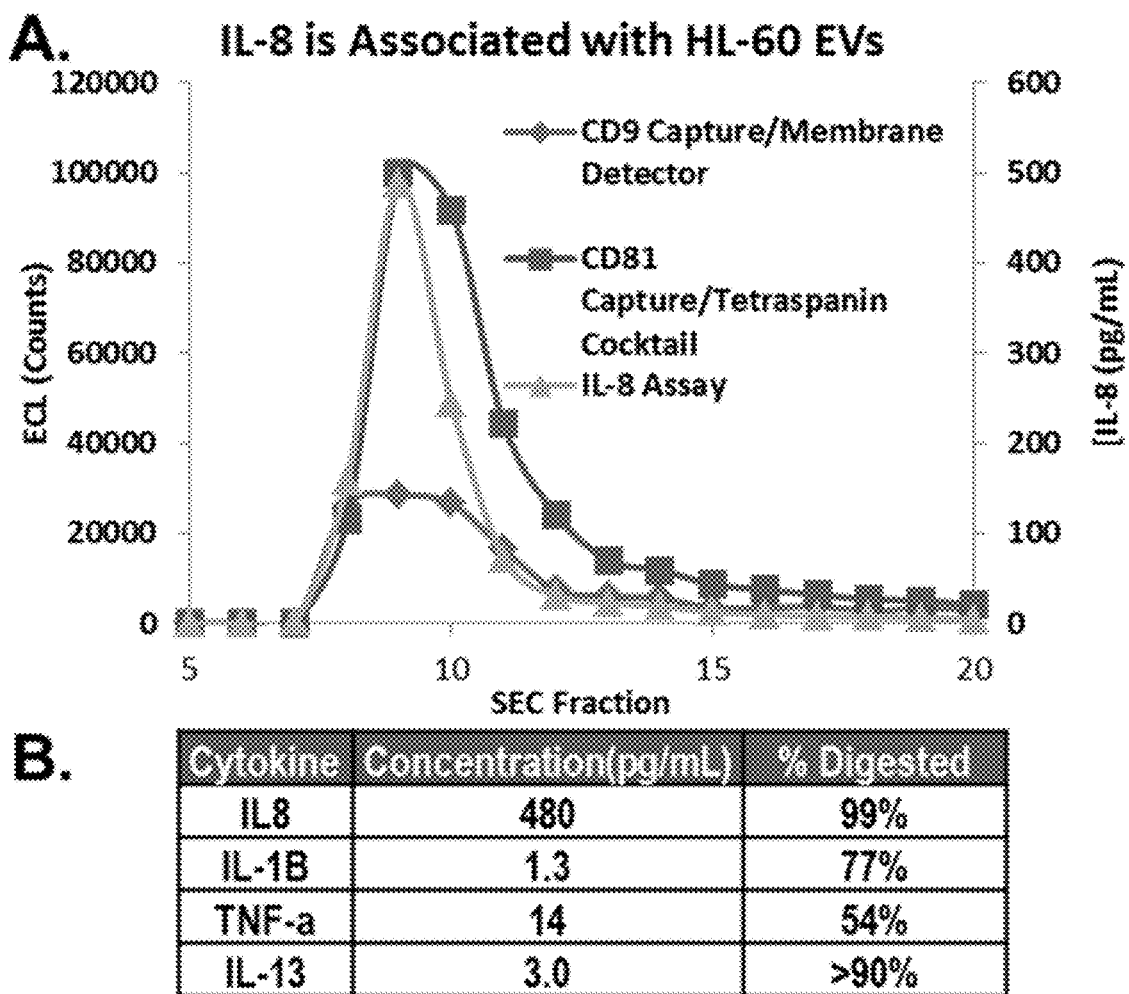

FIGS. 55A and 55B relate to Example 26. FIG. 55A shows an elution profile of EVs purified from stimulated HL-60 cells and subjected to size exclusion chromatography. FIG. 55B shows results of a trypsin digest of the fractions shown in FIG. 55A to determine the localization of the cytokines on cytokine associated EVs.

Figure 56:
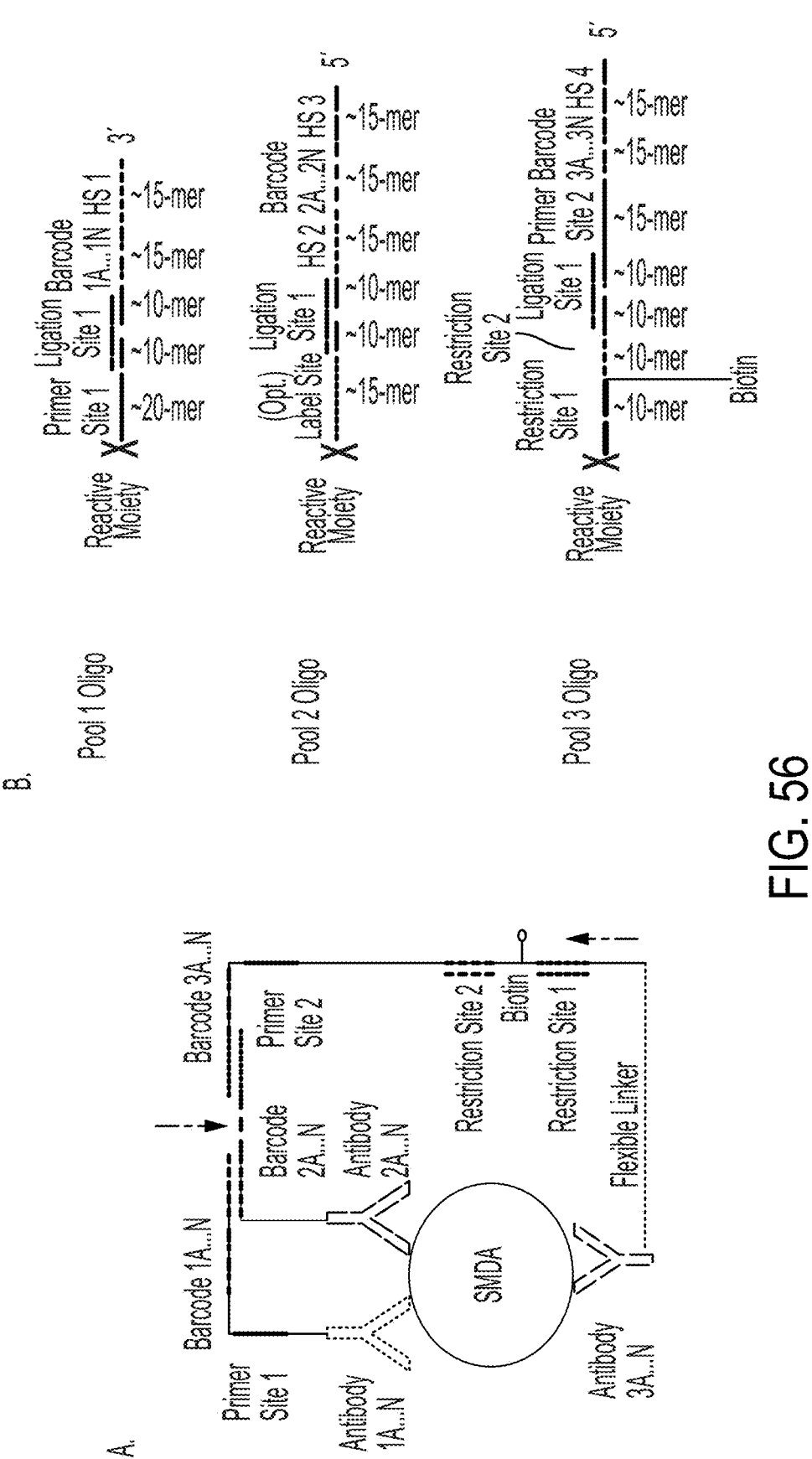
Figure 56:
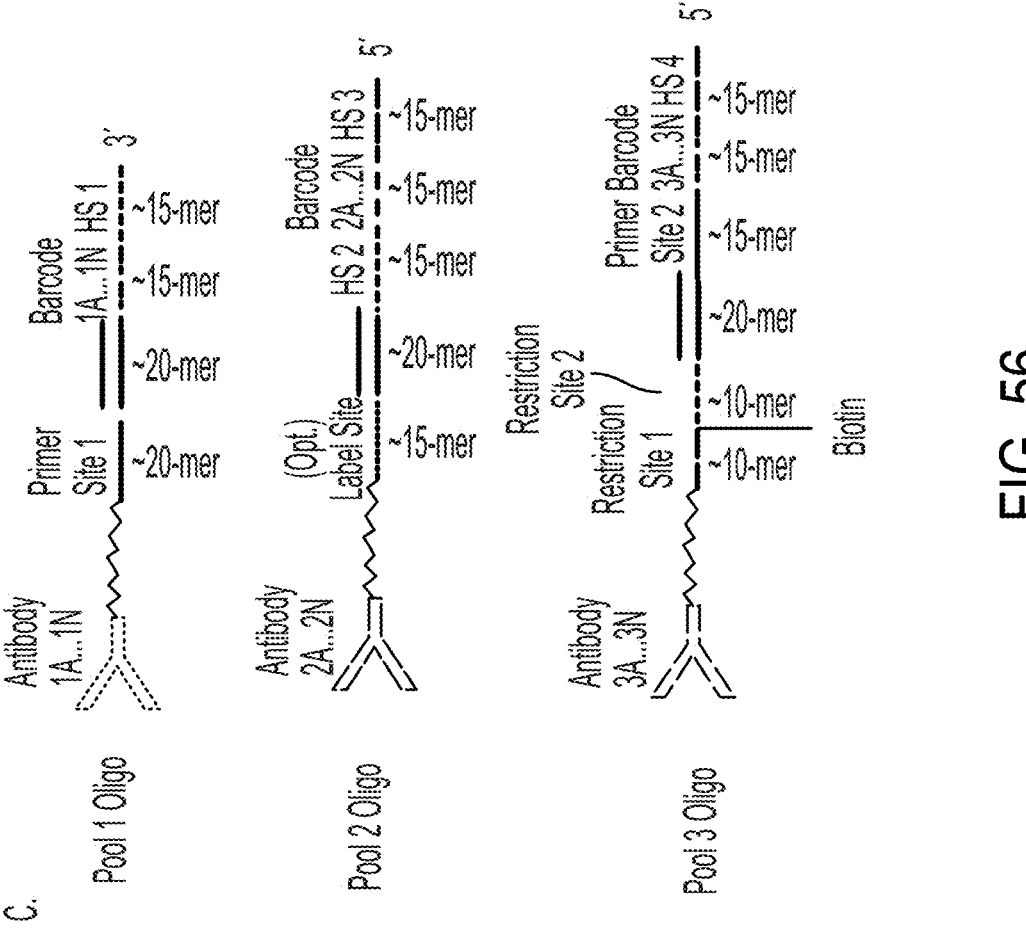

FIGS. 56A-56C illustrate example libraries for determining surface markers of a surface marker displaying agent as described in embodiments herein. FIG. 56A shows a surface marker displaying agent bound to three binding reagents (antibodies), each comprising oligonucleotides with a barcode sequence, to a surface marker displaying agent of interest. FIG. 56B shows a schematic of the various features, e.g., primer sites, ligation sites, barcode sequences, and hybridization sequences (HS), of an example oligonucleotide library. FIG. 56C shows a schematic of an example binding reagent library, wherein the binding reagents are conjugated to the oligonucleotides illustrated in FIG. 56B.

Figure 57:
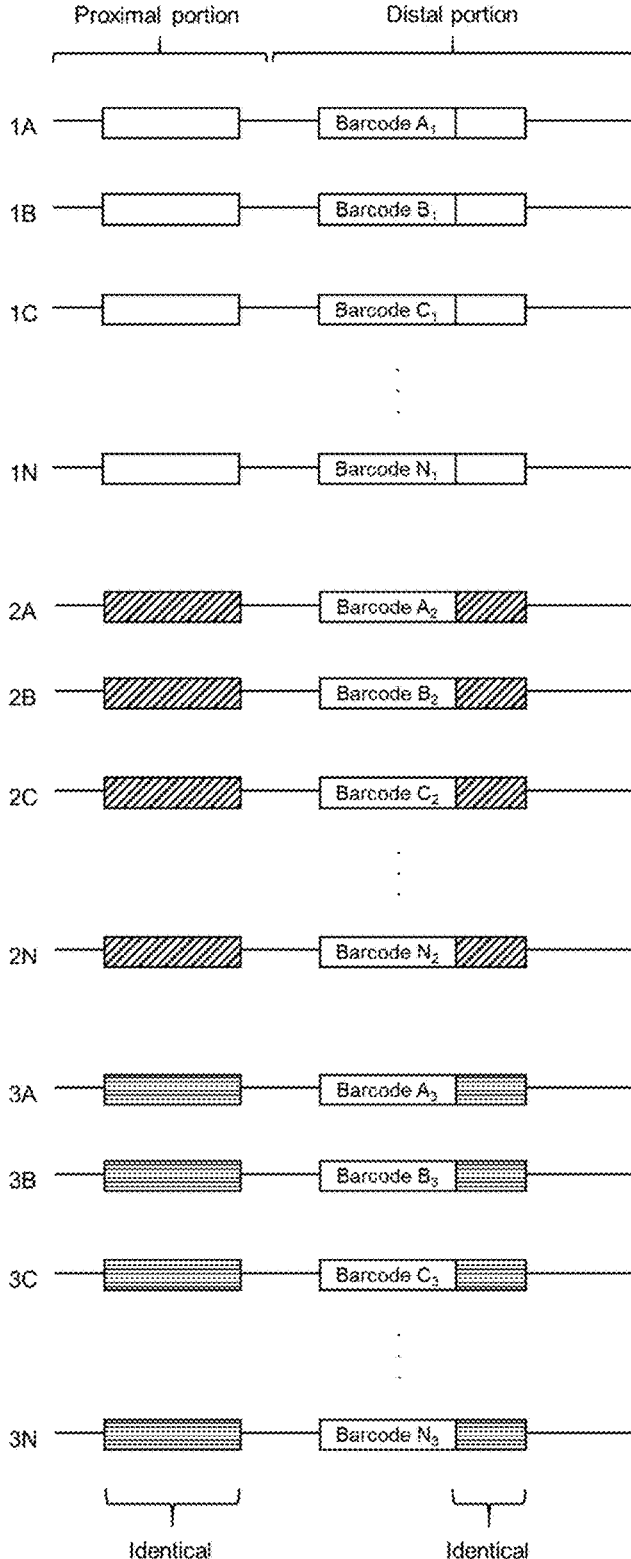

FIG. 57 shows a schematic of the various features of oligonucleotides attached to binding reagents in the binding reagent library, as described in embodiments herein. Each oligonucleotide includes a proximal portion and a distal portion, wherein all proximal portions corresponding to a same pool (denoted as the numbers 1, 2, 3, etc.) are identical, and wherein all distal portions comprise a barcode sequence for the unique binding reagent (denoted as letters A, B, C, etc.) to which the oligonucleotide is attached.

FIGS. 58A and 58B illustrate exemplary reaction schematics for preparing the library of binding reagents as described in embodiments herein. In FIG. 58A, a binding reagent is modified with a heterobifunctional cross-linking agent in Step 1a, then conjugated to an oligonucleotide in Step 1b without an intermediate purification step, and finally purified in Step 2. In FIG. 56B, binding reagent is modified with a heterobifunctional cross-linking agent in Step 1, then the modified binding reagent is purified in Step 2. The purified modified binding reagent is conjugated to the oligonucleotide in Step 3, and finally purified in Step 4. FIGS. 58C and 58D show exemplary reaction products of the reactions in FIGS. 58A and 58B. FIG. 58C shows the products from a reaction in which the limiting reagent is the heterobifunctional cross-linking agent. FIG. 58D shows the products from a reaction in which the limiting reagent is the oligonucleotide.

DETAILED DESCRIPTION OF THE INVENTION

I. Overview

The present disclosure provides methods of isolating and/or characterizing surface marker displaying agents. Surface marker displaying agents can be naturally-occurring, partially synthetic, or fully synthetic. In embodiments, a surface marker displaying agent is a biologically relevant material or component. In general, a surface marker displaying agent comprises a surface, typically a lipid bilayer, membrane, cell wall, or envelope, on which one or more markers are displayed. In embodiments, the surface marker displaying agent encapsulates components such as, e.g., proteins, nucleic acids, lipids, carbohydrates, small molecules such as hormones, cofactors, vitamins, minerals, salts, metals, metal-containing compounds, or combination thereof. Examples of surface marker displaying agents include cells (including prokaryotic cells such as bacterial cells or archaeal cells; eukaryotic cells such as mammalian cells, insect cells, or plant cells); viruses and viral particles; cellular organelles such as nucleus, endoplasmic reticulum, Golgi apparatus, mitochondria, vacuoles, or chloroplast; vesicles such as lysosome, endosome, peroxisome, and liposome; and extracellular vesicles (EVs) or exosomes. Although the present specification may refer to EVs in certain embodiments, the disclosure contemplates that such aspects also apply to any surface marker displaying agent provided herein without limitation.

A variety of analytical methods have been used to characterize EVs and their encapsulated contents (i.e., cargo) including, most commonly, immunoassays (Western blotting, flow cytometry, sandwich immunoassays), electron microscopy, mass spectrometry, PCR and sequencing, and nanoparticle tracking. One of the most significant limitations to characterizing EVs has been the difficulty of separating EVs from the other components in complex biofluids.

EV isolation, enrichment, and purification have been the subject of extensive discussion and publication yet there is still not one universally-accepted method. Ultracentrifugation, ultrafiltration, size-exclusion chromatography, and immuno-affinity based methods all have their strengths and shortcomings. Each must be applied in the appropriate situation with full recognition of the potential for introducing bias or allowing contamination by non-EV components of the sample. Analytical methods that avoid pre-purification steps are advantageous as they introduce no bias in the EV population subject to analysis; however, they have the highest risk of negative effects due to non-EV related molecular interactions and artifacts.

The inventors have discovered a surprisingly effective and highly specific method of isolating EVs of interest from samples. In embodiments, and by way of example, the method indirectly attaches an EV to a surface using at least two separate EV surface markers. In embodiments, first, an EV is indirectly attached to a surface using an EV surface marker, then a second indirect attachment point is formed by way of a second EV surface marker. In embodiments, following removal of unwanted components, the first indirect attachment point is broken, leaving the EV indirectly attached to the surface by only the second surface marker. In this way, EVs not having either surface marker, or EVs having only the first surface marker, are also released from the surface, leaving only EVs having both markers.

II. Methods

In embodiments, the invention provides a method of isolating a surface marker displaying agent of interest in a sample, comprising: (a). contacting the sample with a surface and selectively binding the surface marker displaying agent of interest to: (i) a capture reagent releasably bound to the surface, wherein the surface further comprises an anchoring reagent; and (ii) a binding reagent; (b). binding the anchoring reagent to the binding reagent, thereby forming a complex on the surface comprising the capture reagent, the surface marker displaying agent and the binding reagent; and (c). releasing the capture reagent from the surface and eluting unwanted components of the sample from the surface, thereby isolating the surface marker displaying agent of interest.

In embodiments, the surface marker displaying agent is a cell. In embodiments, the cell is a prokaryotic cell such as, e.g., a bacterial cell or an archaeal cell. In embodiments, the cell is a eukaryotic cell such as, e.g., a mammalian cell, an insect cell, or a plant cell. In embodiments, the cell is a human cell. In embodiments, the surface marker displaying agent is a virus or viral particle. In embodiments, the surface marker displaying agent is an organelle. In embodiments, the organelle is a nucleus, endoplasmic reticulum, Golgi apparatus, mitochondria, vacuoles, or chloroplast. In embodiments, the surface marker displaying agent is a vesicle. In embodiments, the vesicle is a lysosome, endosome, peroxisome, liposome, extracellular vesicle, or exosome. In embodiments, the surface marker displaying agent is an extracellular vesicle or exosome.

In embodiments, the invention provides a method of isolating an extracellular vesicle (EV) of interest in a sample, comprising: (a). contacting the sample with a surface and selectively binding the EV of interest to: (i) a capture reagent releasably bound to the surface, wherein the surface further comprises an anchoring reagent; and (ii) a binding reagent; (b). binding the anchoring reagent to the binding reagent, thereby forming a complex on the surface comprising the capture reagent, the EV and the binding reagent; and (c). releasing the capture reagent from the surface and eluting unwanted components of the sample from the surface, thereby isolating the EV of interest.

In embodiments, the anchoring reagent indirectly binds to the binding reagent. In embodiments, the anchoring reagent is releasably bound to the binding reagent. In embodiments, the intermolecular force by which the capture reagent is releasably bound to the surface is different than the intermolecular force by which the anchoring reagent is releasably bound to the binding reagent. Thus, in embodiments, releasing the capture reagent from the surface does not cause release of the anchoring reagent from the binding reagent, and vice versa.

In embodiments, the binding reagent comprises an antibody or antigen binding fragment thereof, antigen, ligand, receptor, oligonucleotide, hapten, epitope, mnimotope, or an aptamer. Thus, the binding reagent/anchoring reagent pairs comprise antibody or antigen binding fragment thereof/ antigen or epitope or hapten or mimotope, antigen/antibody or antigen binding fragment thereof, ligand/receptor, receptor/ligand, oligonucleotide/oligonucleotide, hapten/antibody or antigen binding fragment thereof, epitope/antibody or antigen binding fragment thereof, mimotope/antibody or antigen binding fragment thereof, or aptamer/target molecule. In embodiments, the binding reagent is an antibody comprising a primer oligonucleotide and the anchoring agent comprises an oligonucleotide. In embodiments, the binding reagent comprises streptavidin or biotin. In these embodiments, the anchoring reagent comprises biotin or streptavidin, respectively. Alternatively, both the binding reagent and the anchoring reagent comprise biotin, and streptavidin or avidin act as a bridging reagent for the two.

In embodiments, the anchoring reagent comprises an oligonucleotide, aptamer, aptamer ligand, antibody, antigen, ligand, receptor, hapten, epitope, or mimotope. Thus, the anchoring reagent/binding reagent pairs comprise an oligonucleotide/oligonucleotide, aptamer/aptamer ligand, aptamer ligand/aptamer, antibody/antigen or hapten or epitope or mimotope, antigen/antibody or antigen binding fragment thereof, ligand/receptor, receptor/ligand, hapten/ antibody or antigen binding fragment thereof, epitope/antibody or antigen binding fragment thereof, or mimotope/ antibody or antigen binding fragment thereof. In embodiments, the anchoring reagent comprises an oligonucleotide and the binding reagent comprises an oligonucleotide. In embodiments, the anchoring reagent comprises streptavidin or biotin. In these embodiments, the binding reagent comprises biotin or streptavidin, respectively. Alternatively, both the binding reagent and the anchoring reagent comprise biotin, and streptavidin or avidin act as a bridging reagent for the two.

Thus, in embodiments, the anchoring reagent is directly or indirectly bound to the surface. In embodiments, the anchoring reagent is releasably or unreleasably bound to the surface.

In further embodiments, the binding reagent comprises an antibody or antigen binding fragment thereof comprising a primer oligonucleotide that generates an amplicon, and the anchoring reagent comprises an oligonucleotide sequence complementary to the amplicon. In embodiments, the binding reagent comprises streptavidin and the anchoring reagent comprises biotin. In embodiments, the binding reagent comprises biotin and the anchoring reagent comprises streptavidin. Alternatively, both the binding reagent and the anchoring reagent comprise biotin, and streptavidin or avidin act as a bridging reagent for the two.

In additional embodiments, the invention provides a method of isolating a surface marker displaying agent of interest in a sample, comprising: (a). contacting the sample with a surface and selectively binding the surface marker displaying agent of interest to: (i) a capture reagent releasably bound to the surface, wherein the surface further comprises an anchoring oligonucleotide; and (ii) a binding reagent, wherein the binding reagent comprises a primer oligonucleotide, thereby forming a complex on the surface comprising the capture reagent, the surface marker displaying agent and the binding reagent; (b). binding a circular oligonucleotide template to the primer oligonucleotide to form an amplicon by rolling circle amplification, wherein the amplicon comprises a sequence that is complementary to the anchoring oligonucleotide; (c). hybridizing the anchoring oligonucleotide to the amplicon to form a second complex on the surface comprising the capture reagent, the surface marker displaying agent, the binding reagent and the anchoring oligonucleotide; and (d). releasing the capture reagent from the surface and eluting unwanted components of the sample from the surface, thereby isolating the surface marker displaying agent of interest.

In additional embodiments, the invention provides a method of isolating a surface marker displaying agent of interest in a sample, comprising: (a). contacting the sample with a surface and selectively binding the surface marker displaying agent of interest to: (i) a capture reagent releasably bound to the surface, wherein the surface further comprises an anchoring oligonucleotide; and (ii) a binding reagent, wherein the binding reagent comprises a primer oligonucleotide, thereby forming a complex on the surface comprising the capture reagent, the surface marker displaying agent and the binding reagent; (b). binding a circular oligonucleotide template to the primer oligonucleotide to form an amplicon by rolling circle amplification, wherein the amplicon comprises a sequence that is complementary to the anchoring oligonucleotide; (c). hybridizing the anchoring oligonucleotide to the amplicon to form a second complex on the surface comprising the capture reagent, the surface marker displaying agent, the binding reagent and the anchoring oligonucleotide; and (d). releasing the capture reagent from the surface and eluting unwanted components of the sample from the surface, thereby isolating the surface marker displaying agent of interest.

In embodiments, the invention further provides a method of isolating a surface marker displaying agent of interest in a sample, comprising: (a). contacting the sample with a surface and selectively binding the surface marker displaying agent of interest to: (i) a capture reagent releasably bound to the surface, wherein the surface further comprises an anchoring oligonucleotide; and (ii) a binding reagent, wherein the binding reagent comprises a tag oligonucleotide, thereby forming a complex on the surface comprising the capture reagent, the surface marker displaying agent and the binding reagent; (b). hybridizing a linker oligonucleotide to the tag oligonucleotide and to the anchoring oligonucleotide to form a second complex on the surface comprising the capture reagent, the surface marker displaying agent, the binding reagent and the anchoring oligonucleotide; and (c). releasing the capture reagent from the surface and eluting unwanted components of the sample from the surface, thereby isolating the surface marker displaying agent of interest.

In embodiments, the unwanted components include surface marker displaying agents that bind to the capture reagent, but not the binding reagent. In the methods of the invention, surface marker displaying agents that bind to the capture reagent, but not the binding reagent, will be eluted following releasing the capture reagent from the surface. In embodiments, the surface marker displaying agent is a cell. In embodiments, the surface marker displaying agent is a virus or viral particle. In embodiments, the surface marker displaying agent is an organelle. In embodiments, the surface marker displaying agent is a vesicle. In embodiments, the surface marker displaying agent is an extracellular vesicle or exosome.

In additional embodiments, the invention provides a method of isolating an extracellular vesicle (EV) of interest in a sample, comprising: (a). contacting the sample with a surface and selectively binding the EV of interest to: (i) a capture reagent releasably bound to the surface, wherein the surface further comprises an anchoring oligonucleotide; and (ii) a binding reagent, wherein the binding reagent comprises a primer oligonucleotide, thereby forming a complex on the surface comprising the capture reagent, the EV and the binding reagent; (b). binding a circular oligonucleotide template to the primer oligonucleotide to form an amplicon by rolling circle amplification, wherein the amplicon comprises a sequence that is complementary to the anchoring oligonucleotide; (c). hybridizing the anchoring oligonucleotide to the amplicon to form a second complex on the surface comprising the capture reagent, the EV, the binding reagent and the anchoring oligonucleotide; and (d). releasing the capture reagent from the surface and eluting unwanted components of the sample from the surface, thereby isolating the EV of interest.

In embodiments, the methods provided herein are generally applicable to isolation of any surface marker displaying agent of interest. In embodiments, the methods provided herein are also generally applicable to isolation of any EV of interest, such as tissue or organ or cell-type specific EVs. In embodiments, the methods use a high throughput 96-well plate format using a single immunoaffinity capture step, followed by a process termed "stapling" or, in the case of EVs, "EV-stapling." In embodiments, the methods use particles, e.g., beads, as a solid phase, followed by stapling. This process uses specific recognition of one or multiple oligo-labeled detection antibodies to template the formation of a ssDNA amplicon that tethers surface marker displaying agents, e.g., EVs, to the surface through formation of multiple identical dsDNA duplexes, termed "staples." Those surface marker displaying agents, e.g., EVs, that were not stapled can then be removed from the surface, thus selectively enriching the surface marker displaying agents, e.g., EVs, of interest.

Figures 1A, 1B:
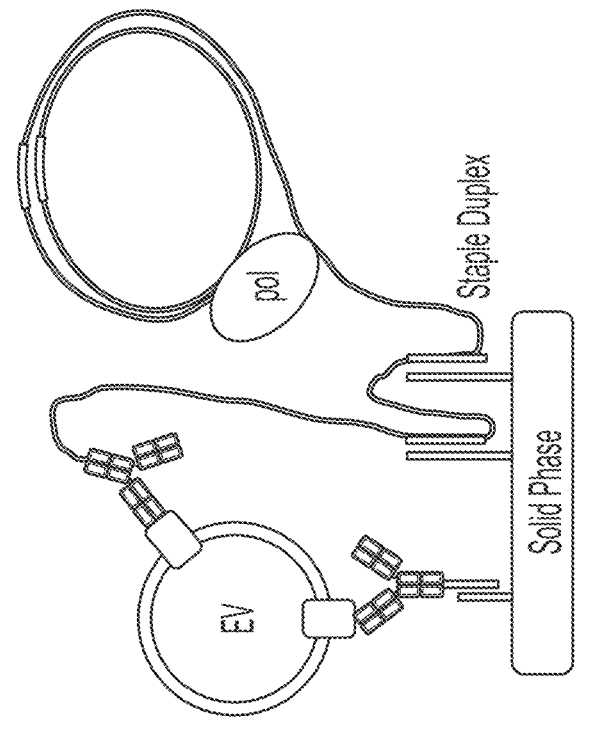

A schematic representation of the "EV-stapling" process is depicted in FIGS. 1A-1C. FIG. 1E shows schematically how this approach uses three markers with the introduction of a ligation site in the circular oligo template and a third antibody conjugated to a splint oligo, akin to the 3-marker assays shown in FIG. 2. In embodiments, four or more antibodies are used, using additional ligation sites and splint-labeled antibodies. Once the non-stapled EVs are removed, in embodiments, the stapled EVs are assayed in situ using an ECL labeled detector antibody. In embodiments, then they are either lysed to assess their cargo, or they may be eluted intact for further off-line characterization.

In summary, the methods provided herein provide high-throughput isolation of very specific populations of surface marker displaying agents, e.g., EVs, from large numbers of samples in parallel, in situ assessment of the surface marker displaying agents, e.g., EVs, isolated from each sample, and compatibility with most downstream analytical techniques.

Isolating specific EVs, such as CNS derived EVs, is important to both understanding the intercellular trafficking of pathogenic proteins via EVs and in identifying highly specific biomarkers of pathogenesis in neurodegenerative diseases. While most existing isolation techniques are difficult to scale to very large sample numbers, particularly those that require centrifugation or chromatography, the methods provided by the invention, in embodiments, are inherently scalable and amenable to automation.

In embodiments, the method of the invention comprises binding the EV to two to ten binding reagents, wherein one binding reagent comprises a primer oligonucleotide, wherein the primer oligonucleotide binds to a circular oligonucleotide template and wherein the remainder of the binding reagents comprise splint oligonucleotides required to assemble the circular template.

Figure 3:
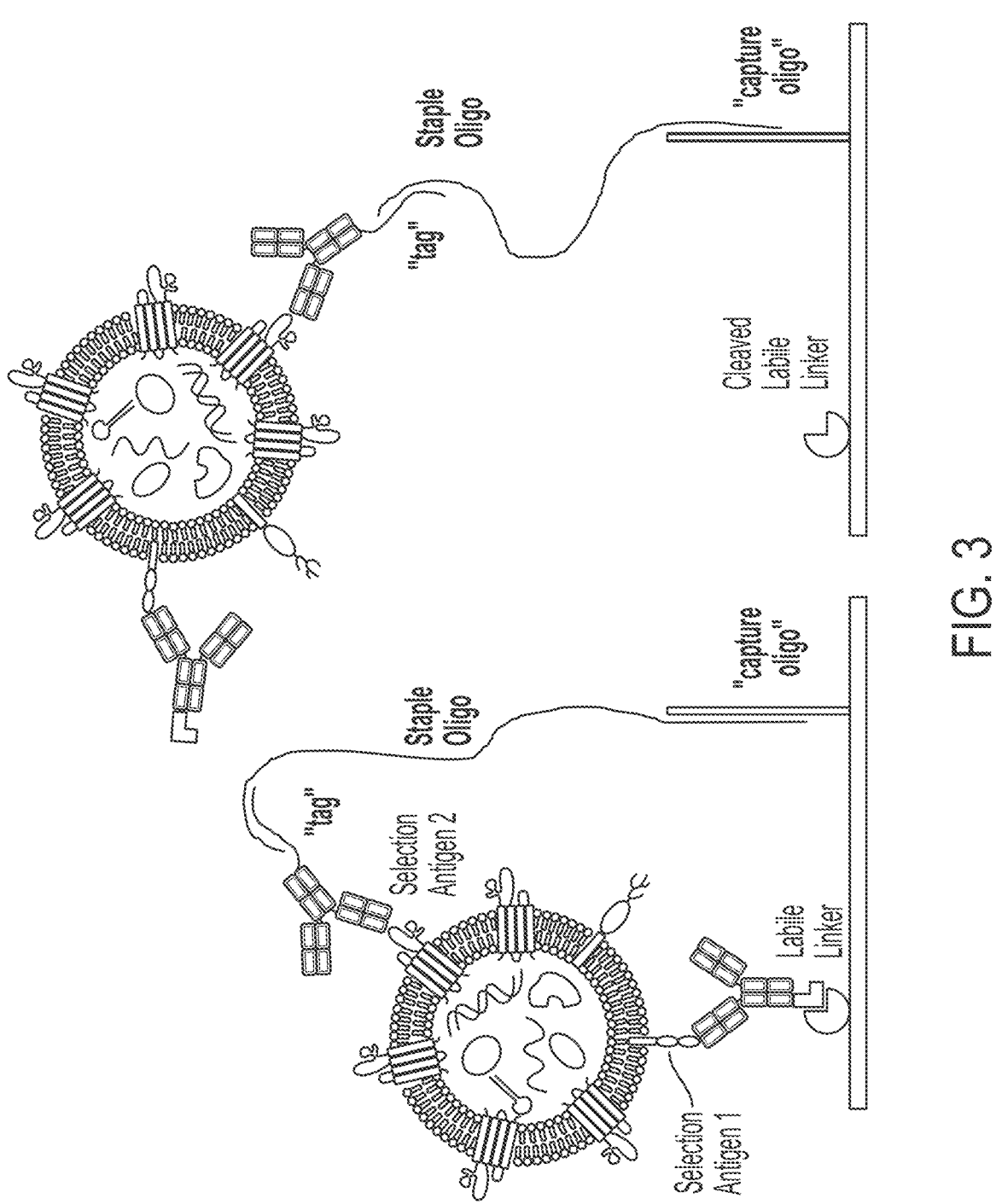
FIG. 3 is a schematic of an example where captured EVs are tethered to surface with a "staple" (linker) oligonucleotide.

In embodiments, the invention further provides a method of isolating an extracellular vesicle (EV) of interest in a sample, comprising: (a). contacting the sample with a surface and selectively binding the EV of interest to: (i) a capture reagent releasably bound to the surface, wherein the surface further comprises an anchoring oligonucleotide; and (ii) a binding reagent, wherein the binding reagent comprises a tag oligonucleotide, thereby forming a complex on the surface comprising the capture reagent, the EV and the binding reagent; (b). hybridizing a linker oligonucleotide to the tag oligonucleotide and to the anchoring oligonucleotide to form a second complex on the surface comprising the capture reagent, the EV, the binding reagent and the anchoring oligonucleotide; and (c). releasing the capture reagent from the surface and eluting unwanted components of the sample from the surface, thereby isolating the EV of interest. This embodiment of the method is exemplified in FIG. 3.

As used herein, the term "isolating" a surface marker displaying agent of interest means to have no more than 5% by weight of any other non-surface marker displaying agents (i.e., unwanted components), and preferably no more than 4%, 3%, 2% or 1% by weight of unwanted components, or preferably no more than 0.8%, 0.6%, 0.4%, 0.2% or 0.1% or less by weight of the unwanted component. In the context of EVs, the term "isolating" an EV of interest means to have no more than 5% by weight of any other non-EV components (i.e., unwanted components), and preferably no more than 4%, 3%, 2% or 1% by weight of unwanted components, or preferably no more than 0.8%, 0.6%, 0.4%, 0.2% or 0.1% or less by weight of the unwanted component. The term "isolating" also encompasses amounts of unwanted components that are undetectable by current methods for detecting such components. As used herein, the term "isolating" is synonymous with enriching and purifying.

Surface Marker Displaying Agents of Interest

Surface marker displaying agents include naturally occurring, partially synthetic, or fully synthetic agents. In embodiments, the surface marker displaying agent is a biologically relevant material or component. In general, a surface marker displaying agent comprises a surface, typically a lipid bilayer, membrane, cell wall, or envelope, on which one or more markers are displayed.

In embodiments, the surface marker displaying agent encapsulates components such as, e.g., proteins, nucleic acids, lipids, carbohydrates, small molecules such as hormones, cofactors, vitamins, minerals, salts, metals, metal-containing compounds, or combination thereof. Examples of surface marker displaying agents include cells (including prokaryotic cells, such as bacterial cells or archaeal cells; eukaryotic cells such as mammalian cells, insect cells, or plant cells); viruses and viral particles; cellular organelles such as nucleus, endoplasmic reticulum, Golgi apparatus, mitochondria, vacuoles, or chloroplast; vesicles such as lysosome, endosome, peroxisome, and liposome; and extracellular vesicles (EVs) or exosomes.

In embodiments, the methods provided herein enable capture of a surface marker displaying agent of interest from a sample, wherein the surface marker displaying agent of interest includes a unique co-localization of surface markers. In embodiments, certain markers can exclude unwanted populations of surface marker displaying agents (e.g., use of a mammalian cell-specific marker to exclude non-mammalian cells).

In embodiments, the surface marker displaying agent is a cell, and the methods provided herein enable isolation and/or characterization of a cell of interest in a population of cells. In embodiments, the cell is a bacterial cell. In embodiments, the cell is an archaeal cell. In embodiments, the cell is a eukaryotic cell. In embodiments, the cell is a mammalian cell. In embodiments, the cell is an animal cell. In embodiments, the cell is a human cell. In embodiments, the cell is an insect cell. In embodiments, the cell is a plant cell. In embodiments, the cell is a yeast cell. In embodiments, the cell is a variant of a particular cell type. For example, the methods provided herein can be used to isolate abnormal cells, e.g., a cancer cell, from a sample of tissue or bodily fluid, for example, blood (e.g., comprising a mixture of cancer and non-cancer cells). In another example, the methods provided herein can be used to isolate a specific type of bacteria from a mixed bacterial sample, e.g., an environmental sample.

In embodiments, the methods provided herein enable identification of populations of cells in a sample. In embodiments, a large number of detection reagents for different surface markers can be screened in a single panel to determine all combinations of the surface markers present on the cells. In one example, a single panel can include antibodies to a selected number of CD markers, each antibody conjugated with a unique oligonucleotide as described herein. In embodiments, a single panel includes antibodies to all 350 CD markers. The unique oligonucleotides can be ligated upon formation of a complex between the cell of interest and the antibodies for the desired number of surface markers (e.g., three surface markers). The ligated oligonucleotides can then be sequenced to identify all cells having the three surface markers. Compared with conventional methods of cell isolation and identification using surface markers that rely upon a fluorescence or colorimetric output such as, e.g., flow cytometry, the present methods provide higher efficiency, e.g., by reducing processing and increasing throughput.

In embodiments, the surface marker displaying agent is a virus or viral particle, and the methods provided herein enable isolation and/or characterization of a particular type of virus or viral particle. The present methods may facilitate the study of viruses or viral particles, as traditional methods (for example, flow cell-based methods) may not be able to accurately distinguish between different small viruses or viral particles.

In embodiments, the surface marker displaying agent is a cellular organelle, and the methods provided herein enable isolation and/or characterization of an organelle of interest from a sample. Organelle isolation typically involves multiple rounds of subcellular fractionation and screening. The present methods may advantageously isolate an organelle of interest by using one or more surface markers unique to the organelle of interest. For example, TGN38 is a marker unique to the Golgi; VDAC1 is a marker unique to the mitochondria; cytochrome c reductase is a marker unique to the endoplasmic reticulum; and NUP98 is a marker unique to the nucleus.

In embodiments, the surface marker displaying agent is a vesicle, and the methods provided herein enable isolation and/or characterization of a vesicle of interest from a sample. In embodiments, the vesicle is a lysosome, an endosome, or a peroxisome. Examples of lysosome-specific markers include, e.g., LAMP1, LC3, and ATG5. Examples of endosome-specific markers include, e.g., EEA1, Rab5, Rab7, and palladin. An example of a peroxisome-specific marker is catalase. In embodiments, the vesicle is a liposome. Liposomes can be artificial vesicles that include engineered surface markers.

In embodiments, the vesicle is an extracellular vesicle (EV) or an exosome. EVs are described herein.

In embodiments, the surface marker displaying agent comprises a surface-associated marker. Unlike surface markers, surface-associated markers are generally not integrally expressed on the surface of a surface marker displaying agent, but may be covalently or non-covalently bound to one or more surface markers and/or structural components of the surface. In embodiments, the surface-associated marker is associated with the membrane of a surface marker displaying agent. In embodiments, the surface-associated marker is associated with a transmembrane protein of a surface marker displaying agent. In embodiments, the surface-associated marker is a surface receptor. In embodiments, the surface marker displaying agent is a cell. In embodiments, the surface marker displaying agent is an EV.

Extracellular Vesicles of Interest

EVs released from a variety of cells target recipient cells for intercellular communication and transfer a subset of genetic materials, proteins, lipids, and metabolites. EVs include a broad spectrum of vesicles secreted by several types of cells and the term is used as a collective one. These include exosomes, ectosomes, oncosomes, shed vesicles, microvesicles, and apoptotic bodies. Thus, EVs represent a broad spectrum of vesicles secreted by several types of cells. Major groups include exosomes (endosomal origin, 40-200 nm), microvesicles/ectosomes (plasma membrane origin, 100-1000 nm) and larger particles such as large-oncosomes (tumor cell origin, >1 um). The exact definition and nomenclature for each of these general vesicles classes has yet to be fully codified by the field due to their heterogeneous nature, herein, the term "EVs" is as defined by the International Society of Extracellular Vesicles (see Gardiner et al., Journal of Extracellular Vesicles 5(1):32945 (2016).

The isolation and assay methods provided herein enable capture of EVs of interest from the sample, wherein the EVs bear a unique co-localization of surface markers. In embodiments, certain markers can exclude certain unwanted populations of EVs (e.g., use of CD81 as detection marker to exclude platelet derived vesicles). In embodiments, some of the cell-type specific surface markers select EVs of particular origin (i.e. exosomes or ectosomes/microvesicles). In embodiments, the isolation methods exclude very large EVs, apoptotic bodies and cell debris from cell culture supernatants using common techniques like differential centrifugation, ultrafiltration and size-exclusion chromatography but do not otherwise distinguish between small EVs of various origin.

While EVs secreted by neurons and various glial populations have been studied in vitro, isolating populations of EVs from biofluids remains elusive because no method of discriminating these cell-specific EVs has yet been developed. This invention provides methods of isolating populations based on the fact that combinations of surface markers define EVs secreted by specific cells such as CNS cells. The methods described herein thus take advantage of the fact that most proteins that are highly expressed on the surface of a particular cell line are also present on the surface of the EVs secreted in cultures of those cells. EVs of interest include cells of the CNS, such as neurons and astrocytes.

In embodiments, the EV of interest is secreted from a cell of the central nervous system (CNS). In embodiments, the cell of the CNS is a neuron, an astrocyte, an oligodendrocyte or microglia.

In embodiments, the EV comprises a surface marker that is common to EVs. In embodiments, the first marker is common to EVs. In further embodiments, the marker common to EVs is a tetraspanin. Exemplary tetraspanins include CD9, CD37, CD63, CD 81, and CD82. In embodiments, a surface marker common to EVs is CD9, CD11a, CD18, CD26, CD29, CD35, CD45, CD46, CD47, CD48, CD50, CD51, CD55, CD63, CD71, CD73, CD81, CD82, CD95, CD104, CD151, CD276, or CD317.

In embodiments, the EV comprises a surface marker that is a surface adhesion protein. Exemplary surface adhesion proteins include, but are not limited to, EpCAM, E-Cadherin, N-cadherin, P-Cadherin, E-selectin, P-selectin, L1CAM, VE-cadherin, ITGB1, MCAM, ICAM-3, ITBG1, MCAM, ALCAM, NCAM1, Nectin-4, PECAM and ICAM-1. In embodiments, the EV comprises a surface marker that is a surface receptor. Exemplary surface receptors include, but are not limited to, EGFR, EphA2, TFRC, FasR, TNFR1, TNFR2, SCFR/Kit, FASR, IL-6R, FLT-1, MET, CXCR4, CXCR5, CCR2, EPCR, and VEGFR2. In embodiments, the EV comprises a surface marker that is an endothelial marker. Exemplary endothelial markers include, but are not limited to, CD146, PECAM, CD276, TEM7, TEM8, thrombomodulin, endoglin, PSGL-1, VE-cadherin, E-selectin, ICAM-1, and ICAM-3. In embodiments, the EV comprises a surface marker that is a tumor antigen. Exemplary tumor antigens include, but are not limited to, CEA, CA19.9, CA50, CA125, CA15.3, mesothelin, cytokeratin-8, E-cadherin, EGFR, EpCAM, EphA2, NCAM, P-cadherin, cMET, Flt-3L, TNFR-2, cKit, ErbB2, FAP-a, and ANXA1. In embodiments, the tumor antigen markers are pancreatic cancer markers. In embodiments, the EV comprises a surface marker that is a platelet EV marker. Exemplary platelet EV markers proteins include, but are not limited to, P-selectin, PECAM, CD63 and CD9.

In embodiments of the invention, at least one of EV surface markers is a central nervous system (CNS) cell marker. In additional embodiments, the EV surface marker is specific to a neuron, an astrocyte, an oligodendrocyte or a microglia. In embodiments, the EV surface marker is specific to a neuron. In embodiments, the EV surface marker specific to a neuron is L1CAM, NCAM, NRCAM, CHL1, Glu-R2, neurofascin, DAT1, CD90, CD24, N-cadherin, PSA-NCAM or synaptophysin. In embodiments, the neuron is a dopaminergic neuron, a GABAergic neuron, a cholinergic neuron, a serotonergic neuron or a glutamatergic neuron.

In embodiments, the EV surface marker is specific to an astrocyte. In embodiments, the surface marker specific to an astrocyte is ALDH1L1, GLT-1, GLAST, CD184, CD44, A2B5, aquaporin-4, ATP1B2 (ASCA-2), ceruloplasmin, CD80 or CD86. In embodiments, the EV surface marker is specific to an oligodendrocyte. In embodiments, the surface marker specific to an oligodendrocyte is O4, PDGFRa, CSPG4, GD3, MOG, or MBP. In embodiments, the EV surface marker is specific to a microglia. In embodiments, the microglia surface marker is Tmem119, CD11bF4/80, CD68, P2RY12, CXC3R1. In embodiments, the EV surface marker is a disease-specific biomarker.

In embodiments, the EV surface marker is specific to astrocytes and neurons. In embodiments, the surface marker specific to astrocytes and neurons is ALCAM CD166, CD40, FGFR3, GJA1 (connexin 43), integrin B1 (CD29), or CD24. In embodiments, the surface marker specific to neurons is CD 11, CD56, CD90, CD166, CD171, CD271, or CD325. In embodiments, the surface marker specific to astrocytes is A2B5, ASCA, GJA1, or GLAST-1.

In embodiments, the EV surface marker is specific to a T cell, a B cell, a dendritic cell, an NK cell, a monocyte, a macrophage, a granulocyte, a platelet, an erythrocyte, an endothelial cell, an epithelial cell, a stem cell precursor cell, a mesenchymal stem cell, a hematopoietic stem cell, a leukocyte, a T lymphocyte, or a B lymphocyte. T cells include, e.g., helper T cells, such as the subtypes Th1, Th2, Th9, Th17, Th22, and Tfh; regulatory T cells; killer T cells; γδ TCR+ T cells; and natural killer T cells.

In embodiments, the EV surface marker is specific to a T cell, a helper T cell, a regulatory T cell, a killer T cell, a γδ TCR+ T cell, or a natural killer T cell. In embodiments, the surface marker specific to a T cell is CD2, CD3, CD4, CD5, CD6, CD8, CD9, CD25, CD28, CD30, CD37, CD38, CD44, CD49b, CD52, CD53, CD56, CD57, CD62L, CD69, CD70, CD103, CD152, CD154, CD162, CD166, CD178, CD181, CD182, CD183, CD223, CD272, CD278, CD314, or CD366. In embodiments, the surface marker specific to a helper T cell is CD5, CD6, CD45, CD62L, CD197(CCR7), or a/b TCR. In embodiments, the surface marker specific to a helper T cell subtype Th1 is CD183(CXCR3), CD119 (IFNy Ra), CD195 (CCR5), CD218a(IL-18Ra), LT-BR, or CD336 (TIM-3). In embodiments, the surface marker specific to a helper T cell subtype Th2 is CD194(CCR4), Crth2, CDwl98(CCR8), CRTH2, IL33-Ra, or CD365(TIM-1). In embodiments, the surface marker specific to a helper T cell subtype Th17 is CD196(CCR6), CD161, or IL-23R. In embodiments, the surface marker specific to a helper T cell subtype Th22 is CCR10. In embodiments, the surface marker specific to a helper T cell subtype Tfh is CD185 (CXCR5), CD84, CD126(IL-6Ra), CD150, CD154, CD252 (OX40L), CD278(ICOS), or CD279(PD1). In embodiments, the surface marker specific to a regulatory T cell is CD25, CD39, CD73, CD103, CD152(CTLA-4), GARP, or GITR. In embodiments, the surface marker specific to a killer T cell is CD8. In embodiments, the surface marker specific to a γδ TCR+ T cell is γδ TCR. In embodiments, the surface marker specific to a natural killer T cell is CD56 (NCAM), CD11b, CD11c, CD16, CD32, CD49b, CD57, CD69, CD94, CD122, CD158, CD161 (NK1.1), CD244, CD314, CD319, CD328, CD355, Ly49, Ly108, or Va24-J18 TCR.

In embodiments, the EV surface marker is specific to a B cell. In embodiments, the surface marker specific to the B cell is CD10, CD19, CD20, CD5, CD9, CDIIa, CD18, CD21, CD23, CD24, CD25, CD26, CD27, CD29, CD30, CD31, CD37, CD38, CD40, CD44, CD45, CD49b, CD49c, CD49d, CD50, CD52, CD53, CD54, CD57, CD58, CD62L, CD70, CD72 CD73, CD79a, CD80, CD95, CD102, CD119, CD120a, CD120b, CD124, CD138, CD166, CD223, CD267, CD269, or CD319.

In embodiments, the EV surface marker is specific to a neutrophil. In embodiments, the surface marker specific to the neutrophil is CD11b, CD11c, CD15, CD16b, CD37, CD44, CD53, CD66b, CD87, CD114, CD116, CD162, CD172, CD181, or CD182.

In embodiments, the EV surface marker is specific to a dendritic cell. In embodiments, the surface marker specific to the dendritic cell is CDIa, CD11c, CD23, CD33, CD40, CD45, CD49d, CD49e, CD52, CD53, CD58, CD73, CD80, CD83, CD115, CD120a, CD120b, CD123, CD201, CD207, CD208, CD209, CD223, or CD271.

In embodiments, the EV surface marker is specific to a NK cell. In embodiments, the surface marker specific to the NK cell is CDIIa, CD11b, CD11c, CD16a, CD18, CD25, CD26, CD29, CD31, CD38, CD45, CD49b, CD49d, CD49e, CD50, CD53, CD56, CD57, CD58, CD59, CD62L, CD69, CD94, CD95, CD96, CD119, CD120a, CD120b, CD178, CD183, CD223, or CD314.

In embodiments, the EV surface marker is specific to a monocyte or a macrophage. In embodiments, the surface marker specific to the monocyte or macrophage is CD4, CD9, CD11a, CD11b (integrin a-M), CD11c, CD13, CD14, CD15, CD16, CD16a, CD18, CD23, CD26, CD29, CD31, CD33, CD36, CD37, CD38, CD40, CD44, CD45, CD49a, CD49b, CD49c, CD49e, CD49f, CD50 (ICAM-3), CD51, CD52, CD53, CD54, CD57, CD58, CD59, CD61, CD62L, CD63, CD64, CD68, CD80, CD86, CD87, CD95, CD102, CD105, CD114, CD115, CD119, CD120a, CD120b, CD123, CD124, CD127, CD162, CD163, CD166, CD172, CD181, CD182, CD184, or CD192 (CCR2).

In embodiments, the EV surface marker is specific to a granulocyte. In embodiments, the surface marker specific to the granulocyte is CD66b, CD4, CD9, CDIIa, CD13, CD14, CD15, CD18, CD29, CD31, CD33, CD44, CD45, CD50, CD58, CD59, CD63, CD95, CD119, CD120a, CD120b, CD123, or CD178.

In embodiments, the EV surface marker is specific to a platelet. In embodiments, the surface marker specific to the platelet is CD23, CD9, CD29, CD31, CD36, CD41, CD44, CD49b, CD49f, CD51, CD61, CD62, CD63, CD102, CD107, CD120a, CD120b, or CD140a.

In embodiments, the EV surface marker is specific to an erythrocyte. In embodiments, the surface marker specific to the erythrocyte is CD36, CD235a, CD49e, CD58, CD59, CD49e, CD58, or CD235a.

In embodiments, the EV surface marker is specific to an endothelial cell. In embodiments, the surface marker specific to the endothelial cell is CD31, CD34, CD54, CD62E, CD90, CD105, CD106, CD141, CD144, CD146, CD162, CD181, CD182, CD01, CD309, PECAM, B7-H3, CD276, TEM7, TEM8, thrombomodulin, endoglin, PSGL-1, ICAM-1, ICAM-3, CD106 (VCAM-1), CD201 (EPCR), CD309 (VEGF-R2), CD40, ESAM, E-selectin, IL-1 R1, THSD1, VE-cadherin (CD144), or VEGF-R1 (FLT-1).

In embodiments, the EV surface marker is specific to an epithelial cell. In embodiments, the surface marker specific to the epithelial cell is CD58, CD111, CD 112, CD166, CD227, CD324, CD326, CD340, EpCAM, EGFR, EphA2, or E-cadherin. In embodiments, the surface marker specific to the endothelial or epithelial cell is CD9, CD10, CD13, CD26, CD29, CD31, CD34, CD49b, CD49c, CD49d, CD49e, CD49f, CD50, CD51, CD54, CD58, CD61, CD62E, CD62P, CD63, CD71, CD90, CD102, CD104, CD105, CD109, CD119, CD120a, CD120b, CD121a, CD123, CD124, CD133, CD140a, CD140b, CD144, CD146, CD166, or CD178.

In embodiments, the EV surface marker is specific to a lymphoid cell. In embodiments, the surface marker specific to the lymphoid cell is CD3, CD4, CD8, or CD19. In embodiments, the EV surface marker is specific to a myeloid cell. In embodiments, the surface marker specific to the myeloid cell is CD15 or CD55b.

In embodiments, the EV surface marker is a cancer antigen. In embodiments, the cancer antigen is 5'-nucleotidase (CD73), B7-H3 (CD276), CA19.9, CA60, cadherin-1 (CD324), CD44v6, ADAM10 (CD156c), basigin (CD147), CD24, CD91, Cripto-1 (TSGF1), E-selectin (CD62e), FLT-3 ligand, AlCAM (CD166), Claudin-3, Claudin-4, EGFR, EGFRvIII, CDCP1 (CD318), CEACAM5 (CD66e), Ephrin receptor A2, FAP-a, Glypican-1, HIST2H2BE, HIST2H2BF, CD44, Galectin-3-binding-protein, MAGE3/6, Gamma-enolase (NSE), IL-2R, KIT (CD117), KNG2DL2 (ULBP-2), EpCAM (CD326), FasR (CD95), FasL, HER-2, ICAM-1 (CD54), Integrin A6 (CD49f), Integrin B4(CD104), Mucin-4, Prominin-1 (CD133), Wnt-2, Mucin-16, Mucin-18 (CD146), Sialyl Lewis X, Syndecan-1 (CD138), TNFR1 (CD120a), upaR (CD87), L1CAM (CD171), MET, MUC1 (CA15-3), Raph Blood group (CD151), Tspan8, EphB4, CEA, ALCAM (CD166), DCC (netrin 1 receptor), LRIG3, Nectin-4, TNFSF8, YES, Galectin-9, Vimentin, or Cytokeratin.

In embodiments, the EV surface marker is specific to a leukocyte. In embodiments, the surface marker specific to a leukocyte is CD3, CD4, CD5, CD8, CD10, CD11b, CD13, CD14, CD15, CD19, CD20, CD24, CD26, CD31, CD40, CD50, CD54, CD56, CD64, CD67, CD71, CD73, CD90, CD105, CD141, CD66b, CD162, or CD166. In embodiments, the EV surface marker is specific to a tumor infiltrating leukocyte. In embodiments, the surface marker specific to a tumor infiltrating leukocyte is LAG-3, TIM-3, PD-1 (CD279), CD44, PD-L1, CTLA-4, or CD28. In embodiments, the EV surface marker is an antigen presenting cell marker. In embodiments, the antigen presenting cell marker is CD80, CD86, or CD83. In embodiments, the surface marker is an immuno-oncology marker. In embodiments, the immune-oncology marker is CD137, CD154, or CD40.

In embodiments, the EV surface marker is specific to a stem cell. In embodiments, the surface marker specific to a stem cell is ABCG2 (CD338), CD9, CD11b, CD20, CD29, CD31, CD34, CD44, CD45, CD49f, CD56, CD73, CD81, CD90, CD95, CD105, CD117, CD118, CD133, CD144, CD146, CD166, CD184, DLK1, STRO-1, TNAP, CD24, SSEA-3, SSEA-4, TRA-1-60, or TRA-1-81. In embodiments, the EV surface marker is specific to a mesenchymal stem cell. In embodiments, the surface marker specific to a mesenchymal stem cell is CD73, CD105, CD90, CD29 (ITGB1), CD44, CD166, CD13, CD14, CD10, CD146, CD24, CD271, DLK1, STRO-1, or TNAP. In embodiments, the EV surface marker is specific to a hematopoietic stem cell. In embodiments, the surface marker specific to the hematopoietic stem cell is CD34, CD117, CD135, or CD201.

In embodiments, the EV surface marker is a cell adhesion molecule, an integrin, a classical cadherin, a desmosomal cadherin, a protocadherin, an unconventional cadherin, a claudin, or a selectin. In embodiments, the cell adhesion molecule is EpCAM, E-cadherin, N-cadherin, P-cadherin, E-selectin, P-selectin, L1CAM, VE-cadherin, ITGB1, MCAM, ICAM1, ICAM2, ICAM3, ICAM4, ICAM5, VCAM1, PECAM-1, NCAM, or ALCAM. In embodiments, the integrin is VLA-1, VLA-2, VLA-3, VLA-4, VLA-5, VLA-6, LFA-1, MAC-1, CD11c/CD18, CD41/CD61, vir-tonectin-R, or CD49d. In embodiments, the classical cad-herin is CDH1, CHD2, CDH12, or CDH3. In embodiments, the desmosomal cadherin is DSG1, DSG2, DSG3, DSG4, DSC1, DSC2, or DSC3. In embodiments, the unconven-tional cadherin is CDH4, CDH5, CDH6, CDH7, CDH8, CDH9, CDH10, CDH11, CDH13, CDH15, CDH16, CDH17, CDH18, CDH19, CDH20, CDH21, CDH22, CDH23, CDH24, CDH26, CDH28. In embodiments, the claudin is CDLN1, CDLN2, CDLN3, CDLN4, CDLN5, CDLN6, CDLN7, CDLN8, CDLN9, CDLN10, CDLN11, CDLN12, CDLN13, CDLN14, CDLN15, CDLN16, CDLN17, CDLN18, CDLN19, CDLN20, CDLN21, CDLN22, CDLN23 or CDLN24. In embodiments, the selec-tin is E-selectin, P-selectin, or L-selectin.

In embodiments, the EV surface marker is specific to a senescent cell. In embodiments, the surface marker specific to the senescent cell is DPP4, CD26, CD57, or CD16.

In embodiments, the EV surface marker is specific to an adipose cell. In embodiments, the surface marker specific to the adipose cell is ALK7, CD300LG, GHR, GLUT4, or TUSC5.

In embodiments, the EV surface marker is specific to a hepatocyte. In embodiments, the surface marker specific to the hepatocyte is ASGR1, ASGR2, ceruloplasmin (RAN-2), FATP5, hepatocyte specific antigen, or LRP1 (A2MR).

In embodiments, the EV surface marker is specific to a myocyte. In embodiments, the surface marker specific to the myocyte is AdipoR2, a-sarcoglycan, d-sarcogylcan, ITGA7, or M-cadherin (Cad 15).

In embodiments, the EV surface marker is specific to a cardiac cell such as a cardiomyocyte, fibroblast, endothelial cell, smooth muscle cell, or combination thereof. In embodi-ments, the surface marker specific to the cardiac cell is Connexin-43, N-Cadherin, ATP1A3, PKP2, Dystrophin, SIPRA, VCAM-1, CD77, Caveolin-3, Desmoglein-2, Angiotensin II type 1 receptors, EMILIN-2, POPDC2, KCNA6, and Desmin. In embodiments, presence of the cardiac cell specific surface marker in a subject is associated with higher risk of cardiovascular disease.

In embodiments, the EV comprises a surface-associated marker. In embodiments, the surface-associated marker is covalently or non-covalently bound to one or more surface markers and/or structural components of the EV surface. In embodiments, the surface-associated marker is associated with the EV membrane. In embodiments, the surface-asso-ciated marker is associated with an EV transmembrane protein. In embodiments, the surface-associated marker is an immunomodulatory molecule. In embodiments, the surface-associated marker is a cytokine. In embodiments, the sur-face-associated marker is a surface receptor. In embodi-ments, the surface-associated marker is a costimulatory molecule, e.g., as described in Hodge et al., *Front Biosci* 11: 788-803 (2006) and Bugeon et al., *Am J Respir Crit Care Med* 162: S164-5168 (2000).

In embodiments, the EV comprises a surface marker or surface-associated marker specific to an infected cell, e.g., infected by a pathogen such as bacteria, fungi, or virus. In embodiments, the EV comprises a surface marker or sur-face-associated marker specific to an HIV-infected cell. In embodiments, the surface-associated marker is IL-2RA, IFN-GR1, TNFR1, TNFR2, IL-1R1, IL-1R2, IL-3R, IL-4Ra, IL-5Ra, IL-6Ra, IL-7Ra, IL-9R, IL-6Rb, Common β subunit, Common γ subunit, 4-1BB, CXCR1, CXCR2, CXCR3, CXCR4, CXCR5, CXCR6, CCR1, CCR2, CCR3, CCR4, CCR5, CCR6, CCR7, CCR8, CCR9, IL-10RA, IL-10RB2 IL-12RB, IL-13RA1, IL-13RA2, IL-15RA, IL-17RA, IL-17RC, IL-18R1, IL18RAP, TRAIL-R3, TACI, BAFF-R, BCMA, VEGF-R1, VEGF-R2, IL-21R, IL-22Ra1, IL-23R, IL-27R, IL-31RA, TGF-B1, TGF-B2, TGF-B3, G-CSFR, GM-CSFR, FasR, OX40, 4-1BB, CTLA-4, LAG3, B7-H3, ICOS, PD-1, TIM-3, TIGIT, GITR, CD27, CD28, or BTLA. In embodiments, the surface-associated marker is IL-1RA, IL-1a, IL-1B, IL-2, IL-3, IL-4, IL-5, IL-6, IL-7, IL-8, IL-9, IL-10, IL-12p70, IL12/IL23p40, IL-13, IL-15, IL-16, IL-17A, IL-18, IL-21, IL-22, IL-23, IL-27, IL-29, IL-31, IL-33, IFN-y, TNF-a, TNF-B, TSLP, Eotaxin, Eotaxin-3, IP-10, MCP-1, MCP-4, MCD, MIP-1a, MIP-1B, MIP-3a, TARC, VEGF-A, GM-CSF, G-CSF, TGF-B1, TGF-B2, TGF-B3, TALL-1, RANTES, CXCL1, TRAIL, APRIL, BAFF, LIGHT, PD-L1, PD-L2, OX40L, GITRL, or 4-1BBL.

In embodiments, the EV comprises a viral envelope protein. In embodiments, the EV comprises an HIV-1 viral protein. In embodiments, the HIV-1 viral protein is surface protein gp120 or transmembrane protein gp41. In embodi-ments, the EV comprises an HCV viral protein. In embodi-ments, the HCV viral protein is envelope glycoprotein E1 or envelope glycoprotein E2. In embodiments, the EV com-prises an HSV-1 viral protein. In embodiments, the HSV-1 viral protein is envelope glycoprotein B (gB), envelope glycoprotein C (gC) or envelope glycoprotein D (gD). In embodiments, the EV comprises an HLTV-1 viral protein. In embodiments, the HIV-1 viral protein is surface protein gp46 or transmembrane protein gp21. In embodiments, the EV comprises an EBV viral protein. In embodiments, the EBV viral protein is membrane antigen gp350, envelope glycoprotein H (gH), envelope glycoprotein L (gL), or LMP1. In embodiments, the EV comprises a combination of viral envelope proteins and immune markers, e.g., about 5 to about 100 viral envelope proteins, about 5 to about 100 immune surface receptors, about 5 to about 100 immune receptor ligands, or combination thereof.

In embodiments, the EV is an exosome, a micro-vesicle or a large-oncosome.

Samples

In embodiments of the methods of the invention, surface marker displaying agents of interest are isolated from samples using the methods of the invention. In embodiments of the invention, the sample comprises the surface marker displaying agents of interest and unwanted components. In embodiments of the methods of the invention, before contacting the sample with a surface and selectively binding the surface marker displaying agents of interest, the sample, e.g., mammalian fluid, secretion, or excretion, is purified by, for instance, differential centrifugation, ultrafiltration, size-exclusion chromatography, immuno-affinity, precipitation, or a combination thereof. In embodiments, the unwanted components are soluble in the sample and/or the washing fluid. Further unwanted components can include, but are not limited to, surface marker displaying agents that do not have the marker that the capture reagent binds to, the marker that the binding reagent binds to, or both. In embodiments, the unwanted components include surface marker displaying agents that bind to the capture reagent, but not the binding reagent. In the methods of the invention, surface marker displaying agents that bind to the capture reagent, but not the binding reagent, will be eluted following releasing the capture reagent from the surface. In embodiments, the surface marker displaying agent is a cell. In embodiments, the surface marker displaying agent is a virus or viral particle. In embodiments, the surface marker displaying agent is an organelle. In embodiments, the surface marker displaying agent is a vesicle. In embodiments, the surface marker displaying agent is an extracellular vesicle or exosome.

In embodiments of the methods of the invention, EVs of interest are isolated from samples using the methods of the invention. In embodiments of the invention, the sample comprises the EVs of interest and unwanted components. In embodiments of the methods of the invention, before contacting the sample with a surface and selectively binding the EV of interest, the sample, e.g., mammalian fluid, secretion, or excretion, is purified by, for instance, differential centrifugation, ultrafiltration, size-exclusion chromatography, immuno-affinity, precipitation, or a combination thereof. In embodiments, the unwanted components are soluble in the sample and/or the washing fluid. Further unwanted components can include, but are not limited to, EVs that do not have the marker that the capture reagent binds to, the marker that the binding reagent binds to, or both. In embodiments, the unwanted components include EVs that bind to the capture reagent, but not the binding reagent. In the methods of the invention, EVs that bind to the capture reagent, but not the binding reagent, will be eluted following releasing the capture reagent from the surface.

In embodiments of the methods of the invention, the sample comprises EVs produced from a cell differentiated from a cell-line, differentiated from an induced pluripotent stem cell, a primary cell, or a combination thereof. Samples further include cell supernatants, such as those from neuronal and astrocyte cultures, which include at least the following: human cortical neurons differentiated from induced pluripotent stem cells (iPSC) and from the HCN-2 cell line, adult NPC derived neurons, and adult primary neurons, as well as mature astrocytes differentiated from iPSC and primary human astrocytes. In embodiments, samples include supernatants from oligodendrocytes derived from iPSC cells, which are commercially available, and from cell lines such as HOG or M03.13 which can be differentiated to mature oligodendrocytes using established protocols. Samples further include iPSC derived microglia, which are commercially available, as well as primary microglia which can be expanded in culture. Non-limiting examples of cell lines include MOLT-4 (differentiated or undifferentiated), Jurkat, HL60 (differentiated or undifferentiated), U-937 (differentiated or undifferentiated), HDLM-2, THP-1 (differentiated or undifferentiated), GA10, Ramos, HUVEC, PANC-1, Expi293, HaCat, HCT-15, H-2228, peripheral blood mononuclear cells (PBMCs), KU-812, MC-04, HT-1376, TT, HCT-1116, MCF-7, Calu-3, and the like. Exemplary monocytic cell lines include THP-1, differentiated THP-1, HL60, and differentiated HL60. An exemplary NK cell line is NK92. Exemplary T cell lines include Jurkat and Molt-4. An exemplary B cell line is GA-10. Exemplary endothelial cell lines include HUVEC and differentiated HUVEC. Exemplary hepatocytic cell lines include HepG2 and differentiated HepG2. Exemplary epithelial cell lines include A549, A431, Caco-2, HT29, LNCap, SKOV3, SW480, PC3, MDMB-468, MDMB-231, MCF7, HT-1376, PANC-1, HCT15, Calu-3, Skov3, Bewo, K562, and HeLa. Further additional cell lines include, e.g., HT-29 sARPE-19, SH-SY5Y, and U87-MG.

In embodiments, the samples comprise EVs produced from a T cell, a B cell, a dendritic cell, an NK cell, a monocyte, a macrophage, a granulocyte, a platelet, an erythrocyte, an endothelial cell (e.g., an aortic endothelial cell), an epithelial cell, a stem cell precursor cell, a mesenchymal stem cell, a hematopoietic stem cell, a leukocyte, a senescent cell, an adipose cell, a hepatocyte, a myocyte, or a skeletal muscle cell. T cells include, e.g., helper T cells, such as the subtypes Th1, Th2, Th9, Th17, Th22, and Tfh; regulatory T cells; killer T cells; γδ TCR+ T cells; and natural killer T cells. Adipose cells include, e.g., normal adipocytes, diabetic adipocytes, omental adipocytes, MSC-derived adipocytes, preadipocytes, and omental preadipocytes.

In embodiments, the sample comprises tissue explants in suspension culture. In embodiments, the tissue explant comprises adipocytes or monocytes.

In embodiments of the invention, the sample is a mammalian fluid, secretion, or excretion. In embodiments, the sample is a purified mammalian fluid, secretion, or excretion.

In embodiments, the mammalian fluid, secretion, or excretion is whole blood, plasma, serum, sputum, lachrymal fluid, lymphatic fluid, synovial fluid, pleural effusion, urine, sweat, cerebrospinal fluid, ascites, milk, stool, bronchial lavage, saliva, amniotic fluid, nasal secretions, vaginal secretions, a surface biopsy, sperm, semen/seminal fluid, wound secretions and excretions. In embodiments, the sample is cerebrospinal fluid.

In embodiments, the sample is obtained from an individual, e.g., a human. In embodiments, the sample comprises a plasma sample from an individual. In embodiments, the sample is obtained from a healthy individual. In embodiments, the sample is obtained from an individual having or at risk of a disease. In embodiments, the disease is a cardiovascular disease, a viral infection, cancer, or combination thereof. For instance, the sample can include a plasma sample from a healthy individual, an individual having but not treated for HIV, and an individual with HIV and treated with antiretroviral therapy (ART). In embodiments, the sample comprises a combination of immune surface receptors, immune receptor ligands, and viral proteins. For example, a sample can include about 5 to about 100 viral envelope proteins, about 5 to about 100 immune surface receptors, about 5 to about 100 immune receptor ligands, or combination thereof. In embodiments, a library comprising multiple pools of binding reagents provided herein is used to detect surface markers described herein, the binding reagents in the pools configured such that any combination of markers in the sample can be detected.

In embodiments, the sample comprises purified EVs. Methods of purification include, but are not limited to, precipitation, ultracentrifugation, size exclusion chromatography, ultrafiltration, or affinity purification. In embodiments, the affinity purification may be performed with magnetic or non-magnetic beads.

Biological samples that may be analyzed include, but are not limited to, physiological samples and/or samples containing suspensions of cells, such as mucosal swabs, tissue aspirates, tissue homogenates, cell cultures, and cell culture supernatant, including cultures of eukaryotic and prokaryotic cells. In embodiments, cells are removed, before contacting the surface with EVs, by, for instance centrifugation or filtration.

In embodiments, different cells are identified and distinguished from each other, based on the EVs detected using the present methods. For example, the present methods may be used to distinguish between differentiated and undifferentiated cells, or between diseased and normal (healthy) cells, based on the EVs secreted by each type of cell. The present methods may also be used to determine the growth stage or stimulated state of a cell or cell population. For example, the present methods may be used to compare multiple growth and stimulation conditions on a single cell line. Advantageously, the present methods facilitate comparison of EV secretion in multiple cell lines and reduce potentially tedious sample preparation. In embodiments, the detection of EVs is used to diagnose or assess risk of a disease in a subject.

In embodiments, EVs detected by the present methods are used to assess the presence of different cell types in a sample. For example, detection of a surface marker known to be on EVs from a particular cell type in a sample would indicate presence of that cell type in the sample. Thus, in embodiments, the present methods are used to detect the presence of contaminating cell types in a sample. For example, a sample derived from CNS cells would not be expected to have a surface marker for an endothelial cell; however, if an EV with a marker for a non-CNS cell, e.g., an endothelial cell-specific surface marker, is detected, the sample may be contaminated with non-CNS cells. Non-limiting examples of surface markers that can be used to assess for the presence of endothelial cells in a sample include endoglin, thrombomodulin, PECAM, ICAM-1, ICAM-3, and CD276. Non-limiting examples of surface markers that can be used to assess for the presence of platelet cells in a sample include P-selectin. Non-limiting examples of surface markers that can be used to assess for the presence of lymphoid cells in a sample include CD3, CD4, CD8, and CD19. Non-limiting examples of surface markers that can be used to assess for the presence of myeloid cells in a sample include CD15 and CD66b. Non-limiting examples of surface markers that can be used to assess for the presence of epithelial cells in a sample include EpCAM, EGFR, EphA2, and E-cadherin.

In embodiments, the relative abundance of surface markers on surface marker displaying agents is determined using a library comprising multiple pools of binding reagents as provided herein, wherein each pool contains a specified number of a same binding reagent. In embodiments, the relative abundance of EVs in a sample can be measured by using a plurality of different capture reagents to capture different EVs expressing different markers, then detecting each type of captured EVs with the same detection reagent to a common marker on the different EVs. In embodiments, the relative abundance of EVs in a sample can be measured by using the same capture reagent to capture different EVs expressing a common marker, then using a plurality of different detection reagents to determine the different markers expressed by the EVs.

Samples may be obtained from a single source described herein, or may contain a mixture from two or more sources, e.g., two or three or four cell lines or other sources described herein.

Surface Comprising Capture Reagent and Anchoring Reagent

In embodiments of the invention, a sample comprising a surface marker displaying agent of interest is contacted with a surface, wherein the surface comprises a releasably bound capture reagent and an anchoring reagent.

In embodiments of the invention, a sample comprising an EV of interest is contacted with a surface, wherein the surface comprises a releasably bound capture reagent and an anchoring reagent. The term "contacting" has its ordinary meaning to one of skill in the art. Methods of contacting samples, e.g., liquids, solids, gels, etc., are known to those of ordinary skill in the art.

In embodiments of the methods of the invention, the capture reagent is releasably bound to the surface by a labile linker. In embodiments, the labile linker is a heat-labile, a photolabile, or a chemically labile linker. In additional embodiments, the labile linker is an oligonucleotide that is complementary to an oligonucleotide bound to the surface or is an oligonucleotide comprising a restriction site cleavable by a restriction endonuclease. In embodiments, the labile linker is a small molecule that binds to a protein on the surface. In embodiments, the capture reagent is biotinylated, and the surface is coated with streptavidin. The surface can be, for example, an MSD plate electrode or a particle. In some embodiments, the surface is directly coated with the capture reagent.

In embodiments, the capture reagent is an antibody, antigen, ligand, receptor, oligonucleotide, hapten, epitope, mimotope, or an aptamer. In embodiments of the methods of the invention, the capture reagent and the binding reagent are antibodies, or epitope binding portions thereof, capable of specifically binding a target molecule in or on the surface of the EV of interest.

In embodiments, the EV surface marker to which the capture reagent binds is common to EVs. Such surface markers include, but are not limited e.g., tetraspanins, such as CD9, CD37, CD63, CD81, CD82. In embodiments, the EV surface marker to which the capture reagent binds is specific to a central nervous system (CNS) EV. In embodiments, the EV surface marker to which the capture reagent binds is specific to a neuron EV, an astrocyte EV, an oligodendrocyte EV or a microglia EV.

In embodiments, the EV surface marker to which the capture reagent binds is specific to a neuron EV. In embodiments, the neuron-specific EV surface marker to which the capture reagent binds is L1CAM, NCAM, NRCAM, CHL1, Glu-R2, neurofascin, DAT1, CD90, CD24, N-cadherin, PSA-NCAM or synaptophysin. In embodiments, the neuron that has an EV surface marker to which the capture reagent binds is a dopaminergic neuron, a GABAergic neuron, a cholinergic neuron, a serotonergic neuron or a glutamatergic neuron.

In embodiments, the EV surface marker to which the capture reagent binds is specific to an astrocyte EV. In embodiments, the astrocyte-specific EV surface marker to which the capture reagent binds is ALDH1L1, GLT-1, GLAST, CD184, CD44, A2B5, aquaporin-4, ATP1B2 (ASCA-2), ceruloplasmin, CD80 or CD86.

In embodiments, the EV surface marker is specific to astrocytes and neurons. In embodiments, the surface marker specific to astrocytes and neurons is ALCAM CD166, CD40, FGFR3, GJA1 (connexin 43), integrin B1 (CD29), or CD24.

In embodiments, the EV surface marker to which the capture reagent binds is specific to an oligodendrocyte EV. In embodiments, the oligodendrocyte-specific EV surface marker to which the capture reagent binds is O4, PDGFRa, CSPG4 (NG2, MCSP), GD3, MOG, or MBP.

In embodiments, the EV surface marker to which the capture reagent binds is specific to a microglia EV. In embodiments, the microglia-specific EV surface marker to which the capture reagent binds is Tmem119, CD11bF4/80, CD68, P2RY12, or CXC3R1.

In embodiments of the invention, the capture reagent is an antibody to a disease-specific target molecule in or on the surface of the EV. In embodiments, the EV surface marker to which the binding reagent binds is a cancer antigen. In embodiments, the cancer antigen to which the capture reagent and/or the binding reagent binds is CEA, CA19.9, CA50, CA125, CA15.3, mesothelin, cytokeratin-8, E-cadherin, EGFR, EpCAM, EphA2, NCAM, P-cadherin, cMET, Flt-3L, TNFR-2, cKit, ErbB2, FAP-a, or ANXA1.

In embodiments of the methods of the invention, the surface comprises an anchoring reagent. In the methods of the invention, the anchoring reagent is attached to the surface to allow linker oligonucleotide binding and/or amplicon binding in order to provide an additional indirect attachment point at the surface for the EV of interest. In embodiments, the anchoring reagent includes an oligonucleotide sequence, aptamer, aptamer ligand, antibody, antigen, ligand, receptor, hapten, epitope, or a mimotope; and optionally, the anchoring region can include an aptamer and the anchoring reagent can include an aptamer ligand/target molecule. The anchoring region, in embodiments, comprises a nucleic acid sequence and/or a DNA- or RNA-binding protein. The anchoring reagent comprises, in embodiments, oligonucleotide sequence and the anchoring reagent can include a complementary oligonucleotide sequence. The anchoring reagent, for example, can be a single stranded oligonucleotide sequence or a double stranded oligonucleotide sequence. In embodiments of the invention, the anchoring reagent features, etc., are disclosed in International Appl. No. PCT/US2015/030925, published as WO 2015/175856, which is incorporated by reference in its entirety.

In additional embodiments, the amplicon is bound to the anchoring reagent at a position within 10 μm, 5 μm, or 100 nm of the location of the complex comprising the EV of interest on the surface.

Suitable surfaces for use in the methods of the present invention are known in the art, including conventional surfaces from the art of binding assays. Suitable surfaces are disclosed, for example, in International Appl. No. PCT/US2015/030925, published as WO 2015/175856. Surfaces may be made from a variety of different materials including polymers (e.g., polystyrene and polypropylene), ceramics, glass, composite materials (e.g., carbon-polymer composites such as carbon-based inks). Suitable surfaces include the surfaces of macroscopic objects such as an interior surface of an assay container (e.g., test tubes, cuvettes, flow cells, FACS cell sorter, cartridges, wells in a multi-well plate, etc.), slides, assay chips (such as those used in gene or protein chip measurements), pins or probes, beads, filtration media, lateral flow media (for example, filtration membranes used in lateral flow test strips), etc.

Suitable surfaces also include particles (including but not limited to colloids or beads) commonly used in other types of particle-based assays e.g., magnetic, polypropylene, and latex particles, hydrogels, e.g. agarose, materials typically used in solid-phase synthesis e.g., polystyrene and polyacrylamide particles, and materials typically used in chromatographic applications e.g., silica, alumina, polyacrylamide, polystyrene. The materials may also be a fiber such as a carbon fibril. Microparticles may be inanimate or alternatively, may include animate biological entities such as cells, viruses, bacterium and the like. A particle used in the present method may be comprised of any material suitable for attachment to one or more capture or anchoring reagents, and that may be collected via, e.g., centrifugation, gravity, filtration or magnetic collection. A wide variety of different types of particles that may be attached to capture or anchoring reagents are sold commercially for use in binding assays. These include non-magnetic particles as well as particles comprising magnetizable materials which allow the particles to be collected with a magnetic field. In one embodiment, the particles are comprised of a conductive and/or semiconductive material, e.g., colloidal gold particles. The microparticles may have a wide variety of sizes and shapes. By way of example and not limitation, microparticles may be between 5 nanometers and 100 micrometers. Preferably microparticles have sizes between 20 nm and 10 micrometers. The particles may be spherical, oblong, rod-like, etc., or they may be irregular in shape.

The particles used in the present method may be coded to allow for the identification of specific particles or subpopulations of particles in a mixture of particles. The use of such coded particles has been used to enable multiplexing of assays employing particles as solid phase supports for binding assays. In one approach, particles are manufactured to include one or more fluorescent dyes and specific populations of particles are identified based on the intensity and/or relative intensity of fluorescence emissions at one or more wave lengths. This approach has been used in the Luminex xMAP systems (see, e.g., U.S. Pat. No. 6,939,720) and the Becton Dickinson Cytometric Bead Array systems. Alternatively, particles may be coded through differences in other physical properties such as size, shape, imbedded optical patterns and the like. One or more particles provided in a mixture or set of particles may be coded to be distinguishable from other particles in the mixture by virtue of particle optical properties, size, shape, imbedded optical patterns and the like.

In a specific embodiment, the methods of the invention can be used in a multiplexed format by binding a plurality of different analytes to a plurality of capture reagents for those analytes, the capture analytes being immobilized on coded bead, such that the coding identifies the capture reagent (and analyte target) for a specific bead. The method may further comprise counting the number of beads that have a bound analyte (using the detection approaches described herein).

Alternatively or additionally, the capture reagents can be bound, directly or indirectly, to different discrete binding domains on one or more solid phases, e.g., as in a binding array wherein the binding domains are individual array elements, or in a set of beads wherein the binding domains are the individual beads, such that discrete assay signals are generated on and measured from each binding domain. If capture reagents for different analytes are immobilized in different binding domains, the different analytes bound to those domains can be measured independently. In one example of such an embodiment, the binding domains are prepared by immobilizing, on one or more surfaces, discrete domains of capture reagents that bind analytes of interest. Optionally, the surface(s) may define, in part, one or more boundaries of a container (e.g., a flow cell, well, cuvette, etc.) which holds the sample or through which the sample is passed. In a preferred embodiment, individual binding domains are formed on electrodes for use in electrochemical or electrochemiluminescence assays. Multiplexed measurement of analytes on a surface comprising a plurality of binding domains using electrochemiluminescence has been used in the Meso Scale Diagnostics, LLC, MULTI-ARRAY® and SECTOR® Imager line of products (see, e.g., U.S. Pat. Nos. 10,201,812, 7,842,246 and 6,977,722, the disclosures of which are incorporated herein by reference in their entireties).

Still further, the capture reagents can be bound, directly or indirectly, to an electrode surface, which optionally includes different discrete binding domains, as described above. The electrode surface can be a component of a multi-well plate and/or a flow cell. Electrodes can comprise a conductive material, e.g., a metal such as gold, silver, platinum, nickel, steel, iridium, copper, aluminum, a conductive allow, or the like. They may also include oxide coated metals, e.g., aluminum oxide coated aluminum. The electrode can include a working and counter electrodes which can be made of the same or different materials, e.g., a metal counter electrode and carbon working electrode. In one specific embodiment, electrodes comprise carbon-based materials such as carbon, carbon black, graphitic carbon, carbon nanotubes, carbon fibrils, graphite, graphene, carbon fibers and mixtures thereof. In one embodiment, the electrodes comprise elemental carbon, e.g., graphitic, carbon black, carbon nanotubes, etc. Advantageously, they may include conducting carbon-polymer composites, conducting particles dispersed in a matrix (e.g. carbon inks, carbon pastes, metal inks, graphene inks), and/or conducting polymers. One specific embodiment of the invention is an assay module, preferably a multi-well plate, having electrodes (e.g., working and/or counter electrodes) that comprise carbon, e.g., carbon layers, and/or screen-printed layers of carbon inks.

In embodiments, the capture reagent is attached to the surface via a pair of short complementary oligonucleotides (one attached to the surface, the other attached to the capture reagent) that form stable duplexes in common biological buffers but can be denatured in a low salt buffer, and modestly elevated temperature is used to allow the capture reagent, e.g., antibody to be released. In embodiments, a restriction site in the complementary oligonucleotides that is cleaved by a restriction endonuclease is used. This has the advantage of being completely orthogonal to the denaturation that will be used, in embodiments, to purposely elute the stapled EVs, though a second restriction enzyme can also be used to elute the stapled EVs. Stapling sequence, diluents, and procedure are optimized to maximize retention of stapled EVs and minimize retention of non-stapled EVs. In embodiments, the captured EVs are co-labeled with STAG-labeled detection antibodies, and the ECL signal is compared with the ECL signal generated with and without elution, or with specific stapling and irrelevant stapling.

In embodiments of the invention, the capture reagent binds to a first surface marker on the EV and the binding reagent binds to a second surface marker on the EV.
Binding Reagents and Stapling Step In embodiments of the invention, following binding of the surface marker displaying agent of interest with a capture reagent that is releasably bound to the surface, at least one binding reagent is contacted with the surface marker displaying agent. In embodiments, a complex is thus formed on the surface comprising the capture reagent, the surface marker displaying agent and a binding reagent. In embodiments, the binding reagent comprises a binding site for a surface marker on the surface marker displaying agent. In embodiments, the binding reagent surface marker is distinct from the surface marker to which the capture reagent is bound. In embodiments, the capture reagent binds to a surface marker common to surface marker displaying agents, and the binding reagent binds to a surface marker displaying agent surface marker specific to a type of surface marker displaying agent, e.g., a cancer cell in a sample of blood cells. In embodiments, the surface marker displaying agent is a cell. In embodiments, the surface marker displaying agent is a virus or viral particle. In embodiments, the surface marker displaying agent is an organelle. In embodiments, the surface marker displaying agent is a vesicle. In embodiments, the surface marker displaying agent is an extracellular vesicle or exosome.

In embodiments of the invention, following binding of the EV of interest with a capture reagent that is releasably bound to the surface, at least one binding reagent is contacted with the EV. In embodiments, a complex is thus formed on the surface comprising the capture reagent, the EV and a binding reagent. In embodiments, the binding reagent comprises a binding site for a surface marker on the EV. In embodiments, the binding reagent surface marker is distinct from the surface marker to which the capture reagent is bound. In embodiments, the capture reagent binds to a surface marker common to EVs, and the binding reagent binds to an EV surface marker specific to a cell, tissue, or organ specific marker such as a CNS marker.

The binding reagent, in embodiments, comprises an antibody, antigen, ligand, receptor, oligonucleotide, hapten, epitope, mimotope, or an aptamer. In embodiments, the binding reagent comprises an antibody or an antigen/epitope-binding portion thereof. In embodiments, the binding reagent comprises a non-neutralizing antibody capable of binding to a receptor. In embodiments, the binding reagent comprises an antibody capable of binding to a receptor in the presence of a ligand. In embodiments, the binding reagent comprises an antibody capable of binding to a receptor-bound ligand.

In embodiments, the EV surface marker to which the binding reagent binds is common to EVs. Such surface markers include, but are not limited e.g., tetraspanins, such as CD9, CD37, CD63, CD81, CD82. In embodiments, the EV surface marker to which the binding reagent binds is specific to a CNS EV. In embodiments, the EV surface marker to which the binding reagent binds is specific to a neuron EV, an astrocyte EV, an oligodendrocyte EV or a microglia EV.

In embodiments, the EV surface marker to which the binding reagent binds is specific to a neuron EV. In embodiments, the EV surface marker to which the binding reagent binds is L1CAM, NCAM, NRCAM, CHL1, Glu-R2, neurofascin, DAT1, CD90, CD24, N-cadherin, PSA-NCAM or synaptophysin. In embodiments, the neuron EV surface marker to which the binding reagent binds is from a dopaminergic neuron, a GABAergic neuron, a cholinergic neuron, a serotonergic neuron or a glutamatergic neuron.

In embodiments, the EV surface marker to which the binding reagent binds is specific to an astrocyte EV. In embodiments, the EV surface marker to which the binding reagent binds is ALDH1L1, GLT-1, GLAST, CD184, CD44, A2B5, aquaporin-4, ATP1B2 (ASCA-2), ceruloplasmin, CD80 or CD86.

In embodiments, the EV surface marker is specific to astrocytes and neurons. In embodiments, the surface marker specific to astrocytes and neurons is ALCAM CD166, CD40, FGFR3, GJA1 (connexin 43), integrin B1 (CD29), or CD24.

In embodiments, the EV surface marker to which the binding reagent binds is specific to an oligodendrocyte EV. In embodiments, the EV surface marker to which the binding reagent binds is O4, PDGFRa, CSPG4 (NG2, MCSP), GD3, MOG, or MBP.

In embodiments, the EV surface marker to which the binding reagent binds is specific to a microglia EV. In embodiments, the EV surface marker to which the binding reagent binds is Tmem119, CD11bF4/80, CD68, P2RY12, CXC3R1.

In embodiments of the invention, at least one of the first or second binding reagents are antibodies to a disease-specific target molecule in or on the surface of the EV. In embodiments, the EV surface marker to which the binding reagent binds is specific to an Alzheimer's biomarker.

In embodiments, in addition to a binding site for an EV surface marker, the binding reagent comprises an oligo-nucleotide that allows the EV of interest to be indirectly attached or linked to the surface. In embodiments, the binding reagent oligonucleotide is a tag oligonucleotide that contains a sequence that is complementary to an anchoring oligonucleotide that is attached to the surface. Thus when the binding reagent oligonucleotide is hybridized to the anchoring oligonucleotide the EV of interest is indirectly bound to the surface by these interactions In embodiments of the methods of the invention the binding reagent oligonucleotide comprises a region comple-mentary to the anchoring nucleotide of about 15 to 35 oligonucleotides. In embodiments, the region is 20-30 oli-gonucleotides. In additional embodiments the capture reagent is also releasably attached to the surface via a pair of hybridized oligonucleotides with one oligonucleotide attached to the capture reagent and one oligonucleotide attached to the surface. In additional embodiments, the complementary portions of the hybridized oligonucleotides attaching the capture reagent to the surface are optimized to be releasable at a lower temperature or less strict conditions than the hybridized regions of the binding reagent oligo-nucleotide and the anchoring oligonucleotide.

In embodiments, the binding reagent oligonucleotide is a tag oligonucleotide that contains a sequence that is comple-mentary to a linker oligonucleotide. In embodiments, the linker oligonucleotide further contains a sequence that is complementary to an anchoring oligonucleotide that is attached to the surface. Thus, when a linker oligonucleotide is hybridized to the tag oligonucleotide and to an anchoring oligonucleotide, the EV of interest is indirectly bound to the surface by these interactions.

In embodiments of the methods of the invention the linker oligonucleotide comprises a first region complementary to the tag nucleotide of about 15 to 35 oligonucleotides and a second region complementary to the anchoring nucleotide of about 15 to 35 oligonucleotides. In embodiments, the first and second region are each 20-30 oligonucleotides. In additional embodiments the capture reagent is also releas-ably attached to the surface via a pair of hybridized oligo-nucleotides with one oligonucleotide attached to the capture reagent and one oligonucleotide attached to the surface. In additional embodiments the complementary portions of the hybridized oligonucleotides attaching the capture reagent to the surface are optimized to be releasable at a lower tem-perature or less strict conditions than the hybridized regions of the linker oligonucleotide and the binding reagent and the hybridized regions of the linker oligonucleotide and the anchoring oligonucleotide.

In additional embodiments, the binding reagent comprises a primer oligonucleotide that contains a sequence that is complementary to an oligonucleotide template, such as a circular oligonucleotide. The primer is used to form an amplicon that comprises a sequence complementary to an anchoring oligonucleotide. Any suitable amplification tech-nique can be used to generate the extended sequence (or amplicon), including but not limited to, PCR (Polymerase Chain Reaction), LCR (Ligase Chain Reaction), and iso-thermal amplification methods, e.g., helicase-dependent amplification, rolling circle amplification (RCA), 3SR (Self-Sustained Synthetic Reaction), transcription mediated amplification (TMA), nucleic acid sequence-based amplifi-cation (NASBA), signal mediated amplification of RNA technology, strand displacement amplification (SDA), loop-mediated isothermal amplification of DNA (LAMP), iso-thermal multiple displacement amplification, single primer isothermal amplification, and circular helicase-dependent amplification. In embodiments, the amplification technique is proximity ligation amplification (PLA) using RCA, which is known in the art, and disclosed in International Appl. No. PCT/US2015/030925, published as WO 2015/175856, which is incorporated by reference in its entirety.

In additional embodiments, the amplicon further com-prises one or more detection sequences and the measuring step further comprises contacting the extended sequence with a plurality of labeled probes complementary to the one or more detection sequences.

In further embodiments, the amplicon remains localized on the surface following the amplification. In further embodiments of the methods of the invention, the amplicon remains bound to the surface after the amplification.

In a preferred embodiment, RCA is used to make the amplicon because it has significant advantages in terms of sensitivity, multiplexing, dynamic range and scalability. Techniques for RCA are known in the art (see, e.g., Baner et al, Nucleic Acids Research, 26:5073 5078, 1998; Lizardi et al., Nature Genetics 19:226, 1998; Schweitzer et al. Proc. Natl. Acad. Sci. USA 97:10113 119, 2000; Faruqi et al., BMC Genomics 2:4, 2000; Nallur et al., Nucl. Acids Res. 29:e118, 2001; Dean et al. Genome Res. 11:1095 1099, 2001; Schweitzer et al., Nature Biotech. 20:359 365, 2002; U.S. Pat. Nos. 6,054,274, 6,291,187, 6,323,009, 6,344,329 and 6,368,801). Several different variants of RCA are known, including linear RCA (LRCA) and exponential RCA (ERCA). RCA generates many thousands of copies of a circular template, with the chain of copies attached to the original target DNA, allowing for spatial resolution of target and rapid amplification of the signal. RCA facilitates (i) detection of single target molecules; (ii) amplification of signals from proteins as well as DNA and RNA; (iii) identifying the location of molecules that have been ampli-fied on a solid surface; (iv) measurement of many different targets simultaneously; and (v) analysis of one or more targets in solution or solid phase. The spatial localization of RCA products with the detection complex is especially advantageous when conducting multiplexed binding assays in an array or particle based format.

Alternative Anchoring Reagents and Staples

In embodiments, the anchoring reagent of the present disclosure comprises an oligonucleotide moiety and a hydrophilic polymer moiety. An anchoring reagent comprising an oligonucleotide moiety and a hydrophilic polymer moiety may be advantageous in some cases over an anchoring reagent comprising an oligonucleotide of the same length. For example, the anchoring reagent comprising the oligonucleotide moiety and the hydrophilic polymer moiety may be easier and more cost-efficient to synthesize. The anchoring reagent comprising the oligonucleotide moiety and the hydrophilic polymer moiety may also have increased stability (e.g., less prone to degradation), higher biocompatibility (e.g., due to the high water solubility of the hydrophilic polymer), and decreased non-specific binding (e.g., due to the anchoring reagent being substantially unreactive with one or more other components, e.g., the surface marker displaying agent, the capture reagent, and/or the binding reagent) when compared with an oligonucleotide-only anchoring reagent. In embodiments, the anchoring reagent comprising the oligonucleotide moiety and the hydrophilic polymer moiety is also advantageous because a longer hydrophilic moiety (e.g., having a molecular weight of about 20 kD) enables a longer anchoring reagent that is more compatible with the expected size of some surface marker displaying agents, such as extracellular vesicles.

Thus, in embodiments, the present disclosure provides a method of isolating a surface marker displaying agent of interest in a sample, comprising: (a) contacting the sample with a surface and selectively binding the surface marker displaying agent of interest to: (i) a capture reagent releasably bound to the surface, wherein the surface further comprises an anchoring reagent, wherein the anchoring reagent comprises an oligonucleotide moiety and a hydrophilic polymer moiety; and (ii) a binding reagent; (b) binding the anchoring reagent to the binding reagent, thereby forming a complex on the surface comprising the capture reagent, the surface marker displaying agent and the binding reagent; and (c) releasing the capture reagent from the surface and eluting unwanted components of the sample from the surface, thereby isolating the surface marker displaying agent of interest. In embodiments, the surface marker displaying agent is a cell. In embodiments, the surface marker displaying agent is a virus or viral particle. In embodiments, the surface marker displaying agent is an organelle. In embodiments, the surface marker displaying agent is a vesicle. In embodiments, the surface marker displaying agent is an extracellular vesicle or exosome.

In embodiments, the oligonucleotide moiety is conjugated to a first end of the hydrophilic polymer moiety. In embodiments, the anchoring reagent is formed by conjugation of an oligonucleotide to a hydrophilic polymer, wherein the oligonucleotide and a first end of the hydrophilic polymer each comprises a reactive group. In embodiments, the reactive group of the oligonucleotide is capable of reacting with the reactive group of the hydrophilic polymer. As used herein, "conjugation," "bioconjugation," or variants thereof refer to the formation of a stable, covalent linkage, also referred to herein as a "conjugation linkage," between two substances, e.g., an oligonucleotide and a hydrophilic polymer. The conjugation can occur via reaction of a pair of reactive groups to form the stable, covalent linkage. Examples of reactive group pairs include, e.g., amine and N-hydroxysuccinimide (NHS) ester or aldehyde; thiol and NHS-ester, maleimide, disulfide, or alkene; alkyne or cycloalkyne and azide; etc. Cross-reactive groups are further discussed in, e.g., *Thermo Scientific Crosslinking Technical Handbook*, printed October 2012, copyright 2012.

As used herein, the term "moiety," as used in the context of a component of a conjugated compound, generally refers to the component as part of the conjugated compound. Thus, the term "oligonucleotide moiety" as used herein in the context of a conjugated compound includes an oligonucleotide conjugated to a hydrophilic polymer or any other substance described herein (e.g., a binding reagent, a capture reagent, or any other component of the methods and/or kits herein). Similarly, a "hydrophilic polymer moiety" refers to a hydrophilic polymer conjugated to an oligonucleotide or any other substance described herein. Thus, the skilled artisan can appreciate that an oligonucleotide moiety would include an oligonucleotide covalently linked to a hydrophilic polymer as described herein, and similarly, a hydrophilic polymer moiety would include a hydrophilic polymer covalently linked to an oligonucleotide as described herein.

In embodiments, the anchoring reagent is formed from a conjugation reaction of an oligonucleotide and a hydrophilic polymer. In embodiments, the conjugation reaction is a polar reaction. Exemplary polar reactions are shown in FIG. 50A. Exemplary hydrophilic polymers comprising reactive groups suitable for polar reactions described herein are shown in FIG. 51A.

In embodiments, the oligonucleotide comprises an amine, and the hydrophilic polymer comprises an N-hydroxysuccinimide (NHS) ester. In embodiments, the oligonucleotide comprises an amine, and the hydrophilic polymer comprises an aldehyde. In embodiments, the oligonucleotide comprises a thiol, and the hydrophilic polymer comprises an NHS ester. In embodiments, the oligonucleotide comprises a thiol, and the hydrophilic polymer comprises a maleimide. In embodiments, the oligonucleotide comprises a thiol, and the hydrophilic polymer comprises a disulfide. In embodiments, the oligonucleotide comprises a thiol, and the hydrophilic polymer comprises an alkene.

In embodiments, the oligonucleotide comprises an NHS ester, and the hydrophilic polymer comprises an amine. In embodiments, the oligonucleotide comprises an aldehyde, and the hydrophilic polymer comprises an amine. In embodiments, the oligonucleotide comprises an NHS ester, and the hydrophilic polymer comprises a thiol. In embodiments, the oligonucleotide comprises a maleimide, and the hydrophilic polymer comprises a thiol. In embodiments, the oligonucleotide comprises a disulfide, and the hydrophilic polymer comprises a thiol. In embodiments, the oligonucleotide comprises an alkene, and the hydrophilic polymer comprises a thiol.

In embodiments, the conjugation reaction is a cycloaddition reaction, e.g., a click reaction. Click chemistry reactions are described in, e.g., Hein et al., Pharm Res 25(10): 2116-2230 (2008). In embodiments, the conjugation reaction occurs in an aqueous solvent in the presence of a copper catalyst and/or a reducing agent. In embodiments, the copper catalyst comprises Cu(I). In embodiments, the reducing agent comprises sodium ascorbate, hydrazine, or tris(2-carboxyethyl)phosphine (TCEP). In embodiments, the oligonucleotide comprises an alkyne, and the hydrophilic polymer comprises an azide. In embodiments, the oligonucleotide comprises a cycloalkyne, and the hydrophilic polymer comprises an azide. In embodiments, the oligonucleotide comprises an azide, and the hydrophilic polymer comprises an alkyne. In embodiments, the oligonucleotide comprises an azide, and the hydrophilic polymer comprises a cycloalkyne. Exemplary cycloaddition reactions are shown in FIG. 50B. Exemplary hydrophilic polymers comprising reactive groups suitable for cycloaddition reactions described herein are shown in FIG. 51B.

In embodiments, the conjugation reaction occurs in an aqueous solvent at pH about 6 to about 9. In embodiments, the conjugation reaction occurs in an aqueous solvent at pH about 7 to about 8. In embodiments, the conjugation reaction occurs in an aqueous solvent at pH about 6 to about 8. In embodiments, the conjugation reaction occurs in an aqueous solvent at pH about 2 to about 8.

In embodiments, the conjugation linkage resulting from the conjugation reaction is an amide, a thioester, a thioether, a disulfide, an imine, or a triazole. For example, NHS ester and an amine form an amide linkage; an NHS ester or an alkene and thiol form a thioester linkage; a maleimide and thiol form a thioether linkage; a disulfide and thiol form a disulfide linkage; an aldehyde and amine form an imine linkage; an alkyne or cycloalkyne and azide form a triazole linkage. Thus, in embodiments, the anchoring reagent comprises a conjugation linkage between the oligonucleotide moiety and the hydrophilic polymer moiety selected from an amide, a thioester, a thioether, a disulfide, an imine, or a triazole.

In embodiments, the oligonucleotide and the hydrophilic polymer are conjugated to form the anchoring reagent, and the anchoring reagent is then purified to remove unreacted and/or unwanted components of the conjugation reaction. In embodiments, the purification comprises chromatography, membrane purification, gel electrophoresis, size exclusion, or combinations thereof. In embodiments, the purification comprises ion exchange chromatography. In embodiments, the purification charge switch membrane purification. Methods of performing purification are known by one of skill in the art.

In embodiments, the binding reagent comprises an oligonucleotide. In embodiments, the oligonucleotide moiety comprises a sequence that is complementary to an oligonucleotide of the binding reagent. Thus, in embodiments, the binding of the binding reagent to the anchoring reagent comprises hybridizing the oligonucleotide moiety of the anchoring reagent to the oligonucleotide of the binding reagent, thereby forming a complex on the surface comprising the capture reagent, the surface marker displaying agent, and the binding reagent.

An exemplary anchoring reagent described in embodiments herein is illustrated in FIG. 49A. A capture reagent (e.g., capture antibody) for a surface marker displaying agent (e.g., EV) is linked to a surface (e.g., bead) via complementary oligonucleotides on the capture reagent and the surface. The surface marker displaying agent also binds to a binding reagent, which is linked to an oligonucleotide. An anchoring reagent comprises an oligonucleotide moiety, a hydrophilic polymer (e.g., PEG) moiety, and a biotin, which is capable of attachment to a streptavidin on the surface. The oligonucleotide moiety of the anchoring reagent comprises a complementary sequence to the oligonucleotide of the binding reagent, thereby binding the binding reagent to the anchoring reagent and forming a complex on the surface comprising the capture reagent, the surface marker displaying agent, and the binding reagent.

In embodiments, the oligonucleotide moiety of the anchoring reagent and an oligonucleotide of the binding reagent each comprises a sequence that is complementary to a splint oligonucleotide. In embodiments, the oligonucleotide moiety of the anchoring reagent and the oligonucleotide of the binding reagent each comprises a sequence complementary to a 5' and a 3' portion of the splint oligonucleotide, respectively, such that the oligonucleotide moiety of the anchoring reagent and the oligonucleotide of the binding reagent do not overlap when hybridized to the splint oligonucleotide. In embodiments, a ligation site is formed when the oligonucleotide moiety of the anchoring reagent and the oligonucleotide of the binding reagent are hybridized to the splint oligonucleotide. In embodiments, the binding of the binding reagent to the anchoring comprises ligating the oligonucleotide moiety of the anchoring reagent and the oligonucleotide of the binding reagent. In embodiments, the binding of the binding reagent to the anchoring reagent comprises forming a stable hybridized complex with the oligonucleotide of the oligonucleotide moiety of the anchoring reagent, the oligonucleotide of the binding reagent, and the splint oligonucleotide.

An exemplary anchoring reagent described in embodiments herein is illustrated in FIG. 49B. FIG. 49B is similar to FIG. 49A, except the oligonucleotide moiety of the anchoring reagent and the oligonucleotide of the binding reagent each comprises a sequence complementary to 5' and 3' portions of a splint oligonucleotide, respectively. Thus, when the oligonucleotide moiety of the anchoring reagent and the oligonucleotide of the binding reagent are hybridized to the splint oligonucleotide, a ligation site between the oligonucleotide moiety of the anchoring reagent and the oligonucleotide of the binding reagent is formed. The ligation site can then be ligated, e.g., via a ligase, thereby binding the binding reagent to the anchoring reagent and forming a complex on the surface comprising the capture reagent, the surface marker displaying agent, and the binding reagent.

In embodiments, the binding reagent of the method is a first binding reagent, and step (a) of the method further comprises binding the surface marker displaying agent of interest to a second binding reagent, wherein the first and second binding reagents each comprises an oligonucleotide, and the oligonucleotide of the first binding reagent and the oligonucleotide moiety of the anchoring reagent each comprises a sequence that is complementary to the oligonucleotide of the second binding reagent. In embodiments, the oligonucleotide of the first binding reagent and the oligonucleotide moiety of the anchoring reagent are complementary to a 5' and a 3' portion of the oligonucleotide of the second binding reagent, respectively, such that the oligonucleotide moiety of the anchoring reagent and the oligonucleotide of the first binding reagent do not overlap when hybridized to the oligonucleotide of the second binding reagent. In embodiments, a ligation site is formed when the oligonucleotide moiety of the anchoring reagent and the oligonucleotide of the first binding reagent are hybridized to the oligonucleotide of the second binding reagent. In embodiments, the binding of the first binding reagent to the anchoring comprises ligating the oligonucleotide moiety of the anchoring reagent and the oligonucleotide of the first binding reagent. In embodiments, the binding of the first binding reagent to the anchoring reagent comprises forming a stable hybridized complex with the oligonucleotide of the oligonucleotide moiety of the anchoring reagent, the oligonucleotide of the first binding reagent, and the oligonucleotide of the second binding reagent.

Thus, in embodiments, the method comprises (a) contacting the sample with a surface and selectively binding the surface marker displaying agent of interest to: (i) a capture reagent releasably bound to the surface, wherein the surface further comprises an anchoring reagent, wherein the anchoring reagent comprises an oligonucleotide moiety and a hydrophilic polymer moiety; and (ii) first and second binding reagents, wherein the first and second binding reagents each comprises an oligonucleotide, and the oligonucleotide of the first binding reagent and the oligonucleotide moiety of the anchoring reagent each comprises a sequence that is complementary to the oligonucleotide of the second binding reagent; (b) binding the anchoring reagent to the first binding reagent, thereby forming a complex on the surface comprising the capture reagent, the surface marker displaying agent and the first and second binding reagents; and (c) releasing the capture reagent from the surface and eluting unwanted components of the sample from the surface, thereby isolating the surface marker displaying agent of interest. In embodiments, the surface marker displaying agent is a cell. In embodiments, the surface marker displaying agent is a virus or viral particle. In embodiments, the surface marker displaying agent is an organelle. In embodiments, the surface marker displaying agent is a vesicle. In embodiments, the surface marker displaying agent is an extracellular vesicle or exosome.

An exemplary anchoring reagent described in embodiments herein is illustrated in FIG. 49C. In FIG. 49C, the surface marker displaying agent is bound to a capture reagent and first and second binding reagents, each binding reagent comprising an oligonucleotide. The oligonucleotide of the first binding reagent and the oligonucleotide moiety of the anchoring reagent each comprises a sequence complementary to the 5' and 3' portions of the oligonucleotide of the second binding reagent, respectively. Thus, when the oligonucleotide of the first binding reagent and the oligonucleotide moiety of the anchoring reagent are hybridized to the oligonucleotide of the second binding reagent, a ligation site between the oligonucleotide of the first binding reagent and the oligonucleotide moiety of the anchoring reagent is formed. The ligation site can then be ligated, e.g., via a ligase, thereby binding the first binding reagent to the anchoring reagent and forming a complex on the surface comprising the capture reagent, the surface marker displaying agent, and the first and second binding reagents.

In embodiments, the hydrophilic polymer moiety is about 0.2 nm to about 200 nm in length. In embodiments, the hydrophilic polymer moiety is about 0.4 nm to about 180 nm in length. In embodiments, the hydrophilic polymer moiety is about 0.2 nm, about 0.4 nm, about 0.6 nm, about 0.8 nm, about 1 nm, about 2 nm, about 3 nm, about 4 nm, about 5 nm, about 6 nm, about 7 nm, about 8 nm, about 9 nm, about 10 nm, about 20 nm, about 30 nm, about 40 nm, about 50 nm, about 60 nm, about 70 nm, about 80 nm, about 90 nm, about 100 nm, about 110 nm, about 120 nm, about 130 nm, about 140 nm, about 150 nm, about 160 nm, about 170 nm, about 180 nm, about 190 nm, or about 200 nm in length.

In embodiments, the hydrophilic polymer moiety comprises polyethylene glycol (PEG), poly(N-isopropylacrylamide) (PNIPAM), polyacrylamide (PAM), poly(2-oxazoline), polyethyleneimine (PEI), poly(acrylic acid), polymethacrylate, acrylic polymers, poly(ethylene oxide), poly(vinyl alcohol) (PVA) and copolymers thereof, poly (vinylpyrrolidone) (PVP) and copolymers thereof, polyelectrolytes, cucurbit[n]uril hydrate, maleic anhydride copolymer, polyether, or any combination, cross- or co-polymer thereof. In embodiments, the hydrophilic polymer is PEG. In embodiments, the PEG is about 10 kD to about 50 kD. In embodiments, the PEG is about 20 kD.

In embodiments, the anchoring reagent further comprises a surface attachment moiety. In embodiments, the hydrophilic polymer moiety of the anchoring reagent comprises a surface attachment moiety at a second end. In embodiments, the surface attachment moiety is biotin. In embodiments, the surface comprises streptavidin.

In further embodiments, the present disclosure provides a method of isolating a surface marker displaying agent of interest in a sample, comprising: (a) contacting the sample with a surface and selectively binding the surface marker displaying agent of interest to: (i) a capture reagent releasably bound to the surface, wherein the surface further comprises an anchoring reagent; and (ii) a binding reagent; (b) binding the anchoring reagent to the binding reagent using an anchor linking reagent, wherein the anchor linking reagent comprises a first oligonucleotide moiety, a hydrophilic polymer moiety, and a second oligonucleotide moiety, thereby forming a complex on the surface comprising the capture reagent, the surface marker displaying agent, the binding reagent, and the anchor linking reagent; and (c) releasing the capture reagent from the surface and eluting unwanted components of the sample from the surface, thereby isolating the surface marker displaying agent of interest. In embodiments, the surface marker displaying agent is a cell. In embodiments, the surface marker displaying agent is a virus or viral particle. In embodiments, the surface marker displaying agent is an organelle. In embodiments, the surface marker displaying agent is a vesicle. In embodiments, the surface marker displaying agent is an extracellular vesicle or exosome.

In embodiments, using an anchor linking reagent to bind the binding reagent to the anchoring reagent provides additional flexibility to the assay, e.g., by using an anchor linking reagent that has a longer or shorter length as needed for forming the complex on the surface comprising the capture reagent, the surface marker displaying agent, and the binding reagent. In embodiments, a plurality of distinct anchor linking reagents can be used to multiplex the methods provided herein.

In embodiments, the first oligonucleotide moiety and the second oligonucleotide moiety of the anchor linking reagent are conjugated respectively to a first end and a second end of the hydrophilic polymer moiety. In embodiments, the anchor linking reagent is formed from a conjugation reaction of a first oligonucleotide to a first end of a hydrophilic polymer, and a second oligonucleotide to a second end of the hydrophilic polymer, wherein the first and second oligonucleotides and the first and second ends of the hydrophilic polymer each comprise a reactive group. Conjugation reactions and reactive groups are described herein.

In embodiments, the conjugation reaction of the first oligonucleotide with the first end of the hydrophilic polymer and the conjugation of the second oligonucleotide with the second end of the hydrophilic polymer are performed simultaneously. In embodiments, the reactive groups of the first and second oligonucleotides are not substantially reactive with one another. In embodiments, the reactive groups of the first and second ends of the hydrophilic polymer are not substantially reactive with one another. In embodiments, the reactive group of the first oligonucleotide is substantially reactive with only one of the first or the second end of the hydrophilic polymer, and the reactive group of the second oligonucleotide is substantially reactive with the other of the first or the second end of the hydrophilic polymer. Thus, in embodiments, the first oligonucleotide and the second oligonucleotide are not substantially reactive with one another. In embodiments, the first oligonucleotide and the second oligonucleotide are each capable of reacting with a different end of the hydrophilic polymer.

In embodiments, the first oligonucleotide and the first end of the hydrophilic polymer are conjugated in a first conjugation reaction, followed by conjugation of the second oligonucleotide with the second end of the hydrophilic polymer in a second conjugation reaction. In embodiments, after the first conjugation reaction, the intermediate (i.e., comprising the first oligonucleotide conjugated with the first end of the hydrophilic polymer) is purified prior to the second conjugation reaction. In embodiments, the intermediate is not purified prior to the second conjugation reaction. In embodiments, the purification comprises ion exchange or charge switch chromatography or membrane purification. In embodiments, after the second conjugation reaction (i.e., forming the anchor linking reagent comprising the first oligonucleotide moiety, the hydrophilic polymer moiety, and the second oligonucleotide moiety), the anchor linking reagent is purified to remove unreacted and/or unwanted components of the conjugation reaction. In embodiments, the purification comprises chromatography, membrane purification, gel electrophoresis, size exclusion, or combinations thereof. Methods of performing purification are known by one of skill in the art.

In embodiments, the first conjugation reaction is a polar reaction, and the second conjugation reaction is a cycloaddition reaction. In embodiments, the first conjugation reaction is a cycloaddition reaction, and the second conjugation reaction is a polar reaction. In embodiments, the first oligonucleotide comprises an amine, the second oligonucleotide comprises a thiol, and the hydrophilic polymer comprises an NHS ester at the first end and a maleimide at the second end. In embodiments, the first oligonucleotide comprises an amine, the second oligonucleotide comprises a thiol, and the hydrophilic polymer comprises an NHS ester at the first end and an alkene at the second end. In embodiments, the first oligonucleotide comprises an amine, the second oligonucleotide comprises a thiol, and the hydrophilic polymer comprises an NHS ester at the first end and a disulfide at the second end.

In embodiments, the first oligonucleotide comprises an amine, the second oligonucleotide comprises an alkyne or cycloalkyne, and the hydrophilic polymer comprises an NHS ester at the first end and an azide at the second end. In embodiments, the first oligonucleotide comprises an amine, the second oligonucleotide comprises an azide, and the hydrophilic polymer comprises an NHS ester at the first end and an alkyne or cycloalkyne at the second end. In embodiments, the first oligonucleotide comprises a thiol, the second oligonucleotide comprises an alkyne or cycloalkyne, and the hydrophilic polymer comprises a maleimide at the first end and an azide at the second end. In embodiments, the first oligonucleotide comprises a thiol, the second oligonucleotide comprises an alkyne or cycloalkyne, and the hydrophilic polymer comprises a halide at the first end and an azide at the second end. In embodiments, the first oligonucleotide comprises a thiol, the second oligonucleotide comprises an azide, and the hydrophilic polymer comprises a maleimide at the first end and an alkyne or cycloalkyne at the second end. In embodiments, the first oligonucleotide comprises a thiol, the second oligonucleotide comprises an azide, and the hydrophilic polymer comprises a halide at the first end and an alkyne or cycloalkyne at the second end. Exemplary polar reactions and hydrophilic polymers suitable for polar reactions are shown in FIGS. 53A and 54A, respectively. Exemplary polar and cycloaddition reactions and hydrophilic polymers suitable for polar and cycloaddition reactions are shown in FIGS. 53B and 54B, respectively.

In embodiments, the conjugation linkage resulting from the first and/or second conjugation reactions is a thioether, a disulfide, an amide, or a triazole. In embodiments, the first conjugation reaction produces a first conjugation linkage, and the second conjugation reaction produces a second conjugation linkage that is different from the first conjugation linkage. Thus, in embodiments, the anchor linking reagent comprises a first conjugation linkage between the first oligonucleotide moiety and the hydrophilic polymer moiety selected from a thioether, a disulfide, an amide, or a triazole; and a second conjugation linkage that is different from the first conjugation linkage and selected from a thioether, a disulfide, an amide, or a triazole between the hydrophilic polymer moiety and the second oligonucleotide moiety.

In embodiments, the binding reagent comprises an oligonucleotide. In embodiments, the first oligonucleotide moiety further comprises a sequence that is complementary to an oligonucleotide of the binding reagent. In embodiments, the anchoring reagent comprises an oligonucleotide. In embodiments, the second oligonucleotide moiety further comprises a sequence that is complementary to an oligonucleotide of the anchoring reagent. Thus, in embodiments, the binding of the binding reagent to the anchoring reagent comprises hybridizing (i) the first oligonucleotide moiety of the anchor linking reagent to the oligonucleotide of the binding reagent and (ii) the second oligonucleotide moiety of the anchor linking reagent to the oligonucleotide of the anchoring reagent, thereby forming a complex on the surface comprising the capture reagent, the surface marker displaying agent, and the binding reagent.

An exemplary anchor linking reagent described in embodiments herein is illustrated in FIG. 52. A capture reagent (e.g., capture antibody) for a surface marker displaying agent (e.g., EV) is linked to a surface (e.g., bead) via complementary oligonucleotides on the capture reagent and the surface. The surface marker displaying agent also binds to a binding reagent, which is linked to an oligonucleotide. The surface also comprises an anchoring reagent comprising an oligonucleotide. The oligonucleotide of the anchoring reagent can have the same or a different sequence as the oligonucleotide hybridized to the oligonucleotide of the capture reagent. A anchor linking reagent comprises a first oligonucleotide moiety complementary to the oligonucleotide of the binding reagent, a hydrophilic polymer (e.g., PEG) moiety, and a second oligonucleotide moiety complementary to the oligonucleotide of the anchoring reagent, thereby binding the binding reagent to the anchoring reagent and forming a complex on the surface comprising the capture reagent, the surface marker displaying agent, and the binding reagent.

In embodiments, the hydrophilic polymer moiety is about 0.2 nm to about 200 nm in length. In embodiments, the hydrophilic polymer moiety is about 0.4 nm to about 180 nm in length. In embodiments, the hydrophilic polymer moiety is about 0.2 nm, about 0.4 nm, about 0.6 nm, about 0.8 nm, about 1 nm, about 2 nm, about 3 nm, about 4 nm, about 5 nm, about 6 nm, about 7 nm, about 8 nm, about 9 nm, about 10 nm, about 20 nm, about 30 nm, about 40 nm, about 50 nm, about 60 nm, about 70 nm, about 80 nm, about 90 nm, about 100 nm, about 110 nm, about 120 nm, about 130 nm, about 140 nm, about 150 nm, about 160 nm, about 170 nm, about 180 nm, about 190 nm, or about 200 nm in length.

In embodiments, the hydrophilic polymer is polyethylene glycol (PEG), poly(N-isopropylacrylamide) (PNIPAM), polyacrylamide (PAM), poly(2-oxazoline), polyethyleneimine (PEI), poly(acrylic acid), polymethacrylate, acrylic polymers, poly(ethylene oxide), poly(vinyl alcohol) (PVA) and copolymers thereof, poly(vinylpyrrolidone) (PVP) and copolymers thereof, polyelectrolytes, cucurbit[n]uril hydrate, maleic anhydride copolymer, polyether, or any combination, cross- or co-polymer thereof. In embodiments, the hydrophilic polymer is PEG. In embodiments, the PEG is about 10 kD to about 50 kD. In embodiments, the PEG is about 20 kD.

Releasing Capture Reagent and Eluting Unwanted Components

In embodiments of the invention, after the surface marker displaying agent of interest is indirectly attached to the surface by at least two attachment points, e.g., by the capture reagent and the binding reagent/anchoring reagent complex, the capture reagent is released from the surface and unwanted components are eluted from the surface using, e.g., a washing solution.

In embodiments of the invention, after the EV of interest is indirectly attached to the surface by at least two attachment points, e.g., by the capture reagent and the binding reagent/anchoring reagent complex, the capture reagent is released from the surface and unwanted components are eluted from the surface using, e.g., a washing solution. The unwanted components include, but are not limited to, components soluble in the washing solution, or components that do not have the surface marker that the binding reagent binds to.

The specific release of the capture reagent depends on how the capture reagent is releasably bound to the surface. For example, if the capture reagent is releasably bound to the surface by complementary oligonucleotides, the releasing comprises denaturation, whereas if the capture reagent is bound to the surface by an oligonucleotide comprising a restriction site, releasing comprises cleaving by a restriction endonuclease.

In embodiment of the methods of the invention, the attachment of the EV to the surface by the binding reagent/anchoring reagent complex is stable during the release of the capture reagent from the surface. For example, the hybridized anchoring oligonucleotide and amplicon is stable during the release of the capture reagent from the surface.

In embodiments of the methods of the invention, the hybridized linker oligonucleotide and tag oligonucleotide and the hybridized linker oligonucleotide and anchoring oligonucleotide are stable during the releasing of the capture reagent from the surface.

Releasing and Eluting Surface Marker Displaying Agents of Interest

In embodiments of the methods of the invention, following release of the capture reagent from the surface and elution of unwanted components of the sample from the surface, the surface marker displaying agent of interest is released from the surface. In embodiments, the surface marker displaying agent is released from the surface and further analyzed. In embodiments, the surface marker displaying agents are eluted with the capture antibody still bound to the surface marker displaying agent surface marker (s). The eluted surface marker displaying agents, for example, can then be assayed with the bound capture antibody, or a low-pH elution can be performed to remove the antibodies.

In embodiments of the methods of the invention, following release of the capture reagent from the surface and elution of unwanted components of the sample from the surface, the EV of interest is released from the surface. In embodiments, the EV is released from the surface and further analyzed. In embodiments, the EVs are eluted with the capture antibody still bound to the EV surface marker(s). The eluted EVs, for example, can then be assayed with the bound capture antibody, or a low-pH elution can be performed to remove the antibodies.

Labeled capture antibodies can be coupled to the solid phase using cleavable linkers or multiplex assay linkers. In embodiments, after releasing the antibodies from the solid phase to elute the surface marker displaying agents, e.g., EVs, the surface marker displaying agents, e.g., EVs, are captured with a second marker on an assay plate. In such instances, the surface marker displaying agents, e.g., EVs, already include the labeled capture antibodies, and thus no extra detection step is necessary. Elimination of the extra detection step is advantageous when the desired capture antibody has a high off-rate, which would create challenges in a typical two-step assay.

In embodiments, the surface marker displaying agent, e.g., EV, of interest is released from the surface by denaturing the tag oligonucleotide and the linker oligonucleotide, or the linker oligonucleotide and the anchoring oligonucleotide, or both. In additional embodiments, the surface marker displaying agent, e.g., EV, of interest is released by denaturing the anchoring oligonucleotide and amplicon. In additional embodiments, the anchoring oligonucleotide is detached from the surface, or cleaved in the case that the anchoring oligonucleotide contains a restriction site. In further embodiments, the sequence of the hybridized tag oligonucleotide and the linker oligonucleotide, or sequence of the hybridized linker oligonucleotide and the anchoring oligonucleotide, or both, comprise a restriction site, and the EV is released upon cleavage of the restriction site by a restriction enzyme. Methods of denaturing oligonucleotides and additional methods of releasing bound components are well known to those of skill in the art.

Release, as used herein, refers to delocalization of a previously collected material. Materials that are held at a localized position through chemical bonds or through specific or non-specific binding interactions may be allowed to delocalize by breaking the bond or interaction so that the materials may diffuse or mix into the surrounding media. There are many well-established cleavable chemical linkers that may be used that provide a covalent bond that may be cleaved without requiring harsh conditions. For example, disulfide containing linkers may be cleaved using thiols or other reducing agents, cis-diol containing linkers may be cleaved using periodate, metal-ligand interactions (such as nickel-histidine) may be cleaved by changing pH or introducing competing ligands. Similarly, there are many well-established reversible binding pairs that may be employed (including those that have been identified in the art of affinity chromatography). By way of example, the binding of many antibody-ligand pairs can be reversed through changes in pH, addition of protein denaturants or chaotropic agents, addition of competing ligands, etc. Other suitable reversible binding pairs include complementary nucleic acid sequences, the hybridization of which may be reversed under a variety of conditions including changing pH, decreasing salt concentration, increasing temperature above the melting temperature for the pair and/or adding nucleic acid denaturants (such as formamide).

Release also includes physical delocalization of materials by, for example, mixing, shaking, vortexing, convective fluid flow, mixing by application of magnetic, electrical or optical forces and the like. Where microparticles or materials bound to microparticles have been collected, such physical methods may be used to resuspend the particles in a surrounding matrix. Release may simply be the reverse of a previous collection step (e.g., by any of the mechanisms described above) or collection and release could proceed by two different mechanisms. In one such example, collection of materials (such as an analyte or a complex comprising an analyte) bound to a particle can be achieved by physical collection of the particle. The materials are then released by cleaving a bond or reversing a binding reaction holding the material on the particle. In a second such example, materials (such as an analyte of a complex comprising an analyte are collected on a surface through a binding interaction with a binding reagent that is linked to the surface. The material is then released by breaking a bond or a second binding interaction linking the binding reagent to the surface.

Collection followed by release may be used to concentrate and/or purify analytes in a sample. By collecting in a first volume and releasing into a second smaller volume, an analyte in a sample can be concentrated. Through concentration, it is often possible to significantly improve the sensitivity of a subsequent measurement step. By collecting from a sample and removing some or all of the uncollected sample, potential assay interferents in the sample may be reduced or eliminated. Optionally, removal of the unbound sample may include washing a collected material with and releasing the collected material into defined liquid reagents (e.g., assay or wash buffers) so as to provide a uniform matrix for subsequent assay steps.

As illustrated in FIG. 3(a) of US 2010/0261292, which is incorporated herein by reference in its entirety, the method includes contacting a sample comprising a target analyte (herein, an EV) with a particle linked to a first binding reagent (herein, a capture reagent) that binds the target analyte, wherein the first binding reagent is linked to a first targeting agent and the particle is linked to a second targeting agent, and the first binding reagent and the particle are linked via a binding reaction between the first and second targeting agents to form a complex comprising said target analyte bound to said first binding reagent. The complex is then collected and unbound components in the sample are separated from the complex.

Alternative Stapling Methods

In embodiments, the present disclosure provides methods of isolating a surface marker displaying agent using multiple (e.g., three, four, or four or more) markers for the same surface marker displaying agent. In embodiments, a method of isolating a surface marker displaying agent of interest in a sample comprises: contacting the sample with a surface and selectively binding the surface marker displaying agent of interest to: (i) first and second binding reagents, wherein the first binding reagent and the second binding reagent comprise complementary nucleotide sequences; (ii) a capture reagent releasably bound to the surface, wherein the surface further comprises an anchoring reagent, and binding the anchoring reagent to the second binding reagent, wherein the anchoring reagent is bound to the second binding reagent by an adaptor oligonucleotide, wherein the adaptor oligonucleotide comprises (1) a nucleotide sequence complementary to a nucleotide sequence of the anchoring reagent, and (2) a nucleotide sequence complementary to a nucleotide sequence of the second binding reagent, thereby forming a complex on the surface comprising the capture reagent, the surface marker displaying agent and the binding reagent; and releasing the capture reagent from the surface and eluting unwanted components of the sample from the surface, thereby isolating the surface marker displaying agent of interest. In embodiments, the surface marker displaying agent is a cell. In embodiments, the surface marker displaying agent is a virus or viral particle. In embodiments, the surface marker displaying agent is an organelle. In embodiments, the surface marker displaying agent is a vesicle. In embodiments, the surface marker displaying agent is an extracellular vesicle or exosome.

In embodiments, a method of isolating a surface marker displaying agent of interest in a sample comprises: contacting the sample with a surface and selectively binding the surface marker displaying agent of interest to: (i) first, second, and third binding reagents, wherein the first binding reagent and the second binding reagent comprise complementary nucleotide sequences; (ii) a capture reagent releasably bound to the surface, wherein the capture reagent and the third binding reagent comprise complementary nucleotide sequences, thereby forming a complex on the surface comprising the capture reagent, the surface marker displaying agent, and the first, second, and third binding reagents; and releasing the capture reagent from the surface and eluting unwanted components of the sample from the surface, thereby isolating the surface marker displaying agent of interest. In embodiments, the surface marker displaying agent can be bound to additional binding reagents, each comprising a nucleotide sequence complementary to a nucleotide sequence of at least one other binding reagent. In embodiments, the surface marker displaying agent is a cell. In embodiments, the surface marker displaying agent is a virus or viral particle. In embodiments, the surface marker displaying agent is an organelle. In embodiments, the surface marker displaying agent is a vesicle. In embodiments, the surface marker displaying agent is an extracellular vesicle or exosome.

In embodiments, a method of isolating a surface marker displaying agent of interest in a sample comprises: contacting the sample with a surface and selectively binding the surface marker displaying agent of interest to: (i) first, second, and third binding reagents, wherein the first binding reagent comprises a nucleotide sequence complementary to a portion of a nucleotide sequence of the second binding reagent, and the third binding reagent comprises a nucleotide sequence complementary to a different portion of the nucleotide sequence of the second binding reagent; (ii) a capture reagent releasably bound to the surface, thereby forming a complex on the surface comprising the capture reagent, the surface marker displaying agent and the first, second, and third binding reagents; and releasing the capture reagent from the surface and eluting unwanted components of the sample from the surface, thereby isolating the surface marker displaying agent of interest. In embodiments, the surface marker displaying agent can be bound to additional binding reagents, each comprising a nucleotide sequence complementary to a nucleotide sequence of at least one other binding reagent. In embodiments, the surface marker displaying agent is a cell. In embodiments, the surface marker displaying agent is a virus or viral particle. In embodiments, the surface marker displaying agent is an organelle. In embodiments, the surface marker displaying agent is a vesicle. In embodiments, the surface marker displaying agent is an extracellular vesicle or exosome.

In embodiments, the present disclosure provides methods of isolating an EV using multiple (e.g., three) markers for the same EV. In embodiments, a method of isolating an EV of interest in a sample comprises: contacting the sample with a surface and selectively binding the EV of interest to: (i) first and second binding reagents, wherein the first binding reagent and the second binding reagent comprise complementary nucleotide sequences; (ii) a capture reagent releasably bound to the surface, wherein the surface further comprises an anchoring reagent, and binding the anchoring reagent to the second binding reagent, wherein the anchoring reagent is bound to the second binding reagent by an adaptor oligonucleotide, wherein the adaptor oligonucleotide comprises (1) a nucleotide sequence complementary to a nucleotide sequence of the anchoring reagent, and (2) a nucleotide sequence complementary to a nucleotide sequence of the second binding reagent, thereby forming a complex on the surface comprising the capture reagent, the EV and the binding reagent; and releasing the capture reagent from the surface and eluting unwanted components of the sample from the surface, thereby isolating the EV of interest.

In embodiments, a method of isolating an EV of interest in a sample comprises: contacting the sample with a surface and selectively binding the EV of interest to: (i) first, second, and third binding reagents, wherein the first binding reagent and the second binding reagent comprise complementary nucleotide sequences; (ii) a capture reagent releasably bound to the surface, wherein the capture reagent and the third binding reagent comprise complementary nucleotide sequences, thereby forming a complex on the surface comprising the capture reagent, the EV, and the first, second, and third binding reagents; and releasing the capture reagent from the surface and eluting unwanted components of the sample from the surface, thereby isolating the EV of interest. In embodiments, the EV can be bound to additional binding reagents, each comprising a nucleotide sequence complementary to a nucleotide sequence of at least one other binding reagent.

In embodiments, a method of isolating an EV of interest in a sample comprises: contacting the sample with a surface and selectively binding the EV of interest to: (i) first, second, and third binding reagents, wherein the first binding reagent comprises a nucleotide sequence complementary to a portion of a nucleotide sequence of the second binding reagent, and the third binding reagent comprises a nucleotide sequence complementary to a different portion of the nucleotide sequence of the second binding reagent; (ii) a capture reagent releasably bound to the surface, thereby forming a complex on the surface comprising the capture reagent, the EV and the first, second, and third binding reagents; and releasing the capture reagent from the surface and eluting unwanted components of the sample from the surface, thereby isolating the EV of interest. In embodiments, the EV can be bound to additional binding reagents, each comprising a nucleotide sequence complementary to a nucleotide sequence of at least one other binding reagent.

In embodiments, the capture reagent is releasably bound to the surface by an oligonucleotide comprising a first cleavage site, e.g., restriction site, and wherein the adaptor oligonucleotide comprises a second cleavage site, e.g., restriction site. In embodiments, the surface is a bead or a planar substrate having multiple binding sites.

In embodiments, the sample comprises at least two EVs of interest, and the surface comprises at least a first bead and a second bead, wherein a first capture reagent releasably bound to the first bead binds to a first EV and a second capture reagent releasably bound to the second bead binds to a second EV.

In embodiments, the sample comprises at least two EVs of interest and the surface comprises at least a first region and a second region, wherein a first capture reagent releasably bound to the first region binds to a first EV and a second capture reagent releasably bound to the second region binds to a second EV.

In embodiments, a method of isolating a surface marker displaying agent, e.g., an EV, of interest from a sample using multiple (e.g., three) markers and a single solid phase is illustrated in FIG. 32 and includes:

1. Contacting the sample containing the surface marker displaying agent, e.g., EV, of interest with: a capture reagent releasably bound to a solid phase (e.g., a bead or a planar surface having multiple binding sites), wherein the surface further comprises an anchoring reagent (e.g., an anchoring oligonucleotide); and first and second binding reagents (e.g., detection antibodies).

In embodiments, the capture reagent is bound to the solid phase via an oligonucleotide sequence comprising a first cleavage site. In embodiments, the first and second binding reagents comprise complementary nucleotide sequences. In embodiments, the adaptor oligonucleotide comprises a complementary nucleotide sequence to a nucleotide sequence of the anchoring reagent, and a complementary nucleotide sequence to a nucleotide sequence of the second binding reagent. In embodiments, the cleavage site is a restriction site. In embodiments, the cleavage site is a labile linker. In embodiments, the labile linker is a heat-labile, photolabile, or chemically-labile linker. In embodiments, the labile linker is an oligonucleotide that is complementary to an oligonucleotide bound to the surface or is an oligonucleotide comprising a restriction site cleavable by a restriction endonuclease. In embodiments, the labile linker is a small molecule that binds to a protein on the surface.

In embodiments, the first binding reagent includes a first oligonucleotide sequence that includes a first barcode sequence and a complementary nucleotide sequence to the second binding reagent. In embodiments, the second binding reagent includes a second oligonucleotide sequence that includes a second barcode sequence, a complementary nucleotide sequence to the first binding reagent, and a complementary nucleotide sequence to an adaptor oligonucleotide. In embodiments, the capture reagent is bound to the solid phase via a third oligonucleotide sequence that includes a third barcode sequence and a first cleavage site. In embodiments, the first cleavage site is a first restriction site. In embodiments, the first cleavage site is a labile linker.

A "barcode sequence" or "barcode oligonucleotide sequence," as used herein, refers to a short nucleotide (typically between about 5 and about 40 nucleotides in length) that allows a corresponding nucleotide or molecule to be identified. In embodiments, the corresponding nucleotide or molecule is attached to the barcode sequence. In embodiments, the molecule is a peptide, a protein, a protein complex, an antibody, or a vesicle. In embodiments, the barcode sequence is a unique nucleotide identifiable by sequencing. In embodiments, the barcode sequence is hybridizable to a complementary detectable probe. In such embodiments, the complementary detectable probe hybridizes to the barcode sequence, allowing the corresponding nucleotide or molecule to be detected. Barcode technologies are described in, e.g., Winzeler et al., Science 285:901-906 (1999), Eason et al., Proc Natl Acad Sci 101(30):11046-11051 (2004), and Fredriksson et al., Nature Methods 4(4): 327-329 (2007), each of which is herein incorporated by reference in its entirety.

2. Adding an adaptor oligonucleotide to the complex. In embodiments, the adaptor oligonucleotide includes a nucleotide sequence complementary to the anchoring oligonucleotide, a second cleavage site (for example, a second restriction site), a fourth barcode sequence, and a complementary nucleotide sequence to the second binding reagent. In some embodiments, the adaptor oligonucleotide hybridizes with the anchoring oligonucleotide and second binding reagent, thereby forming a complex on the solid phase comprising: the capture reagent, EV, first and second binding reagents, and the adaptor oligonucleotide.

In embodiments, the second oligonucleotide sequence does not include a barcode sequence.

3. Eluting unwanted components (e.g., unbound surface marker displaying agent, e.g., EVs or binding reagents) from the sample.

4. Adding polymerase, ligase, or both to the sample to ligate together the second, third, and fourth oligonucleotides at the ligation site, thereby forming a "staple."

In embodiments, the complementary nucleotide sequences of the second, third, and fourth oligonucleotides are extended with a polymerase and/or ligated together with a ligase to remove any gaps in the sequence. In embodiments, the complementary nucleotide sequences of the second, third, and fourth oligonucleotides are ligated together using additional short oligonucleotides that are complementary to any gaps in the sequence.

5. Releasing the capture binding reagent from the solid phase by cleaving at the first cleavage site and eluting unwanted components (e.g., unbound surface marker displaying agent, e.g., EVs) from the sample.

6. Isolating the surface marker displaying agent, e.g., EV, by cleaving at the second cleavage site, or by eluting the adaptor oligonucleotide from the solid phase, to release the surface marker displaying agent, e.g., EV, of interest.

In embodiments, visualization or quantification of the surface marker displaying agents, e.g., EVs, can be performed using detectably labeled oligonucleotides complementary to the first, second, third, or fourth barcode sequences, prior to releasing the surface marker displaying agents, e.g., EVs, from the solid phase. In embodiments, the capture reagent, the first binding reagent, and/or the second binding reagent can be detected using a detectable probe as described herein, for example, a fluorescent or electrochemiluminescent probe. In embodiments, surface marker displaying agents, e.g., EVs, can be fixed and permeabilized for in situ immunoassays or FISH, prior to releasing the surface marker displaying agents, e.g., EVs, from the solid phase.

In embodiments, two or more different populations of surface marker displaying agents, e.g., EVs, of interest (i.e., different surface marker displaying agents, e.g., EVs) can be isolated. In embodiments, two or more different surface marker displaying agents, e.g., EVs, of interest are immobilized on two different solid phases (e.g., different sets of beads or a planar substrate having multiple binding sites). In embodiments, a single sample is mixed with all of the solid phases in a single reaction capturing different populations of surface marker displaying agents, e.g., EVs, on each solid phase. In embodiments, two or more sets of capture and binding reagents (with each set having one capture and two binding reagents per population of surface marker displaying agent, e.g., EV) are added to the reaction to capture different surface marker displaying agents, e.g., EVs, on different solid phases. The different solid phases may be separated by physical properties (e.g., magnetism, size, or color), or the different surface marker displaying agents, e.g., EVs, may be eluted together. In embodiments, the different EVs are distinguished using detectably labeled oligonucleotides as described herein.

In embodiments, the method includes isolating two different surface marker displaying agents, e.g., EVs, of interest (i.e., first and second surface marker displaying agents, e.g., EVs) from the sample, wherein the two different surface marker displaying agents, e.g., EVs, of interest bind to the same detection reagents, and to different capture reagents on two different solid phases, as illustrated in FIG. 33. Thus, in embodiments, the capture reagent (which may include the third barcode sequence and the first cleavage site), and the adaptor oligonucleotide (which may include the fourth barcode sequence and the second cleavage site) are different for the two different surface marker displaying agents, e.g., EVs, of interest, while the first and second binding reagents (and therefore the second and third barcode sequences) are the same for the two different surface marker displaying agents, e.g., EVs, of interest. In embodiments, the two different surface marker displaying agents, e.g., EVs, of interest are isolated separately by cleaving with the first restriction site for the first surface marker displaying agent, e.g., EV, then cleaving with the first restriction site for the second surface marker displaying agent, e.g., EV. In embodiments, the two different surface marker displaying agents, e.g., EVs, of interest are isolated separately by using two different types of solid phases (e.g., beads) that can be separated by size, gravity, magnetism (e.g., magnetic beads for the first surface marker displaying agent, e.g., EV and non-magnetic beads for the second surface marker displaying agent, e.g., EV), bead color, and the like. In embodiments, the two different surface marker displaying agents, e.g., EVs, of interest are isolated together by elution, and the first barcodes are used to distinguish between the two different surface marker displaying agents, e.g., EVs, since the first barcodes for the first and second surface marker displaying agents, e.g., EVs, are different. In embodiments, the second, third, and fourth barcodes can be sequenced to determine the total number of the two different types of surface marker displaying agents, e.g., EVs.

In embodiments, the method includes isolating two different surface marker displaying agents, e.g., EVs, of interest (i.e., first and second surface marker displaying agents, e.g., EVs) from the sample, wherein the two different surface marker displaying agents, e.g., EVs, of interest bind to one of the same binding reagents, and to different capture reagents and one different binding reagent on different solid supports, as illustrated in FIG. 34. Thus, in embodiments, the capture reagent (which may include the third barcode sequence and the first cleavage site), and one of the two binding reagents (which may include the first barcode sequence or the second barcode sequence), and the adaptor oligonucleotide (which may include the fourth barcode sequence, the second cleavage site, and the complementary nucleotide sequence to the anchoring oligonucleotide) are different for the two surface marker displaying agents, e.g., EVs, of interest, while the other of the two binding reagents (which may include the first barcode sequence or the second barcode sequence) are the same for the two different surface marker displaying agents, e.g., EVs, of interest. In embodiments, the second, third, and fourth barcodes can be sequenced to determine the relative ratio of the two different surface marker displaying agents, e.g., EVs, of interest in the sample.

In embodiments, the method includes isolating two different surface marker displaying agents, e.g., EVs, of interest (i.e., first and second surface marker displaying agents, e.g., EVs) from the sample, wherein the two different surface marker displaying agents, e.g., EVs, of interest bind to different capture reagents on different solid supports, and to different first and second binding reagents as illustrated in FIG. 35. Thus, in embodiments, the capture reagent (which may include the third barcode sequence and the first cleavage site), the first and second binding reagents (which may include the first and second barcode sequences), and the adaptor oligonucleotide (which may include the fourth barcode sequence, the second cleavage site, and the complementary nucleotide sequence to the anchoring oligonucleotide) are different for the two surface marker displaying agents, e.g., EVs, of interest. In embodiments, the second, third, and fourth barcodes can be sequenced to determine the relative ratio of the two different surface marker displaying agents, e.g., EVs, of interest in the sample.

In embodiments, the method includes isolating two different surface marker displaying agents, e.g., EVs, of interest (i.e., first and second surface marker displaying agents, e.g., EVs) from the sample, wherein the two different surface marker displaying agents, e.g., EVs, of interest bind to different capture reagents on different solid supports, and to different first and second binding reagents, and wherein the second oligonucleotide further includes a first amplification primer site before the second barcode sequence, and the adaptor oligonucleotide further includes a second amplification primer site after the fourth barcode sequence as illustrated in FIG. 36. Thus, in embodiments, the second, third, and fourth barcode sequences are joined together by extension and ligation of the first and second amplification primer sites.

In embodiments, the present disclosure provides a method of isolating a surface marker displaying agent of interest in a sample, comprising: contacting the sample with, and selectively binding the surface marker displaying agent of interest to: (i) first and second binding reagents, wherein the first binding reagent and the second binding reagent comprise complementary nucleotide sequences, and (ii) a capture reagent, wherein the capture reagent is linked to an anchoring reagent, wherein the anchoring reagent comprises: (1) a nucleotide sequence complementary to the second binding reagent nucleotide sequence and (2) at least one cleavage site, and wherein the anchoring reagent is bound to the surface; hybridizing the anchoring reagent with the second binding reagent, thereby forming a complex on the surface comprising the capture reagent, the surface marker displaying agent, and the first and second binding reagents; and releasing the anchoring reagent from the surface and eluting unwanted components of the sample from the surface, thereby isolating the surface marker displaying agent of interest. In embodiments, the surface marker displaying agent is a cell. In embodiments, the surface marker displaying agent is a virus or viral particle. In embodiments, the surface marker displaying agent is an organelle. In embodiments, the surface marker displaying agent is a vesicle. In embodiments, the surface marker displaying agent is an extracellular vesicle or exosome.

In embodiments, the present disclosure provides a method of isolating an EV of interest in a sample, comprising: contacting the sample with, and selectively binding the EV of interest to: (i) first and second binding reagents, wherein the first binding reagent and the second binding reagent comprise complementary nucleotide sequences, and (ii) a capture reagent, wherein the capture reagent is linked to an anchoring reagent, wherein the anchoring reagent comprises: (1) a nucleotide sequence complementary to the second binding reagent nucleotide sequence and (2) at least one cleavage site, and wherein the anchoring reagent is bound to the surface; hybridizing the anchoring reagent with the second binding reagent, thereby forming a complex on the surface comprising the capture reagent, the EV, and the first and second binding reagents; and releasing the anchoring reagent from the surface and eluting unwanted components of the sample from the surface, thereby isolating the EV of interest.

In embodiments, the anchoring reagent comprises biotin, and the surface comprises streptavidin. In embodiments, the at least one cleavage site is a restriction site. In embodiments, the anchoring reagent comprises two cleavage sites. In embodiments, the anchoring reagent comprises two restriction sites.

In embodiments, the capture reagent is linked to the anchoring reagent with PEG, poly(A), or a polynucleotide sequence.

In embodiments, a method of isolating an EV of interest from a sample using multiple (e.g., three) markers and a single solid phase is illustrated in FIG. 31A. In embodiments, the first binding reagent includes a nucleotide sequence comprising a first amplification primer site, a first barcode sequence, and a complementary nucleotide sequence to the second binding reagent nucleotide sequence. In embodiments, the second binding reagent includes a nucleotide sequence comprising a complementary nucleotide sequence to the first binding reagent, a second barcode sequence, and a complementary nucleotide sequence to the anchoring reagent nucleotide sequence. In embodiments, the capture reagent is linked via a flexible linker to an anchoring reagent, and the anchoring reagent comprises two cleavage sites (e.g., first and second restriction sites), a second amplification primer site, a third barcode sequence, a complementary nucleotide sequence to the second binding reagent nucleotide sequence, and biotin. In embodiments, the anchoring reagent is anchored to a solid phase that comprises streptavidin.

Assaying the EV

In embodiments of the invention, the surface marker displaying agent of interest is assayed. In embodiments, the assay is an ultrasensitive assay. In embodiments of the invention, the surface marker displaying agent of interest is assayed while bound to the surface, either by both attachment points, e.g., by the capture reagent and by the binding reagent/anchoring reagent, or after the capture reagent is released from the surface. In embodiments, the surface marker displaying agent is a cell. In embodiments, the surface marker displaying agent is a virus or viral particle. In embodiments, the surface marker displaying agent is an organelle. In embodiments, the surface marker displaying agent is a vesicle. In embodiments, the surface marker displaying agent is an extracellular vesicle or exosome.

In embodiments of the invention, the EV of interest is assayed. In embodiments, the assay is an ultrasensitive assay. In embodiments of the invention, the EV of interest is assayed while bound to the surface, either by both attachment points, e.g., by the capture reagent and by the binding reagent/anchoring reagent, or after the capture reagent is released from the surface. In embodiments, the assaying comprises contacting a detectably labeled oligonucleotide with the surface, wherein the oligonucleotide is complementary to the amplicon. In embodiments, the binding reagent is detectably labeled.

In embodiments of the invention, bound surface marker displaying agents, e.g., EVs, of interest are subjected to a measuring step, which are known to those of skill in the art, for example, as disclosed in International Appl. No. PCT/US2015/030925, published as WO 2015/175856, which is incorporated by reference in its entirety. This application describes an ultrasensitive assay format for soluble proteins that marry a variation of proximity ligation amplification (PLA) with ECL detection to provide state-of-the-art sensitivity. The measuring step of the method can comprise imaging an optical signal from the surface to generate an image that consists of a plurality of pixels, wherein each resolvable binding region maps to one or more pixels or groups of pixels in the image. Image analysis to identify pixels or sets of pixels having a signal indicative of a binding event (detection complex) can be accomplished using art recognized methods.

In one embodiment, the resolvable binding regions are elements of an array. In embodiments, the array is an array of micro-wells or nanowells, e.g., individual depressions or wells of a unitary substrate. Preferably, the volume of the wells is less than 500 uL, 300 uL, 150 uL, 100 uL, 10 uL, 1 uL, 100 nL, preferably less than 50 nL. In one embodiment, the volume of the wells ranges from approximately 10 aL-100 pL. Optionally, the wells may be configured to hold a microparticle.

In one embodiment, at least 50% of the resolvable binding regions positioned on a substrate and addressed during an assay contain either zero or one analyte molecule. Preferably, at least 80%, more preferably at least 95%, and most preferably at least 99% of the resolvable binding regions contain either zero or one analyte molecule. The concentration of analyte molecules in the sample is determined at least in part using a calibration curve, a Poisson distribution analysis and/or a Gaussian distribution analysis of the number of binding regions that contain at least one or one analyte molecule. In a specific embodiment, the surface comprises a plurality of particles each including a plurality of capture reagents for an analyte molecule and the plurality of particles is distributed across a plurality of resolvable binding regions (e.g., an array of micro- or nano-wells). Therefore, the method includes: (i) binding one or more analyte molecules to one or more capture reagents on the surface, (ii) distributing the plurality of particles across an array of resolvable binding regions; and (iii) determining the presence or absence of an analyte molecule in each resolvable binding regions, so as to identify the number of binding domains that contain an analyte molecule and/or the number of binding domains that do not contain an analyte molecule.

Alternatively, labels used to detect analyte molecules can be fluorescent species that can be used in single molecule fluorescence detection, e.g., fluorescence correlation spectroscopy, and/or fluorescence cross-correlation spectroscopy. Single molecule fluorescence detection comprises flowing an eluent that includes a detectable species through a capillary, focusing a light source on a volume within the capillary to create an interrogation zone and observing the interrogation zone with a light detector to detect the passage of fluorescent molecules through the interrogation zone.

In one embodiment, the surface marker displaying agent, e.g., EV, of interest in the sample may be measured using electrochemiluminescence-based assay formats, e.g. electro-chemiluminescence (ECL) based immunoassays. Species that can be induced to emit ECL (ECL-active species) have been used as ECL labels, e.g., i) organometallic compounds where the metal is from, for example, the noble metals of group VIII, including Ru-containing and Os-containing organometallic compounds such as the tris-bipyridyl-ruthenium (RuBpy) moiety and ii) luminol and related compounds. Species that participate with the ECL label in the ECL process are referred to herein as ECL coreactants. Commonly used coreactants include tertiary amines (e.g., see U.S. Pat. No. 5,846,485 and U.S. Provisional Application No. 62/787,892, filed on Jan. 3, 2019), oxalate, and persulfate for ECL from RuBpy and hydrogen peroxide for ECL from luminol (see, e.g., U.S. Pat. No. 5,240,863). In embodiments, the ECL coreactant is tripropylamine (TPA). In embodiments, the ECL coreactant is N-Butyldiethanolamine (BDEA). In embodiments, the ECL coreactant is N,N-dibutylethanolamine (DBAE). In embodiments, the ECL coreactant is included in a read buffer for the ECL assay. In embodiments, the read buffer comprises an ECL coreactant and a surfactant. In embodiments, the surfactant is TRITON X-100. In embodiments, the read buffer does not comprise TRITON X-100. In embodiments, the surfactant does not disrupt a surface of the surface marker displaying agent. In embodiments, the surfactant does not disrupt a lipid bilayer membrane. In embodiments, the surfactant does not disrupt a membrane of an EV. In embodiments, the surfactant is BRIJ, TWEEN, PLURONIC or KOLLIPHOR. In embodiments, the surfactant is TWEEN. In embodiments, the read buffer does not comprise a surfactant.

The light generated by ECL labels can be used as a reporter signal in diagnostic procedures (Bard et al., U.S. Pat. No. 5,238,808, herein incorporated by reference). For instance, an ECL label can be covalently coupled to a binding agent such as an antibody, nucleic acid probe, receptor or ligand; the participation of the binding reagent in a binding interaction can be monitored by measuring ECL emitted from the ECL label. Alternatively, the ECL signal from an ECL-active compound may be indicative of the chemical environment (see, e.g., U.S. Pat. No. 5,641,623 which describes ECL assays that monitor the formation or destruction of ECL coreactants).

The methods of the invention may be applied to single-plex or multiplex formats where multiple assay measurements are performed on a single sample. Multiplex measurements that can be used with the invention include, but are not limited to, multiplex measurements i) that involve the use of multiple sensors; ii) that use discrete assay domains on a surface (e.g., an array) that are distinguishable based on location on the surface; iii) that involve the use of reagents coated on particles that are distinguishable based on a particle property such as size, shape, color, etc.; iv) that produce assay signals that are distinguishable based on optical properties (e.g., absorbance or emission spectrum) or v) that are based on temporal properties of assay signal (e.g., time, frequency or phase of a signal).

The invention includes methods for detecting and counting individual detection complexes. In a specific embodiment, the surface can comprise a plurality of capture reagents for one or more surface marker displaying agents, e.g., EVs, that are present in a sample and the plurality of capture reagents are distributed across a plurality of resolvable binding regions positioned on the surface. Under the conditions used to carry out and analyze a measurement, a "resolvable binding region" is the minimal surface area associated with an individual binding event that can be resolved and differentiated from another area in which an additional individual binding event is occurring. Therefore, the method consists of binding one or more surface marker displaying agents, e.g., EVs, of interest to one or more capture reagents on the surface, determining the presence or absence of the surface marker displaying agent, e.g., EV, in a plurality of resolvable binding regions on the surface, and identifying the number of resolvable binding regions that contain a surface marker displaying agent, e.g., EV, of interest and/or the number of analyte domains that do not contain a surface marker displaying agent, e.g., EV, of interest.

The resolvable binding regions can be optically interrogated, in whole or in part, i.e., each individual resolvable binding region can be individually optically interrogated and/or the entire surface comprising a plurality of resolvable binding regions can be imaged and one or more pixels or groupings of pixels within that image can be mapped to an individual resolvable binding region. A resolvable binding region may also be a microparticle within a plurality of microparticles. The resolvable binding regions exhibiting changes in their optical signature can be identified by a conventional optical detection system. Depending on the detected species (e.g., type of fluorescence entity, etc.) and the operative wavelengths, optical filters designed for a particular wavelength can be employed for optical interrogation of the resolvable binding regions. In embodiments where optical interrogation is used, the system can comprise more than one light source and/or a plurality of filters to adjust the wavelength and/or intensity of the light source. In some embodiments, the optical signal from a plurality of resolvable binding regions is captured using a CCD camera. Other non-limiting examples of camera imaging systems that can be used to capture images include charge injection devices (CIDs), complementary metal oxide semiconductors (CMOSs) devices, scientific CMOS (sCMOS) devices, and time delay integration (TDI) devices, as will be known to those of ordinary skill in the art. In some embodiments, a scanning mirror system coupled with a photodiode or photomultiplier tube (PMT) can be used for imaging.

Additional methods of interrogating whole surface marker displaying agents, e.g., EVs, are known in the art, such as by bioluminescence, and NMR. In additional embodiments, for example, the surface marker displaying agent, e.g., EV, of interest is assessed by sequencing and/or polymerase-based methods, e.g., quantitative polymerase chain reaction, next generation sequencing, or both.

Thus, an exemplary protocol for the methods described herein includes: coating a surface, e.g., a plate having a plurality of wells, each well comprising streptavidin, with a capture reagent, e.g., a biotinylated capture antibody, and incubating the biotinylated capture antibody on the plate, e.g., about 1 hour to about 12 hours; washing the plate, adding dilution buffer and a sample containing the EV of interest to the plate, and incubating the sample for about 1 hour to capture the EVs in the sample with the capture antibody; washing the plate, adding a detection reagent, e.g., a detection antibody, and incubating the sample with the detection antibody for about 1 hour to label the captured EVs; and washing the plate, adding assay buffer, and detecting the EVs labeled with the detection antibody with an instrument, e.g., an instrument configured to detect electrochemiluminescence.

In a multiplex variant of the exemplary protocol described above, the plate is coated with a plurality of different capture antibodies, which may capture different EVs of interest in one sample, and the different EVs of interest are detected with a common detection antibody. The multiplexed methods described herein advantageously allow the same sample containing multiple EVs of interest to be assayed in one experiment, which may help to reduce the amount of sample required and also decrease sample-to-sample variability. In embodiments, a multiplexed method is used to compare multiple capture reagents to the same target and facilitate selection of a preferred capture antibody.

Multiplex methods can also facilitate comparison of different EVs in a same sample, e.g., determining the relative abundance of different EVs. In embodiments, the relative abundance of EVs in a sample can be measured by using a plurality of different capture reagents to capture different EVs expressing different markers, then detecting each type of captured EVs with the same detection reagent to a common marker on the different EVs. In embodiments, the relative abundance of EVs in a sample can be measured by using the same capture reagent to capture different EVs expressing a common marker, then using a plurality of different detection reagents to determine the different markers expressed by the EVs.

Controls

In an additional embodiment, the assay format described herein further includes one or more control assays. A negative control can be included on a binding domain which includes a capture antibody that does not have a corresponding detection antibody, thereby providing a consistent background signal for all samples. Measurement of signal above a preset threshold value can indicate improper assay processing or the presence of a sample-dependent matrix effect causing non-specific binding of labeled detection probe. Moreover, a specimen control can also be included in the assay for a human target antigen (such as a secreted or intracellular protein) that performs multiple control functions. A positive signal will indicate the presence of human material, and therefore test for sample addition and quality. Measurement of a signal below a predefined threshold would indicate that no sample was added, that a failure in the reagents or process occurred, or that substances that interfere with amplification or detection are present. In addition to internal controls, external positive and negative controls can also be used with the method and/or kit. The negative control comprises a representative matrix without any target proteins.

In embodiments, a control surface marker displaying agent is used to establish the performance of the assay or provide a reliable sample for normalizing data, or both. In embodiments, control surface marker displaying agents facilitate comparison of results between plates or experiments, or both. In embodiments, a control surface marker displaying agent is used for correction of nonlinearity of an assay at upper and lower ends of the calibration curve.

In embodiments, a control EV is used to establish the performance of the assay or provide a reliable sample for normalizing data, or both. In embodiments, control EVs facilitate comparison of results between plates or experiments, or both. In embodiments, a control EV is used for correction of nonlinearity of an assay at upper and lower ends of the calibration curve. For example, it may be advantageous to utilize a synthetic EV, which allows for selection of surface antigens, and the copy number can be tuned to match the biological material of interest. In embodiments, the control EV has similar size and density to the EV of interest. In embodiments, the synthetic EV is produced using polymer beads of similar size and density to small EVs. In embodiments, tetraspanin proteins are attached to the surface of the synthetic EV.

In embodiments, well-characterized, biologically-derived EVs that are used as controls. In embodiments, control EVs are produced from a cell line selected for its efficiency at producing EVs. In embodiments, EVs from cell lines or biofluids are used as negative controls, such as from platelets, PBMCs, THP-1 cells, Expi293 cells, and HCT-15 cells. In embodiments, synthetic EVs, such as unilamellar vesicles or beads that have similar physiochemical properties as the EVs of interest, are used as controls.

In embodiments, a control cell line produces EVs that express at least one specific surface marker. In embodiments, a control cell line suitable for astrocyte specific surface markers, e.g., A2B5, ATP1B2 or CD44, is Expi293, TT, or THP-1. In embodiments, a control cell line suitable for neuron specific surface markers, e.g., L1CAM, N-cadherin, NCAM, NRCAM, CD27, CD90, or synaptophysin, is MCF7, PANC-1, SW480, THP-1, Expi293, U87-MG, NK92, SH-SY5Y, TT, U2-OS, or HCT-15. In embodiments, a control cell line suitable for astrocyte and neuron specific surface markers, e.g., ALCAM CD166, CD40, FGFR3, GJA1 (connexin 43), integrin B1 (CD29), or CD24, is Exp293, U87-MG, HCT116, TT, THP-1, or MDMB-468.

Cargo Analysis

The invention further provides methods of identifying, quantitating, or both, a protein, a nucleic acid, a liquid, or a combination thereof, encapsulated by a surface marker displaying agent of interest in a sample, comprising: (a). contacting the sample with a surface and selectively binding the surface marker displaying agent of interest to: (i) a capture reagent releasably bound to the surface, wherein the surface further comprises an anchoring reagent; and (ii) a binding reagent; (b). binding the anchoring reagent to the binding reagent, thereby forming a complex on the surface comprising the capture reagent, the surface marker displaying agent and the binding reagent; (c). releasing the capture reagent from the surface and eluting unwanted components of the sample from the surface, thereby isolating the surface marker displaying agent of interest; and (d). conducting an assay to identify, quantitate, or both, the encapsulated protein, nucleic acid, lipid, or combination thereof. In embodiments, the assay is an ultrasensitive assay.

In additional embodiments, the invention provides methods of identifying, quantitating, or both, a protein, a nucleic acid, a lipid, or combination thereof, encapsulated by a surface marker displaying agent, comprising: (a). contacting the sample comprising an surface marker displaying agent with a surface, wherein the surface marker displaying agent encapsulates the target protein, nucleic acid or metabolite, and selectively binding the surface marker displaying agent to: (i) a capture reagent releasably bound to the surface, wherein the surface further comprises an anchoring oligonucleotide; and (ii) a binding reagent, wherein the binding reagent comprises a primer oligonucleotide, thereby forming a complex on the surface comprising the capture reagent, the surface marker displaying agent and the binding reagent; (b). binding a circular oligonucleotide template to the primer oligonucleotide to form an amplicon by rolling circle amplification, wherein the amplicon comprises a sequence that is complementary to the anchoring oligonucleotide; (c). hybridizing the anchoring oligonucleotide to the amplicon to form a second complex on the surface comprising the capture reagent, the surface marker displaying agent, the binding reagent and anchoring oligonucleotide; (d). releasing the capture reagent from the surface and eluting unwanted components of the sample from the surface, thereby isolating the surface marker displaying agent of interest; and (e). conducting an assay to identify, quantitate, or both, the protein, nucleic acid, lipid, or combination thereof. In embodiments, the assay is an ultrasensitive assay.

The invention further provides a method of identifying, quantitating, or both, a protein, a nucleic acid, a lipid, or a combination thereof, encapsulated by a surface marker displaying agent in a sample, comprising: (a). contacting the sample comprising a surface marker displaying agent with a surface, wherein the surface marker displaying agent encapsulates a protein, a nucleic acid, a lipid, or a combination thereof, and selectively binding the surface marker displaying agent to: (i) a capture reagent releasably bound to the surface, wherein the surface further comprises an anchoring oligonucleotide; and (ii) a binding reagent, wherein the binding reagent comprises a tag oligonucleotide, thereby forming a complex on the surface comprising the capture reagent, the surface marker displaying agent, and the binding reagent; (b). hybridizing a linker oligonucleotide to the tag oligonucleotide and to the anchoring oligonucleotide to form a second complex on the surface comprising the capture reagent, the surface marker displaying agent, the binding reagent, and the anchoring oligonucleotide; (c). releasing the capture reagent from the surface and eluting unwanted components of the sample from the surface, thereby isolating the surface marker displaying agent of interest; and (d). conducting an assay to identify, quantitate, or both, the encapsulated protein, nucleic acid, lipid, metabolite, or a combination thereof. In embodiments, the assay is an ultrasensitive assay.

In embodiments, the surface marker displaying agent is a cell. In embodiments, the surface marker displaying agent is a virus or viral particle. In embodiments, the surface marker displaying agent is an organelle. In embodiments, the surface marker displaying agent is a vesicle. In embodiments, the surface marker displaying agent is an extracellular vesicle or exosome.

The invention further provides methods of identifying, quantitating, or both, a protein, a nucleic acid, a liquid, or a combination thereof, encapsulated by an EV of interest in a sample, comprising: (a). contacting the sample with a surface and selectively binding the EV of interest to: (i) a capture reagent releasably bound to the surface, wherein the surface further comprises an anchoring reagent; and (ii) a binding reagent; (b). binding the anchoring reagent to the binding reagent, thereby forming a complex on the surface comprising the capture reagent, the EV and the binding reagent; (c). releasing the capture reagent from the surface and eluting unwanted components of the sample from the surface, thereby isolating the EV of interest; and (d). conducting an assay to identify, quantitate, or both, the encapsulated protein, nucleic acid, lipid, or combination thereof. In embodiments, the assay is an ultrasensitive assay.

In additional embodiments, the invention provides methods of identifying, quantitating, or both, a protein, a nucleic acid, a lipid, or combination thereof, encapsulated by an EV, comprising: (a). contacting the sample comprising an EV with a surface, wherein the EV encapsulates the target protein, nucleic acid or metabolite, and selectively binding the EV to: (i) a capture reagent releasably bound to the surface, wherein the surface further comprises an anchoring oligonucleotide; and (ii) a binding reagent, wherein the binding reagent comprises a primer oligonucleotide, thereby forming a complex on the surface comprising the capture reagent, the EV and the binding reagent; (b). binding a circular oligonucleotide template to the primer oligonucleotide to form an amplicon by rolling circle amplification, wherein the amplicon comprises a sequence that is complementary to the anchoring oligonucleotide; (c). hybridizing the anchoring oligonucleotide to the amplicon to form a second complex on the surface comprising the capture reagent, the EV, the binding reagent and anchoring oligonucleotide; (d). releasing the capture reagent from the surface and eluting unwanted components of the sample from the surface, thereby isolating the EV of interest; and (e). conducting an assay to identify, quantitate, or both, the protein, nucleic acid, lipid, or combination thereof. In embodiments, the assay is an ultrasensitive assay.

The invention further provides a method of identifying, quantitating, or both, a protein, a nucleic acid, a lipid, or a combination thereof, encapsulated by an EV in a sample, comprising: (a). contacting the sample comprising an EV with a surface, wherein the EV encapsulates a protein, a nucleic acid, a lipid, or a combination thereof, and selectively binding the EV to: (i) a capture reagent releasably bound to the surface, wherein the surface further comprises an anchoring oligonucleotide; and (ii) a binding reagent, wherein the binding reagent comprises a tag oligonucleotide, thereby forming a complex on the surface comprising the capture reagent, the EV, and the binding reagent; (b). hybridizing a linker oligonucleotide to the tag oligonucleotide and to the anchoring oligonucleotide to form a second complex on the surface comprising the capture reagent, the EV, the binding reagent, and the anchoring oligonucleotide; (c). releasing the capture reagent from the surface and eluting unwanted components of the sample from the surface, thereby isolating the EV of interest; and (d). conducting an assay to identify, quantitate, or both, the encapsulated protein, nucleic acid, lipid, metabolite, or a combination thereof. In embodiments, the assay is an ultrasensitive assay.

The contents of surface marker displaying agents, e.g., vesicles, vary with respect to mode of biogenesis, cell type, and physiologic conditions. In embodiments, the contents of surface marker displaying agents include proteins, nucleic acids, lipids, carbohydrates, small molecules such as hormones, cofactors, vitamins, minerals, salts, metals, metal-containing compounds, or combination thereof. In general, EVs encapsulate (i.e., are loaded with cargo) various proteins, lipids, nucleic acids and metabolites. The loading of the different types of cargo can be specific per vesicle and cell type. Research conducted to characterize the content of EVs has resulted in the assembly of different databases collecting the datasets from the many EV studies. Three different databases are publicly accessible: Exocarta, Vesiclepedia, and EVpedia (Kim et al., EVpedia: an integrated database of high-throughput data for systemic analyses of extracellular vesicles, J Extracell Vesicles 2:1-7 (2013); Kalra et al., Vesiclepedia: a compendium for extracellular vesicles with continuous community annotation, PLoS Biol. 2012; Mathivanan S, Simpson R J. ExoCarta: a compendium of exosomal proteins and RNA, Proteomics 9:4997-5000 (2009); Simpson et al., ExoCarta as a resource for exosomal research, J Extracell Vesicles. 2012; Mathivanan et al., ExoCarta 2012: database of exosomal proteins RNA and lipids, Nucleic Acids Res. 2012, each of which is incorporated by reference in its entirety). All databases include the protein, nucleic acid, and lipid content together with the isolation and purification procedures used to generate the data.

In embodiments, the protein that is encapsulated within the EV is of CNS cell origin, for example, neuron, astrocyte, oligodendrocyte, or microglia cells. Exemplary proteins include, but are not limited to, TSG101, HSP70, ALIX/PDCD6IP, Flotillin, Tuj 1, Tyr hydroxylase, NSE, NF-L, NF-H, GFAP, 51000, GluSyn, CNPase, Oligo2, TMEM119, Rab5a, HAS, ApoA1, ApoA2, ApoB, or a combination thereof.

In embodiments, the protein that is encapsulated within the EV is a cardiovascular disease marker. Exemplary cardiovascular disease markers include, but are not limited to, troponin, GDF-15 (MIC-1), myeloperoxidase (MPO), galectin-3, PlGF, topoisomerase 20, ST-2, sFlt-1, neuregulin, and inflammation markers such as hsCRP, IL-1β, IL-6, TNFα, neuregulin, ST2, NT-proBNP, BNP, and galectin 3.

Figure 4A:
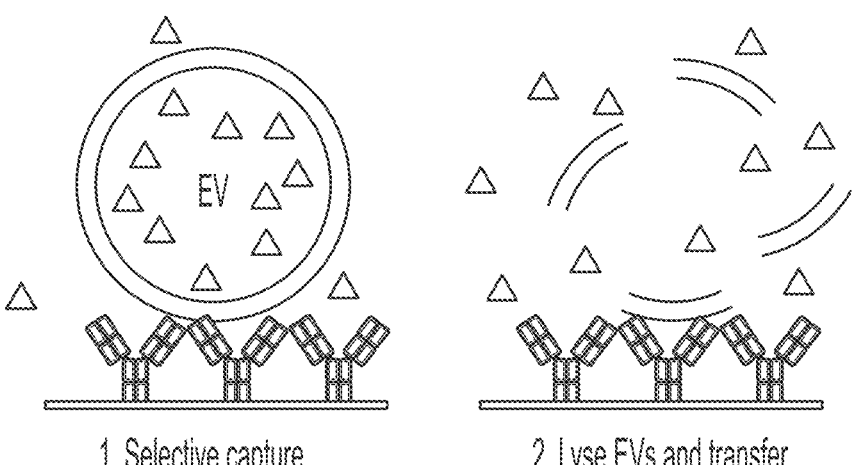
FIG. 4A. Cell culture EVs are captured on affinity capture plate with EV-specific or irrelevant antibodies and washed, followed by lysis and transfer to an ultrasensitive assay for EGFR cytoplasmic domain. The supernatant has detectable levels of the analyte outside the EVs (no lysis), but after lysis the signal increases to 3-fold, indicating roughly twice as much analyte within the EVs as outside. Nearly all of the EGFR containing EVs are captured on the CD9 plate, while the CD81 and CD63 only yield about half of the total EV associated EGFR. Very few EVs are captured by the control antibody so the EGFR signal is quite low.
Figure 4B:
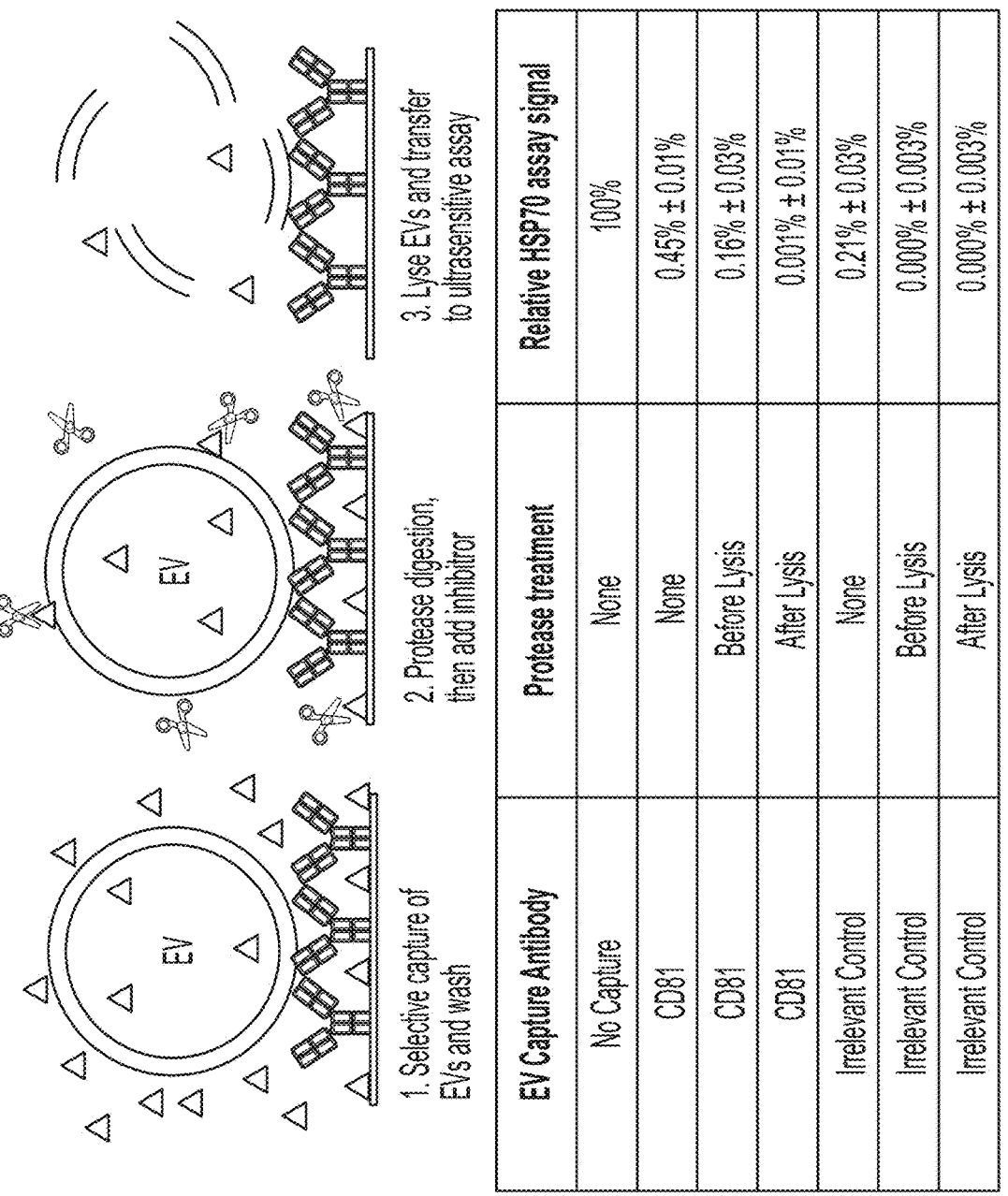
FIG. 4B. Cargo proteins can be difficult to measure accurately when the same protein species is abundant in soluble form. A cell conditioned medium with >500-fold more HSP70 in soluble form than in the EV cargo was selected to mitigate the effect of this soluble protein. When the EVs are captured with CD81 antibodies or an irrelevant control antibody and then lysed, a fraction of the soluble HSP70 binds non-specifically to the well and are transferred to the assay plate along with the true cargo, which would lead to an overestimation of the true EV cargo. After proteolysis, only the true EV cargo are transferred to the assay well. When the captured EVs are lysed before protease treatment, all of the cargo is digested as well.

In embodiments exemplified in FIG. 4A, the encapsulated molecules within the EV of interest are subjected to an assay, e.g., an ultrasensitive assay, that comprises lysing the EV, and conducting an assay on the lysate. In embodiments, assays may comprise additional steps to digest non-EV associated proteins, as exemplified in FIG. 4B. Such a method may include contacting the surface with a protease, inactivating the protease, lysing the EV and transferring the lysate to a second surface, wherein the lysate is detected, analyzed or both using an assay. Assays for proteins, oligonucleotides and lipids are well known in the art. In embodiments, the EV of interest encapsulates a protein, a nucleic acid, a lipid, or a combination thereof. In embodiments, the nucleic acid is RNA. In embodiments the RNA is a mature miRNA.

Many biomarkers proposed in the CNS-EV literature are expected to originate within the cytosol of neurons or glia and be secreted inside EVs as "cargo". The concentration of these cargo proteins can be exceedingly low, and the difficulty of making accurate measurements can be compounded by the existence of non-EV associated (soluble) forms of the same protein in biofluid samples. To a first approximation, EVs are found in human plasma at a concentration of about $1\times10^{10}$ particles/mL and CNS-EVs should represent only a small fraction of all EVs. For measurements of a cargo protein in a specific population of CNS-EVs representing 0.1% of the total EVs in circulation, assuming that each CNS-EV has a single copy of the target protein, a concentration of <1 pg/mL for a protein of average molecular weight would be expected, which is generally below the sensitivity of conventional assays. Thus ultrasensitive assays are usually required to detect, measure, or both, these low concentration analytes.

Ultrasensitive assay format for soluble proteins that marry a variation of proximity ligation amplification with ECL detection to provide state-of-the-art sensitivity for protein assays are known in the art, see, e.g., as disclosed in International Appl. No. PCT/US2015/030925, published as WO 2015/175856. Such assays have detection limits as low as the pg/mL to sub pg/mL level, detecting as low as 1000 molecules per 25 uL sample.

In embodiments, to verify the identity of the EVs isolated using each specific surface marker signature, cargo proteins specifically expressed in each of the CNS-EV types are identified and measured. In embodiments, EV surface proteins are identified and measured, for example, if no specific intracellular proteins are available for a cell type, but they should not be one of the same proteins used in the specific EV isolation.

Kits

The invention further provides kits for isolating, detecting, measuring, or combinations thereof, a surface marker displaying agent in a sample comprising, in one or more vials, containers, or compartments: (a) a surface comprising (i) a capture reagent for the surface marker displaying agent, wherein the capture reagent is releasably bound to the surface, and (ii) an anchoring reagent; and (b) a binding reagent for the surface marker displaying agent.

The invention further provides kits for detecting a surface marker displaying agent in a sample comprising, in one or more vials, containers, or compartments: (a) a surface comprising (i) a capture reagent for the surface marker displaying agent, wherein the capture reagent is releasably bound to the surface, and (ii) an anchoring oligonucleotide; (b) binding reagent for the surface marker displaying agent that is linked to a primer oligonucleotide; and (c) a circular oligonucleotide template comprising a sequence complementary to the primer oligonucleotide.

The invention further provides kits for detecting a surface marker displaying agent in a sample comprising, in one or more vials, containers, or compartments: (a) a surface comprising a binding domain; (b) a linking reagent capable of binding to the binding domain; and (c) an anchoring reagent capable of binding to the binding domain, wherein the anchoring reagent comprises an oligonucleotide moiety and a hydrophilic polymer moiety.

In some embodiments, the anchoring reagent comprises a conjugation linkage between the oligonucleotide moiety and the hydrophilic polymer moiety selected from an amide, a thioester, a thioether, a disulfide, an imine, or a triazole. In embodiments, the anchoring reagent in the kit is provided as an oligonucleotide and a hydrophilic polymer. In embodiments, the anchoring reagent is formed from a conjugation reaction between an oligonucleotide and a hydrophilic polymer, wherein the oligonucleotide and the hydrophilic polymer each comprises a reactive group as described herein. Conjugation reactions and reactive groups are described herein.

In embodiments, the oligonucleotide comprises an amine, and the hydrophilic polymer comprises an N-hydroxysuccinimide (NHS) ester or an aldehyde. In embodiments, the oligonucleotide comprises a thiol, and the hydrophilic polymer comprises an NHS ester, a maleimide, a disulfide, or an alkene. In embodiments, the oligonucleotide comprises an N-hydroxysuccinimide (NHS) ester or an aldehyde, and the hydrophilic polymer comprises an amine. In embodiments, the oligonucleotide comprises an NHS ester, a maleimide, a disulfide, or an alkene, and the hydrophilic polymer comprises a thiol. In embodiments, the oligonucleotide comprises an alkyne or cycloalkyne, and the hydrophilic polymer comprises an azide. In embodiments, the oligonucleotide comprises an azide, and the hydrophilic polymer comprises an alkyne or cycloalkyne.

In embodiments, the anchoring reagent comprises biotin and the surface comprises streptavidin.

The invention further provides kits for detecting a surface marker displaying agent in a sample comprising, in one or more vials, containers, or compartments: (a) a surface comprising a binding domain; (b) a surface comprising a binding domain; (c) an anchoring reagent capable of binding to the binding domain; and (d) an anchor linking reagent capable of binding to the anchoring reagent. In embodiments, the anchor linking reagent comprises a first oligonucleotide moiety, a hydrophilic polymer moiety, and a second oligonucleotide moiety.

In embodiments, the anchor linking reagent comprises a first conjugation linkage between the first oligonucleotide moiety and the hydrophilic polymer moiety selected from a thioether, a disulfide, an amide, or a triazole; and a second conjugation linkage that is different from the first conjugation linkage and selected from a thioether, a disulfide, an amide, or a triazole between the hydrophilic polymer moiety and the second oligonucleotide moiety.

In embodiments, the anchor linking reagent in the kit is provided as a first oligonucleotide, a hydrophilic polymer, and a second oligonucleotide. In embodiments, the anchor linking reagent is formed from conjugation of the first oligonucleotide to a first end of the hydrophilic polymer, and the second oligonucleotide to a second end of the hydrophilic polymer, wherein the first and second oligonucleotides and the first and second ends of the hydrophilic polymer each comprise a reactive group as described herein.

In embodiments, the first oligonucleotide comprises an amine, the second oligonucleotide comprises a thiol, and the hydrophilic polymer comprises an NHS ester at the first end and a maleimide at the second end. In embodiments, the first oligonucleotide comprises an amine, the second oligonucleotide comprises a thiol, and the hydrophilic polymer comprises an NHS ester at the first end and an alkene at the second end. In embodiments, the first oligonucleotide comprises an amine, the second oligonucleotide comprises a thiol, and the hydrophilic polymer comprises an NHS ester at the first end and a thiol at the second end.

In embodiments, the first oligonucleotide comprises an amine, the second oligonucleotide comprises an alkyne or cycloalkyne, and the hydrophilic polymer comprises an NHS ester at the first end and an azide at the second end. In embodiments, the first oligonucleotide comprises an amine, the second oligonucleotide comprises an azide, and the hydrophilic polymer comprises an NHS ester at the first end and an alkyne or cycloalkyne at the second end.

In embodiments, the first oligonucleotide and the second oligonucleotide are not substantially reactive with one another. In embodiments, the first oligonucleotide and the second oligonucleotide are each capable of reacting with a different end of the hydrophilic polymer.

In embodiments, the surface marker displaying agent is a cell. In embodiments, the surface marker displaying agent is a virus or viral particle. In embodiments, the surface marker displaying agent is an organelle. In embodiments, the surface marker displaying agent is a vesicle. In embodiments, the surface marker displaying agent is an extracellular vesicle or exosome.

The invention further provides kits for isolating, detecting, measuring, or combinations thereof, an EV in a sample comprising, in one or more vials, containers, or compartments: (a) a surface comprising (i) a capture reagent for the EV, wherein the capture reagent is releasably bound to the surface, and (ii) an anchoring reagent; and (b) a binding reagent for the EV.

The invention further provides kits for detecting an EV in a sample comprising, in one or more vials, containers, or compartments: (a) a surface comprising (i) a capture reagent for the EV, wherein the capture reagent is releasably bound to the surface, and (ii) an anchoring oligonucleotide; (b) binding reagent for the EV that is linked to a primer oligonucleotide; and (c) a circular oligonucleotide template comprising a sequence complementary to the primer oligonucleotide.

In embodiments, the disclosure further provides a kit for detecting an EV in a sample comprising, in one or more vials, containers, or compartments: (a) a surface comprising a binding domain; (b) a linking reagent capable of binding to the binding domain; and (c) an anchoring reagent capable of binding to the binding domain. In embodiments, the kit further comprises a capture reagent for a surface marker, e.g., an EV surface marker, wherein the capture reagent is capable of binding to the linking reagent.

In embodiments, the disclosure further provides a kit for detecting an EV in a sample comprising, in one or more vials, containers, or compartments: (a) a surface comprising a targeting reagent complement in a binding domain; (b) a linking reagent connected to a targeting reagent, wherein the targeting reagent is a binding partner of the targeting reagent complement; and (c) an anchoring reagent comprising a supplemental linking reagent, wherein the supplemental linking reagent is capable of binding to the linking reagent. In embodiments, the kit further comprises a capture reagent for a surface marker, e.g., an EV surface marker, wherein the capture reagent comprises a supplemental linking reagent capable of binding to the linking reagent.

In embodiments, the surface comprises a plurality of binding domains, wherein each binding domain comprises a different targeting reagent complement; and wherein the kit further comprises a plurality of linking reagents, each linking reagent connected to a different targeting reagent for each of the different targeting reagent complements. In embodiments, the kit further comprises a plurality of capture reagents, each capture reagent comprising a supplemental linking reagent capable of binding to the linking reagent. Exemplary surfaces are described in, e.g., U.S. Pat. Nos.

10,201,812; 7,842,246 and 6,977,722, the disclosures of which are hereby incorporated by reference in their entireties.

In embodiments of a kit comprising a plurality of binding domains, the kit further comprises a plurality of capture reagents, each capture reagent comprising a supplemental linking reagent capable of binding to the linking reagent. In embodiments, the surface comprises an array with a plurality of different targeting reagent complements immobilized on one or more solid phase supports, each array element comprising a different targeting reagent complement, and each of the different targeting reagent complements being the binding partner of a different targeting reagent. In embodiments, the capture reagents are connected to one of the different targeting reagents, and each of the capture reagents is connected to a different targeting reagent. Furthermore, the anchoring reagent is divided into a plurality of portions each having at least a copy of the anchoring reagent, and the anchoring reagent in each portion is connected to a different targeting reagent. Thus, in embodiments, the solid phase support comprises a targeting reagent complement, and each of the capture reagent and anchoring reagent comprises a targeting reagent. In embodiments, each capture reagent and anchoring reagent portion may be provided separately, all reagents/portions linked to the same targeting reagent are provided as a mixture and separate from the other reagents, all capture reagents are provided as a mixture and all anchor reagent portions are provided as a mixture, or all capture reagents and anchor reagent portions are provided as one mixture.

In embodiments, the capture reagent comprises a supplemental linking reagent; the anchoring reagent comprises a supplemental linking reagent; the targeting reagents are connected to a linking reagent; and the linking reagent is a binding partner of the supplemental linking reagent. Thus, in embodiments, the surface comprises a targeting reagent complement, which binds to the targeting reagent that is connected to the linking reagent, which binds to the supplemental linking reagent on the capture reagent and anchoring reagent.

In embodiments, the targeting reagent and targeting reagent complement are two members of a binding partner pair selected from avidin-biotin, streptavidin-biotin, antibody-hapten, antibody-antigen, antibody-epitope tag, nucleic acid-complementary nucleic acid, aptamer-aptamer target, and receptor-ligand. In embodiments, the targeting reagent is biotin and the targeting reagent complement is streptavidin. In embodiments, the linking reagent and supplemental linking reagent pair is a different binding partner pair than the targeting reagent and targeting reagent complement pair. In embodiments, the linking reagent is avidin or streptavidin, and the supplemental linking reagent is biotin. In embodiments, the targeting reagent and targeting reagent complement are complementary oligonucleotides.

In embodiments, the linking reagent and supplemental linking reagent are two members of a binding partner pair selected from avidin-biotin, streptavidin-biotin, antibody-hapten, antibody-antigen, antibody-epitope tag, nucleic acid-complementary nucleic acid, aptamer-aptamer target, and receptor-ligand. In embodiments, the linking reagent is biotin and the supplemental linking reagent is streptavidin. In embodiments, the linking reagent is avidin or streptavidin, and the supplemental linking reagent is biotin.

In embodiments, the array comprising the plurality of binding domains is on one solid phase support, and the solid phase support is an electrode. In embodiments, the solid phase support is a carbon-based electrode. In embodiments, the kit comprises a multi-well plate assay consumable, and each well of the plate comprises a carbon ink electrode. In some embodiments, the solid phase supports are particles. In embodiments, each element of the array is on a different solid phase support, and the solid phase supports are beads.

In embodiments, the anchoring reagent includes an anchoring sequence that is directly or indirectly bound (e.g., through binding reactions) to the surface. In embodiments, the anchoring reagent comprises a protein linked or otherwise bound to the anchoring sequence. In embodiments, any protein can be used that can be immobilized on a surface (covalently or non-covalently) and modified by an anchoring oligonucleotide. Non-limiting examples include streptavidin, avidin, or bovine serum albumin (BSA). In embodiments, the anchoring reagent comprises BSA. Methods of immobilizing anchoring reagents are described in, e.g., WO 2015/175856, herein incorporated by reference in its entirety.

In embodiments, the capture reagent in the kit comprises an antibody, antigen, ligand, receptor, oligonucleotide, hapten, epitope, mimotope, or aptamer. In embodiments, the binding reagent in the kit comprises an antibody, antigen, ligand, receptor, oligonucleotide, hapten, epitope, mimotope, or aptamer. In embodiments, both the capture reagent and the binding reagent are antibodies, or an epitope binding portion of an antibody.

In additional embodiments, the surface of the kit comprises a plurality of distinct binding domains and the capture reagent and the anchoring reagent, e.g., anchoring oligonucleotide, are located on two distinct binding domains on the surface. In further embodiments, the surface of the kit comprises a plurality of distinct binding domains and the capture reagent and the anchoring reagent, e.g., anchoring oligonucleotide are located on the same binding domain on the surface. In additional embodiments, the surface comprises a plurality of distinct binding domains and the capture reagent and the anchoring reagent, e.g., anchoring oligonucleotide are located on the same binding domain.

In embodiments, the kit comprises a surface wherein the capture reagent and the anchoring reagent, e.g., anchoring oligonucleotide are within 10 μm, 5 μm, or 100 nm on the surface.

In embodiments, the surface in the kit comprises an electrode.

In embodiments, the capture reagent comprised in the kit binds a common target protein to a specific type of surface marker displaying agents (e.g., a common marker for all cells, viruses, organelles, or vesicles). In embodiments, the capture reagent comprised in the kit binds a common EV target protein selected from CD9, CD37, CD63, CD81, CD82.

In embodiments, the kit comprises one or more buffers. In embodiments, the kit comprises one or more of a wash buffer, an assay buffer, and a read buffer. In embodiments, the same buffer can be used for the wash, assay, and detection (i.e., "read") steps. In embodiments, the kit comprises a Tris buffer and/or a phosphate buffer. Non-limiting examples of wash buffers, assay buffers, and/or read buffers include phosphate buffer, Tris buffer, HEPES buffer, and the like. In embodiments, the wash buffer and/or the read buffer comprises a surfactant. In some embodiments, the surfactant is TRITON-X. In embodiments, the surfactant is TWEEN-20. In embodiments, the wash buffer and/or the read buffer comprises a co-reactant. In embodiments, the co-reactant is tripropylamine (TPA). In embodiments, the read buffer is a Tris buffer comprising TRITON-X and TPA. In embodiments, the read buffer comprises N-Butyldiethanolamine (BDEA). In embodiments, the read buffer comprises N,N-dibutylethanolamine (DBAE). In embodiments, the read buffer comprises a surfactant that does not disrupt a surface of the surface marker displaying agent. In embodiments, the read buffer comprises a surfactant that does not disrupt a lipid bilayer membrane. In embodiments, the read buffer comprises a surfactant that does not disrupt a membrane of an EV. In embodiments, the surfactant is BRIJ, TWEEN, PLURONIC or KOLLIPHOR. In embodiments, the read buffer does not comprise a surfactant. In embodiments, the read buffer is a read buffer provided in, e.g., U.S. Provisional Application No. 62/787,892, filed on Jan. 3, 2019.

Automated High Throughput EV Isolation and Cargo Screening

The invention further provides an automated version of the methods of the invention using a high-throughput robotic liquid handling system. This system allows simultaneous preparation of up to 480 samples with accuracy and reproducibility unmatched by a human operator. In embodiments, the automated system is a free-standing, fully integrated system for carrying out immunoassays using ECL technology. This system, capable of simultaneously running up to five 96-well assay plates, consists of a robotic lab automation workstation for liquid handling and plate manipulation, physically integrated with an ECL reader.

In embodiments, the workflow conducts the methods of the invention with minimal human intervention. In embodiments, a single 96-well source plate is loaded with 120 uL each of 96 plasma samples in each well. 25 uL per sample is dispensed along with appropriate diluents into each of four different capture plates, each for isolating a single CNS-EV type. Plates are incubated about two hours on shakers while EVs are captured. Next, the plates are washed and the binding reagents are then added and incubated for about one hour. Plates are washed again followed by addition of reagents for staple amplification and 15 minute incubation for stapling. Plates are washed again followed by addition of elution reagent for removing non-stapled EVs. After a final wash, each of the four plates contain a unique type of CNS EVs. Lysis buffer is optionally added to each well followed by a short incubation. Lysates from each plate are transferred along with appropriate diluents to one of four identical 4-plex cargo assay plates and the standard assay, e.g., ultrasensitive assay, procedure then follows to complete the assays. At the end of an about an 8 hour day each of the 96 samples are fractionated into 4 EV types and each type assayed for four different EV cargo analytes. The operator only has to set up the source plate, and load reagents into the instrument. No further intervention is required. In embodiments, the procedure is run three days in a row on the same samples with the same plate and reagent lots to assess run-to-run variability.

Screening for Multiple Markers to a Same Target

One of the challenges associated with multi-marker isolation (i.e., using two or more capture and/or detection reagents) of target molecules, for example, macromolecules such as proteins, protein complexes, surface marker displaying agents, or extracellular vesicles (EVs), is the need to efficiently identify multi-marker signatures that correspond to the targets of interest. Multiple markers may need to be identified in any immunoassay requiring three, four, or four or more binding reagents on a single protein, protein complex, large macromolecule such as EVs, or surface marker displaying agents such as cells, viruses, organelles, or vesicles. For example, multiple binding reagents may be desired for binding to different epitopes on the same protein. Multiple binding reagents may also be desired for binding to different surface markers on the same EV. Multiple binding reagents may further be desired for binding to different surface markers on the same surface marker displaying agent. In another example, multiple binding reagents may be desired for binding to the same epitope in a multimeric target (e.g., protein or protein complex), and it may be desirable to use one or more of the same binding reagents for binding to the same epitope in different monomers of the multimeric target. In a further example, multiple binding reagents may be desired for identifying and/or isolating a subpopulation of surface marker displaying agents, e.g., the surface marker displaying agent can be a cell, and the subpopulation can be a certain cell type or cellular state (e.g., whether the cell is healthy, infected or inflamed). The present disclosure provides methods of screening large libraries of binding reagents to identify combinations of binding reagents that bind to the same target. In embodiments, the target is a surface marker displaying agent, and the binding reagents can target different surface markers (e.g., proteins) on the same surface marker displaying agent. In embodiments, the target is an EV, and the binding reagents can target different surface markers (e.g., proteins) on the same EV. In embodiments, the target is a large macromolecule, for example, a single protein, and the binding reagents can target different epitopes on the same protein. In embodiments, the target is a protein complex comprising one or more of the same protein monomers, and the binding reagents can target the same epitope on different monomers.

Accordingly, the present disclosure also provides methods of determining target epitopes on proteins, comprising: contacting the protein with a plurality of unique binding reagents, wherein each unique binding reagent comprises a detection sequence comprising a unique barcode oligonucleotide sequence, wherein if at least three unique binding reagents bind to three unique protein epitopes, an output oligonucleotide is generated that comprises the barcode oligonucleotide sequences of each of the three unique binding reagents; and sequencing the output oligonucleotide to identify the barcode oligonucleotide sequences, thereby determining the at least three unique target protein epitopes.

In embodiments, the present disclosure provides methods of determining target epitopes on proteins, comprising: contacting the protein with a plurality of unique binding reagents, wherein each unique binding reagent comprises a detection sequence comprising a unique barcode oligonucleotide sequence, wherein if at least four unique binding reagents bind to four unique protein epitopes, an output oligonucleotide is generated that comprises the barcode oligonucleotide sequences of each of the four unique binding reagents; and sequencing the output oligonucleotide to identify the barcode oligonucleotide sequences, thereby determining the at least four unique target protein epitopes.

Accordingly, the present disclosure also provides methods of determining surface markers of a surface marker displaying agent, comprising: contacting the surface marker displaying agent with a plurality of unique binding reagents, wherein each unique binding reagent comprises a detection sequence comprising a unique barcode oligonucleotide sequence, wherein if at least three unique binding reagents bind to three unique surface markers of a surface marker displaying agent, an output oligonucleotide is generated that comprises the barcode oligonucleotide sequences of each of the three unique binding reagents; and sequencing the output oligonucleotide to identify the barcode oligonucleotide sequences, thereby determining the at least three unique surface markers of a surface marker displaying agent.

In embodiments, the present disclosure provides methods of determining surface markers of a surface marker displaying agent, comprising: contacting the surface marker displaying agent with a plurality of unique binding reagents, wherein each unique binding reagent comprises a detection sequence comprising a unique barcode oligonucleotide sequence, wherein if at least four unique binding reagents bind to four unique surface markers of a surface marker displaying agent, an output oligonucleotide is generated that comprises the barcode oligonucleotide sequences of each of the four unique binding reagents; and sequencing the output oligonucleotide to identify the barcode oligonucleotide sequences, thereby determining the at least four unique surface markers of a surface marker displaying agent.

The present disclosure also provides methods of determining EV surface markers, comprising: contacting the EV with a plurality of unique binding reagents, wherein each unique binding reagent comprises a detection sequence comprising a unique barcode oligonucleotide sequence, wherein if at least three unique binding reagents bind to three unique EV surface markers, an output oligonucleotide is generated that comprises the barcode oligonucleotide sequences of each of the three unique binding reagents; and sequencing the output oligonucleotide to identify the barcode oligonucleotide sequences, thereby determining the at least three unique EV surface markers.

In embodiments, the present disclosure provides methods of determining EV surface markers, comprising: contacting the EV with a plurality of unique binding reagents, wherein each unique binding reagent comprises a detection sequence comprising a unique barcode oligonucleotide sequence, wherein if at least four unique binding reagents bind to four unique EV surface markers, an output oligonucleotide is generated that comprises the barcode oligonucleotide sequences of each of the four unique binding reagents; and sequencing the output oligonucleotide to identify the barcode oligonucleotide sequences, thereby determining the at least four unique EV surface markers.

In embodiments, at least one of the plurality of binding reagents comprises a detection sequence that comprises a hybridization sequence that is complementary to at least a portion of the detection oligonucleotide sequence of at least one other binding reagent.

In embodiments, each of the plurality of binding reagents comprises a detection sequence that comprises a hybridization sequence that is complementary to either at least a portion of a detection sequence of at least other binding reagent, or at least a portion of a splint oligonucleotide.

In embodiments, the plurality of binding reagents comprises: a first binding reagent comprising a first detection sequence that comprises a first hybridization sequence, and a first amplification primer site; a second binding reagent comprising a second detection sequence that comprises a second hybridization sequence, and a third hybridization sequence; and a third binding reagent comprising a third detection sequence that comprises a fourth hybridization sequence, and a second amplification primer site, wherein the first hybridization sequence and the second hybridization sequence are complementary; wherein the third hybridization sequence and the fourth hybridization sequence complementary; and wherein generating the single output oligonucleotide comprises ligating, extending, or both, the hybridized first detection sequence, second detection sequence, and third detection sequence.

In embodiments, the plurality of binding reagents further comprises a fourth binding reagent comprising an anchoring reagent. In embodiments, the anchoring reagent is capable of attachment to a surface. Anchoring reagents and surfaces are provided herein. In embodiments, the anchoring reagent comprises biotin, and the surface comprises streptavidin. In such embodiments, the fourth binding reagent captures the surface marker displaying agent onto the surface. In embodiments, the fourth binding reagent is known to bind to the surface marker displaying agent, e.g., via a known epitope and/or surface marker, and the at least three other binding reagents are identified by the method provided herein. For example, the surface marker displaying agent, e.g., an EV, can have a known surface marker for a specific disease, e.g., a marker specific to EVs derived from HIV-infected cells, and the method can be used to determine additional surface markers that may be present on EVs from HIV-infected cells.

In embodiments, the plurality of binding reagents comprises: a first binding reagent comprising a first detection sequence that comprises a first hybridization sequence, a first barcode sequence, and a first amplification primer site; a second binding reagent comprising a second detection sequence that comprises a second hybridization sequence, a second barcode sequence, and a 5' splint complement sequence; a third binding reagent comprising a third detection sequence that comprises a 3' splint complement sequence, a third barcode sequence, and a third hybridization sequence; and a fourth binding reagent comprising a fourth detection sequence that comprises a fourth hybridization sequence, a fourth barcode sequence, and a second amplification primer site, wherein the first hybridization sequence and the second hybridization sequence are complementary; wherein the third hybridization sequence and the fourth hybridization sequence complementary; wherein the 5' splint complement sequence and the 3' splint complement sequence are complementary, respectively, to 5' and 3' ends of a splint oligonucleotide; and wherein generating the single output oligonucleotide comprises ligating, extending, or both, the hybridized first detection sequence, second detection sequence, splint oligonucleotide, third detection sequence, and fourth detection sequence.

In embodiments, additional binding reagents bind to additional unique surface markers on the surface marker displaying agent, e.g., for a total of 5, 6, 7, 8, 9, 10 . . . n binding reagents. In embodiments, the detection sequences of the binding reagents are connected by hybridization to at least a portion of a different binding reagent, or to at least a portion of a splint oligonucleotide. In embodiments, the number of splint oligonucleotides that are used to connect the detection sequences of all the binding reagents is n-3.

In embodiments, at least one of the plurality of binding reagents comprises an anchoring reagent. In embodiments, the fourth binding reagent comprises an anchoring reagent. In embodiments, the anchoring reagent is capable of attachment to a surface. In embodiments, the anchoring reagent is present on the detection sequence of the binding reagent. Anchoring reagents and surfaces are provided herein. In embodiments, the anchoring reagent comprises biotin, and the surface comprises streptavidin.

In embodiments, the plurality of unique binding reagents comprises at least ten unique binding reagents. In embodiments, the plurality of unique binding reagents comprises about 10 to about 10,000 unique binding reagents. In embodiments, the plurality of unique binding reagents comprises about 3 to about 10,000 unique binding reagents. In embodiments, the plurality of unique binding reagents comprises about 5 to about 5,000 unique binding reagents. In embodiments, the plurality of unique binding reagents comprises about 10 to about 1,000 unique binding reagents. In embodiments, the plurality of unique binding reagents comprises about 20 to about 500 unique binding reagents. In embodiments, the plurality of unique binding reagents comprises about 50 to about 100 unique binding reagents. In embodiments, the plurality of unique binding reagents comprises about 10 to about 100 unique binding reagents.

In embodiments, the sequencing is performed by next-generation sequencing. In embodiments, sequencing the output oligonucleotide comprises: adding one or more adapter sequences to the single output oligonucleotide; and sequencing the single output oligonucleotide using the adapter sequence.

In embodiments, the multiplexed method is conducted in solution.

In embodiments, the methods described herein enable combinatorial screening of more than 10, more than 20, more than 30, more than 40, more than 50, more than 60, more than 70, more than 80, more than 90, more than 100, more than 500, or more than 1000 binding reagents (e.g., antibodies) for EV surface markers in a single reaction. Thus, in embodiments, at least $10^3$, $20^3$, $30^3$, $40^3$, $50^3$, $60^3$, $70^3$, $80^3$, $90^3$, $100^3$, $500^3$, or $1000^3$ possible three-marker combinations can be screened in a single reaction. In embodiments, at least $10^4$, $20^4$, $30^4$, $40^4$, $50^4$, $60^4$, $70^4$, $80^4$, $90^4$, $100^4$, $500^4$, or $1000^4$ possible four-marker combinations can be screened in a single reaction. In embodiments, the multiple (e.g., three, four, or four or more) binding reagents also serve as a secondary tether, allowing selective removal of EVs lacking the combination of the three, four, or four or more surface markers, thereby providing additional specificity.

In embodiments, the surface markers are identified by next-generation sequencing of the barcode oligonucleotide sequences associated with the binding reagents specific for the surface markers. In embodiments, the same multiple (e.g., three) binding reagents (e.g., antibodies) identified by next-generation sequence are used for isolation of the surface marker displaying agent, e.g., EV, thereby simplifying reagent preparation and ensuring that the binding reagents (e.g., antibodies) behave similarly during both screening and isolation processes.

In embodiments, the EVs are isolated from monocytes. In embodiments, the EVs are isolated from B cells. In embodiments, the EVs are isolated from CD4+ T cells. In embodiments, the EVs are isolated from CD8+ T cells. In embodiments, the EVs are isolated from vascular endothelial cells.

A non-limiting, exemplary process for a method of determining surface markers on a target is illustrated in FIGS. 31A-31B. Further non-limiting, exemplary processes of methods of determining surface markers on a target are illustrated in FIGS. 48A-48B. The processes illustrated in FIGS. 31A, 31B. 48A, and 48B are not limited to EVs, but can also be used with any surface marker displaying agents described herein. Thus, the exemplary process includes:

1. Creating a binding reagent library. This includes coupling binding reagents to three different types of detection sequences to generate a first binding reagent, a second binding reagent, and a third binding reagent, each of which has a unique barcode oligonucleotide sequence. The detection sequences may be coupled to the binding reagents via flexible linkers, or coupled directly to the binding reagent. In embodiments, the binding reagent is an aptamer, and a single oligonucleotide is synthesized containing the aptamer and the detection sequence. Binding reagent libraries are further described in embodiments herein.

In embodiments, each binding reagent in the binding reagent library is coupled to each of the three types of detection sequences, in order to allow all combinations of three binding reagents to be tested. In embodiments, the combinations of three binding reagents comprise three different binding reagents. In embodiments, the combinations of three binding reagents comprise two or more of the same binding reagent, wherein each binding reagent is coupled to each of the three types of detection sequences. In embodiments, the combination of three binding reagents comprise three of the same binding reagent, wherein each binding reagent is coupled to each of the three types of detection sequences. In embodiments, the barcode oligonucleotide sequence is unique to each binding reagent-detection sequence combination, allowing the binding reagent to be identified by sequencing.

2. Contacting the binding reagent library with the target and incubating to allow binding of the binding reagents to the EV.

3. Capturing the target bound to the binding reagents and washing away unbound binding reagents. The binding reagent can be captured, for example, if one of the three binding reagents is biotinylated, to a solid support (e.g., a bead or surface) coated with streptavidin. The target can also be captured, for example, using an additional, common binding marker, such as a tetraspanin on an EV. In embodiments, a fourth binding reagent is used to capture the target, e.g., as illustrated in FIG. 48B. In embodiments, a stringent wash is used to disrupt interactions between the detection sequences.

4. Wherein at least one first binding reagent, one second binding reagent, and one third binding reagent is bound to the same target (e.g., EV or protein), complementary regions of the detection sequences hybridize (see, e.g., FIG. 31A).

5. Adding polymerase and ligase to the reaction mixture to join the first, second, and third detection sequences, creating a single output oligonucleotide that includes all three barcode sequences (see, e.g., FIG. 31B).

6. Amplifying the single output oligonucleotide and incorporating sequencing primer sites.

7. Sequencing the single output oligonucleotides to identify combinations of the barcode oligonucleotide sequences.

In embodiments, the first detection sequence comprises a first amplification primer site and a first hybridization sequence. In embodiments, the second detection sequence comprises a second hybridization sequence and a third hybridization sequence. In embodiments, the third detection sequence comprises a fourth hybridization sequence and a second amplification primer site. In embodiments, the first hybridization sequence and the second hybridization sequences are complementary. In embodiments, the third hybridization sequence and the fourth hybridization sequences are complementary. Thus, in embodiments, the first and third detection sequences can each hybridize to the second detection sequence. In embodiments, after the first and third detection sequences hybridize to the second detection sequence, ligase is added to ligate the first, second, and third detection sequences into a single output oligonucleotide. In embodiments, polymerase extension followed by ligation remove any gaps in the ligated sequence and extend the output oligonucleotide using the first and second amplification primer sites. In embodiments, the ligation and polymerization are performed at the same time (e.g., proximity ligation/extension). In embodiments, the amplification further comprises adding one or more sequencing primer sites to the ends of the output oligonucleotide. In embodiments, sequencing is performed using the sequencing primer sites.

Each sequencing read contains three barcode oligonucleotide sequences, which will be mapped to the identity of the binding reagent. In embodiments, the frequency of a specific combination of binding reagents will be related to the abundance of the three markers (e.g., surface markers on an EV or epitopes on a protein). In embodiments, the abundance of a single marker (e.g., surface markers on an EV or epitopes on a protein) can be determined from the frequency with which the marker is identified from the barcode oligonucleotide sequencing results. In embodiments, multiple binding reagents targeting the same marker can be compared using the barcode oligonucleotide sequencing results. For example, the highest affinity binding reagent can be identified as the binding reagent most represented by its barcode in the sequencing data.

In FIG. 48A, four binding reagents (e.g., antibodies) each comprises a detection sequence that comprises a complementary region to at least a portion of a detection sequence of a different binding reagent, or to at least a portion of a splint oligonucleotide.

In embodiments, the first detection sequence comprises a first amplification primer site, a first barcode sequence, and a first amplification site. In embodiments, the second detection sequence comprises a second hybridization sequence, a second barcode sequence, and a 5' splint complement sequence. In embodiments, the third detection sequence comprises a 3' splint complement sequence, a third barcode sequence, and a third hybridization sequence. In embodiments, the fourth detection sequence comprises a fourth hybridization sequence, a fourth barcode sequence, and a second amplification primer site. In embodiments, the first hybridization sequence and the second hybridization sequences are complementary. In embodiments, the third hybridization sequence and the fourth hybridization sequences are complementary. In embodiments, the 5' splint complement sequence and the 3' splint complement sequence are complementary, respectively, to 5' and 3' ends of a splint oligonucleotide. Thus, in embodiments, the second and third detection sequences each hybridize to the splint oligonucleotide. In embodiments, after the splint oligonucleotide and the first, second, third, and fourth detection sequences hybridize to their respective hybridization partners, a ligase is added to ligate the splint oligonucleotide and the first, second, third, fourth detection sequences into a single output oligonucleotide. In embodiments, polymerase extension followed by ligation removes any gaps in the ligated sequence and extend the output oligonucleotide using the first and second amplification primer sites. In embodiments, the ligation and polymerization are performed at the same time (e.g., proximity extension/ligation). In embodiments, the amplification further comprises adding one or more sequencing primer sites to the ends of the output oligonucleotide. In embodiments, sequencing is performed using the sequencing primer sites.

In embodiments wherein four binding reagents bind to four unique surface markers on the surface marker displaying agent, each sequencing read contains four barcode sequences that are mapped to the identity of the binding reagents, thereby identifying the four unique surface markers. In embodiments wherein more than four binding reagents bind to more than four unique surface markers on the surface marker displaying agent, the binding reagents are identified by sequencing reads that include the detection sequences of each of the binding reagents, thereby identifying the more than four unique surface markers. In embodiments, the abundance of one or more of the surface markers is determined from the frequency with which the surface marker(s) are identified from the output oligonucleotide sequencing results. In embodiments, subpopulations of surface marker displaying agents are determined based on the combinations of the surface markers detected from the sequencing results.

In embodiments, the sequencing is performed with high-throughput sequencing. In embodiments, the sequencing produces at least $10^6$ reads. In embodiments, the sequencing produces at least $10^7$ reads. In embodiments, the sequencing produces at least $10^8$ reads. In embodiments, the sequencing produces at least $10^9$ reads. Methods of sequencing are known to one of ordinary skill in the art and can be performed, e.g., using a next-generation sequencing platform such as the MINISEQ (Illumina).

Binding Reagent Library

In embodiments, the present disclosure provides a library comprising multiple pools of binding reagents, wherein each pool of binding reagents is conjugated to an oligonucleotide comprising i) a unique proximal portion and ii) a unique distal portion comprising a barcode sequence.

An exemplary embodiment of the oligonucleotides in the binding reagent library is illustrated in FIG. 57. Each pool in the library is denoted by a number, e.g., 1, 2, 3, etc., and each unique binding reagent in the library is denoted by a letter, e.g., A, B, C, etc. The proximal portion of the oligonucleotide is the portion of the oligonucleotide closest to the binding reagent. In embodiments, the proximal portion comprises a reactive moiety (e.g., as described herein) for conjugating to the binding reagent. In embodiments, the proximal portion and distal portion of an oligonucleotide are separated by a ligation site.

In embodiments, the barcode sequences is used to identify the binding reagent. In embodiments, the position of the barcode sequence within an output oligonucleotide is used to identify the binding reagent. In embodiments, each unique binding reagent corresponds to one or more barcode sequences. In embodiments, each unique binding reagent corresponds to one unique barcode sequence, and the unique barcode sequence is present on an oligonucleotide conjugated to the unique binding reagent in each pool. In embodiments, a binding reagent is present in multiple pools in the library, and the barcode sequence of the oligonucleotide conjugated to the binding reagent in each pool of the library is identical. In embodiments, each unique binding reagent corresponds to multiple barcode sequences, wherein barcode sequences corresponding to a unique binding reagent in different pools are different. In embodiments, no barcode sequences are repeated in the library. In embodiments, each barcode sequence of oligonucleotides conjugated to binding reagents in the library is unique. For example, as illustrated in FIG. 57, barcode sequences corresponding to binding reagent A in the first pool (pool 1) are labeled Barcode $A_1$, barcode sequences corresponding to binding reagent A in the second pool (pool 2) are labeled Barcode $A_2$, and barcode sequences corresponding to binding reagent A in the third pool (pool 3) are labeled Barcode $A_3$, and Barcode $A_1$, Barcode $A_2$, and Barcode $A_3$ can be identical or different. In embodiments when the barcode sequence corresponding to the same binding reagent in each pool is identical, the position of the barcode within the output oligonucleotide identifies the binding reagent.

In embodiments, the oligonucleotides conjugated to binding reagents in different pools comprise different sequences, e.g., amplification primer sites, complementary sequences to one or more other oligonucleotides, restriction sites, etc., in order to form an output oligonucleotide after the binding reagents bind to surface markers (e.g., as illustrated in FIGS.

31A-B and 56A). Briefly, FIG. 56A shows a method of determining surface markers as described herein, which includes binding three unique binding reagents, each comprising oligonucleotides with a barcode sequence for identifying the binding reagent, to a surface marker displaying agent of interest. An output oligonucleotide can be generated from the oligonucleotides of the binding reagents, which can then be sequenced to determine the surface markers of the surface marker displaying agent.

In the exemplary embodiment illustrated in FIG. 56C, the oligonucleotide conjugated to a binding reagent corresponding to pool 1 comprises a first amplification primer site, a barcode for the binding reagent, and a first hybridization sequence ("HS 1"). The oligonucleotide conjugated to a binding reagent corresponding to pool 2 comprises a label site, a second hybridization sequence ("HS 2"), a barcode for the binding reagent, and a third hybridization sequence ("HS 3"). The oligonucleotide conjugated to a binding reagent corresponding to pool 3 comprises first and second restriction sites, and, in embodiments, a chemical, biochemical, or hapten moiety, to allow binding to a solid support, a second amplification primer site, a barcode for the binding reagent, and a fourth hybridization sequence ("HS 4"). In embodiments, the chemical, biochemical, or hapten moiety comprises biotin. In embodiments, the chemical, biochemical, or hapten moiety facilitates attachment of the oligonucleotide to a surface, e.g., a solid support. In embodiments, an output oligonucleotide is generated only an oligonucleotide from each pool is present. In embodiments, multiple copies of a particular binding reagent are present in the library, wherein each copy of the binding reagent is present in a different pool of the library.

In embodiments, the distal portion of the oligonucleotide from any given pool comprises a sequence complementary to at least part of a distal portion of the oligonucleotide of a separate pool. For example, as illustrated in FIGS. 56B and 56C, which respectively show oligonucleotides and binding reagent-oligonucleotide conjugates in the library described herein, HS 1 of the oligonucleotide corresponding to pool 1 is complementary to HS 2 of the oligonucleotide corresponding to pool 2. HS 3 of the oligonucleotide corresponding to pool 2 is complementary to HS 4 of the oligonucleotide corresponding to pool 3. For example, as illustrated in FIGS. 56B and 56C, HS 1 of the oligonucleotide corresponding to pool 1 is complementary to HS 2 of the oligonucleotide corresponding to pool 2. HS 3 of the oligonucleotide corresponding to pool 2 is complementary to HS 4 of the oligonucleotide corresponding to pool 3.

In embodiments, certain portions of all oligonucleotides conjugated to binding reagents in the same pool are identical. In embodiments, all oligonucleotides conjugated to binding reagents in the same pool comprise identical proximal portions, e.g., as illustrated in FIG. 57. For example, as shown in FIGS. 56B and 56C, the proximal portion of oligonucleotides in pool 1 includes the first primer site; the proximal portion of oligonucleotides in pool 2 includes a label site; and the proximal portion of oligonucleotides in pool 3 includes first and second restriction sites and, in embodiments, a chemical, biochemical, or hapten moiety. In embodiments, the chemical, biochemical, or hapten moiety comprises biotin. In embodiments, the chemical, biochemical, or hapten moiety facilitates attachment of the oligonucleotide to a surface, e.g., a solid support. In embodiments, the unique proximal portions corresponding to each pool simplify preparation of the binding reagent library.

In embodiments, all oligonucleotides conjugated to binding reagents in the same pool comprise identical distal portions except for the barcode sequence, e.g., as illustrated in FIG. 57. For example, as shown in FIGS. 56B and 56C, the distal portion of oligonucleotides in pool 1 includes HS 1; the distal portion of oligonucleotides in pool 2 includes HS 2 and HS 3; and the distal portion of oligonucleotides in pool 3 includes HS 4. In embodiments, the unique distal portions corresponding to each pool simplify preparation of the binding reagent library.

In embodiments, the library comprises a first binding reagent conjugated to a first oligonucleotide comprising (i) a proximal portion comprising a first amplification primer site and (ii) a distal portion comprising a barcode sequence and a first hybridization sequence; a first binding reagent conjugated to a second oligonucleotide comprising (i) a proximal portion and (ii) a distal portion comprising a second hybridization sequence, a barcode sequence, and a third hybridization sequence; a first binding reagent conjugated to a third oligonucleotide comprising (i) a proximal portion and (ii) a distal portion comprising a second amplification primer site, a barcode sequence, and a fourth hybridization sequence; wherein the first hybridization sequence and the second hybridization sequence are complementary, and the third hybridization sequence and the fourth hybridization sequence complementary. In embodiments, the first, second, and/or third oligonucleotide comprises a proximal portion comprising a chemical, biochemical, or hapten moiety. In embodiments, the chemical, biochemical, or hapten moiety comprises biotin. In embodiments, the chemical, biochemical, or hapten moiety facilitates attachment of the oligonucleotide to a surface, e.g., a solid support.

In embodiments, a binding reagent in any given pool of the library is also present in one or more other pools of the library. For example, the library can comprise a first pool comprising binding reagents A, B, and C, each conjugated to an oligonucleotide comprising a unique proximal portion and unique distal portion for the first pool, and a barcode sequence for each binding reagent; a second pool comprising binding reagents A, B, and C, each conjugated to an oligonucleotide comprising a unique proximal portion and unique distal portion for the first pool, and a barcode sequence for each binding reagent; a third pool comprising binding reagents A, B, and C, each conjugated to an oligonucleotide comprising a unique proximal portion and unique distal portion for the first pool, and a barcode sequence for each binding reagent; and so on. In embodiments, the binding reagent in each pool is conjugated to an oligonucleotide comprising different barcode sequences for the binding reagent. In embodiments, the binding reagent in each pool is conjugated to an oligonucleotide comprising the same barcode sequence for the binding reagent. In embodiments wherein the binding reagent in each pool is conjugated to an oligonucleotide comprising the same barcode sequence, in some embodiments, the position of the barcode sequence in the output oligonucleotide identifies the binding reagent.

In embodiments, the library comprises a first binding reagent conjugated to a first oligonucleotide comprising (i) a proximal portion comprising a first amplification primer site (ii) a distal portion comprising a barcode sequence and a first hybridization sequence; a first binding reagent conjugated to a second oligonucleotide comprising (i) a proximal portion and (ii) a distal portion comprising a second hybridization sequence, a barcode sequence, and a 5' splint complement sequence; a first binding reagent conjugated to a third oligonucleotide comprising (i) a proximal portion and (ii) a distal portion comprising, a 3' splint complement sequence, a barcode sequence, and a third hybridization sequence; a first binding reagent conjugated to a fourth oligonucleotide comprising (i) a proximal portion and (ii) a distal portion comprising a second amplification primer site, a barcode sequence, and a fourth hybridization sequence; wherein the first hybridization sequence and the second hybridization sequence are complementary; the third hybridization sequence and the fourth hybridization sequence complementary; and the 5' splint complement sequence and the 3' splint complement sequence are complementary respectively to 5' and 3' ends of a splint oligonucleotide. In embodiments, the first, second, third and/or fourth oligonucleotide comprises a proximal portion comprising a chemical, biochemical, or hapten moiety. In embodiments, the chemical, biochemical, or hapten moiety comprises biotin. In embodiments, the chemical, biochemical, or hapten moiety facilitates attachment of the oligonucleotide to a surface, e.g., a solid support.

In embodiments, the library further comprises one or more additional unique binding reagents conjugated to first, second, third, and/or fourth oligonucleotides comprising identical first, second, third, and/or fourth oligonucleotides, respectively, of the first binding reagent, except that the barcode sequence of oligonucleotides conjugated to the one or more unique additional binding reagents are unique to the particular binding reagent. As exemplified in FIG. 56A, there are three pools (1, 2, 3) in the library, and thus each unique binding reagent (A . . . N) in the library is independently conjugated with three different oligonucleotides, as shown in FIG. 56B, to form three binding reagent-oligonucleotide conjugates, one corresponding to each pool (e.g., 1A . . . 1N, 2A . . . 2N, 3A . . . 3N).

In embodiments, a binding reagent in any given pool of the library is not present in any other pool of the library. For example, the library can comprise a first pool comprising binding reagents A, B, and C, each conjugated to an oligonucleotide comprising a unique proximal portion and unique distal portion for the first pool, and a barcode sequence for each binding reagent; a second pool comprising binding reagents D, E, and F, each conjugated to an oligonucleotide comprising a unique proximal portion and unique distal portion for the first pool, and a barcode sequence for each binding reagent; a third pool comprising binding reagents G, H, and I, each conjugated to an oligonucleotide comprising a unique proximal portion and unique distal portion for the first pool, and a barcode sequence for each binding reagent; and so on, such that no binding reagent is duplicated cross any pools of the library.

In embodiments, the library comprises first binding reagent conjugated to a first oligonucleotide comprising (i) a proximal portion comprising a first amplification primer site and (ii) a distal portion comprising a barcode sequence and a first hybridization sequence; a second binding reagent conjugated to a second oligonucleotide comprising (i) a proximal portion and (ii) a distal portion comprising a second hybridization sequence, a barcode sequence, and a third hybridization sequence; a third binding reagent conjugated to a third oligonucleotide comprising (i) a proximal portion and (ii) a distal portion comprising a second amplification primer site, a barcode sequence, and a fourth hybridization sequence; wherein the first hybridization sequence and the second hybridization sequence are complementary, and the third hybridization sequence and the fourth hybridization sequence complementary. In embodiments, the first, second, and/or third oligonucleotide comprises a proximal portion comprising a chemical, biochemical, or hapten moiety. In embodiments, the chemical, biochemical, or hapten moiety comprises biotin. In embodiments, the chemical, biochemical, or hapten moiety facilitates attachment of the oligonucleotide to a surface, e.g., a solid support.

In embodiments, the library comprises a first binding reagent conjugated to a first oligonucleotide comprising (i) a proximal portion comprising a first amplification primer site (ii) a distal portion comprising a barcode sequence and a first hybridization sequence; a second binding reagent conjugated to a second oligonucleotide comprising (i) a proximal portion and (ii) a distal portion comprising a second hybridization sequence, a barcode sequence, and a 5' splint complement sequence; a third binding reagent conjugated to a third oligonucleotide comprising (i) a proximal portion and (ii) a distal portion comprising, a 3' splint complement sequence, a barcode sequence, and a third hybridization sequence; a fourth binding reagent conjugated to a fourth oligonucleotide comprising (i) a proximal portion and (ii) a distal portion comprising a second amplification primer site, a barcode sequence, and a fourth hybridization sequence; wherein the first hybridization sequence and the second hybridization sequence are complementary; the third hybridization sequence and the fourth hybridization sequence complementary; and the 5' splint complement sequence and the 3' splint complement sequence are complementary respectively to 5' and 3' ends of a splint oligonucleotide. In embodiments, the first, second, third and/or fourth oligonucleotide comprises a proximal portion comprising a chemical, biochemical, or hapten moiety. In embodiments, the chemical, biochemical, or hapten moiety comprises biotin. In embodiments, the chemical, biochemical, or hapten moiety facilitates attachment of the oligonucleotide to a surface, e.g., a solid support.

In embodiments, the library comprises a plurality of binding reagents comprising at least 3 unique binding reagents. In embodiments, the plurality of binding reagents comprises about 4 to about 10,000 unique binding reagents. In embodiments, the plurality of binding reagents comprises about 3 to about 1,000 unique binding reagents. In embodiments, the plurality of binding reagents comprises at least 10 unique binding reagents. In embodiments, the plurality of binding reagents comprises about 10 to about 10,000 unique binding reagents. In embodiments, the plurality of binding reagents comprises about 10 to about 1,000 unique binding reagents. In embodiments, the plurality of binding reagents comprises about 50 to about 500 unique binding reagents. In embodiments, the plurality of binding reagents comprises about 10 to about 100 unique binding reagents. In embodiments, the plurality of binding reagents comprises about 50 to about 100 unique binding reagents. In embodiments, the plurality of binding reagents comprises at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 500, at least 1,000, at least 5,000, or at least 10,000 unique binding reagents.

In embodiments, the library comprises a plurality of binding reagents for a sample described herein. In embodiments, the library comprises binding reagents to markers present on immune cells, such as, e.g., cytokine receptors and immune checkpoint substances, and the sample is from an individual having or at risk of a disease. For example, the library can include binding reagents to disease markers on cells, e.g., immune cells, relevant to a viral infection, e.g., by HIV, HCV, HSV, EBV, or combination thereof. In embodiments, the markers are present on the surface of the surface marker displaying agent. In embodiments, the markers are associated with the surface marker displaying agent, as provided herein. In embodiments, the markers are secreted onto the surface from the surface marker displaying agent, e.g., viral proteins.

In embodiments, the proximal portion and distal portion are provided as separate proximal and distal oligonucle- otides and assembled prior to conjugating the oligonucle- otide to the binding reagent. Thus, in embodiments, the disclosure provides an oligonucleotide library, e.g., as illus- trated in FIG. 56B. Providing separate proximal and distal oligonucleotides can advantageously reduce costs and increase synthesis fidelity, compared with synthesizing a longer single oligonucleotide comprising both the proximal and distal portions. In embodiments, the proximal oligo- nucleotide includes a first reactive moiety for conjugating to the binding reagent. As used herein, "reactive moiety" refers to a chemical group capable of further modification or reaction with another chemical functionality. As synthesis of oligonucleotides modified with reactive moieties can be costly, reducing the length of the oligonucleotide can pro- vide significant cost savings. Having identical proximal portions for each oligonucleotide correspond to a single pool of unconjugated oligonucleotides can further simplify the design and synthesis of the separate proximal oligonucle- otide. For example, if an oligonucleotide from each pool is required to form the output oligonucleotide, three different proximal portions would be needed. Without the separate proximal and distal oligonucleotides, however, the number of different oligonucleotides would be three times the num- ber of different unique binding reagents in the library. Synthesis of three different proximal oligonucleotides that include a reactive moiety for conjugating to the binding reagent, would be considerably less costly than synthesis of multiple longer, single oligonucleotides each corresponding to a single binding reagent and having the reactive moiety for conjugating to the binding reagent. For example, in the case of 10 or 100 unique binding reagents, only three different proximal portions with the reactive moiety would need to be produced, while 30 or 300 unique, longer oligonucleotides with the reactive moiety would need to be produced if the proximal and distal portions are not provided as separate oligonucleotides. Synthesis of longer oligonucle- otides may further pose technical challenges, for example, due to a higher failure rate of synthesis, increased impurities (for instance, impurities that may have similar sequences as the desired oligonucleotide), higher probability of muta- tions, etc., and may require additional quality control and validation steps and technical expertise, leading to overall decreased efficiency and increased cost. Likewise, having identical parts of the distal portions can simplify the design and reduce the cost of synthesis of the separate distal oligonucleotide.

Thus, in embodiments, the disclosure provides a method of generating an oligonucleotide library comprising a plu- rality of oligonucleotides, comprising: (a) providing i) a plurality of proximal oligonucleotides, each proximal oli- gonucleotide comprising a first reactive moiety and a first ligation site; ii) a plurality of distal oligonucleotides, wherein each distal oligonucleotide comprises (1) a barcode sequence; (2) a sequence complementary to at least part of another distal oligonucleotide; and (3) a second ligation site; (b) ligating the first ligation site of a proximal oligonucle- otide to the second ligation site of a distal oligonucleotide to obtain a ligated oligonucleotide comprising the first reactive moiety and the barcode sequence.

In embodiments, the first ligation site of the proximal oligonucleotide and second ligation site of the distal oligo- nucleotide are capable of being ligated together. In embodiments, the first and second ligation sites are ligated by chemical or enzymatic ligation, to form the oligonucleotide comprising proximal and distal portions as described herein. Methods of ligating oligonucleotides are known in the art and described herein and include, e.g., using a DNA ligase such as the T4 ligase. In embodiments, the ligated oligo- nucleotide comprises the first reactive moiety (i.e., on the proximal portion) and the barcode sequence (i.e., on the distal portion).

In embodiments, the oligonucleotide library is generated in a plate, e.g., a multi-well plate. In embodiments, each proximal oligonucleotide is provided or added to a well of a multi-well plate, and distal oligonucleotide(s) is then added to the appropriate wells containing their correspond- ing proximal oligonucleotides. In alternative embodiments, each distal oligonucleotide is provided or added to a well of a multi-well plate, and proximal oligonucleotide(s) is then added to the appropriate wells containing their correspond- ing distal oligonucleotides. In embodiments, a ligase is then added to the wells to generate the ligated oligonucleotide.

In embodiments, the disclosure further provides a method of generating a binding reagent library, comprising conju- gating a plurality of binding reagents to the ligated oligo- nucleotide described herein via the first reactive moiety. In embodiments, the ligated oligonucleotide is conjugated to the binding reagent via the first reactive moiety on the proximal portion. In embodiments, the binding reagent is modified with a second reactive moiety capable of reacting with the first reactive moiety on the proximal portion of the oligonucleotide. In embodiments, the binding reagent is modified with a heterobifunctional cross-linking agent. In embodiments, the binding reagent is modified prior to the conjugation. In embodiments, the heterobifunctional cross- linking agent comprises (1) a second reactive moiety at a first end capable of reacting with the first reactive moiety on the proximal portion (2) a third reactive moiety at a second end capable of reacting with the binding reagent. In embodi- ments, the second and third reactive moieties are not sub- stantially reactive with one another. In embodiments, the second reactive moiety is not substantially reactive with the binding reagent. In embodiments, the third reactive moiety of the heterobifunctional cross-linking agent is not substan- tially reactive with the proximal portion. In embodiments, the second reactive moiety is an azide, and the first reactive moiety is an alkyne or cycloalkyne, e.g., cyclooctyne. In embodiments, the second reactive moiety is an alkyne or cycloalkyne, e.g., cyclooctyne, and the first reactive moiety is an azide. In embodiments, the third reactive moiety is not substantially reactive with the first reactive moiety. In embodiments, the third reactive moiety is capable of react- ing with a thiol, an amine, an aromatic amino acid residue, an aldehyde, a ketone, a polysaccharide, a strained cycloalk- ene, an alkene or a tetrazine on the binding reagent. In embodiments, the third reactive moiety is capable of react- ing with an amine on the binding reagent. In embodiments, the third reactive moiety is capable of reacting with a thiol on the binding reagent. In embodiments, the third reactive moiety is a maleimide. In embodiments, the third reactive moiety is a N-hydroxysuccinimide (NHS) ester.

In embodiments, the heterobifunctional cross-linking agent further comprises a hydrophilic spacer moiety. In embodiments, the hydrophilic spacer moiety comprises a hydrophilic polymer moiety. Hydrophilic polymer moieties are described herein and include, e.g., polyethylene glycol (PEG), poly(N-isopropylacrylamide) (PNIPAM), polyacry- lamide (PAM), poly(2-oxazoline), polyethyleneimine (PEI), poly(acrylic acid), polymethacrylate, acrylic polymers, poly (ethylene oxide), poly(vinyl alcohol) (PVA) and copolymers thereof, poly(vinylpyrrolidone) (PVP) and copolymers thereof, polyelectrolytes, cucurbit[n]uril hydrate, maleic anhydride copolymer, polyether, or any combination, cross- or co-polymer thereof. In embodiments, the hydrophilic polymer moiety comprises PEG.

In embodiments, the binding reagent is first modified with the heterobifunctional cross-linking agent, and the modified binding reagent is then conjugated to the ligated oligonucle- otide via reacting the first and second reactive moieties without an intermediate purification step. In embodiments, the binding reagent-oligonucleotide conjugate is purified by filtration (e.g., ultrafiltration), buffer exchange (e.g., desalt- ing), chromatography, or combinations thereof. In embodi- ments, the purification removes unreacted and/or unwanted components of the reactions, e.g., unreacted heterobifunc- tional cross-linking agent, oligonucleotide, and/or binding reagent; catalysts and co-reactants from the reaction, and unwanted byproducts or side products. Methods of conju- gation are known in the art and also further provided herein.

In embodiments, the binding reagent is first modified with the heterobifunctional cross-linking agent, and the modified binding reagent is then purified from unreacted components, e.g., the unreacted heterobifunctional cross-linking agent and/or the unmodified binding reagent in an intermediate purification step. In embodiments, the intermediate purifi- cation step comprises filtration (e.g., ultrafiltration), buffer exchange (e.g., desalting), chromatography, or combination thereof. An exemplary embodiment is illustrated in FIG. 58A, showing a heterobifunctional cross-linking agent com- prising an NHS-ester, PEG moiety, and alkyne, which is attached to amines on the binding reagent and reacted with an oligonucleotide comprising an azide.

In embodiments, the purified modified binding reagent is then conjugated to the ligated oligonucleotide via reacting the first and second reactive moieties, and the binding reagent-oligonucleotide conjugate is purified by filtration (e.g., ultrafiltration), buffer exchange (e.g., desalting), chro- matography, or combination thereof, as described herein. An exemplary embodiment is illustrated in FIG. 58B, showing an intermediate purification of the modified binding reagent and the final reaction product after the conjugation step. In embodiments, the intermediate purification step provides a library of modified binding reagents. The library of modified binding reagents can then be conjugated to any oligonucle- otides comprising a first reactive moiety capable of conju- gating to the second reactive moiety of the heterobifunc- tional cross-linking agent. For example, the library of modified binding reagents can be useful when testing sub- sets of the binding reagents for a particular surface marker displaying agent; rather than conjugating all of the binding reagents to oligonucleotides, only the subset to be tested needs to be conjugated, which reduces processing time and leaves the unconjugated modified binding reagents in the library available for conjugating to other oligonucleotides.

In embodiments, a single binding reagent is conjugated to multiple copies of the oligonucleotide. In embodiments, the multiple oligonucleotides conjugated to a single binding reagent are identical. In embodiments, having multiple oli- gonucleotides on a single binding reagent provides addi- tional degrees of freedom, e.g., when generating the output oligonucleotide. In embodiments, the number of oligonucle- otides per binding reagent is controlled during the modifi- cation of the binding reagent with the heterobifunctional cross-linking agent. In such embodiments, the number of oligonucleotides per binding reagent is limited by the num- ber of heterobifunctional cross-linking agents attached to the binding reagent. In embodiments, the number of oligonucle- otides per binding reagent is controlled during the conjuga- tion of the modified binding reagent with the oligonucle- otide. In such embodiments, the number of oligonucleotides per binding reagent is limited by the number of oligonucle- otides added in the conjugation reaction. An exemplary product from reactions wherein the number of oligonucle- otides per binding reagent is limited by the number of heterobifunctional cross-linking agent attached to the bind- ing reagent is shown in FIG. 58C. An exemplary product from reactions wherein the number of oligonucleotides per binding reagent is limited by the number of oligonucleotides added to the conjugation reaction is shown in FIG. 58D. As exemplified in FIG. 58D, in situations where the number of oligonucleotides added to the conjugation reaction is fewer than the number of heterobifunctional cross-linking agents attached to the binding reagent, the binding reagent can include additional unconjugated reactive moieties (e.g., the free alkynes on the binding reagent shown in FIG. 58D) which can then be used to react with other substances.

In embodiments, the binding reagent library is generated on a solid support, e.g., in a plate, for instance, a multi-well plate. In embodiments, the modifying of each binding reagent with the heterobifunctional cross-linking agent is performed in parallel. In embodiments, each binding reagent is in a well of a multi-well plate, and the heterobifunctional cross-linking agent is added to each well of the plate. In embodiments, the conjugating of modified binding reagents with the ligated oligonucleotide is performed in parallel. In embodiments, purification of the modified binding reagent and/or the binding reagent-oligonucleotide conjugate are performed in parallel. In embodiments, the parallel purifi- cation is performed by transferring the reaction mixtures from the multi-well plate to a multi-well purification plate, e.g., a filtration plate or buffer exchange plate. The transfer can be further performed in parallel, e.g., using a multi- channel device such as a multi-channel pipette or automated liquid handling device. In embodiments, the filtration plate is an ultrafiltration plate. In embodiments, the buffer exchange plate is a desalting plate.

In embodiments, the present disclosure further provides kits for generating the oligonucleotide library and/or the binding reagent library described herein. In embodiments, the kit comprises a plate, e.g., a multi-well plate. In embodi- ments, the kit comprises separate plates for generating the oligonucleotide library and the binding reagent library. In embodiments, separate kits are provided for generating the oligonucleotide library and the binding reagent library. In embodiments, a single kit is provided for generating the oligonucleotide library and the binding reagent library.

In embodiments, the kit comprises a plurality of proximal oligonucleotides. In embodiments, the proximal oligonucle- otides are provided on the plate. In embodiments, the proximal oligonucleotides are provided in a container, and a user of the kit adds the proximal oligonucleotides to the plate. In embodiments, a kit for generating the binding reagent library comprises pools of ligated oligonucleotides as described herein. In embodiments, the kit comprises a plurality of modified binding reagents as described herein. In embodiments, the kit comprises a library of binding reagents, wherein each binding reagent is conjugated to an oligonucleotide as described herein. For example, the kit can contain a library comprising multiple pools of binding reagents conjugated to oligonucleotides, wherein the bind- ing reagents bind to markers in a sample of interest, e.g., CD antigens, immune markers, disease markers, receptors and ligands, cell-type specific markers, and the like.

In embodiments, the kit further comprises one or more of a splint oligonucleotide, a ligase, a heterobifunctional cross-linking agent, a buffer (e.g., ligase buffer, conjugation buffer, assay buffer, storage buffer, reconstitution buffer, and the like), and a purification device (e.g., column, filter, resin, and the like). In embodiments, the purification device comprises a purification plate, e.g., a multi-well plate. In embodiments, the purification plate comprises a resin and/or filter for purifying the ligated oligonucleotide, the binding reagent-oligonucleotide conjugate, or both. In embodiments, the purification plate is a buffer exchange plate. In embodiments, the purification plate is a filtration, e.g., ultrafiltration plate. In embodiments, the kit further comprises one or more reagents for screening and/or sequencing, e.g., an amplification primer, a polymerase, a restriction enzyme, a sequencing buffer, and/or a read buffer. Further components of the kits described herein can include liquid handling devices, vials, tubes, and the like. In embodiments, the components of the kits described herein are provided in one or more vials, containers, or compartments.

All references cited herein, including patents, patent applications, papers, textbooks and the like, and the references cited therein, to the extent that they are not already, are hereby incorporated herein by reference in their entirety.

III. Examples

Example 1. Methods of Extracellular Vesicle (EV) Capture

Example 1.1. Plate-Based Solid Phase Immunoaffinity Capture

Exosomes and other EVs can be captured on a solid support using affinity ligands that target known protein or carbohydrate moieties on their surface. The moiety most often used is the tetraspanin proteins, which are hypothesized to be present on the surface of most EVs. It has been disclosed that various beads or microtiter plates can be used for immunoaffinity precipitation of EVs. A plate-based approach is preferred when many samples must be handled in parallel or when stringent washing is desired to remove non-specific binding, which may be more difficult to perform on beads.

Antibodies used to capture EVs from fluid samples were displayed on Meso Scale Discovery plates. Streptavidin gold plates were typically used to display biotinylated antibodies. In order to capture as many EVs as possible, large spot streptavidin gold plates were used (MSD GOLD Immuno-assay Plates). The large capture area improved capture kinetics (because capture rate is proportional to surface area) and EV binding capacity. Plates with directly coated antibodies could also be used.

Figure 5A:
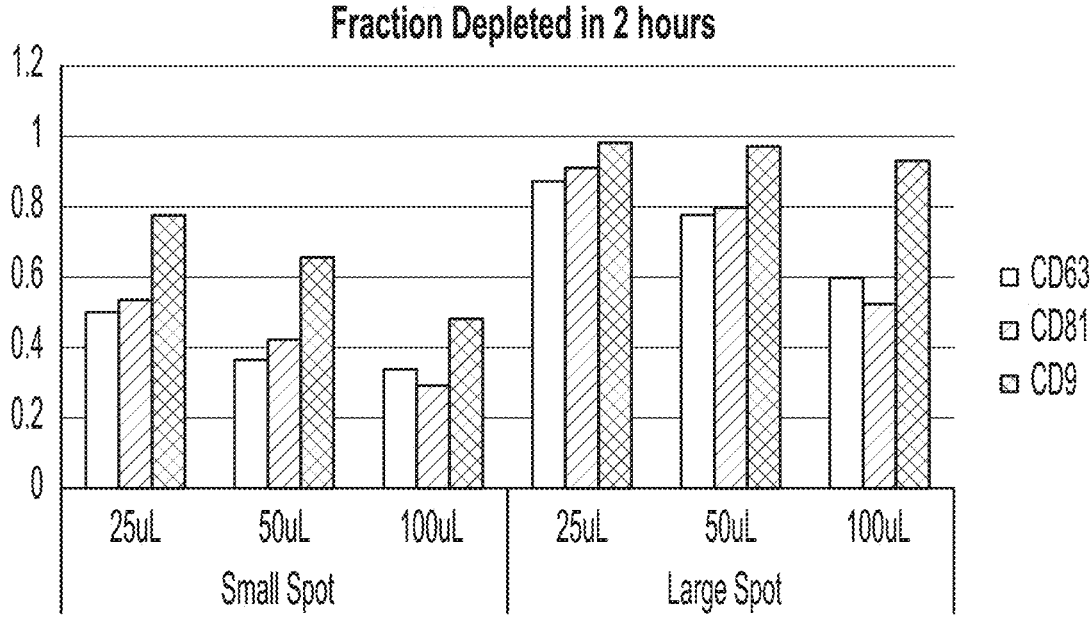
FIGS. 5A-5B show the results of the experiments described in Example 1.1.
Figure 5B:
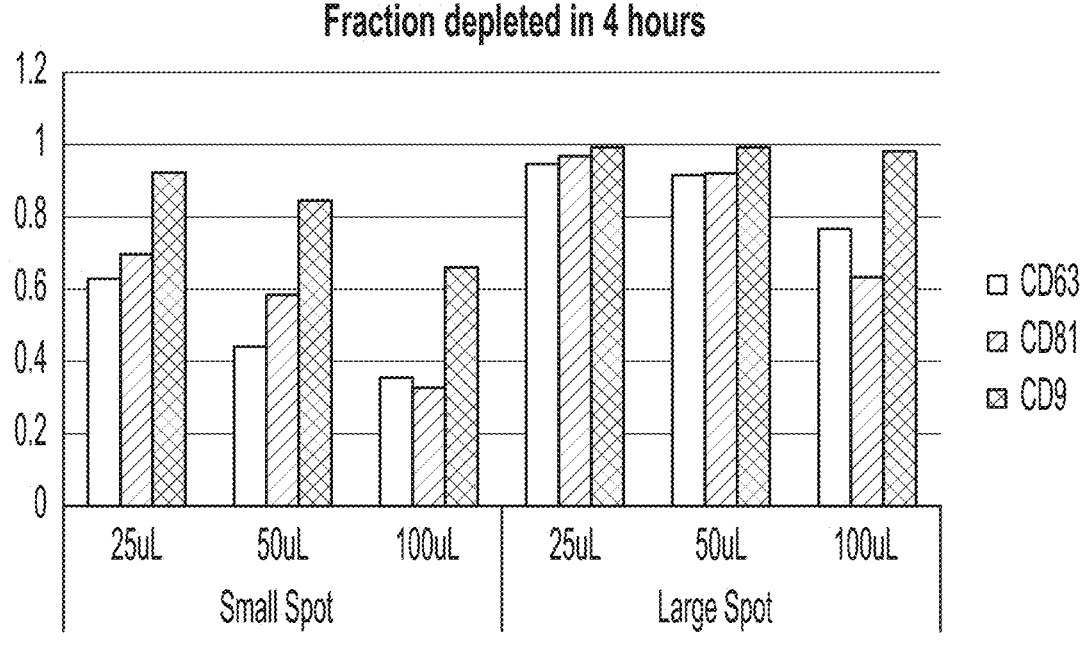

EVs from a typical sample of cell culture medium could also be captured on a large spot electrode within a few hours using antibodies targeting any of the three tetraspanin proteins. Depleted media and fresh (non-depleted) sample were assayed using tetraspanin sandwich assays, and signal from depleted media is plotted as a fraction of the signal in the fresh (non-depleted) sample. Results are shown in FIGS. 5A and 5B.

Example 1.2. Immunoaffinity Capture and Elution

EVs have been found to be difficult to elute from a solid phase once they have been captured by antibodies. This occurrence is mostly likely due to high avidity arising from multiple interactions between the capture antibodies and EV surface markers that can occur when the capture antibody is present at a high surface concentration.

Figure 6A:
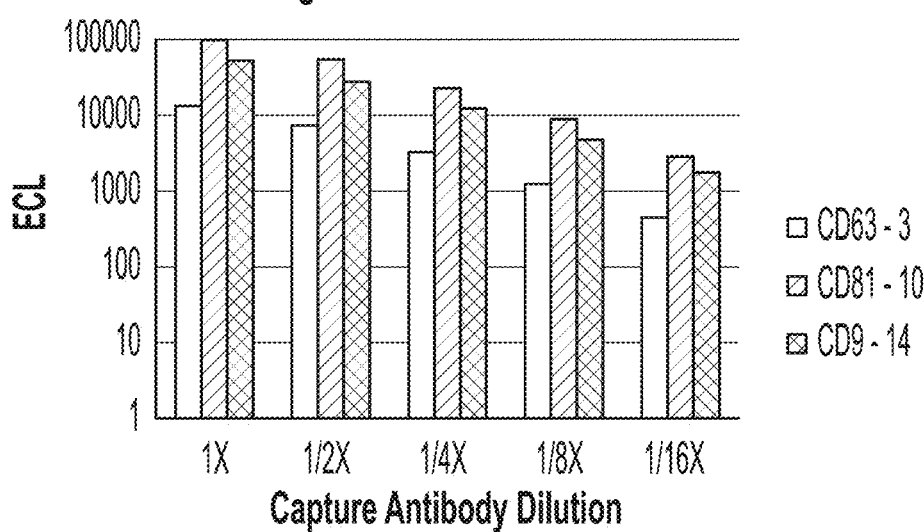
FIGS. 6A-6B show the results of the experiments described in Example 1.2.
Figure 6B:
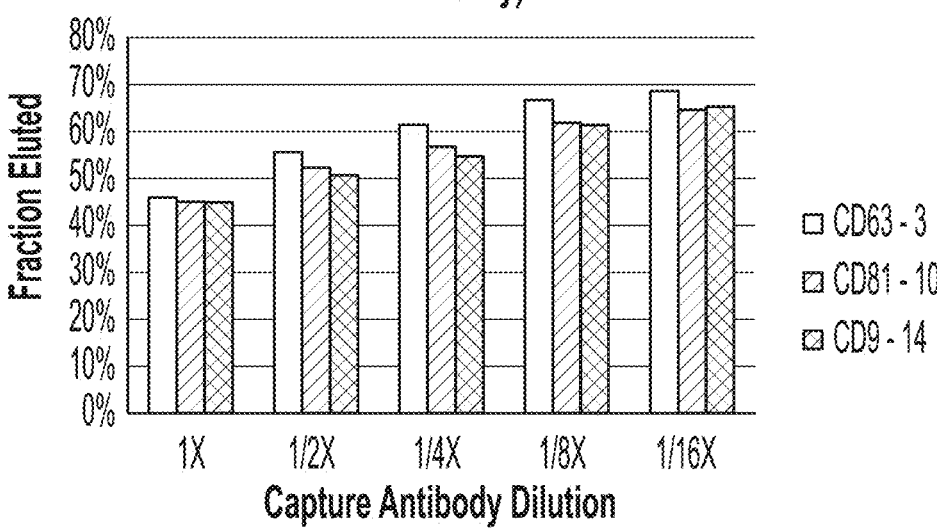

Typical elution strategies involve lowering the pH to decrease the affinity of the antibody-antigen binding. When the valency of the interaction is high, lowering the individual antibody affinity may not lower the overall avidity sufficiently to allow efficient elution of the EVs, as demonstrated in FIGS. 6A and 6B. Elution efficiency was inversely proportional to capture antibody concentration. Decreasing the capture concentration also significantly decreases the binding capacity of the surface and slows the capture kinetics.

Figure 7:
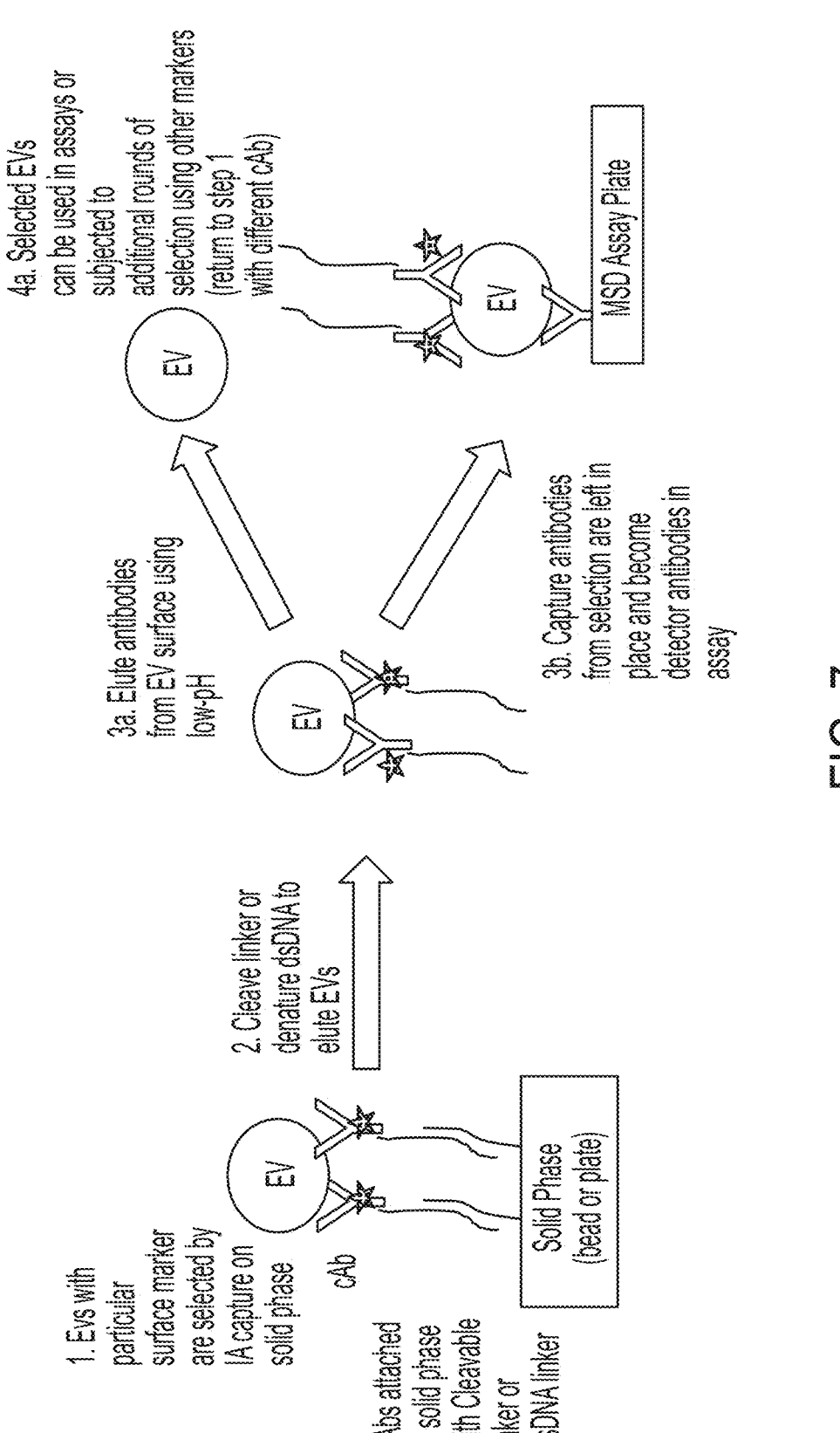
FIG. 7 illustrates an embodiment described in Example 1.2, wherein EVs are captured by labeled capture antibodies immobilized on a solid surface. The EV-capture antibody complex is first eluted from the solid surface, and the capture antibody can then optionally be released from the EV for further characterization, or the EV-capture antibody complex can be used directly in detection assays.

As exemplified in FIG. 7, EVs are captured by STAG labeled-capture antibodies via immunocapture onto a solid phase, e.g., a bead or plate. The capture antibodies are immobilized on the solid surface with a cleavable linker or a double-stranded DNA (dsDNA) linker. The linker is then cleaved, or the dsDNA is denatured, to elute the EVs still bound to the capture antibodies. The capture antibodies are then either: eluted from the EVs using low pH, then the EVs can be used in assays or subjected to additional rounds of selection using other markers; or remain bound to the EVs and serve as detection antibodies in the assay using the STAG label.

Example 1.3. Bead-Based Immunoaffinity Capture

In this Example, solid-phase immunoaffinity capture was performed using beads as the solid phase. CD81 antibodies and a non-specific isotype matched antibody were separately immobilized on beads, and each antibody was incubated with exosomes isolated from normal human serum by PEG precipitation. The exosomes were then eluted at low pH and assayed with CD63, CD81, and CD9 sandwich assays. The non-depleted sample, the depleted sample, and the eluted fraction were all assayed.

Figure 8:
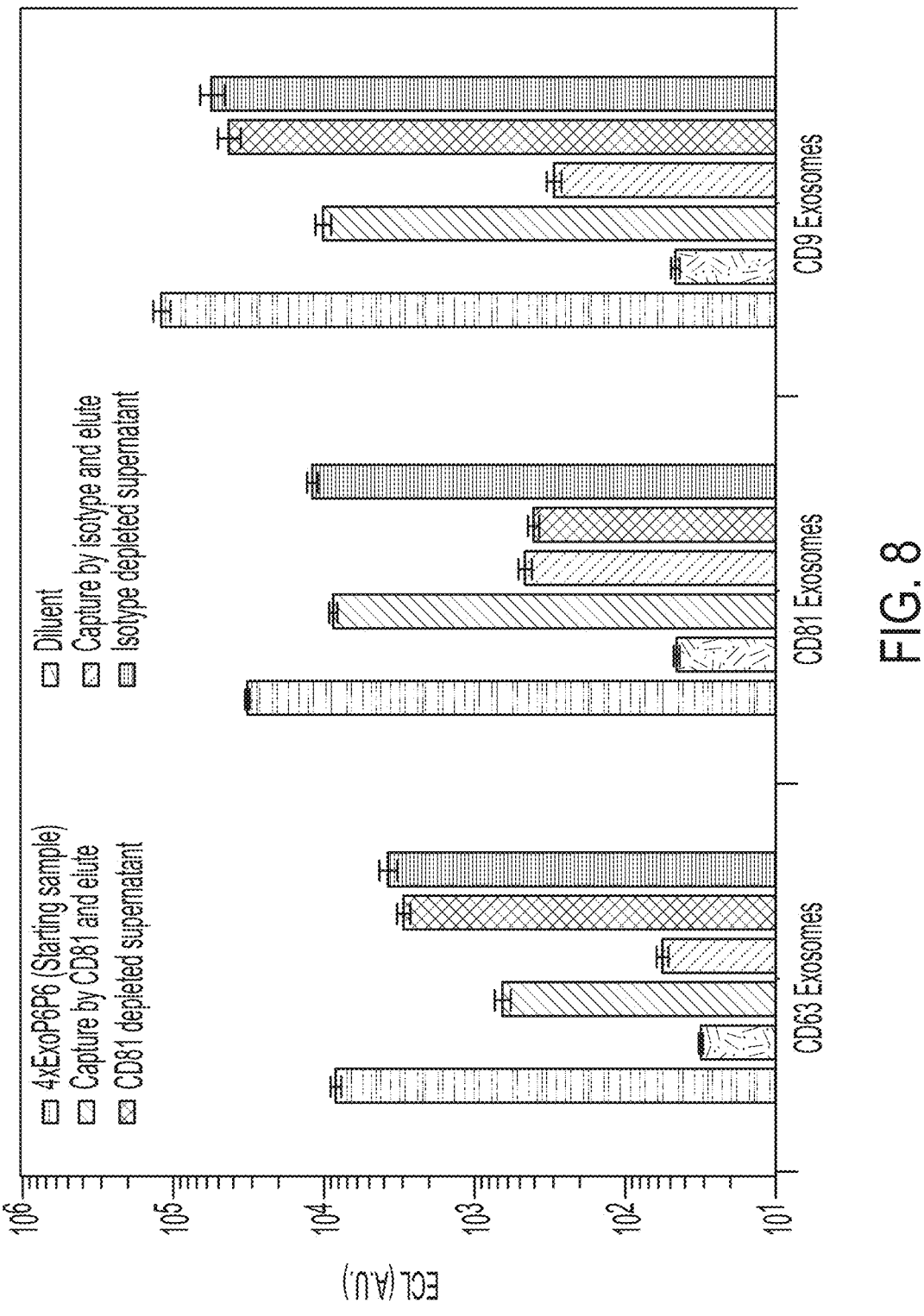
FIG. 8 shows the results of the experiments described in Example 1.3. EVs were captured by bead-based immuno-affinity capture using either CD81 antibody or a non-specific isotype-matched antibody. The EVs were eluted at low pH, and the non-depleted sample, and depleted supernatant sample were evaluated using tetraspanin (CD63, CD81, and CD9) sandwich assays. Bar graph represents the ECL signal from each sample.

Results are shown in FIG. 8. More than 98% of the EV-associated CD81 was depleted from the sample by the CD81 beads. Only approximately 1/3 of the captured EVs were eluted and subsequently recaptured, most likely due to inefficient elution.

Example 2. Sandwich Immunoassay Formats for Intact EVs

Immunoassay formats and methods for characterizing intact EVs based on surface protein or carbohydrate markers are described in Examples 2.1-2.4.

The following is an overview of the method for quantifying EVs or EV-associated proteins using ECL-based sandwich immunoassays.

Capture antibodies with reactivity to suspected EV-associated proteins are displayed on the surface of MSD plate electrodes, using either direct coating, biotinylated antibodies on streptavidin-coated plates, or a multispot system as described in U.S. Pat. Nos. 10,201,812; 7,842,246 and 6,977,722 (the disclosure of which are hereby incorporated by reference in their entireties), to display the capture antibodies.

A fluid sample suspected to contain EVs and particularly exosomes is applied to the surface. The wells of the plate may be prefilled with a small amount of a diluent to improve the assay characteristics. Many surfactants will disrupt the membranes of EVs should be considered when selecting diluent composition. Most often, DPBS with 2% bovine serum albumin is used as the assay diluent and added at a ratio of 1:1 with the sample (see Example 5.1 for further description of diluent composition). The plate is then incubated to allow EVs to be captured by the capture antibodies. The depletion of EVs from the sample is diffusion-limited due to the size of the EVs, thus, the time required to deplete the sample of EVs is dependent on spot size, EV size, plate agitation, and capture antibody concentration. Typically, a sample can be >90% depleted by a large spot plate in 2 hours, while a small spot plate may take 4 to 8 hours, and a 10-spot plate may take longer than 12 hours. A short capture time (1 hour) is typically used, particularly when a large number of EVs are expected to be in the sample, because complete depletion of EVs is impractical.

The plate is washed with water, or preferably a wash buffer, most preferably containing a small amount of Tween-20 (0.05% v/v) to aid in removal of physiosorbed EVs from the plate surface.

Detection antibody is added in a diluent and incubated for a sufficient time to allow a significant fraction of the bound exosomes to be decorated. This detection antibody can target the same protein species as the capture antibody or a different protein. Where the same protein is targeted by both capture and detector antibodies, it is preferable to use the same clone or two clones that target the same epitope. This ensures that soluble monomeric protein will not be detected and minimizes the false positive signal that may be generated if the protein of interest is present in a dimerized or aggregated form. Certain diluent compositions may also reduce the false positive signal generated by soluble dimers (see Example 5.1). Where different species are targeted by the capture and detection antibodies, it is preferable to target two species that are known to not form heterodimers or higher order structures with one another, as the co-localization of the two proteins should only occur when both are embedded in an EV membrane. For samples with high soluble levels of one of the species used for capture or detection, a purification method such as ultrafiltration, ultra-centrifugation, precipitation, or size exclusion chromatography should be used to reduce the soluble protein to avoid competition and the potential for false positive signals.

The most commonly used proteins for capturing and detection EVs are CD81, CD63 and CD9, so-called tetraspanin proteins because they have 4 membrane spanning alpha-helices. One or more of these proteins are believed to be present on nearly all EVs.

Example 2.1.1. Intact EV Sandwich Assays for CD63+ EVs, CD81+ EVs, and CD9+ EVs 50 µL of 1 µg/mL biotinylated CD63, CD81, or CD9 antibodies were added to a small spot streptavidin plate and shaken overnight to be immobilized.

The plates were washed with PBST to remove unbound antibody. Unlike typical sandwich assays, these assays use the same epitope for the capture and detection antibodies, so any unbound capture antibody left in the well can compete with the detection antibody and cause a loss of signal. This is also true of any bound antibody that desorbs from the surface using the capture step.

A soaking/blocking step in diluent after the plate is coated with capture antibody was found to yield more consistent results. A shorter capture time also appeared to minimize this competition, as there is less time for the capture antibody to desorb.

After blocking, the plate is washed and 25 µL of diluent A is added to each well, followed by 25 µL of each sample. In the results (FIG. 11), the samples were a dilution series of cell conditioned medium from Expi293 cells, which produce a large number of EVs expressing a high level of CD81. These EVs also express the surface proteins CD9 and CD63 to a lesser degree.

The samples were incubated on a shaker at room temperature for 1 hour, followed by washing with PBST in a plate washer.

The detection antibodies (the same as the capture antibody in each case) were added at 1 µg/mL in 25 µL of diluent A and incubated on a shaker at room temperature for 1 hour, followed by a PBST wash. The plate was then read with read buffer B on a SECTOR imager.

Figure 9A:
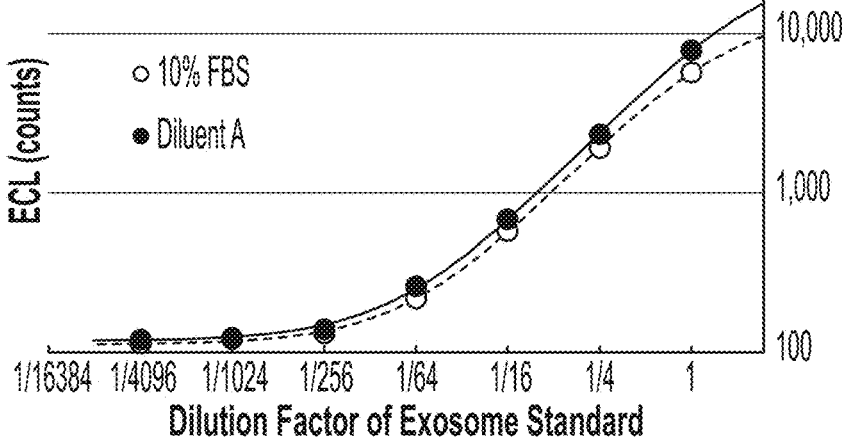
FIGS. 9A-9C relate to the experiments described in Example 2.1.1. Calibration curves for tetraspanin (CD63, CD81, and CD9) sandwich assays are shown in FIGS. 9A, 9B, and 9C, respectively. Calibration curves for the assay in diluent A with and without 10% fetal bovine serum (FBS) were generated for each sample.
Figure 9B:
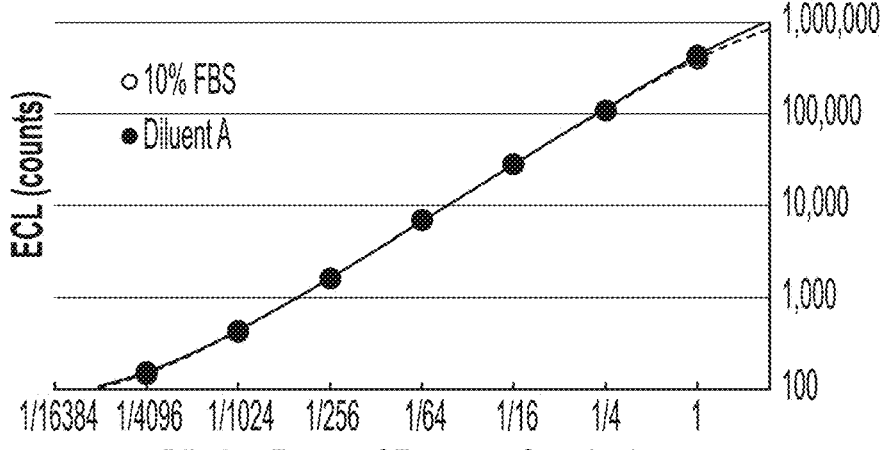
Figure 9C:
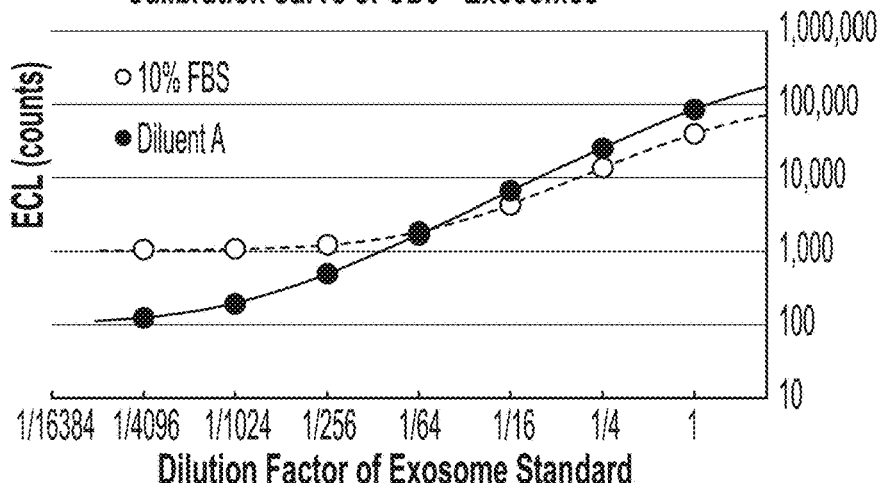

As shown in FIGS. 9A-9C, CD63 and CD81 assays were largely unaffected by the presence of 10% fetal bovine serum, while the CD9 assay had some adverse reaction to FBS due to cross-reactivity of the detection antibody to bovine CD9.

Table 1 shows the LLODs, the maximum dilution factor of neat exosome standard that is detectable (2.5 standard deviations above background).

TABLE 1

| | LLODs for Intact EV Sandwich Assays. | | | |
| Assay | Hill Slope (Dil A) | Hill Slope (10% FBS) | LLOD (Dil A) | LLOD (10% FBS) |
| --- | --- | --- | --- | --- |
| CD63 | 1.05 | 1.08 | 166-fold | 149-fold |
| CD81 | 1.04 | 1.04 | 8830-fold | 8940-fold |
| CD9 | 1.02 | 1.02 | 2220-fold | 490-fold |

Figure 10:
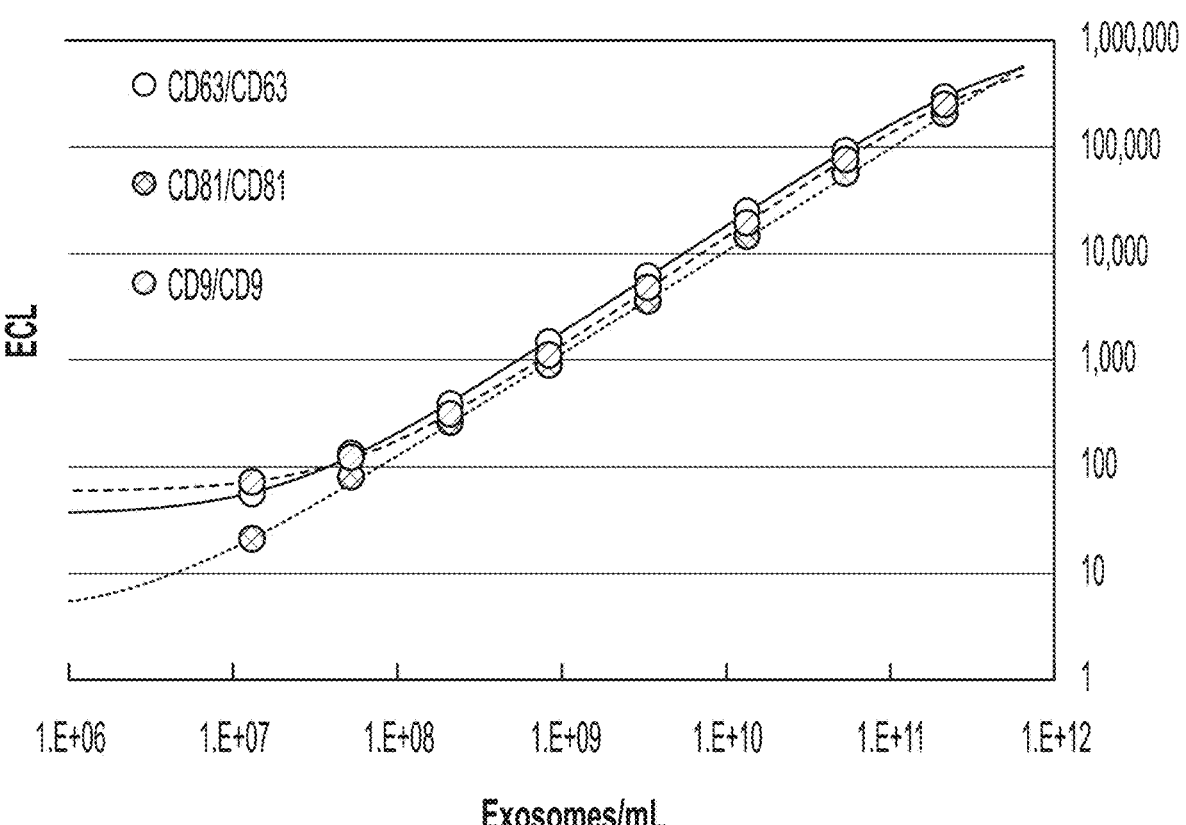
FIG. 10 relates to experiments described in Example 2.1.2. Calibration curves for tetraspanin (CD63, CD81, and CD9) sandwich assays for exosomes from THP-1 cells are shown.

Example 2.1.2. Intact EV Assays Measuring Concentrated Exosomes from THP-1 Cells THP-1 cells were grown in serum-free conditions with PMA to induce monocyte-like differentiation. Cell conditioned medium was collected on Day 4 and concentrated approximately 10-fold using Nanosep 300 kDa centrifugation units. Sample was serially diluted in 4-fold steps and assayed with each of the tetraspanin assays. Results are shown in FIG. 10 and demonstrate that the intact EV assays exhibit wide dynamics when used to measure concentrated exosomes from THP-1 cells. Table 2 is a summary of the LLODs.

TABLE 2

| | LLODs for Assays of Exosomes from THP-1 Cells. | | | |
| Assay | Hill Slope | LLOD (Dilution Factor) | LLOD (Exosomes/mL) | LLOD (Exosomes/well) |
| --- | --- | --- | --- | --- |
| CD63 | 1.02 | 3500-fold | 6e7 | 1.5e6 |
| CD81 | 0.97 | 2000-fold | 1e8 | 2.5e6 |
| CD9 | 1.05 | 2000-fold | 1e8 | 2.5e6 |

Example 2.2 Two-Marker Assays for Intact EVs

Intact EV assays were run using all pairwise combinations of CD63, CD81, and CD9 as capture and detection antibodies.

Procedure:

CD63, CD81, and CD9 capture antibodies were each displayed in separate wells of a streptavidin gold plate or multispot plate. Samples were added and incubated to capture EVs with each of the tetraspanins. Plates were washed with PBST in a plate washer. Detection antibodies for CD63, CD81, CD9, or a cocktail of all three were added to various wells of the plate to yield all possible combinations of capture and detection antibodies.

Figure 11:
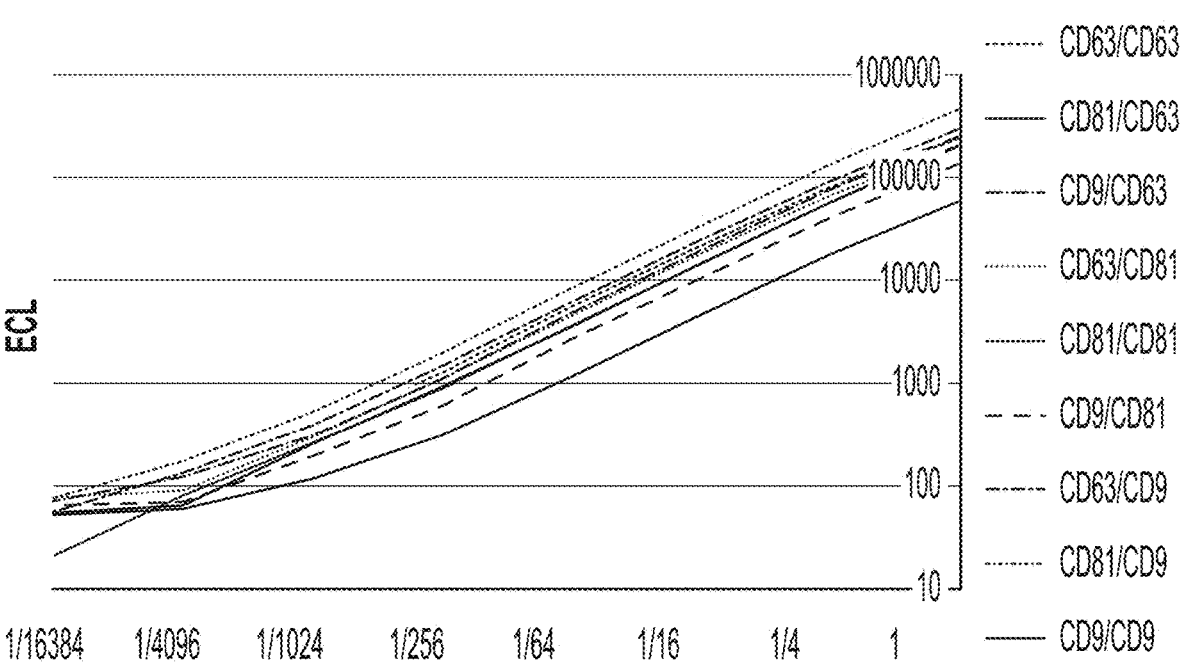
FIG. 11 shows the results of the experiments described in Example 2.2. Intact EV assays were performed using all pairwise combinations of CD63, CD81, and CD9 as capture and detection antibodies.

Results are shown in FIG. 11. Interpretation of the signals is further discussed in Example 5.1. The signal roughly corresponds to the amount of the detection antibody target present on the population of EVs bearing the capture antibody target. For example, for CD81 capture/CD63 detection, the signal corresponds to the amount of CD63 protein present on the surface of all CD81+ vesicles.

Example 2.2.1. Screening Cell Supernatants and Purified Exosomes

Cell conditioned media (CCM) samples and EVs purified by differential ultracentrifugation were assayed for all combinations of CD63, CD81, CD9, and EpCAM (except EpCAM/EpCAM) as capture and detection antibody.

Results are shown in FIG. 12. Very different patterns for two-marker assay reactivity between the cell lines were observed. For the Panc-1 and HUVEC EVs, the pattern of reactivity is remarkably similar between the CCM and purified EVs, although the EVs have not been concentrated. For the tumor-derived exosomes, a significant change was observed, i.e., all CD81+ EVs were lost during ultracentrifugation. Notably, the HUVEC CCM and exosomes had no detectable EpCAM+ EVs, while all other samples had detectable levels of EpCAM+ EVs, which was expected because HUVEC are endothelial cells and do not typically express EpCAM.

Example 2.2.2. Use of Isotype Control Antibodies

Isotype control antibodies are frequently used in flow cytometry to assess non-specific binding of the antibody to the cell surface. Isotype control antibodies were used to assess non-specific binding of EVs to capture antibodies, and also used to assess non-specific binding of detection antibodies to specifically captured exosomes. These isotype control antibodies are typically raised against the KLH antigen. Antibodies raised against other antigens not expected to be present in the sample have also been used with success.

As illustrated in FIG. 13A, tetraspanin capture antibody was combined with isotype-matched non-specific control antibody detector to assess non-specific binding of detection antibodies to specifically-captured EVs.

As illustrated in FIG. 13B, isotype-matched non-specific control antibody was displayed on a plate as capture antibody and combined with tetraspanin detection antibodies to assess non-specific binding of exosomes to the surface, which were then specifically detected.

The results in FIG. 13C show low non-specific binding of EVs to IgG1-control capture antibody (last column), and low binding of IgG1-control antibody to captured EVs (4$^{th}$ row).

Example 2.3.1. Multiplexed Assays for Common Markers on Intact EVs

The capture antibodies targeting CD63, CD81, and CD9 were displayed within the same well using the multispot system as described in U.S. Pat. Nos. 10,201,812; 7,842,246 and 6,977,722 (the disclosures of which are hereby incorporated by reference in their entireties). Spots 1, 3, and 8 were used due to their radial symmetry, and similar mass-transport should occur during mixing.

A 4-fold dilution series of Expi293 cell conditioned medium was generated, and assays were performed using all pairwise combinations of tetraspanin capture and detection antibodies. Easy assay was performed in singleplex as well as in a multiplex with all three capture antibodies in each well, but only a single detection antibody in each well.

FIG. 14 shows the ratios of the multiplex signal to the singleplex. In most cases, the signal for the multiplexed assays is within 10% of the singleplex assays.

Example 2.3.2. Multiplexed Assays for Rare EVs

Specific populations of EVs have been proposed as bio-markers of disease. Often, these populations are a small fraction of the total EVs in a sample and are characterized by the presence of a surface marker that is absent from most EVs.

A powerful screening tool for biomarker discovery and quantitative comparison of rare EV populations between samples has been developed by multiplexing capture antibodies for up to 10 surface antigens and then using common detector antibodies (tetraspanins or other common markers) for detection.

(A). Cell Line Screening with EV Cancer Markers

To develop a 10-plex of assays for tumor-associated EVs, 16 antibodies were arrayed against 13 different antigens suspected to be present on tumor-derived EVs in two 8-plexes.

Supernatants from 15 different culture conditions representing 10 different cell lines were assayed. Each sample was captured with both 8-plexes and detected with each of the tetraspanin detection antibodies separately.

Cell lines that produced EVs with 11 of the 13 markers were identified. See FIG. 15.

(B). Pancreatic Cancer EV Screening

Control samples from pancreatic cancer-derived cell lines and patient derived xenograft models (PDX) cultures were screened using 10-plex of cancer antigen capture antibodies and triplex of tetraspanin capture antibodies. Detection was performed using a cocktail of all three tetraspanin antibodies to maximize signal and minimize the amount of sample required.

Results are shown in FIG. 16A. All of the markers were detectable in at least one of the control samples.

Plasma samples from 10 pancreatic ductal adenocarcinoma patients and 10 healthy controls were diluted 1:10 and assayed on both the 10-plex cancer antigen array and the tetraspanin triplex.

Results are shown in FIG. 16B. Most of the cancer antigen+EV populations were barely detectable in most of the samples. A notable exception was CEA, which showed significant elevation in the PDAC patients relative to healthy controls. Some other markers had individual cancer patients with high signals, such as P-Cadherin, CA15.3 E-Cadherin, and CA125, which could be indicative of a particular phenotype of the tumor cells that produced the EVs.

Markers that were too low to detect in both the healthy subjects and PDAC patients (e.g., EphA2, CA50, EpCAM, EGFR, CA19-9) are good candidates for further screening with a high-sensitivity amplified assay (see Example 2.4).

(C). Multiplexing on Printed Plates

Samples of cell conditioned medium (CCM) and exosomes from various cell lines and serum pools were captured using three 6-plex panels of cancer antigens. Not all of these antigens are expected to be on the surface of EVs as some are secreted in a soluble form. The captured EVs were detected using a cocktail of tetraspanin detection antibodies.

Results are shown in FIG. 17. Surface markers EGFR, CA15-3, CA19-9 were detected in pancreatic cancer cell line samples.

Example 2.4. Amplified Assays for EV Surface Proteins

The following detection schemes that used rolling-circle amplification to boost the signal from surface antigens on captured EVs were demonstrated, as further discussed in Examples 2.4.1 and 2.4.2:

Single Detection Antibody with Rolling Circle Amplification (RCA): A single antibody conjugate is used to both splint the DNA ligation and prime the DNA extension for rolling circle amplification. This can also be performed using a preformed rolling circle template and omitting the ligation step.

Homo-Pair Proximity Ligation: The same tetraspanin antibody is used for proximity probe 1 (PP1) and proximity probe 2 (PP2) in a proximity ligation/rolling circle amplification reaction.

Hetero-Pair Proximity Ligation: Antibodies against two different surface antigens are used for PP1 and PP2, respectively, in a proximity ligation/rolling circle amplification reaction.

PLA/RCA Cocktail: A PP1 for each of the tetraspanins and a PP2 for each of the tetraspanins is combined (6 proximity probes in all) to allow all combinations of CD63, CD81, and CD9 to produce amplified signal.

Figure 18A:
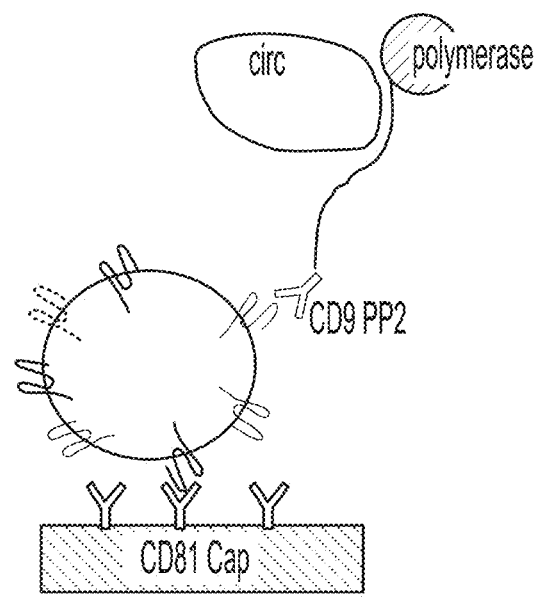
FIGS. 18A-18B relate to the experiments described in Example 2.4.1 (A).

Example 2.4.1. Singleplex Assays (A). Single Antibody RCA Detection of EV-Associated Antigens A dilution series of Expi293 cell conditioned medium (CCM) was captured on two plates with CD81 co-spotted with anchor oligonucleotide. Captured EVs were detected with STAG-labeled detection antibodies (CD63, CD81, or CD9) or PP2 conjugates (CD63, CD81, or CD9). RCA reaction was then performed on the plate with detection conjugates. The procedure is illustrated in FIG. 18A.

Figure 18B:
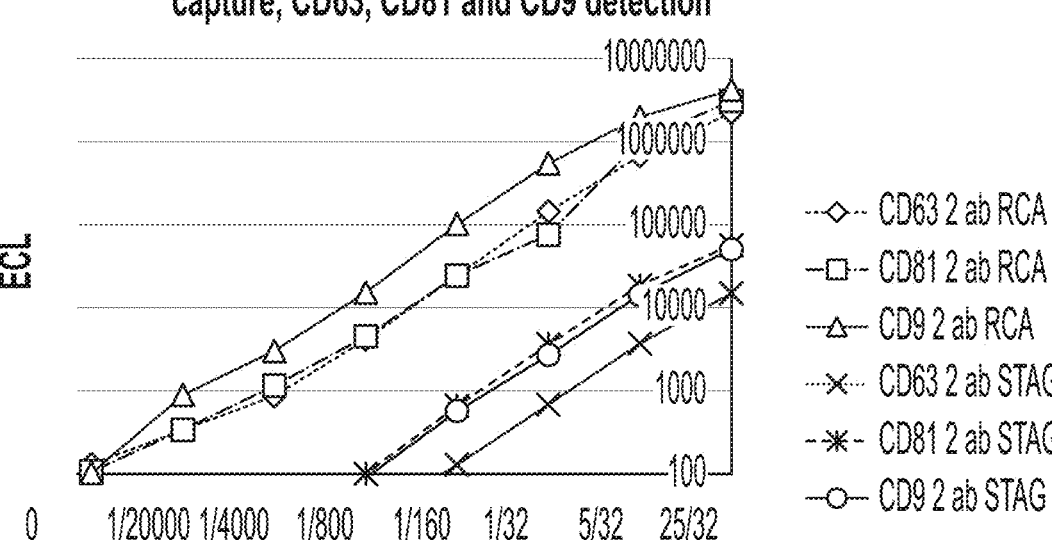

Results are shown in FIG. 18B. The assay shows linear amplification (50× for CD81, 200× for CD63 and CD9) across a wide range of dilutions with no observable elevation in background signal. The low amplification ratio for CD81 is likely due to low labeling ratio of CD81-PP2 conjugate, the presence of unconjugated antibody, or competition by desorbed capture antibody.

(B). Homo- and Hetero-Pair Proximity Ligation/RCA for EV Surface Antigens

Expi293 EVs were captured on CD81 capture plates with anchor oligonucleotide and detected with all pairwise combinations of CD63, CD81, and CD9 PP1 and CD63, CD81, and CD9 PP2. The procedures for a homo-pair and a hetero-pair of proximity probes are illustrated in FIGS. 19A and 19B, respectively.

Results are shown in FIG. 19C. Low non-specific binding (ECL signal of 250 or less) was observed for all combinations of proximity probes.

(C). PLA/RCA Cocktail

EVs from 4 CCM samples were captured on plates printed with an anti-EphA2 capture antibody. MC02 (PANC-1) and HCT-15 cells were expected to express high levels of EphA2 exosomes relative to the other two cell lines.

Captured EVs were detected with either homo-pairs of proximity probes in a PLA/RCA assay (e.g., CD9/CD9), hetero-pairs (e.g., CD9/CD81), or cocktails comprising CD63, CD81, and CD9 PP1s and CD63, CD81, and CD9 PP2s at either 0.33 μg/mL each or 1 μg/mL each.

Note: 1 μg/mL is the standard concentration for each PP1 and PP2 when assays are performed with a pair of PPs. 0.33 μg/mL was tested to keep the total concentration of PP1s and PP2s in the cocktail equivalent to the standard concentration.

Figure 20:
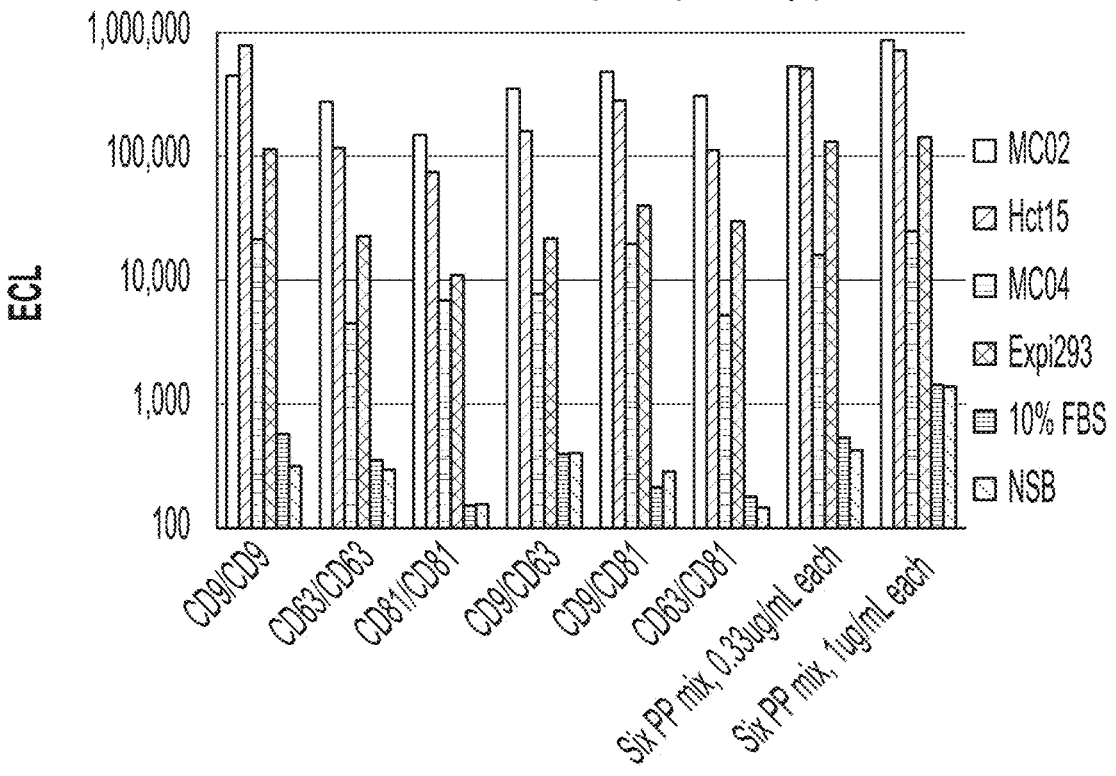
FIG. 20 shows the results of the experiments described in Example 2.4.1 (C). EVs from four cell conditioned medium samples were captured on plates printed with an anti-EphA2 capture antibody. Captured EVs were detected with homo-pairs of proximity probes in a PLA/RCA assay (e.g., CD9/

Results are shown in FIG. 20. The signal and background both appear to scale according to the concentration PPs in the cocktail.

Example 2.4.2. Multiplexed Amplified Assays for EVs

Each of the amplified detection methods described in Example 2.4.1 can be applied with multiplexed EV capture on a multispot plate: Single Detection Antibody with RCA; Homo-Pair Proximity Ligation; Hetero-Pair Proximity Ligation; and PLA/RCA Cocktail.

(A). Homo-Pair PLA/RCA Detection on Multiplexed Tetraspanin Capture Array

EVs from a 10-fold dilution of THP-1 cell conditioned medium (CCM) were captured on multispot plates with either a single tetraspanin cAb (CD63, CD81, or CD9) in each well, or all 3 tetraspanin plus isotype control captures multiplexed in each well using the U-PLEX linkers.

Multispot plates were coated using the typical protocol except that the anchor oligonucleotide was also linked to each of the linkers for the spots that were being used and were then added to the antibody mix at ⅛ of the molarity of each the capture antibodies.

EVs were captured for 1 hour. Captured EVs were detected using one of the following homo-pairs: CD63 PP1/CD63 PP2, CD81 PP1/CD81 PP2, CD9 PP1/CD9 PP2 in each well.

Results are shown in FIG. 21A. The multiplex signals were nearly identical to the singleplex signals. This was accomplished by keeping the capture time short and by using the extra blocking step described in Example 2.1.1. This is important when the same capture antibody and detection antibody are used anywhere in the well.

Another assay was performed without the blocking step, and ~20% lower signal in the multiplex was observed as compared to the singleplex assays. See FIG. 21B. In this assay, only the CD63/CD63 pair for detection was used.

The CD9/CD63 and CD81/CD63 assays lose signal in the multiplex relative to the singleplex because in the singleplex, there is no CD63 cAb present in the well as interference, whereas in the multiplex, the CD63 capture antibody is present on another spot and can leach off of the surface, causing interference with detection. These assays were performed using the multispot system as described in U.S. Pat. Nos. 10,201,812; 7,842,246 and 6,977,722 (the disclosures of which are hereby incorporated by reference in their entireties). For comparison, a singleplex assay was performed on a plate with a single directly coated CD81 spot, and yielded very similar performance to the corresponding multispot assay.

(B). Cell Line Screening for EV Surface Markers 3 multiplexed capture panels were assembled using the multispot system to display capture antibodies. Biotinylated anchor oligonucleotide was added into each antibody/linker coupling reaction at ¹⁄₁₀₀th of the concentration (w/v) of the antibody. The stop solution was added, and finally the individual antibody/linker+oligonucleotide/linker reactions were mixed together to form the multiplex.

Panel 1 contained the three tetraspanins and isotype control. Panel 2 contained six proteoglycan surface markers plus the isotype control. Panel 3 contained five cell adhesion proteins and two surface receptors as well as the isotype control.

CCM from 12 cell lines, selected with the expectation of having least one positive for each of the surface markers, were centrifuged for 60 mins at 10,000 g to remove large EVs and cell debris, then captured on each of the panels. Normal serum pools, 10% FBS, and DPBS blanks were included as controls.

1-hour and 4-hour captures were performed for each sample on each panel. Each CCM/panel combination was detected with each of the tetraspanin homo-pairs of PPs using PLA/RCA detection.

Results for selected cell lines for each panel are shown in FIGS. 22A and 22B. Each of the marker/PP pair combinations had low background except for the GPC1, which had a background signal of ~4000 counts regardless of which PPs were used. This GPC1 antibody was the only polyclonal capture on either panel and appeared to be capturing some component of the PLA/RCA amplification system. Reactivity of each cell line agreed with non-amplified data set run previously, albeit with ~25-fold signal amplification.

Example 3. Assays for EV "Cargo Proteins"

Measuring the levels of proteins that are inside EVs (i.e., cargo proteins) can be difficult for several reasons. First, many of these proteins are also present outside the EVs in a soluble or aggregated form, sometimes in much higher concentration than in the EV lumen. Thus, a method to separate EV-associated protein from soluble protein is required. Second, the EVs must be lysed to access the cargo proteins. Lysis conditions must be compatible with the assay. Third, some common cargo proteins (e.g., Alix, TSG101) have numerous binding partners that can occlude epitopes or can adopt various conformations that can affect antibody binding.

Typical methods to assess cargo proteins include the following:

Ultracentrifuge purification, with or without density gradient floatation: strength—can produce very pure samples; weaknesses—potential to co-sediment protein aggregates, potential to smash or rupture EV or force aggregation, time-consuming, poor scalability and low yield. Density gradient results in much more pure samples but is very time-consuming.

PEG precipitation: strength—moderately scalable; weaknesses—co-precipitates some proteins, causes aggregation of EVs.

Bead immunoprecipitation: strength—very scalable; weakness—co-elution of non-specifically bound proteins due to high surface area.

Size exclusion chromatography: strength—EVs are not disrupted or aggregated; weaknesses—co-elution of protein aggregates, poor resolution between large proteins and small EVs.

The above methods may be combined with a lysis step, followed by a standard or ultrasensitive MSD assay.

A preferred method for assaying EV cargo is as follows, and illustrated in FIG. 23:

1. Solid-phase immunoprecipitation using a biotinylated capture antibody on a large spot streptavidin plate. As shown in Example 1.1-1.3, nearly all the EVs from a sample can be depleted using one or more of the tetraspanin antibodies.

2. Removal of soluble proteins: wash plate thoroughly, which removes most of the soluble protein from the well. For some proteins, additional treatment such as protease treatment is required (see Example 3.3).

3. Lysis of bound EVs: detergents are used to lyse the captured EVs and solubilize the cargo proteins.

4. Assay: solubilized protein is transferred to a secondary assay plate for standard or ultrasensitive assay.

Example 3.1.1. IL-6 Cargo Measurement in Transfected Expi293 Cell Derived EVs Expi293 cells were transfected with a plasmid to express a recombinant IL-6/targeting peptide fusion that was designed to target the fusion to the lumen of the exosomes. The targeting vector was purchased from System Biosciences. Cell conditioned medium from wild type and transfected Expi293 cells was lysed with TRITON X-100 and assayed on V-PLEX IL-6 plates.

Results are shown in FIG. 24A. Wild-type Expi293 cells did not secrete measurable levels of IL-6, so any measurable IL-6 was due to the transfection. Transfected cells expressed high levels of IL-6, though the IL-6 was present at high levels outside the exosomes, since the "no-TRITON" condition had high signal.

To determine whether IL-6 was present within the exosomes of the transfected cells, EVs were captured using biotinylated CD63, CD81, CD9, or an isotype control antibody on a large spot streptavidin plate. The plate was then washed, and the captured EVs were lysed with TRITON X-100. The lysate was transferred to a V-PLEX IL-6 plate to assess IL-6.

Results are shown in FIG. 24B. IL-6 appeared to be present within the CD81+ and CD9+EV populations.

A small fraction of soluble IL-6 in the original sample was expected to non-specifically bind to the large-spot streptavidin plate and then be eluted by the lysis buffer, which may confound the measurement of the exosomal IL-6. To assess this non-specific binding, recombinant IL-6 calibrator was added onto the large-spot capture plate with each of the tetraspanin antibodies. These wells were treated identically to the exosome capture experiment, in that the plate was then washed and lysis buffer was added and transferred to the IL-6 assay plate.

Results are shown in FIG. 24C. All capture antibodies showed similar low levels of non-specific binding. Thus, it is very likely that the enrichment of IL-6 in the CD81 and CD9 captured samples relative to the isotype control is due to IL-6 being inside the EVs. The signal level is expected to be less than 2000 counts if less than 0.05% of the soluble IL-6 was carried over to the assay.

Example 3.1.2. EGFR Cytoplasmic Domain

An ultrasensitive assay for EGFR (cytoplasmic domain) is described. EGFR cytoplasmic domain is not known to be secreted as a soluble protein, thus, most EGFR cytoplasmic domain in cell conditioned medium is expected to be contained in exosomes. The ultrasensitive assay was used to compare levels of EGFR cytoplasmic domain measurable in a cell conditioned medium sample before and after EV lysis. Results in FIG. 25A show that the measurable EGFR cytoplasmic domain increased more than 2-fold after lysis.

EVs from a sample of the same cell conditioned medium was captured using CD63, CD81, CD9, and isotype control antibodies. The captured EVs were then lysed and transferred to the EGFR assay plate. For CD9, nearly all of the EV-associated EGFR signal was recovered (lysed total— unlysed total from FIG. 25A). See FIGS. 25B and 25C.

Example 3.2. Enzymatic "Clean-Up" of Non-Cargo Proteins

In the experiments described in Examples 3.1.1 and 3.1.2, it was possible for some soluble (non-EV cargo) proteins to bind non-specifically to the plate walls or electrode surface in the capture plates and to remain even after thorough washing. Some of this protein may then be released during the lysis step, as the lysis detergent may disrupt the interaction between the non-specifically bound protein and plate surface. Released protein would be transferred along with the solubilized cargo proteins and would lead to an overrepresentation of the amount of cargo protein.

To mitigate this effect, a clean-up method using proteolytic enzymes was developed. Several enzymes were tested, including trypsin, chymotryspin, pepsin, and proteinase K. The desirable qualities for the enzyme were promiscuity, i.e., ability to digest many different proteins, and ease of inhibition, i.e., an enzyme inhibitor was available that would be compatible with the assay.

In this Example, trypsin was used to digest residual soluble HSP70 or IL-6, allowing a more accurate measurement of the levels of HSP70 or IL-6 in the cargo of captured EVs.

The procedure is illustrated in FIG. 26A. The EVs were captured from Expi293 cell conditioned medium on a large spot streptavidin plate coated with either anti-CD81 capture antibody or an isotype control antibody. The samples were then either treated with 1 mg/mL trypsin, 5 mg/mL trypsin, or no enzyme, either before or after the captured EVs were lysed. The resulting lysate/digest was treated with a protease inhibitor to halt the proteolytic activity of the trypsin and then transferred to an assay plate for either HSP70 or IL-6.

Results are shown in FIG. 26B (HSP70) and 26C (IL-6). The signal from the isotype control captured sample is likely due to residual soluble protein since this capture antibody does not capture EVs. For both protein species, the isotype control signal decreased ~5 fold after enzyme digestion. The signal from the CD81 capture represents the true cargo signal plus the signal due to residual soluble protein. After enzymatic clean-up, most of the soluble protein is digested. Thus, the signal from after enzymatic clean-up represents the true cargo protein level.

Example 3.3. In Situ Measurement of Cargo Proteins

Cargo molecules can be measured in situ in EVs that have been captured on a solid phase, e.g., an antibody coated plate. The EV cargo must be "fixed" to keep it from washing away after the membrane of the EV is permeabilized, similar to immunocytochemistry or intracellular flow cytometry. Previously, it was unknown that EVs can be fixed and permeabilized, since EVs are believed to lack the cytoskeletal proteins that allow cells to retain their structure after fixation.

The procedure is shown in FIG. 27A. Captured EVs were fixed in a 10% solution of formaldehyde in DPBS, then permeabilized with multiple concentrations of TRITON X-100 to partially dissolve the membrane of the EVs.

Results in FIG. 27B show that without permeabilization, no HSP70 is detectable. Without fixation, permeabilization most likely solubilizes most of the cargo proteins, so the detectable HSP70 is very low. After fixation and permeabilization, the HSP70 is detectable. Thus, in principle, cargo proteins can be detected in situ.

Example 4. Read Buffers for Intact EV Assays

All of the MSD standard read buffers contain TRITON X-100 at sufficient concentration to lyse some EVs. Two different read buffers were developed for intact EV assays.

The first read buffer was a mixture of MSD 1× read buffer T with surfactant-free read buffer T to yield a TRITON concentration at 1/10 of the concentration in standard 1× read buffer T. This formulation appears to lyse the EVs very slowly.

The second read buffer was assessed for use with intact EVs. The second read buffer was based on the MSD Read Buffer B. TRITON X-100 was titrated into read buffer B.

Results are shown in FIG. 28. While the signal decreased with increasing TRITON X-100 concentration, no TRITON X-100 was necessary for efficient ECL generation. The surfactant-free formulation generated as much signal as the low levels of TRITON X-100. Tween was added to improve the wetting of the plastic and thus improve the reproducibility of the shape of the air/liquid interface. The addition of Tween increased the signal, likely due to the optical effect, and possible mitigation of trans-dimers and also improved the reproducibility.

Thus, read buffer B with 0.5 mM Tween was determined to be the preferred read buffer for intact EV assays.

Example 4.1. Read Buffers Surfactants for Intact EV Assays

MSD 1× read buffer T and read buffer B containing varying concentrations of TRITON X-100 were tested for performance in an intact EV assay. The EV assay signal change for each buffer type and TRITON X-100 concentration was measured.

Results are shown in FIG. 46. With MSD 1× read buffer T, assay performance improved as the concentration of TRITON X-100 was decreased from 0.1% to 0.01%. The MSD 1× read buffer T assay performance declined as TRITON X-100 concentration was further decreased from 0.01% to 0%. MSD read buffer B with 0.1% TRITON X-100 had low assay performance, while MSD read buffer B with 0% TRITON X-100 had the best assay performance out of all the tested buffer types and TRITON X-100 concentrations.

MSD read buffer A, which contains a surfactant that does not lyse EVs, was tested for assay performance variability. Titration curves using known concentrations of CD81+ EVs were generated for two different lots of MSD read buffer A.

Results are shown in FIG. 47. The two tested lots of MSD read buffer A had very similar titration curves, indicating low lot-to-lot variability in performance.

Example 5. Interpretation of Intact EV Assay Data

Several challenges are present in interpreting EV data. Interpretation of data from intact EV sandwich assays is not as straightforward as for soluble protein analytes. This is because, unlike a soluble analyte assay where the signal generated for a given capture duration is only dependent on the analyte concentration, the signal for intact EVs depends on at least two parameters: the concentration of EVs with the capture moiety (a surface marker); and the total number of copies of the detectable moiety (the capture moiety or a different surface marker) on the captured EVs.

Further, the capture efficiency most likely varies with copy number, i.e., EVs with many copies of a surface marker will be captured more quickly than those with only a few copies.

Diffusion coefficient and thus the capture efficiency depends on the size of the EVs.

When the same marker is used as the capture and detection moiety, there are additional complexities because when the number of copies of the surface marker per EV is low, most (or all) of those copies will be occupied by the capture antibodies and thus will not be detectable. Therefore, at low copy number the signal falls off faster than the copy number.

Example 5.1. Possible Analyses of EVs Based on Two-Marker Assays

In Example 2.2.2, two ways of interpreting data from two-marker intact EV assays were discussed. These methods are useful for making comparisons of EV populations between multiple samples (e.g., cell supernatants or clinical samples) or comparing multiple populations or surface markers within a single sample.

The following types of comparisons can be enabled by using intact EV assays:

1. Compare quantity of EVs with a particular phenotype (surface marker or combination of surface markers) between multiple samples.

Comparison of the quantity of EpCAM+ EVs between samples is exemplified with reference to FIG. 29. In FIG. 29, sample B has very few EpCAM+ EVs relative to other 3 samples. This is ascertained by comparing the EpCAM capture columns of the data tables for each sample. None of the tetraspanin detectors yield appreciable signal for sample B when combined with EpCAM capture. Therefore, very few EVs were captured by the EpCAM capture antibody, indicating a lack of EpCAM+ EVs in this sample. Further, comparison of the quantities of EpCAM+ EVs between samples can determine that sample D has a higher total quantity of EpCAM+ EVs than sample A and C, although it has very few EVs with CD81, so the quantity of EpCAM+ CD81+ EVs is lower in sample D than sample A or C.

2. Compare average copy number per EV of particular marker between multiple samples (or total amount of EV associated marker).

Comparison of the level of EV-associated EpCAM between samples is exemplified with reference to FIG. 29. In FIG. 29, sample D has the highest total level of EV-associated EpCAM, determined by summing across the EpCAM detector row.

3. Compare quantity of EVs with one particular surface marker to quantity of EVs with a different surface marker within a given sample.

Referring to FIG. 29, comparison of the quantity of EVs with CD63 to those with CD9 and CD81 in sample D can be performed. By summing each column, the total EV population captured using each surface marker can be compared. CD9+ vesicles are most abundant, and CD81+ vesicles are least abundant.

4. Compare average copy numbers of two or more markers within a given sample.

Referring to FIG. 29, comparison of the relative levels of EV-associated CD63, CD81, CD9, and EpCAM in a particular sample can be performed. By summing across the rows of the tables (constant detection antibody), it was determined that for sample A, the relative levels of CD63, CD81, and CD9 are close to one another, while the level of EV-associated EpCAM is much lower. For sample C, EV-associated CD9 is much higher than the other three markers. For sample D, EV-associated CD63 is relatively low, CD81 is non-existent, but CD9 and EpCAM are both present at similarly high levels.

Example 5.2. Calibrators or Controls

Because the EVs in a biological sample are most likely to be in a heterogeneous population having varying sizes and copy numbers of each surface antigen, it is difficult to have a true calibrator material for intact EV assays in the same manner as for soluble protein assays, wherein each analyte is an identical macromolecule.

However, reference materials, i.e., controls can still be provided. The controls can be actual biologically-derived EVs that are well-characterized, or synthetic materials such as unilamellar vesicles or beads that have similar physio-chemical properties as the EVs of interest.

The control material can establish the performance of the assay and provide a reliable sample for normalizing data between plates or experiments and enables correcting for nonlinearity of the assay at the upper and lower ends of the calibration curve. The synthetic materials may be particularly useful, because the surface antigens present can be selected, and the copy number can be tuned to match the biological material of interest, thus functioning as a traditional calibrator.

A useful control material should conform as closely as possible to the size and density of the EVs of interest. Synthetic calibrators have been produced using polymer beads of similar size and density to small EVs and attached tetraspanin proteins to the surface for use as control materials.

Three cell lines have also been selected as particularly efficient at producing EVs: THP-1, Expi293, and HCT-15. See FIG. 30A. The EVs produced by these cell lines have been characterized for use as control material. Nanoparticle tracking analysis was used to quantitate the EVs in the raw material and purified material. FIG. 30B shows the expected size distribution of exosomes, which can be diluted linearly over a wide range in the assays described herein.

Example 6

Cell lines that can be used in this Example include, for example, human cortical neurons differentiated from induced pluripotent stem cells (iPSCs) and from the HCN-2 cell line, and mature astrocytes differentiated from iPSCs and primary human astrocytes. By screening cultured cells from these cell lines, those markers that are overrepresented on either neuronal or astrocyte EVs relative to non-CNS-EVs will be identified for further consideration. For each of these markers, the clone that yields the highest signal and lowest non-specific binding of both the detection antibody and irrelevant EVs will be selected. The sensitivity of each marker will be estimated by comparing the fraction of neuronal or astrocyte-EVs captured by each marker-specific antibody to a tetraspanin cocktail known to capture nearly all EVs. The specificity of each marker will be estimated by comparing the fraction of the off-target population isolated (e.g. astrocyte EVs isolated with proposed neuronal markers). The neuron and astrocyte EVs with at least ten capture antibodies targeting proteins frequently detected on non-CNS EVs (e.g. markers such as PECAM, P-Selectin, EpCAM, E-Cadherin, EphA2, EGFR) will also be screened using tetraspanin detection antibodies. The capture targets will be chosen to represent various sources of non-neuronal EVs, including platelet derived EVs, erythrocyte EVs, endothelial EVs, epithelial EVs. Markers from this screen that are found not to be expressed on either neural or astrocyte EVs will be selected, and a single multiplex panel will be assembled to assess the level of non-CNS EVs in a sample.

Based on the results of the single marker screening, any useful individual markers for capturing either neuronal or astrocyte EVs will be identified. At least a few markers for each cell population will likely be selected for further consideration. All pairwise and triplet combinations of these markers will be assessed using the three-marker assay format shown in FIG. 2. For pairwise combinations, the capture and one of the detection antibodies will be the specific markers while the second detection marker will be a common EV marker or cocktail thereof (e.g. tetraspanins). Pairs will be tested in both orientations. Each combination will be used to assay both neuronal and glial EVs and the specificity will be assessed based on comparing the signal for the non-targeted EV population to the signal for the targeted population. For triplets, all three antibodies will be directed at distinct specific markers and all three orientations will be tested. Combinations that have higher specificity than any individual marker are expected to be identified.

Subject to the results of the single- and multi-marker screening, the most promising individual, pairwise and triplet marker combinations for each target CNS-EV type will be selected. First, the sensitivity of each marker or combination will be tested for capturing pure neuronal or astrocyte EVs isolated from the culture supernatants via ultrafiltration. The selectively captured EV fraction will be assayed in situ using a common EV detector and quantified relative to the total EV population captured by tetraspanin antibody cocktail. Next, a known quantity of neuronal and astrocyte EVs will be spiked into normal human plasma, normal human serum and human CSF. Each of the promising individual markers and combinations will be used for isolation and the EV spike-recovery from each matrix will be assessed by assaying the recovered EVs in situ and comparing to a total EV capture of the same EV sample spiked into clean diluent. For combinations of markers and matrices where spike recovery is high, the spike recovery in EV depleted matrix will be repeated in order to assess whether a fraction of the observed signal was actually due to CNS-EVs native to the matrix which would lead to an overestimation of the spike recovery. Specificity will be further assessed by eluting the recovered EVs and assaying them using the non-CNS-EV panel developed in aim 1. Spike recovery and specificity measurements will also be performed on CNS-EVs recovered using the existing technique practiced in the Kapogiannis Lab (benchmark) for enriching neuronal or astrocyte EVs. It is expected that there are combinations of markers that result in higher specificity for each CNS-EV population than any individual markers.

Any rigorous study of biomarkers must consider biological variables such as sex and the potential for association of these variables with any potential biomarkers. While sex is not expected to be significantly correlated with the surface markers expressed on EVs of the CNS, it will be considered where possible to avoid biasing our screening. In established cell lines, sex will not be considered as a biological variable as there are very few choices for established human cell lines that can be differentiated to functional mature neurons or mature oligodendrocytes (R33 phase). Primary cells from both sexes will be obtained, subject to availability.

Example 7—EV Immunoassays

Intact EV Assays: The basis of the technology in this is example is the sandwich immunoassay with electrochemiluminescence (ECL) detection. This technique is applied by capturing and detecting intact EVs using both common EV markers (e.g. CD81, CD9, CD63) and markers for specific EV populations (e.g. cancer antigens or neuronal markers). Assays for nearly 30 EV surface antigens have been developed, which highlights the ability to rapidly screen antibodies and develop new assays. Up to 10 capture antibodies in each well of a 96 well assay plate can be multiplexed. Combining capture antibody arrays targeting specific EV populations with a common detection antibody or mixture of detection antibodies targeting generic EV markers (like CD81, CD9 and/or CD63) enables the rapid screening of antibody clones for new EV marker discovery and development as well as measurement of multiple EV populations in a single sample. This approach was used to develop assays for EVs bearing L1CAM and NCAM1, two previously reported markers of CNS-EVs in peripheral circulation. L1CAM and NCAM1 antibodies were screened, including specific clones reported in literature as useful in isolating CNS-EVs, against EVs from cell lines known to express each protein. For each protein, a clone was identified that appeared to have higher affinity than the published clones and low non-specific binding of total EVs. These clones were used to assess the fraction of total circulating EVs that were L1CAM+ or NCAM+ as well as to demonstrate good spike recovery of cell-culture derived L1CAM+ and NCAM+ EVs in plasma. The fraction of total EVs bearing neuronal markers (<1%) was considerably lower that what was reported in several published studies (~10%) and it is concluded that high levels of non-specific binding in the published bead-based isolation techniques may lead to a dramatic overestimation of the EV fraction that are NCAM1+ or L1CAM+.

Figures 2A, 2B:
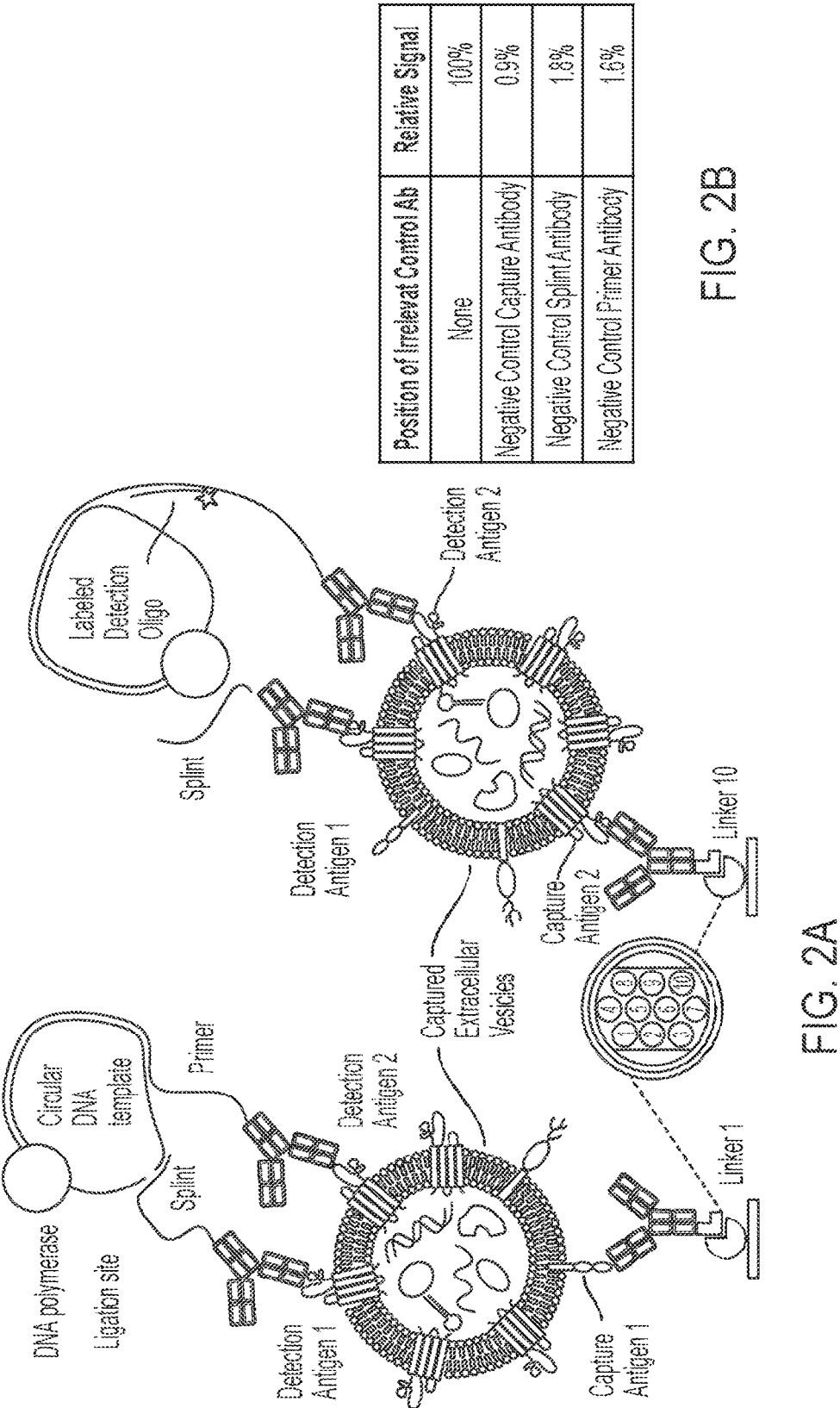
FIG. 2A is a schematic of an example of a 3 marker EV sandwich assay: Specific capture antibody(s) are displayed on the surface of MSD ECL plates. EVs are captured and then detected with two oligonucleotide-labeled antibodies. Typically, one of these targets a common EV surface marker while the other targets a second EV population specific marker. All three antibodies must bind to the same EV to generate an assay signal.
FIG. 2B. Effect of replacing each antibody in three marker assay with irrelevant control antibodies. Assays were performed on cell culture derived EVs with distinct antigens for the three antibody targets.

Ultrasensitive EV Assays: To achieve the sensitivity and specificity needed to reliably measure low-abundance populations of EVs, an ultrasensitive assay format (FIG. 2) was developed based on a variation of proximity ligation amplification. This innovative amplification method generates signal only when two detection antibodies are brought into proximity on the surface of a single captured EV. In practice, after EV capture, two oligonucleotide-labeled detection antibodies directed at distinct molecular targets on the surface of the EVs are added, which mediate the formation and ligation of a circular DNA template and subsequently prime its amplification. A DNA polymerase then creates a long DNA strand covalently linked to one of the antibody-bound oligonucleotides. DNA products are detected using oligonucleotide probes with ECL labels (MSD SULFO-TAG™) and measured using MSD's commercial ECL assay instrumentation. The ultrasensitive assay detection scheme typically yields a 100- to 1000-fold improvement in assay sensitivity versus a sandwich immunoassay and an improvement in specificity due to the use of two distinct detection antibodies58. To demonstrate the requirement that all three antibodies must bind EV proteins in order to generate signal, the antibody at each position was substituted with an irrelevant control antibody and observed nearly a complete loss of signal in each case (FIG. 2B). This technique was used to measure EVs from plasma bearing six different surface proteins (CEA, EGFR, EpCAM, EphA2, mesothelin and transferrin receptor). Signals from EVs in raw plasma vs. EVs purified from the plasma by SEC were similar except for small but consistent signal drops in the SEC samples due to purification yields, indicating that the plasma measurements were truly indicative of the EV population and discriminated against soluble forms of the surface markers.

Example 8

EV cargo proteins were assayed by first capturing the EVs on an immune-capture plate, washing away non-EV associated proteins, then lysing the captured EVs and transferring the lysate to a separate assay well. FIG. 4A demonstrates the application of this concept to measure the cytoplasmic domain of EGFR within captured EVs. For EV cargo targets where non-EV associated levels of the target protein are much higher than the EV-cargo level, the use of a novel protease clean-up method was demonstrated to minimize the amount of soluble protein contamination that may cause inaccurate cargo quantitation. This technique is illustrated for the EV cargo protein HSP70 in FIG. 4B. Briefly, the EVs were captured and washed to remove soluble protein. Protease was added to digest any residual analyte protein that was bound non-specifically in the well. Cargo proteins were protected from digestion by the intact EV membrane. Some of the EVs were released from the surface by digestion of the antibodies but were retained within the well so the assay is not affected. The protease is chemically inactivated, EVs are lysed by detergent and the lysate is transferred to a second plate for the ultra-sensitive assay. The entire process including EV capture, digestion and cargo assay was performed in a single day.

Example 9

To demonstrate the feasibility of the stapling technique CD9 capture antibodies were coupled to the surface of a plate using a pair of short complementary oligonucleotides. A sample of cell-culture derived EVs was selected that was previously shown to have high levels of CD9 and CD81 and low levels of CD63 on their surface and captured these with the CD9 antibodies. The captured EVs were incubated with an ECL-labeled CD9 antibody to render all the captured EVs detectable. Oligo-labeled "stapling" antibodies were added with either CD81, CD63 or an irrelevant control antibody; alternatively, no stapling antibody was added. After amplification by DNA polymerase, the plate was washed in a low salt buffer that enabled the capture antibody oligos to be denatured while the duplex staples, having a higher melting temperature, remained intact. FIG. 1D shows that with CD81 stapling, all the captured EVs were retained, as was expected given the high level of CD81 expression in the sample, while with no stapling ~80% of the captured EVs were eluted.

CD63 stapling allowed retention of a fraction of the EVs, which is consistent with the low level of EV-associated CD63 in this sample. The irrelevant control antibody also enabled some EV retention, which is likely due to non-specific binding of this antibody to an antigen on the EVs.

Example 10

To demonstrate the EV capture capacity, small EVs (<200 nm diameter) were isolated from a cell line shown to produce high levels of small EVs and concentrated them using ultrafiltration. These EVs were quantified by nanoparticle tracking analysis then added $0.5\times10^9$-$2\times10^9$ EVs to wells of a capture plate coated with anti-CD9 antibodies. After 2 hours, the depleted supernatant was transferred to an assay plate and compared it to fresh, non-depleted supernatant to assess the fraction of EVs remaining unbound. For the most concentrated sample, 93% of the EVs had been depleted and for the least concentrated sample, which was still above the expected concentration of total EVs in blood, over 98% of the EVs were depleted. This strongly supports that capture plates have sufficient capture capacity, particularly for the CNS-EV capture application, where only a small fraction of the total EVs from a biofluid sample are expected to be targeted. It also supports the fact that the majority of EVs can be captured from a sample in a relatively short time (2 hours).

Example 11

This example illustrates that the capture surface in each well has sufficient capacity to capture all the EVs with a given marker. Based on simple geometrical considerations each well of the capture plates should have the capacity to bind at least $2\times10^9$ particles with a 100 nm diameter, roughly the average size of exosomes. In a typical 25 uL or 50 uL plasma sample, about $1$-$2\times10^8$ EVs are expected, so capture surface should have sufficient capacity, even if a fraction of the particles are much larger than exosomes. To demonstrate the EV capture capacity, small EVs (<200 nm diameter) were isolated from a cell line shown to produce high levels of small EVs and concentrated them using ultrafiltration. These EVs were quantified by nanoparticle tracking analysis then added $0.5\times10^9$-$2\times10^9$ EVs to wells of a capture plate coated with anti-CD9 antibodies. After 2 hours, the depleted supernatant was transferred to an assay plate and compared it to fresh, non-depleted supernatant to assess the fraction of EVs remaining unbound. For the most concentrated sample, 93% of the EVs had been depleted and for the least concentrated sample, which was still above the expected concentration of total EVs in blood, over 98% of the EVs were depleted. This strongly supports that our capture plates have sufficient capture capacity, particularly for the CNS-EV capture application, where only a small fraction of the total EVs from a biofluid sample was expected to be targeted. It also supports the fact that the majority of EVs can be captured from a sample in a relatively short time (2 hours).

Example 12—Screening Cell Lines for EV Production

In this Example, an EV assay was used to compare EV secretion from various cell lines in different cellular states (e.g., differentiated or undifferentiated), as listed in the left-most column of FIG. 37A. As shown in FIG. 37A, all cell lines secreted detectable levels of CD63+ EVs, demonstrating CD63 as a near-universal EV marker. More variability was observed in the ability of cell lines to express EVs with CD81 or CD9.

Another EV assay was used to compare multiple growth or stimulation conditions on a single cell line, THP-1. FIG. 37B shows the EVs detected from multiple cultures of THP-1 cells, seeded at various densities, and with or without stimulation by phorbol 12-myristate 13-acetate (PMA) to induce differentiation. Culture medium was sample at multiple time points to observe accumulation of EVs over time.

Example 13—Assay Performance in Biofluids

In this Example, EV assay performance was tested in various biofluids. Cell culture-derived EVs were spiked into various clinical matrices (biofluids) of interest, and the biofluids were then subjected to an EV assay to measure for CD9+, CD63+, and CD81+ EVs. Spike levels were chosen to be approximately equivalent to native levels in a diluted sample of the same matrix. FIG. 38 shows the results of the assay with EV-spiked human serum, plasma, CSF, and urine.

Example 14—Additional Two-Marker EV Assays

In this Example, two-marker EV assays were performed on a THP-1 cell line for all combinations of CD63, CD81, and CD9 as capture and detection antibodies. A dilution curve with each of the combinations of CD63, CD81, and CD9 is shown in FIG. 39A. FIG. 39B shows the results of single-marker and two-marker assays for four different cell lines to compare EV subpopulation abundance and relative levels of each EV-associated tetraspanin (i.e., CD63, CD81, and CD9). The relative abundance of EVs bearing each tetraspanin marker in a sample can be estimated by comparing different capture antibodies with the same detection antibody (e.g., as shown in FIG. 39B, many EVs from TT cells, detected by CD9, are captured by CD63, whereas very few are captured by CD81). Relative abundance of each marker on a particular population of EVs can be estimated by comparing different detection antibodies with the same capture antibody (e.g., as shown in FIG. 39B, EVs from Expi293 cells captured with CD63 have low levels of CD63, abundant levels of CD81, and moderate levels of CD9). Abundance of an EV population in multiple samples can be also be compared (e.g., as shown in FIG. 39B, Expi293 cells have the highest abundance of CD81+ EVs, followed by HCT-15 cells, BeWo cells, and lastly TT cells).

Example 15—Additional Two-Marker EV Assays with Biofluids

In this Example, matched human serum and plasma EVs for tetraspanins were tested using single-marker and two-marker EV assays. SEC-purified EVs from matched human serum and plasma from ten healthy donors were assayed with nine combinations of capture and detection antibodies. As shown in FIG. 40, assays that included the marker CD81 as either the capture or detection antibody showed high agreement between matched serum and plasma, most likely because CD81 is not present on platelet-derived EVs and is thus insensitive to variations in phlebotomy and sample handling that affect platelet EV secretion. Conversely, CD63 and CD9 are both abundant on platelet-derived EVs, which are often elevated in plasma relative to serum, depending on post-phlebotomy sample-handling.

Example 16—Singleplex Versus Multiplexed Assays

In this Example, the performance of singleplex and multiplex EV assays were compared. EVs from a THP-1 cell line were assayed using all combinations of CD63, CD81, and CD9 as capture and detection antibodies, using both singleplex and multiplex formats. In addition, an isotype-matched negative control antibody was included to estimate the non-specific binding of EVs to the antibody-coated spots. Each capture antibody was also combined with a cocktail of all three detection antibodies. Results in FIG. 41 show that in all cases, the singleplex and multiplex assays produce equivalent measurements of EVs in the sample.

Example 17—Developing EV Screening Panels

This Example describes development of a new EV screening panel using a multiplex format, which facilitates comparison of multiple capture antibodies targeting the same markers and enables rapid screening for preferred antibodies in an assay. Several cell lines known to express CD4 were selected, and several cell lines known not to express CD4 were chosen as negative controls. Multiple anti-CD4 antibodies were present in each well of a multiplex assay plate. Conditioned medium from each cell line was precleared by centrifugation to remove cell debris, and cleared supernatant was added to each well. Captured EVs were detected with a combination of CD63, CD81, and CD9 detection antibodies in order to maximize detection signal. As shown in FIG. 42A, of the four clones tested, "clone D" yielded the highest signal in all the expected positive cell lines and the lowest or equivalent signal in the negative cell lines and controls. Thus, clone D was selected as the preferred antibody for capturing CD4+ EVs. This screening process was performed for the cell surface markers shown in FIG. 42B.

Example 18—Screening of Culture Conditioned Media

In this Example, EVs were captured from cell conditioned medium using the antibody panels described in Example 17 and shown in FIG. 42B. Captured EVs were detected with a combination of CD63, CD81, and CD9. FIGS. 43A and 43B show the ratio between the background-subtracted ECL signal on each specific capture spot and the negative control antibody spot in the same well, which enabled identification of samples producing EVs bearing each of the target surface markers. Light gray-highlighted cells had ratio greater than five-fold, and dark gray-highlighted cells had ratio greater than ten-fold.

Example 19—Screening of Human Biofluid Samples

In this Example, human biofluids were screened for EVs using the antibody panels described in Example 17 and shown in FIG. 42B. Captured EVs were detected with a combination of CD63, CD81, and CD9. FIG. 44 shows the ratio between the background-subtracted signal on each specific capture spot and the negative isotype-control spot in the same well which enabled identification of samples producing EVs bearing each of the target surface markers. Light gray-highlighted cells had ratio greater than five-fold, and dark gray-highlighted cells had ratio greater than ten-fold. Twenty-three of the 45 markers were detectable in one or more of the different types of human biofluid samples tested.

Example 20—Analysis of EV Screening Data

Hierarchical clustering analysis was performed on the cell line and human biofluid EV screening data from Examples 18 and 19 (and corresponding FIGS. 43A-43B and FIG. 44). Results in FIG. 45 show that epithelial cell lines form one cluster, while a second cluster includes all the leukocytes and endothelial cells. All of the human biofluids clustered with the leukocytes.

Example 21—Multi-Marker Screening with Complex Screening Pools

For large antibody-conjugate pools, or large numbers of samples, a high-throughput sequencing platform will be needed to obtain sufficient sequencing counts to observe the low frequency triplets formed from combinations of low-abundance markers. For these experiments, libraries will be prepared and sequenced using a next-generation sequencing platform. The estimated dynamic range will tolerate between the least and most abundant markers for a given number of sequencing reads available in our surface signature approach. Only those markers that are present on nearly every EV (≥95%) of a given population will be determined, and the number of copies (k) of a marker on individual EVs is expected to follow a Poisson distribution: $P(k)=e(\lambda^k)/k!$, where $\lambda$ is the average number of copies of the marker per EV. Thus, only markers where $\lambda \geq 3$ are considered to ensure $P(0)<5\%$, i.e. if ≥95% of the EVs to have at least 1 copy of a given marker is desired, the average number of copies of that marker must be at least 3, based on Poisson statistics.

There has been no definitive measure of the number of total surface proteins per EV. However, based simply on geometry, if 10% of the surface area on each 100 nm EV were occupied by the proteins targeted by antibodies in a screening pool (~300 protein molecules), the least abundant markers to be detected ($\lambda \geq 3$) would represent 1% of these total proteins and a combination of three of these "low abundance markers" would account for 1 read in 106 (0.013). To avoid missing these low abundance events due to sequencer sampling noise, several million reads would be required, which is readily achievable using modern sequencing technology. In reality, this is likely an overestimation of the sequencing depth needed since the surface area of EVs occupied by targeted proteins is likely less than 10%, particularly since highly abundant and common EV proteins, such as the tetraspanins, would be excluded from the screening pools as they would be unlikely to provide specificity. In the unlikely event that one or a few particular highly abundant proteins account for all of the reads in a sequencing run but do not yield cell type specificity, these would be removed from the screening pool and the experiment re-run to provide the depth to observe the less abundant markers.

To illustrate the advanced capability of the multi-marker screening technique, a higher complexity screening pool will be used to identify multi-marker EV signatures in 5 cell types that secrete relatively high levels of EVs into blood: monocytes, vascular endothelium, B-Cells, CD4+ T-cell and CD8+ T-cells, as well as platelets, which are a common source of contaminating EVs in blood. This will demonstrate the ability of the technique to identify and discriminate signatures between EVs secreted by closely related cell populations (e.g. CD4 and CD8 T-cells). When working with new assay targets, multiple antibody clones for the same target marker are often included, to identify the highest affinity clone. In a screening conjugate pool, these will compete with one another and the most represented barcodes will indicate the highest affinity clone for each target. A screening pool will be generated using ~60 antibodies, with up to 3 clones against each of at least 20 surface marker targets, to create ~180 uniquely barcoded conjugates. At least 4 target markers for each of the cell types will be selected based on previous studies and publications. EVs from at least two cell lines representing each cell type, likely including THP-1, HL-60, Ramos, GA-10, Jurkat, Molt-4 and HUVEC, plus primary cells from ATCC for each type will be assayed using the antibody pool to generate one sequencing library per sample. Individual sample types will receive identifying sample barcodes during installation of sequencing adaptors. The ~18 sample libraries will be normalized, combined, and sequenced in a single next generation sequencing run, which should yield ~1M reads per sample. Selecting specific multi-marker signatures for EVs of a given cell type will require selecting combinations of two or three markers that are well represented in each of the samples for the given cell type while being absent or poorly represented in the samples for all other cell types. There may be multiple 3-marker combinations that define a cell type. These would need to be tested in the actual isolation protocols described below to determine which has the highest specificity and recovers the greatest number of vesicles from the relevant population. Thus, while this technique will be most useful when some prior knowledge of the likeliest useful surface markers is available, the method could make unbiased screening possible for new cell types by using very large libraries of antibody-conjugates.

Example 22—Singleplex and Multiplex Screening to Identify EV Populations

A "digital surface-omics" method for simultaneously assaying EVs with thousands of unique combinations of up to four co-localized surface markers in a sample, as illustrated in FIG. 48A, will be developed. A pool of antibody conjugates targeting known or suspected EV surface molecules will be generated. Each antibody is labeled with uniquely barcoded versions of up to four different oligonucleotide constructs. When antibodies presenting each of the four different oligonucleotides constructs are held in proximity on the surface of a single EV, a proximity extension/ligation (PEL) reaction forms a single molecular construct. This construct contains the unique combination of four barcodes that specifies the identity of the four antibodies and, therefore, the four target surface molecules on the EV. Each of the four oligo constructs will have multiple uniquely barcoded variants, each linked to a single antibody, with multiple of these antibody oligo conjugates combined to form a subpool. For a relatively small number of antibodies, each antibody can be coupled to all four oligo constructs (four redundant subpools), such that any combination of four antibodies, termed a quadruplet or "quad" is possible. Since this quad may include 1-4 copies of the same target marker, the approach yields a single library of amplicons for sequencing that include one to four unique barcodes and provides a snapshot of the relative abundances of these combinations of markers on the EVs. When using larger numbers of antibodies, it will probably be necessary to eliminate the redundancy of some of the subpools. For example, two pairs of redundant subpools would allow detection of any combination of the two markers from the first pair of subpools, and any combination of two markers from the second two subpools. There are many possible combinations, for example, two redundant subpools for pairwise combinations of cell-type specific markers (CD antigens), a third subpool for detecting immune-related receptors or ligands, and the last marker for viral proteins. Depending on the application, other approaches can be employed, e.g. receptors in one subpool and ligands in another to detect receptor/ligand complexes, or a single conjugate in one of the positions to more fully constrain the library, e.g. HIV GP120 to only detect EVs from infected cells or CD3 to only detect T cell derived EVs.

Figure 48:
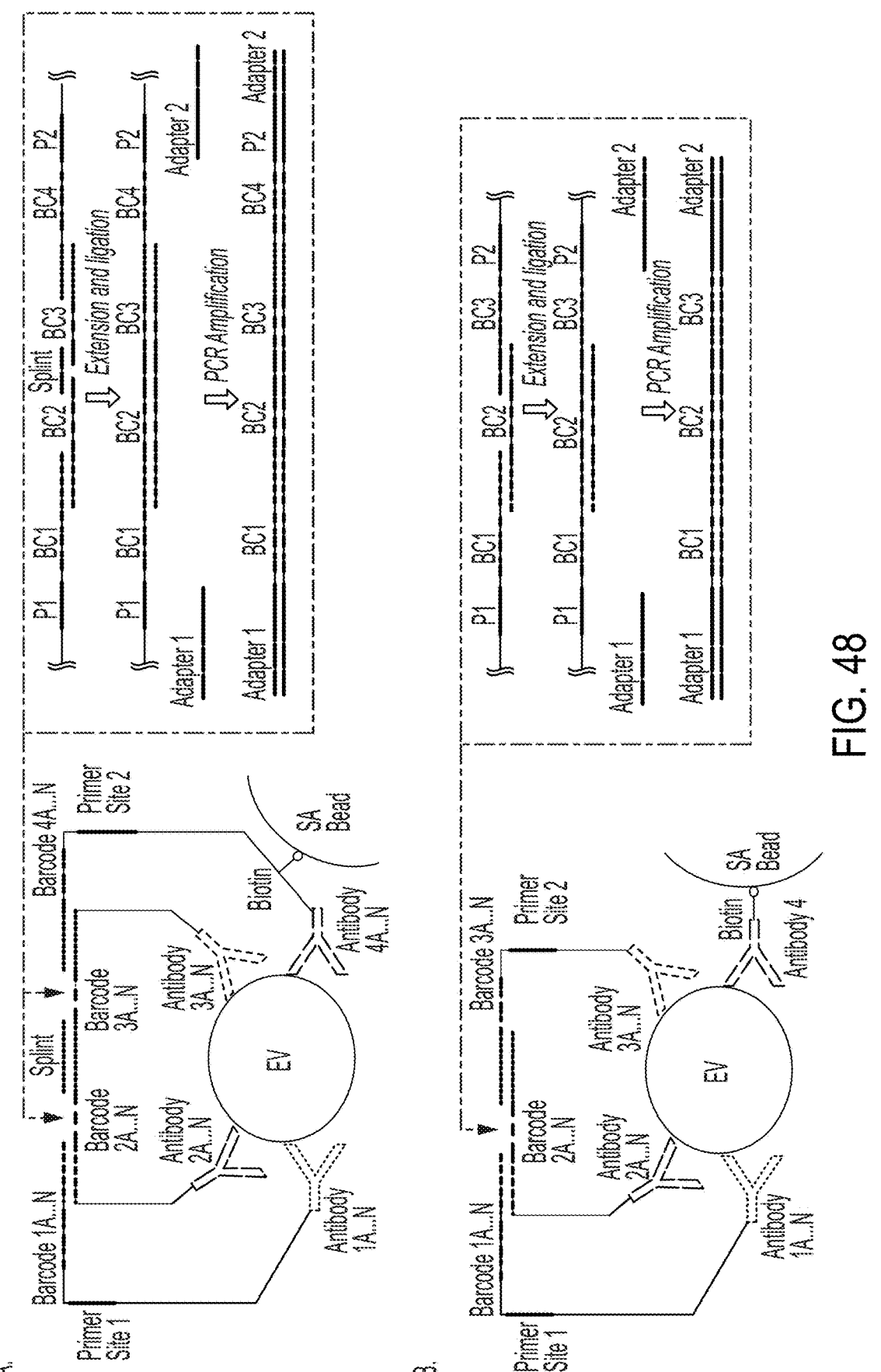
Figure 48:
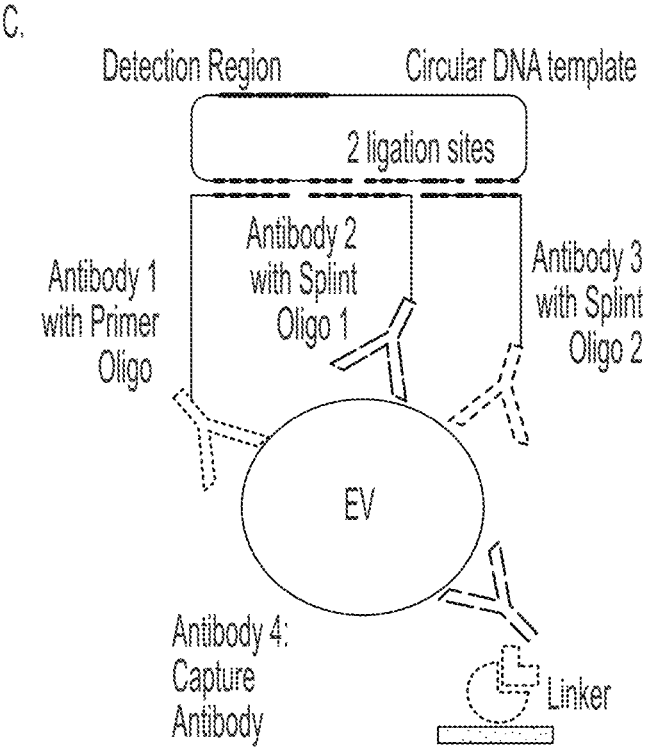

Formation of the four-marker-dependent construct will be performed in singleplex using well-characterized markers and a synthetic bead based system that allows full control over the specific antigens and number of copies per bead. Biotinylated recombinant antigens displayed on 100 nm diameter magnetic streptavidin beads will be used as a surrogate for EVs. The construct will be detected and quantified via qPCR using the amplification primer sites as shown in FIG. 48. Antibody and enzyme concentrations, reaction conditions and time, wash stringency and blockers can be optimized. Non-specific negative control antibodies will be used in each position of the quad to ensure that four specific interactions are used to form the construct, as well as estimate the contribution of non-specific interactions. The singleplex system will also be demonstrated in a cell culture EV model, THP-1 cells, with known abundant surface markers.

A small targeted multiplexed pool using next-generation sequencing, rather than qPCR, will then be used to detect the constructs. Four non-redundant subpools of three antibodies each will be prepared. Biotinylated antigens to each of the 12 antibodies will be used to generate approximately 20 types of beads with mixtures of antigens. qPCR can be used first to ensure that the construct is only formed with the bead contains at least one antigen from each subpool. The beads will then be mixed for next-generation sequencing (NGS), which will be performed using NGS analysis scripts to decode the barcodes.

Four fully redundant subpools will also be used for screening cell culture EVs from three cell models that have been characterized extensively using ECL-based immuno-assays. Ten surface markers will be selected for screening, including markers known to be uniquely present on EVs from only one of the cell models, and markers that are present on EVs from multiple cell models. Each antibody in the panel will be used to create four different antibody-oligo conjugates, one for each position in the PEL reaction (sub-pool), and each with a unique barcode identifying the antibody. Having each antibody in all four positions ensures that all combinations of four antibodies are sampled. This screen will also be performed on EVs from a pool of normal human serum.

Antibody/oligo conjugates will be assembled from mul-tiple synthesized oligos. The oligo portion of each conjugate will be assembled by ligation of two short oligos: one with the common sequences and a distal azide and a second comprising a unique barcode. The assembled oligo will then be purified and conjugated to antibody through a long PEG spacer using orthogonal thia-Michael and azide/cyclooctyne "click" conjugation chemistry. Assembly and purification steps will be performed concurrently using parallel plate-based reactions and purifications that should be easily scal-able for very large screening pools.

An exemplary workflow includes: an EV sample from each of the three cell lines or a mixture of all three will be incubated with the Ab-conjugate pool, captured on strepta-vidin beads, and washed to remove unbound antibodies and EVs. A mixture of polymerase and ligase will be used to form the complete construct containing all four barcodes. Formed constructs will then be amplified by PCR to create a sequencing library, using the common PCR primer sites to install adaptors for sequencing with unique adaptor barcodes for each sample. For the low-complexity pool of antibodies, sequencing will be performed on the MINISEQ (ILLU-MINA), which is suited to short amplicon sequencing. MINISEQ mid-output kits will provide a sufficient number of reads at a reasonable cost for low complexity pools.

For high-complexity antibody-conjugate pools, or large numbers of samples, sufficient sequencing counts are needed to observe the low frequency quads formed from combina-tions of low-abundance markers. For these experiments, either the high-output MINISEQ kits will be used, or librar-ies will be prepared for sequencing on a higher output instrument. A combination of four low abundance markers (1% fractional abundance for each subpool) would account for 1 read in 108 (0.014). To avoid missing these low abundance events due to sequencer sampling noise, hun-dreds of millions of reads would be required, which is readily achievable using modern sequencing technology.

If one or a few particular highly abundant proteins account for most of the reads in a sequencing run, these would be removed from the screening pool and the experi-ment will be re-run to provide the depth to observe the less abundant markers. The number of reads needed can also be limited by employing one or more low complexity subpools and by grouping low abundance markers within a single pool so they don't compete with high abundance markers.

Example 23—Assays for Specific Multi-Marker EV Populations

An ECL assay will be used for EVs with 4-marker combinations. The existing 3-antibody assay circular DNA template will be modified to include a second ligation site, as shown in FIG. 48C. Splint 1, splint 2 and primer oligos will each be conjugated to CD63, CD81 and CD9. The assay construct will be tested and reaction conditions optimized using the synthetic beads used in Example 22 with recom-binant CD63, CD81, CD9 and a fourth antigen used to capture the beads. The quantitation of the ECL based assays will be tested using various dilutions of beads and copies of antigen per bead and compare this to the relative quantita-tion generated by the NGS screening technique. The signal should also be minimal when any of the 4 target antigens is absent from the beads.

Using additional antibodies selected from those used in Example 22, various combinations of four markers will be tested. At least three 4 marker assays will be selected for populations that were detected in both the cell culture model and in serum. Assay cross-reactivity will be assessed using beads with the sets of specific antigens for each of the assays, and diluents and blockers will be adjusted to mini-mize cross reactivity. The multiplexed assays will then be tested on beads spiked into EV depleted human serum and purified EV from human serum, and finally tested in com-plete human serum.

Example 24—Development of Library of Conjugates for EV Surface Markers

A library of antibody-oligo conjugates for at least one hundred Example 23—Assays for Specific Multi-Marker EV Populations will be developed. These will include at least 50 cell-of-origin specific markers, e.g. CD antigens, with a focus on cells relevant to HIV infection, approxi-mately 25 surface receptors including cytokine receptors and immune checkpoint molecules, approximately 25 receptor ligands suspected to be carried on EVs (e.g. EV bound cytokines, checkpoint molecule ligands), as well as ~10 viral proteins (from HIV and common coinfections including HCV, HSV and EBV) that have been shown to be secreted on the surface of EVs. The performance of the conjugates will be evaluated using EVs from cell lines and primary cells. Cell lines known to express the surface marker or receptor will be selected, and EVs will be isolated from the cell supernatant. Up to 10 antibodies for the target will be biotinylated and displayed multiplexed plates to be used as capture antibodies. EVs from the supernatant will be cap-tured and then labeled with either a cocktail of ECL-labeled detection antibodies against common EV proteins (CD63, CD81, CD9), or with an ECL reagent that specifically binds lipid membranes. The best performing clone(s) will be selected based on highest signal and lowest background. For receptors, antibodies that are known to be non-neutralizing will be selected, as these are likely to detect the receptor even in the presence of the ligand. This will be tested by running the screen with and without the presence of the ligand (recombinant) at a concentration sufficient to bind most of the receptor ($5*K_d$ for the receptor ligand interaction).

Screening antibodies for EV associated ligands can include selecting ligands for receptors that have already been detected on EVs. In this case, the recombinant ligand can be added to bind the receptor-bearing EVs, and the EVs can then be captured with antibodies directed against the ligand. Only those antibodies that can recognize the ligand in complex with the receptor will be able to capture EVs, which will then be detected in the same fashion as the previously described antibody screening. For receptor/ligand pairs where a cell line expressing the receptor cannot be easily identified, antibodies that can recognize the ligand when complexed to the receptor will be selected. Antibodies targeting one half of the ligand/receptor pair will be displayed on the surface of the plate, and the antibodies targeting the other half will be used as detection antibodies. Recombinant receptor and ligand will be mixed and used to simultaneously screen all pairs of capture and detection antibodies for those that can recognize the receptor and ligand in complex.

Viral envelope proteins that can be conjugated are described in Table 3, several of which are known to be secreted on the surface of EVs from infected cells. The ability of antibodies to capture EVs from virus infected cell lines such as J1.1(HIV-1), MT2(HTLV-1), Huh-7.5 (HCV) cells, Raji(EBV) will be tested. Antibodies will then be conjugated as described in Example 22. Various combinations of reduced numbers of conjugates using beads, mixtures of cell line EVs, and in human plasma EVs will be tested before establishing each subpool.

TABLE 3

| Viral Envelope Proteins from HIV-1 and Common Co-infections | |
| --- | --- |
| HIV-1 | Surface Protein/gp120 |
| | Transmembrane Protein/gp41 |
| HCV | Envelope Glycoprotein E1 |
| | Envelope Glycoprotein E2 |
| HSV-1 | Envelope Glycoprotein B/gB |
| | Envelope Glycoprotein C/gC |
| | Envelope Glycoprotein D/gD |
| HTLV-1 | Surface Protein/gp46 |
| | Transmembrane Protein/gp21 |
| EBV | Membrane Antigen/gp350 |
| | Envelope Glycoprotein H/gH |
| | Envelope Glycoprotein L/gL |
| | LMP1 |

Complete subpools will be tested in isolation from one another using a single antibody or small subpool of common EV markers in place of each of the other subpools. Finally the sub-pools will be combined and tested in a small number of normal and infected human plasma samples to demonstrate the performance and estimate the number of sequencing reads needed per sample. The effect of pooling the samples from each sample before screening, or running the samples individually then barcoding each during the sequencing library prep and pooling for sequencing will also be compared.

Example 25—Assessing HIV-1 Infection Related EV Populations in Human Samples

Digital surface marker screening of EVs will be performed using assays described in Examples 22-24. Plasma samples will be obtained from normal, untreated HIV, and antiretroviral therapy (ART) treated individuals.

10 uninfected individuals and 10 from each of the infected, ART naive and infected ART treated populations will be selected for the digital screening. These samples will be split evenly between sexes to avoid bias and to allow identification of whether the levels of any of the EV populations are significantly correlated with sex. Samples will be blinded and randomized, and EVs will be isolated from each sample by SEC and each will be assessed using the digital screening technique with the complete library of conjugates generated in Example 24. Each EV sample will be used to generate a sequencing library, which will have a unique adaptor barcode allowing the libraries to be combined and sequenced. These data will be unblinded after barcodes are decoded but before analysis. A single high output MINISEQ run will be performed to assess the library quality and observe gross differences in the samples. This will allow ~1M reads per sample. If additional sequencing depth is needed to detect low abundance EV populations, a higher output sequencer run, such as a NOVASEQ, will be used, which will allow billions of reads at less than 1/10th of the cost per read as the MINISEQ.

From the sequencing data, rank-ordered lists of multi-marker EV populations detectable in normal patients as well as those expressed in HIV patients and those bearing HIV viral proteins indicating they are secreted by latently infected cells can be established. Non-parametric tests such as Mann-Whitney U-test will be used to identify populations with significant differences between the sample types. A subset of ~10 differentially expressed EV populations will be selected for development of multi-marker ECL assays for each of those populations according to the methods developed in Example 23.

Example 26—EV-Associated Cytokines

EVs derived from stimulated HL-60 cells were purified by precipitation, then fractionated by SEC. Results for intact EV assays using tetraspanin proteins or membrane stain are shown in FIG. 55A and indicate that EVs elute mainly in fractions 8-11. IL-8 (green triangles) and other cytokines (not shown) elute in EV-containing fractions indicating stable association (fractions lysed before assay). Fractions were digested with trypsin prior to lysis to determine whether cytokines were encapsulated or surface bound. Results in FIG. 55B show that all cytokines were at least partially digested, indicating they are not fully encapsulated.

What is claimed is:

1. A method of determining surface markers of a surface marker displaying agent, comprising:
 a. contacting a sample comprising a surface marker displaying agent with:
  (i) a first binding reagent comprising a first oligonucleotide comprising a first unique barcode sequence and a first hybridization sequence;
  (ii) a second binding reagent comprising a second oligonucleotide comprising a second hybridization sequence, a second unique barcode sequence, and a 5' splint complement sequence;

(iii) a third binding reagent comprising a third oligonucleotide comprising a 3' splint complement sequence, a third unique barcode sequence, and a third hybridization sequence;

(iv) a splint oligonucleotide; and (v) a capture reagent, wherein the capture reagent is linked to an anchoring reagent, wherein the anchoring reagent is releasably bound to a surface and comprises:

a first cleavage site;

a second cleavage site; and a fourth oligonucleotide comprising a fourth hybridization sequence and a fourth unique barcode sequence, wherein the first hybridization sequence and the second hybridization sequence are complementary, the third hybridization sequence and the fourth hybridization sequence are complementary, and the 5' splint complement sequence and the 3' splint complement sequence are respectively complementary to 5' and 3' ends of the splint oligonucleotide, wherein if the surface marker displaying agent binds to the capture reagent linked to the anchoring reagent, and to the first, second, and third binding reagents, then an output oligonucleotide is generated that comprises the first, second, third, and fourth unique barcode sequences, and wherein the first cleavage site is configured to be cleaved under conditions at which the second cleavage site is not cleaved;

b. cleaving at the first cleavage site and eluting unwanted components from the sample, wherein the surface marker displaying agent is retained on the surface after cleaving at the first cleavage site; and c. sequencing the output oligonucleotide to identify the first, second, third, and fourth barcode sequences therein, thereby determining at least four unique surface markers of the surface marker displaying agent.

2. The method of claim 1, wherein the first oligonucleotide further comprises a first primer site, and the fourth oligonucleotide further comprises a second primer site.

3. The method of claim 1, wherein at least one cleavage site is a restriction site.

4. The method of claim 1, wherein the capture reagent is linked to the anchoring reagent with polyethylene glycol (PEG) or with a polynucleotide sequence.

5. The method of claim 4, wherein the capture reagent is linked to the anchoring reagent with a polynucleotide sequence, wherein the polynucleotide sequence comprises poly(A).

6. The method of claim 1, wherein the surface marker displaying agent is a cell, a virus or viral particle, an organelle, a vesicle, or combination thereof.

7. The method of claim 1, further comprising cleaving at the second cleavage site to release the surface marker displaying agent from the surface.

8. The method of claim 1, further comprising adding adaptor sequences to the output oligonucleotide for PCR amplification and sequencing.

9. The method of claim 1, wherein the anchoring reagent further comprises a surface attachment moiety.

10. The method of claim 9, wherein the surface attachment moiety comprises biotin.

11. The method of claim 1, wherein the surface comprises streptavidin.

* * * * *